US008981180B2

(12) United States Patent
Laga et al.

(10) Patent No.: US 8,981,180 B2
(45) Date of Patent: Mar. 17, 2015

(54) *BRASSICA* PLANT COMPRISING MUTANT FATTY ACYL-ACP THIOESTERASE ALLELES

(75) Inventors: Benjamin Laga, Wingene (BE); Bart Den Boer, Merelbeke (BE); Bart Lambert, Ieper (BE)

(73) Assignee: Bayer CropScience N.V., Diegem (BE)

( * ) Notice: Subject to any disclaimer, the term of this patent is extended or adjusted under 35 U.S.C. 154(b) by 774 days.

(21) Appl. No.: 12/668,303

(22) PCT Filed: Jul. 7, 2008

(86) PCT No.: PCT/EP2008/005551
§ 371 (c)(1),
(2), (4) Date: Jan. 8, 2010

(87) PCT Pub. No.: WO2009/007091
PCT Pub. Date: Jan. 15, 2009

(65) Prior Publication Data
US 2011/0145944 A1    Jun. 16, 2011

Related U.S. Application Data

(60) Provisional application No. 60/958,945, filed on Jul. 10, 2007.

(30) Foreign Application Priority Data

Jul. 9, 2007 (EP) .................................. 07075568

(51) Int. Cl.
| A01H 5/10 | (2006.01) |
| C07H 21/04 | (2006.01) |
| C12N 15/82 | (2006.01) |
| A01H 1/02 | (2006.01) |
| A01H 1/04 | (2006.01) |
| C12N 9/16 | (2006.01) |
| C12Q 1/68 | (2006.01) |

(52) U.S. Cl.
CPC .............. *C12N 15/8247* (2013.01); *A01H 1/02* (2013.01); *A01H 1/04* (2013.01); *A01H 5/10* (2013.01); *C12N 9/16* (2013.01); *C12Q 1/6895* (2013.01)
USPC ........... 800/264; 800/298; 800/306; 536/23.1

(58) Field of Classification Search
None
See application file for complete search history.

(56) References Cited

U.S. PATENT DOCUMENTS

| 5,530,186 A | 6/1996 | Hitz |
| 5,945,585 A | 8/1999 | Hitz et al. |
| 5,955,650 A * | 9/1999 | Hitz .............................. 800/281 |
| 5,985,557 A | 11/1999 | Prudent et al. |
| 2004/0132189 A1 | 7/2004 | Dehesh |

FOREIGN PATENT DOCUMENTS

| EP | 534858 | 3/1993 |
| WO | WO 91/15578 | 10/1991 |
| WO | WO 91/16421 | 10/1991 |
| WO | WO 92/20236 | 11/1992 |
| WO | WO 94/10288 | 5/1994 |
| WO | WO 95/13390 | 5/1995 |
| WO | WO 96/06936 | 3/1996 |
| WO | WO 96/23892 | 8/1996 |
| WO | WO 2006/042049 | 4/2006 |

OTHER PUBLICATIONS

Bonaventure et al, Plant Cell, Apr. 2003, vol. 15, pp. 1020-1033.*
Barker et al, Plant Physiology, published online Jun. 2007, vol. 144, cited in the IDS filed Apr. 8, 2010, abstract.*
Lysak et al 2005 Genome Research 15: p. 516-525.*
Loader et al 1993 Plant Molecular Biology 23: p. 769-778.*
Bonaventure et al 2003 The Plant Cell 15: p. 1020-1033.*
Alonso et al 2003 Science 301: p. 653-657 supplemental information also provided.*
Bonaventure et al 2003 Plant Cell, 15: p. 1020-1033.*
Alonso et al 2003 Science 301: p. 653-657.*
McCallum et al 2000 123: p. 439-442.*
SALK_020856 2003 The *Arabidopsis* Information Resource homepage.*
Filichkin et al 2006 European Journal of Lipid Science and Technology 108: p. 979-990.*
Barker et al., 2007, Plant Physiology, vol. 144, No. 4, pp. 1827-1842.
Beisson et al., 2003, Plant Physiol. 132, pp. 681-697.
Bonaventure et al., 2003, Plant Cell 15, pp. 1020-1033.
Bonaventure et al., 2004, Plant Physiology 135, pp. 1269-1279.
Gibson et al., 1994, Plant Cell Environ 17, pp. 627-637.
Dehesh et al., 1996, Plant J. 9(2), pp. 167-172.
Doermann et al., 1995, Arch Biochem Biophys 316, pp. 612-618.
Doennann et al., 2000, Plant Physiology 123, pp. 637-643.
Eccleston and Ohlrogge, 1998, Plant Cell 10, pp. 613-622.
GenBank accession No. DQ847275.
GenBank accession No. DQ856315.
Hellyer et al., 1992, Plant Mol. Biology. 20, pp. 763-780.
Henikoff et al., 2004, Plant Physiology 135(2), pp. 630-636.
Jones et al., 1995, Plant Cell 7, pp. 359-371.
Li and Zhang, 2002, Funct Integr. Genomics 2, pp. 254-258.
Li et al., 2001, Plant Journal 27, pp. 235-242.
Lysak et al., 2005, Genome Research, vol. 15, 4, pp. 516-525.
Loader et al., 1993, Plant Mol. Biol. 23(4), pp. 769-778.
Lohden and Frentzen, 1988, Planta 176, pp. 506-512.
Mandal et al., 2000, Bioch. Soc. Transactions 28(6), pp. 967-969.
Martini et al., 1995, In Proc. 9th Int. Rapeseed Cong, Cambridge, UK, pp. 461-463.
Mayer and Shanklin, 2005, Journal Biol. Chem. 280(5), pp. 3621-3627.

(Continued)

*Primary Examiner* — Brent T Page
*Assistant Examiner* — Matthew Keogh
(74) *Attorney, Agent, or Firm* — Hunton & Williams LLP

(57) ABSTRACT

The invention relates to crop plants comprising novel seed lipid compositions. Provided are both wild type and mutant nucleic acid molecules encoding *Brassica* fatty acyl-acyl carrier protein (ACP) thioesterase B proteins (FATB) and the proteins as such. Also provided are *Brassica* plants, tissue and seeds comprising at least three mutant fatB alleles in their genome, whereby the seed oil fatty acid composition or profile is significantly altered.

15 Claims, 9 Drawing Sheets

(56) References Cited

OTHER PUBLICATIONS

Mayer and Shanklin, 2007, BMC Plant Biology 7(1), pp. 1-11.
McCallum et al., 2000, Plant Physiology. 123, pp. 439-442.
McCallum et al., 2000, Nat Biotechnology 18, pp. 455-457.
Mekhedov et al., 2000, Plant Physiol. 122, pp. 389-402.
Needleman and Wunsch, 1970, Journal Mol. Biology 48(3), pp. 443-453.
Osborn et al, 2003, Trends in Genetics, vol. 19, No. 3, 141-147.
Pandian et al., 2004, poster abstract, 4th Int. Crop Science Cong.
Raney et al., 1999, In Proc. 10th Int. Rapeseed Cong.: New horizons for an old crop.
Rice et al., 2000, Trends in Genetics 16 (6), pp. 276-277.
Salas and Ohlrogge, 2002, Archives of Biochemistry and Biophysics 403, pp. 25-34.
Scarth and Tang, 2006, Crop Science 46, pp. 1225-1236.
Scheffler et al., 1997, Theoretical and Applied Genetics, vol. 94, No. 5, pp. 583-591.
Snowdon, 2007, Chromosome research 15, pp. 85-95.
Voelker et al. 1992, Science 257, pp. 72-74.
Voelker et al., 1996, Plant J. 9, pp. 229-241.
Voelker et al., 1997, Plant Physiology 114, pp. 669-677.
Vos et al., 1995, Nucleic Acids Research 23 (21), pp. 4407-4414.
Yuan et al., 1995, PNAS vol. 92, pp. 10639-10643.

* cited by examiner

SEQUENCE LISTING

<160> NUMBER OF SEQ ID NOS: 103

<210> SEQ ID NO 1
<211> LENGTH: 1563
<212> TYPE: DNA
<213> ORGANISM: Brassica napus
<220> FEATURE:
<221> NAME/KEY: CDS
<222> LOCATION: (1)..(504)
<220> FEATURE:
<221> NAME/KEY: mat_peptide
<222> LOCATION: (1)..(1560)
<223> OTHER INFORMATION: mature peptide starts at amino acid 91
<220> FEATURE:
<221> NAME/KEY: misc_feature
<222> LOCATION: (490)..(492)
<223> OTHER INFORMATION: conserved Met
<220> FEATURE:
<221> NAME/KEY: CDS
<222> LOCATION: (590)..(723)
<220> FEATURE:
<221> NAME/KEY: misc_feature
<222> LOCATION: (611)..(613)
<223> OTHER INFORMATION: conserved Lys
<220> FEATURE:
<221> NAME/KEY: misc_feature
<222> LOCATION: (683)..(685)
<223> OTHER INFORMATION: conserved Val
<220> FEATURE:
<221> NAME/KEY: CDS
<222> LOCATION: (798)..(911)
<220> FEATURE:
<221> NAME/KEY: misc_feature
<222> LOCATION: (850)..(852)
<223> OTHER INFORMATION: conserved Met
<220> FEATURE:
<221> NAME/KEY: CDS
<222> LOCATION: (981)..(1152)
<220> FEATURE:
<221> NAME/KEY: misc_feature
<222> LOCATION: (1018)..(1020)
<223> OTHER INFORMATION: conserved Ser
<220> FEATURE:
<221> NAME/KEY: CDS
<222> LOCATION: (1243)..(1560)
<220> FEATURE:
<221> NAME/KEY: misc_feature
<222> LOCATION: (1249)..(1251)
<223> OTHER INFORMATION: conserved Trp
<220> FEATURE:
<221> NAME/KEY: misc_feature
<222> LOCATION: (1267)..(1269)

<223> OTHER INFORMATION: conserved Asn
<220> FEATURE:
<221> NAME/KEY: misc_feature
<222> LOCATION: (1273)..(1275)
<223> OTHER INFORMATION: conserved His
<220> FEATURE:
<221> NAME/KEY: misc_feature
<222> LOCATION: (1378)..(1380)
<223> OTHER INFORMATION: conserved Cys

<400> SEQUENCE: 1

```
atg gtg gcc acc tca gct aca tcc tca ttc ttc cct ctc cca tct ttc      48
Met Val Ala Thr Ser Ala Thr Ser Ser Phe Phe Pro Leu Pro Ser Phe
1               5                   10                  15 ccc ctc gac ccc acc gca aaa acc aac aaa gtc acc acc tcc acc aac      96
Pro Leu Asp Pro Thr Ala Lys Thr Asn Lys Val Thr Thr Ser Thr Asn
                20                  25                  30 ttc tcc ggc ctc tcc ccc act cca aac tcc tcc ggc agg atg aag gtt     144
Phe Ser Gly Leu Ser Pro Thr Pro Asn Ser Ser Gly Arg Met Lys Val
        35                  40                  45 aaa cca aac gct cag gcc cca ccc aag atc aac ggc aag aga gtc ggt     192
Lys Pro Asn Ala Gln Ala Pro Pro Lys Ile Asn Gly Lys Arg Val Gly
50                  55                  60 ctc cct tct ggc tcg gtg aag cct gat aac gag acg tcc tca cag cat     240
Leu Pro Ser Gly Ser Val Lys Pro Asp Asn Glu Thr Ser Ser Gln His
65                  70                  75                  80 ccc gca gca ccg agg acg ttc atc aac cag ctg cct gac tgg agc atg     288
Pro Ala Ala Pro Arg Thr Phe Ile Asn Gln Leu Pro Asp Trp Ser Met
                85                  90                  95 ctt ctt gct gca ata aca acc gtc ttc ttg gcg gct gag aag cag tgg     336
Leu Leu Ala Ala Ile Thr Thr Val Phe Leu Ala Ala Glu Lys Gln Trp
                100                 105                 110 atg atg ctt gac tgg aaa ccg agg cgc tct gac gtg att atg gat ccg     384
Met Met Leu Asp Trp Lys Pro Arg Arg Ser Asp Val Ile Met Asp Pro
            115                 120                 125 ttt ggg tta ggg agg atc gtt cag gat ggg ctt gtg ttc cgt cag aat     432
Phe Gly Leu Gly Arg Ile Val Gln Asp Gly Leu Val Phe Arg Gln Asn
        130                 135                 140 ttc tct att cgg tct tat gag ata ggt gct gat cgc tct gcg tct ata     480
Phe Ser Ile Arg Ser Tyr Glu Ile Gly Ala Asp Arg Ser Ala Ser Ile
145                 150                 155                 160 gaa acg gtt atg aat cat tta cag gtactgatta tgattatgat tatgattgta    534
Glu Thr Val Met Asn His Leu Gln
                165 gttgcttgtt gttactggac aaagttaata tgtattgctg ttatggttat gatag gaa    592
                                                              Glu acg gca ctc aac cat gtt aag act gct gga ctg ctt gga gat ggg ttt     640
Thr Ala Leu Asn His Val Lys Thr Ala Gly Leu Leu Gly Asp Gly Phe
170                 175                 180                 185 ggt tct act cct gag atg gtt aag aag aac ttg att tgg gtt gtt act     688
Gly Ser Thr Pro Glu Met Val Lys Lys Asn Leu Ile Trp Val Val Thr
                190                 195                 200 cgt atg cag gtt gtc gtt gat aaa tat cct act tg gtaagctatt           733
Arg Met Gln Val Val Val Asp Lys Tyr Pro Thr Trp
                205                 210 ctcaagcaac cctgagaatc actgcttcct ttgtcatttg cttattcaaa tatctgtctc   793 acag g gga gat gtt gtg gaa gta gat aca tgg gtg agc cag tct gga      840
      Gly Asp Val Val Glu Val Asp Thr Trp Val Ser Gln Ser Gly
          215                 220                 225 aag aac ggt atg cgt cgt gat tgg cta gtt cga gat ggc aat act gga     888
Lys Asn Gly Met Arg Arg Asp Trp Leu Val Arg Asp Gly Asn Thr Gly
```

```
                230                 235                 240
gaa att tta aca aga gca tca ag gttagatttt tatttatcgg ttaggtatct          941
Glu Ile Leu Thr Arg Ala Ser Ser
    245                 250 gaaaatttga gttactaatg caaaatatta tttttgcag t gtg tgg gtg atg atg         996
                                             Val Trp Val Met Met
                                                             255 aat aaa ctg aca aga aga tta tca aag att cct gaa gag gtt cga ggg         1044
Asn Lys Leu Thr Arg Arg Leu Ser Lys Ile Pro Glu Glu Val Arg Gly
            260                 265                 270 gag ata gag cct tac ttt gtt aat tca gac cca gtc ctt gct gag gac         1092
Glu Ile Glu Pro Tyr Phe Val Asn Ser Asp Pro Val Leu Ala Glu Asp
        275                 280                 285 agc aga aag tta act aaa ctt gat gac aag act gct gac tat gtt cgt         1140
Ser Arg Lys Leu Thr Lys Leu Asp Asp Lys Thr Ala Asp Tyr Val Arg
    290                 295                 300 tct ggt ctc act gtaagtatgc atactttctc tatgtttcat caaagcctgt            1192
Ser Gly Leu Thr
305 aaacttctga gattcttaca gtttttattt ggtaatttaa acttttgcag ccg cgt          1248
                                                      Pro Arg
                                                          310 tgg agt gac ttg gat gtt aac cag cac gtt aac aat gtg aag tac atc        1296
Trp Ser Asp Leu Asp Val Asn Gln His Val Asn Asn Val Lys Tyr Ile
                315                 320                 325 ggg tgg ata ctg gag agt gca cct gtg ggg atg atg gag agt cag aag        1344
Gly Trp Ile Leu Glu Ser Ala Pro Val Gly Met Met Glu Ser Gln Lys
            330                 335                 340 ctg aaa agc atg act ctg gag tat cgc agg gag tgc ggg agg gac agt        1392
Leu Lys Ser Met Thr Leu Glu Tyr Arg Arg Glu Cys Gly Arg Asp Ser
        345                 350                 355 gtg ctt cag tcc ctc acc gcg gtt tcg ggc tgc gat gtt ggt agt ctt        1440
Val Leu Gln Ser Leu Thr Ala Val Ser Gly Cys Asp Val Gly Ser Leu
    360                 365                 370 ggg aca gct ggt gaa gtg gaa tgt cag cac ctg ctc cgt ctc cag gat        1488
Gly Thr Ala Gly Glu Val Glu Cys Gln His Leu Leu Arg Leu Gln Asp
375                 380                 385                 390 gga gct gaa gtg gtg aga gga aga aca gag tgg agt tcc aaa aca tca        1536
Gly Ala Glu Val Val Arg Gly Arg Thr Glu Trp Ser Ser Lys Thr Ser
                395                 400                 405 aca aca act tgg gac att aca ccg tga                                    1563
Thr Thr Thr Trp Asp Ile Thr Pro
            410

<210> SEQ ID NO 2
<211> LENGTH: 414
<212> TYPE: PRT
<213> ORGANISM: Brassica napus

<400> SEQUENCE: 2

Met Val Ala Thr Ser Ala Thr Ser Ser Phe Phe Pro Leu Pro Ser Phe
1               5                   10                  15

Pro Leu Asp Pro Thr Ala Lys Thr Asn Lys Val Thr Thr Ser Thr Asn
            20                  25                  30

Phe Ser Gly Leu Ser Pro Thr Pro Asn Ser Ser Gly Met Lys Val
        35                  40                  45

Lys Pro Asn Ala Gln Ala Pro Pro Lys Ile Asn Gly Lys Arg Val Gly
    50                  55                  60

Leu Pro Ser Gly Ser Val Lys Pro Asp Asn Glu Thr Ser Ser Gln His
```

```
            65                  70                  75                  80
        Pro Ala Ala Pro Arg Thr Phe Ile Asn Gln Leu Pro Asp Trp Ser Met
                        85                  90                  95

Leu Leu Ala Ala Ile Thr Thr Val Phe Leu Ala Ala Glu Lys Gln Trp
                    100                 105                 110

Met Met Leu Asp Trp Lys Pro Arg Arg Ser Asp Val Ile Met Asp Pro
                115                 120                 125

Phe Gly Leu Gly Arg Ile Val Gln Asp Gly Leu Val Phe Arg Gln Asn
            130                 135                 140

Phe Ser Ile Arg Ser Tyr Glu Ile Gly Ala Asp Arg Ser Ala Ser Ile
        145                 150                 155                 160

Glu Thr Val Met Asn His Leu Gln Glu Thr Ala Leu Asn His Val Lys
                        165                 170                 175

Thr Ala Gly Leu Leu Gly Asp Gly Phe Gly Ser Thr Pro Glu Met Val
                    180                 185                 190

Lys Lys Asn Leu Ile Trp Val Val Thr Arg Met Gln Val Val Asp
                195                 200                 205

Lys Tyr Pro Thr Trp Gly Asp Val Val Glu Val Asp Thr Trp Val Ser
            210                 215                 220

Gln Ser Gly Lys Asn Gly Met Arg Arg Asp Trp Leu Val Arg Asp Gly
        225                 230                 235                 240

Asn Thr Gly Glu Ile Leu Thr Arg Ala Ser Ser Val Trp Val Met Met
                        245                 250                 255

Asn Lys Leu Thr Arg Arg Leu Ser Lys Ile Pro Glu Glu Val Arg Gly
                    260                 265                 270

Glu Ile Glu Pro Tyr Phe Val Asn Ser Asp Pro Val Leu Ala Glu Asp
                275                 280                 285

Ser Arg Lys Leu Thr Lys Leu Asp Asp Lys Thr Ala Asp Tyr Val Arg
            290                 295                 300

Ser Gly Leu Thr Pro Arg Trp Ser Asp Leu Asp Val Asn Gln His Val
        305                 310                 315                 320

Asn Asn Val Lys Tyr Ile Gly Trp Ile Leu Glu Ser Ala Pro Val Gly
                        325                 330                 335

Met Met Glu Ser Gln Lys Leu Lys Ser Met Thr Leu Glu Tyr Arg Arg
                    340                 345                 350

Glu Cys Gly Arg Asp Ser Val Leu Gln Ser Leu Thr Ala Val Ser Gly
                355                 360                 365

Cys Asp Val Gly Ser Leu Gly Thr Ala Gly Glu Val Glu Cys Gln His
            370                 375                 380

Leu Leu Arg Leu Gln Asp Gly Ala Glu Val Val Arg Gly Arg Thr Glu
        385                 390                 395                 400

Trp Ser Ser Lys Thr Ser Thr Thr Trp Asp Ile Thr Pro
                        405                 410

<210> SEQ ID NO 3
<211> LENGTH: 1659
<212> TYPE: DNA
<213> ORGANISM: Brassica napus
<220> FEATURE:
<221> NAME/KEY: CDS
<222> LOCATION: (1)..(504)
<220> FEATURE:
<221> NAME/KEY: mat_peptide
<222> LOCATION: (1)..(1656)
<223> OTHER INFORMATION: mature peptide starts at amino acid 91
<220> FEATURE:
<221> NAME/KEY: misc_feature
```

```
<222> LOCATION: (490)..(492)
<223> OTHER INFORMATION: conserved Met
<220> FEATURE:
<221> NAME/KEY: CDS
<222> LOCATION: (584)..(717)
<220> FEATURE:
<221> NAME/KEY: misc_feature
<222> LOCATION: (605)..(607)
<223> OTHER INFORMATION: conserved Lys
<220> FEATURE:
<221> NAME/KEY: misc_feature
<222> LOCATION: (677)..(679)
<223> OTHER INFORMATION: conserved Val
<220> FEATURE:
<221> NAME/KEY: CDS
<222> LOCATION: (812)..(925)
<220> FEATURE:
<221> NAME/KEY: misc_feature
<222> LOCATION: (864)..(866)
<223> OTHER INFORMATION: conserved Met
<220> FEATURE:
<221> NAME/KEY: CDS
<222> LOCATION: (1059)..(1230)
<220> FEATURE:
<221> NAME/KEY: misc_feature
<222> LOCATION: (1096)..(1098)
<223> OTHER INFORMATION: conserved Ser
<220> FEATURE:
<221> NAME/KEY: CDS
<222> LOCATION: (1309)..(1656)
<220> FEATURE:
<221> NAME/KEY: misc_feature
<222> LOCATION: (1315)..(1317)
<223> OTHER INFORMATION: conserved Trp
<220> FEATURE:
<221> NAME/KEY: misc_feature
<222> LOCATION: (1333)..(1335)
<223> OTHER INFORMATION: conserved Asn
<220> FEATURE:
<221> NAME/KEY: misc_feature
<222> LOCATION: (1339)..(1341)
<223> OTHER INFORMATION: conserved His
<220> FEATURE:
<221> NAME/KEY: misc_feature
<222> LOCATION: (1444)..(1446)
<223> OTHER INFORMATION: conserved Cys

<400> SEQUENCE: 3 atg gtg gct act tgc gct acg tcg tcg ttt ttt cat gtt cca tct tct      48
Met Val Ala Thr Cys Ala Thr Ser Ser Phe Phe His Val Pro Ser Ser
1               5                   10                  15 tcc tcg ctt gat acg aat ggg aag ggg aac aga gtt ggg tcc act aat      96
Ser Ser Leu Asp Thr Asn Gly Lys Gly Asn Arg Val Gly Ser Thr Asn
            20                  25                  30 ttt gct gga ctt aac tca acg cca agc tct ggg agg atg aag gtt aag     144
Phe Ala Gly Leu Asn Ser Thr Pro Ser Ser Gly Arg Met Lys Val Lys
        35                  40                  45 cca aac gct cag gct cca ccc aag atc aac ggg aag aaa gct aac ttg     192
Pro Asn Ala Gln Ala Pro Pro Lys Ile Asn Gly Lys Lys Ala Asn Leu
50                  55                  60 cct ggc tct gta gag ata tca aag gct gac aac gag act tcg cag ccc     240
Pro Gly Ser Val Glu Ile Ser Lys Ala Asp Asn Glu Thr Ser Gln Pro
65                  70                  75                  80 gca cac gca ccg agg acg ttt atc aac cag ctg cct gac tgg agt atg     288
Ala His Ala Pro Arg Thr Phe Ile Asn Gln Leu Pro Asp Trp Ser Met
                85                  90                  95 ctg ctt gct gct ata act acc att ttc ttg gca gcg gag aaa cag tgg     336
Leu Leu Ala Ala Ile Thr Thr Ile Phe Leu Ala Ala Glu Lys Gln Trp
            100                 105                 110 atg atg ctt gac tgg aaa ccg agg cgt tct gat atg att atg gat cct     384
Met Met Leu Asp Trp Lys Pro Arg Arg Ser Asp Met Ile Met Asp Pro
```

|  |  |
|---|---:|
| 115 120 125 | |
| ttt ggt tta ggg aga att gtt cag gat ggt ctt gtg ttc cgt cag aat<br>Phe Gly Leu Gly Arg Ile Val Gln Asp Gly Leu Val Phe Arg Gln Asn<br>130 135 140 | 432 |
| ttt tcc att agg tct tat gaa ata ggt gct gat cgc tct gcg tct ata<br>Phe Ser Ile Arg Ser Tyr Glu Ile Gly Ala Asp Arg Ser Ala Ser Ile<br>145 150 155 160 | 480 |
| gaa act gtc atg aat cat tta cag gtactgcttt gattgtggtt acactcacat<br>Glu Thr Val Met Asn His Leu Gln<br>165 | 534 |
| gttgtcccaa tagatatatg ctcatgacaa gctcttatgc taatgacag gaa acg gcg<br>Glu Thr Ala<br>170 | 592 |
| ctt aat cat gtg aag tct gcc gga ctg ctg gaa aat ggg ttt ggg tcc<br>Leu Asn His Val Lys Ser Ala Gly Leu Leu Glu Asn Gly Phe Gly Ser<br>175 180 185 | 640 |
| act cct gag atg ttt aag aag aat ttg ata tgg gtc gtt gct cgt atg<br>Thr Pro Glu Met Phe Lys Lys Asn Leu Ile Trp Val Val Ala Arg Met<br>190 195 200 | 688 |
| cag gtt gtc gtt gat aaa tat cct act tg gtaagccatt gttagtctta<br>Gln Val Val Val Asp Lys Tyr Pro Thr Trp<br>205 210 | 737 |
| gcacttgact taaaatcatt ttgcatatta cagtgtgcgt agatcatttg cttattcaaa | 797 |
| tatctgactc acag g gga gat gtt gtg gaa gtg gat act tgg gtt agt cag<br>Gly Asp Val Val Glu Val Asp Thr Trp Val Ser Gln<br>215 220 225 | 848 |
| tct gga aag aat ggt atg cgt cgt gat tgg cta gtt cgg gat tgc aat<br>Ser Gly Lys Asn Gly Met Arg Arg Asp Trp Leu Val Arg Asp Cys Asn<br>230 235 240 | 896 |
| act gga gaa att gta acg cga gca tca ag gtcagagttc ttatattttg<br>Thr Gly Glu Ile Val Thr Arg Ala Ser Ser<br>245 250 | 945 |
| gtttactcca gctattatcg ttttgctctc tgtttgtatt gttcctctg ccattagttt | 1005 |
| gataattgag tctttatagt tgtatatgta tggcaatttt cttctttttg cag t ttg<br>Leu | 1062 |
| tgg gtg atg atg aat aaa ctc aca agg aga ttg tca aag att cct gaa<br>Trp Val Met Met Asn Lys Leu Thr Arg Arg Leu Ser Lys Ile Pro Glu<br>255 260 265 | 1110 |
| gag gtt cga ggg gaa ata gag cct tat ttt gtg aac tct gat cct gtc<br>Glu Val Arg Gly Glu Ile Glu Pro Tyr Phe Val Asn Ser Asp Pro Val<br>270 275 280 | 1158 |
| att gcc gaa gac agc aga aag tta aca aaa ctt gat gac aag act gct<br>Ile Ala Glu Asp Ser Arg Lys Leu Thr Lys Leu Asp Asp Lys Thr Ala<br>285 290 295 300 | 1206 |
| gac tat gtt cgt tct ggt ctc act gtaagtacct tacctttcga caagcctgtc<br>Asp Tyr Val Arg Ser Gly Leu Thr<br>305 | 1260 |
| aaaactcttg aggttctaat ggtttggtaa tgaacttttt tttggcag ccg agg tgg<br>Pro Arg Trp<br>310 | 1317 |
| agt gac ttg gat gtt aac cag cat gtt aac aat gta aag tac att ggg<br>Ser Asp Leu Asp Val Asn Gln His Val Asn Asn Val Lys Tyr Ile Gly<br>315 320 325 | 1365 |
| tgg ata ctg gag agt gct cca gca ggg atg ctg gag agt cag aag ctg<br>Trp Ile Leu Glu Ser Ala Pro Ala Gly Met Leu Glu Ser Gln Lys Leu<br>330 335 340 | 1413 |
| aaa agc atg act ctg gag tat cgc agg gag tgc ggg aga gac agt gtg<br>Lys Ser Met Thr Leu Glu Tyr Arg Arg Glu Cys Gly Arg Asp Ser Val | 1461 |

```
            345                 350                 355
ctt cag tct ctc acc gca gtc tct gga tgt gat gtc ggt aac ctc ggg      1509
Leu Gln Ser Leu Thr Ala Val Ser Gly Cys Asp Val Gly Asn Leu Gly
360                 365                 370                 375 aca gcc ggg gaa gtg gag tgt cag cat ttg ctt cga ctc cag gat gga      1557
Thr Ala Gly Glu Val Glu Cys Gln His Leu Leu Arg Leu Gln Asp Gly
                380                 385                 390 gct gaa gtg gtg aga gga aga aca gag tgg agc tcc cag aca gga gca      1605
Ala Glu Val Val Arg Gly Arg Thr Glu Trp Ser Ser Gln Thr Gly Ala
            395                 400                 405 aca act tgg gga cac tac tac atc gta aac att ggt cct ttg gtt cct      1653
Thr Thr Trp Gly His Tyr Tyr Ile Val Asn Ile Gly Pro Leu Val Pro
        410                 415                 420 ttg taa                                                               1659
Leu

<210> SEQ ID NO 4
<211> LENGTH: 424
<212> TYPE: PRT
<213> ORGANISM: Brassica napus

<400> SEQUENCE: 4

Met Val Ala Thr Cys Ala Thr Ser Ser Phe His Val Pro Ser Ser
1               5                   10                  15

Ser Ser Leu Asp Thr Asn Gly Lys Gly Asn Arg Val Gly Ser Thr Asn
                20                  25                  30

Phe Ala Gly Leu Asn Ser Thr Pro Ser Ser Gly Arg Met Lys Val Lys
            35                  40                  45

Pro Asn Ala Gln Ala Pro Pro Lys Ile Asn Gly Lys Lys Ala Asn Leu
        50                  55                  60

Pro Gly Ser Val Glu Ile Ser Lys Ala Asp Asn Glu Thr Ser Gln Pro
65                  70                  75                  80

Ala His Ala Pro Arg Thr Phe Ile Asn Gln Leu Pro Asp Trp Ser Met
                85                  90                  95

Leu Leu Ala Ala Ile Thr Thr Ile Phe Leu Ala Ala Glu Lys Gln Trp
            100                 105                 110

Met Met Leu Asp Trp Lys Pro Arg Arg Ser Asp Met Ile Met Asp Pro
        115                 120                 125

Phe Gly Leu Gly Arg Ile Val Gln Asp Gly Leu Val Phe Arg Gln Asn
    130                 135                 140

Phe Ser Ile Arg Ser Tyr Glu Ile Gly Ala Asp Arg Ser Ala Ser Ile
145                 150                 155                 160

Glu Thr Val Met Asn His Leu Gln Glu Thr Ala Leu Asn His Val Lys
                165                 170                 175

Ser Ala Gly Leu Leu Glu Asn Gly Phe Gly Ser Thr Pro Glu Met Phe
            180                 185                 190

Lys Lys Asn Leu Ile Trp Val Val Ala Arg Met Gln Val Val Val Asp
        195                 200                 205

Lys Tyr Pro Thr Trp Gly Asp Val Val Glu Val Asp Thr Trp Val Ser
    210                 215                 220

Gln Ser Gly Lys Asn Gly Met Arg Arg Asp Trp Leu Val Arg Asp Cys
225                 230                 235                 240

Asn Thr Gly Glu Ile Val Thr Arg Ala Ser Ser Leu Trp Val Met Met
                245                 250                 255

Asn Lys Leu Thr Arg Arg Leu Ser Lys Ile Pro Glu Glu Val Arg Gly
            260                 265                 270
```

Glu Ile Glu Pro Tyr Phe Val Asn Ser Asp Pro Val Ile Ala Glu Asp
            275                 280                 285

Ser Arg Lys Leu Thr Lys Leu Asp Asp Lys Thr Ala Asp Tyr Val Arg
290                 295                 300

Ser Gly Leu Thr Pro Arg Trp Ser Asp Leu Asp Val Asn Gln His Val
305                 310                 315                 320

Asn Asn Val Lys Tyr Ile Gly Trp Ile Leu Glu Ser Ala Pro Ala Gly
                325                 330                 335

Met Leu Glu Ser Gln Lys Leu Lys Ser Met Thr Leu Glu Tyr Arg Arg
            340                 345                 350

Glu Cys Gly Arg Asp Ser Val Leu Gln Ser Leu Thr Ala Val Ser Gly
            355                 360                 365

Cys Asp Val Gly Asn Leu Gly Thr Ala Gly Glu Val Glu Cys Gln His
        370                 375                 380

Leu Leu Arg Leu Gln Asp Gly Ala Glu Val Val Arg Gly Arg Thr Glu
385                 390                 395                 400

Trp Ser Ser Gln Thr Gly Ala Thr Thr Trp Gly His Tyr Tyr Ile Val
                405                 410                 415

Asn Ile Gly Pro Leu Val Pro Leu
            420

<210> SEQ ID NO 5
<211> LENGTH: 1733
<212> TYPE: DNA
<213> ORGANISM: Brassica napus
<220> FEATURE:
<221> NAME/KEY: CDS
<222> LOCATION: (1)..(507)
<220> FEATURE:
<221> NAME/KEY: mat_peptide
<222> LOCATION: (1)..(1730)
<223> OTHER INFORMATION: mature peptide starts at amino acid 92
<220> FEATURE:
<221> NAME/KEY: misc_feature
<222> LOCATION: (493)..(495)
<223> OTHER INFORMATION: conserved Met
<220> FEATURE:
<221> NAME/KEY: CDS
<222> LOCATION: (740)..(873)
<220> FEATURE:
<221> NAME/KEY: misc_feature
<222> LOCATION: (761)..(763)
<223> OTHER INFORMATION: conserved Lys
<220> FEATURE:
<221> NAME/KEY: misc_feature
<222> LOCATION: (833)..(835)
<223> OTHER INFORMATION: conserved Val
<220> FEATURE:
<221> NAME/KEY: CDS
<222> LOCATION: (947)..(1060)
<220> FEATURE:
<221> NAME/KEY: misc_feature
<222> LOCATION: (999)..(1001)
<223> OTHER INFORMATION: conserved Met
<220> FEATURE:
<221> NAME/KEY: CDS
<222> LOCATION: (1141)..(1312)
<220> FEATURE:
<221> NAME/KEY: misc_feature
<222> LOCATION: (1178)..(1180)
<223> OTHER INFORMATION: conserved Ser
<220> FEATURE:
<221> NAME/KEY: CDS
<222> LOCATION: (1413)..(1730)
<220> FEATURE:
<221> NAME/KEY: misc_feature
<222> LOCATION: (1419)..(1421)
<223> OTHER INFORMATION: conserved Trp

```
<220> FEATURE:
<221> NAME/KEY: misc_feature
<222> LOCATION: (1437)..(1439)
<223> OTHER INFORMATION: conserved Asn
<220> FEATURE:
<221> NAME/KEY: misc_feature
<222> LOCATION: (1443)..(1445)
<223> OTHER INFORMATION: conserved His
<220> FEATURE:
<221> NAME/KEY: misc_feature
<222> LOCATION: (1548)..(1550)
<223> OTHER INFORMATION: conserved Cys

<400> SEQUENCE: 5
```

| | | | | | | | | | | | | | | | | |
|---|---|---|---|---|---|---|---|---|---|---|---|---|---|---|---|---|
| atg | gtg | gcc | acc | tct | gct | aca | tcc | tca | ttc | ttc | cct | ctc | cca | tct | tcc | 48 |
| Met | Val | Ala | Thr | Ser | Ala | Thr | Ser | Ser | Phe | Phe | Pro | Leu | Pro | Ser | Ser | |
| 1 | | | | 5 | | | | | 10 | | | | | 15 | | |
| tct | ctc | gac | ccc | aat | ggc | aaa | acc | aac | aaa | ctc | acc | tcc | acc | aac | ttc | 96 |
| Ser | Leu | Asp | Pro | Asn | Gly | Lys | Thr | Asn | Lys | Leu | Thr | Ser | Thr | Asn | Phe | |
| | | | 20 | | | | | 25 | | | | | 30 | | | |
| tcc | gga | ctc | aac | ccc | aca | cca | aac | tct | tcc | ggc | agg | tta | aag | gtc | aaa | 144 |
| Ser | Gly | Leu | Asn | Pro | Thr | Pro | Asn | Ser | Ser | Gly | Arg | Leu | Lys | Val | Lys | |
| | | 35 | | | | | 40 | | | | | 45 | | | | |
| cca | aac | gcc | caa | gct | cca | tcc | aag | atc | aac | ggc | aag | aaa | gtc | tct | ctg | 192 |
| Pro | Asn | Ala | Gln | Ala | Pro | Ser | Lys | Ile | Asn | Gly | Lys | Lys | Val | Ser | Leu | |
| | 50 | | | | | 55 | | | | | 60 | | | | | |
| cca | ggc | tca | gta | cac | atc | gta | aag | act | gat | aat | aac | cac | gat | ctc | tcg | 240 |
| Pro | Gly | Ser | Val | His | Ile | Val | Lys | Thr | Asp | Asn | Asn | His | Asp | Leu | Ser | |
| 65 | | | | 70 | | | | | 75 | | | | | 80 | | |
| caa | caa | cac | gca | ccc | aga | acg | ttc | atc | aac | cag | ctg | cct | gac | tgg | agc | 288 |
| Gln | Gln | His | Ala | Pro | Arg | Thr | Phe | Ile | Asn | Gln | Leu | Pro | Asp | Trp | Ser | |
| | | | | 85 | | | | | 90 | | | | | 95 | | |
| atg | ctt | ctc | gcc | gcc | atc | aca | acg | gtc | ttc | tta | gca | gct | gag | aag | cag | 336 |
| Met | Leu | Leu | Ala | Ala | Ile | Thr | Thr | Val | Phe | Leu | Ala | Ala | Glu | Lys | Gln | |
| | | | 100 | | | | | 105 | | | | | 110 | | | |
| tgg | atg | atg | ctt | gat | act | aaa | ccg | aga | cgc | tcc | gac | atg | att | atg | gat | 384 |
| Trp | Met | Met | Leu | Asp | Thr | Lys | Pro | Arg | Arg | Ser | Asp | Met | Ile | Met | Asp | |
| | | 115 | | | | | 120 | | | | | 125 | | | | |
| ccg | ttt | ggg | tta | ggg | aga | atc | gtt | cag | gat | ggg | ctt | gtg | tac | cgt | cag | 432 |
| Pro | Phe | Gly | Leu | Gly | Arg | Ile | Val | Gln | Asp | Gly | Leu | Val | Tyr | Arg | Gln | |
| | 130 | | | | | 135 | | | | | 140 | | | | | |
| aat | ttc | gat | atc | agg | tct | tat | gaa | ata | ggt | gct | gat | cgc | tct | gca | tct | 480 |
| Asn | Phe | Asp | Ile | Arg | Ser | Tyr | Glu | Ile | Gly | Ala | Asp | Arg | Ser | Ala | Ser | |
| 145 | | | | | 150 | | | | | 155 | | | | | 160 | |
| ata | gaa | act | gtc | atg | aat | cac | tta | cag | gtatattaca | | atcacactcg | | | | | 527 |
| Ile | Glu | Thr | Val | Met | Asn | His | Leu | Gln | | | | | | | | |
| | | | | 165 | | | | | | | | | | | | |

```
tttgatacta tagcttgacc cgcactgatg ttggttttta tatttttata aattatttag    587
tgacatatag ataggttta ttagatatt tctaggttcc tacgaaccta cccggactca      647
aaccctgtcc gtaaaattga gtttaatttt aaaccaaaaa aatccgatac cgaaaaaac    707 cgatctgtat ctaactcttg tcctcatgac ag
```

| | | | | | | | | | | | | | | | | |
|---|---|---|---|---|---|---|---|---|---|---|---|---|---|---|---|---|
| | | | | | | | | | | gaa | acg | gca | ctc | aac | cat | gtg | 760 |
| | | | | | | | | | | Glu | Thr | Ala | Leu | Asn | His | Val | |
| | | | | | | | | | | 170 | | | | | 175 | | |
| aag | tct | gca | gga | ctg | ctg | gga | gat | ggg | ttt | ggt | tct | acg | cct | gag | atg | 808 |
| Lys | Ser | Ala | Gly | Leu | Leu | Gly | Asp | Gly | Phe | Gly | Ser | Thr | Pro | Glu | Met | |
| | | 180 | | | | | 185 | | | | | 190 | | | | |
| gtt | aag | aag | aac | ttg | ata | tgg | gtc | gtt | act | cgt | atg | cag | gtt | gtc | gtt | 856 |
| Val | Lys | Lys | Asn | Leu | Ile | Trp | Val | Val | Thr | Arg | Met | Gln | Val | Val | Val | |
| | 195 | | | | | 200 | | | | | 205 | | | | | |
| gat | aaa | tat | cct | act | tg | | gtaagctctc | | ttgccactta | | accttaaaca | | | | | 903 |
| Asp | Lys | Tyr | Pro | Thr | Trp | | | | | | | | | | | |

```
      210
atatgcatga atcatttgct tattcaaatg tctgtttcac cag g gga gat gtt gtt      959
                                                  Gly Asp Val Val
                                                      215 gaa gta gat aca tgg gtc agt aag tct ggg aag aac ggt atg cgt cgt     1007
Glu Val Asp Thr Trp Val Ser Lys Ser Gly Lys Asn Gly Met Arg Arg
    220                 225                 230 gat tgg cta gtt cgg gat tgc aat acc gga gaa atc tta aca cgt gca     1055
Asp Trp Leu Val Arg Asp Cys Asn Thr Gly Glu Ile Leu Thr Arg Ala
235                 240                 245                 250 tca ag  gttagcttct ttttgttttt ttgtttactc cagctattat ctgatgattg       1110
Ser Ser agttataacc atctctatgt tacaaaacag t gtg tgg gtg atg atg aat aaa      1162
                                  Val Trp Val Met Met Asn Lys
                                                      255 ctg aca agg aga tta tca aag ctt cct gaa gag gtt cga ggg gaa ata     1210
Leu Thr Arg Arg Leu Ser Lys Leu Pro Glu Glu Val Arg Gly Glu Ile
260                 265                 270                 275 gag cct tac ttt gtg aac tct gac cca atc ctt gcc gag gac agc aga     1258
Glu Pro Tyr Phe Val Asn Ser Asp Pro Ile Leu Ala Glu Asp Ser Arg
                280                 285                 290 aag tta aca aag cta gat gac aag act gct gac tat gtt cgc tct ggt     1306
Lys Leu Thr Lys Leu Asp Asp Lys Thr Ala Asp Tyr Val Arg Ser Gly
            295                 300                 305 ctc acc gtaagtataa atattcaact ctttatcttt tagcgtgtaa aactcttgag      1362
Leu Thr agattcttat gagtttagat tcttatgagt ttggtgatga acttttgcag ccg aga    1418
                                                              Pro Arg
                                                                  310 tgg agt gac ttg gat gtt aac cag cat gtt aac aac gtg aag tac att     1466
Trp Ser Asp Leu Asp Val Asn Gln His Val Asn Asn Val Lys Tyr Ile
                315                 320                 325 ggt tgg ata ctc gag agt gct cca gta gag atg atg gag aag cat aag     1514
Gly Trp Ile Leu Glu Ser Ala Pro Val Glu Met Met Glu Lys His Lys
            330                 335                 340 ctg aaa agc atg act ctg gag tat agg agg gaa tgc ggg aga gac agt     1562
Leu Lys Ser Met Thr Leu Glu Tyr Arg Arg Glu Cys Gly Arg Asp Ser
        345                 350                 355 gtg ctt cag tct ctc acc gcg gtt tcg gga tgc gat gtt ggt agc ctc     1610
Val Leu Gln Ser Leu Thr Ala Val Ser Gly Cys Asp Val Gly Ser Leu
360                 365                 370                 375 ggg aca gct ggt gaa gtg gaa tgt cag cat ttg ctt cga ctc cag gat     1658
Gly Thr Ala Gly Glu Val Glu Cys Gln His Leu Leu Arg Leu Gln Asp
                380                 385                 390 gga gct gaa gtg gtg aag gga cga aca gtg tgg agt tcg aaa aca cca     1706
Gly Ala Glu Val Val Lys Gly Arg Thr Val Trp Ser Ser Lys Thr Pro
            395                 400                 405 tca acg act tgg gac act aca tcg taa                                 1733
Ser Thr Thr Trp Asp Thr Thr Ser
        410                 415

<210> SEQ ID NO 6
<211> LENGTH: 415
<212> TYPE: PRT
<213> ORGANISM: Brassica napus

<400> SEQUENCE: 6

Met Val Ala Thr Ser Ala Thr Ser Ser Phe Phe Pro Leu Pro Ser Ser
1               5                   10                  15
```

```
Ser Leu Asp Pro Asn Gly Lys Thr Asn Lys Leu Thr Ser Thr Asn Phe
             20                  25                  30

Ser Gly Leu Asn Pro Thr Pro Asn Ser Ser Gly Arg Leu Lys Val Lys
         35                  40                  45

Pro Asn Ala Gln Ala Pro Ser Lys Ile Asn Gly Lys Lys Val Ser Leu
     50                  55                  60

Pro Gly Ser Val His Ile Val Lys Thr Asp Asn Asn His Asp Leu Ser
 65                  70                  75                  80

Gln Gln His Ala Pro Arg Thr Phe Ile Asn Gln Leu Pro Asp Trp Ser
                 85                  90                  95

Met Leu Leu Ala Ala Ile Thr Thr Val Phe Leu Ala Ala Glu Lys Gln
            100                 105                 110

Trp Met Met Leu Asp Thr Lys Pro Arg Arg Ser Asp Met Ile Met Asp
        115                 120                 125

Pro Phe Gly Leu Gly Arg Ile Val Gln Asp Gly Leu Val Tyr Arg Gln
    130                 135                 140

Asn Phe Asp Ile Arg Ser Tyr Glu Ile Gly Ala Asp Arg Ser Ala Ser
145                 150                 155                 160

Ile Glu Thr Val Met Asn His Leu Gln Glu Thr Ala Leu Asn His Val
                165                 170                 175

Lys Ser Ala Gly Leu Leu Gly Asp Gly Phe Gly Ser Thr Pro Glu Met
            180                 185                 190

Val Lys Lys Asn Leu Ile Trp Val Val Thr Arg Met Gln Val Val Val
        195                 200                 205

Asp Lys Tyr Pro Thr Trp Gly Asp Val Val Glu Val Asp Thr Trp Val
    210                 215                 220

Ser Lys Ser Gly Lys Asn Gly Met Arg Arg Asp Trp Leu Val Arg Asp
225                 230                 235                 240

Cys Asn Thr Gly Glu Ile Leu Thr Arg Ala Ser Ser Val Trp Val Met
                245                 250                 255

Met Asn Lys Leu Thr Arg Arg Leu Ser Lys Leu Pro Glu Glu Val Arg
            260                 265                 270

Gly Glu Ile Glu Pro Tyr Phe Val Asn Ser Asp Pro Ile Leu Ala Glu
        275                 280                 285

Asp Ser Arg Lys Leu Thr Lys Leu Asp Asp Lys Thr Ala Asp Tyr Val
    290                 295                 300

Arg Ser Gly Leu Thr Pro Arg Trp Ser Asp Leu Asp Val Asn Gln His
305                 310                 315                 320

Val Asn Asn Val Lys Tyr Ile Gly Trp Ile Leu Glu Ser Ala Pro Val
                325                 330                 335

Glu Met Met Glu Lys His Lys Leu Lys Ser Met Thr Leu Glu Tyr Arg
            340                 345                 350

Arg Glu Cys Gly Arg Asp Ser Val Leu Gln Ser Leu Thr Ala Val Ser
        355                 360                 365

Gly Cys Asp Val Gly Ser Leu Gly Thr Ala Gly Glu Val Glu Cys Gln
    370                 375                 380

His Leu Leu Arg Leu Gln Asp Gly Ala Glu Val Val Lys Gly Arg Thr
385                 390                 395                 400

Val Trp Ser Ser Lys Thr Pro Ser Thr Thr Trp Asp Thr Thr Ser
                405                 410                 415

<210> SEQ ID NO 7
<211> LENGTH: 1572
<212> TYPE: DNA
```

```
<213> ORGANISM: Brassica napus
<220> FEATURE:
<221> NAME/KEY: CDS
<222> LOCATION: (1)..(498)
<220> FEATURE:
<221> NAME/KEY: mat_peptide
<222> LOCATION: (1)..(1569)
<223> OTHER INFORMATION: mature peptide starts at amino acid 89
<220> FEATURE:
<221> NAME/KEY: misc_feature
<222> LOCATION: (484)..(486)
<223> OTHER INFORMATION: conserved Met
<220> FEATURE:
<221> NAME/KEY: CDS
<222> LOCATION: (579)..(712)
<220> FEATURE:
<221> NAME/KEY: misc_feature
<222> LOCATION: (610)..(612)
<223> OTHER INFORMATION: conserved Lys
<220> FEATURE:
<221> NAME/KEY: misc_feature
<222> LOCATION: (672)..(674)
<223> OTHER INFORMATION: conserved Val
<220> FEATURE:
<221> NAME/KEY: CDS
<222> LOCATION: (791)..(904)
<220> FEATURE:
<221> NAME/KEY: misc_feature
<222> LOCATION: (843)..(845)
<223> OTHER INFORMATION: conserved Met
<220> FEATURE:
<221> NAME/KEY: CDS
<222> LOCATION: (995)..(1166)
<220> FEATURE:
<221> NAME/KEY: misc_feature
<222> LOCATION: (1032)..(1034)
<223> OTHER INFORMATION: conserved Ser
<220> FEATURE:
<221> NAME/KEY: CDS
<222> LOCATION: (1252)..(1569)
<220> FEATURE:
<221> NAME/KEY: misc_feature
<222> LOCATION: (1258)..(1260)
<223> OTHER INFORMATION: conserved Trp
<220> FEATURE:
<221> NAME/KEY: misc_feature
<222> LOCATION: (1276)..(1278)
<223> OTHER INFORMATION: conserved Asn
<220> FEATURE:
<221> NAME/KEY: misc_feature
<222> LOCATION: (1282)..(1284)
<223> OTHER INFORMATION: conserved His
<220> FEATURE:
<221> NAME/KEY: misc_feature
<222> LOCATION: (1387)..(1389)
<223> OTHER INFORMATION: conserved Cys

<400> SEQUENCE: 7 atg gtg gcc acc tca gct aca tcc tca ttc ttc cct ctc cca tct tcc      48
Met Val Ala Thr Ser Ala Thr Ser Ser Phe Phe Pro Leu Pro Ser Ser
1               5                   10                  15 ccc ctc gac ccc acc gca aaa acc aac aaa gtc acc acc tcc acc aac      96
Pro Leu Asp Pro Thr Ala Lys Thr Asn Lys Val Thr Thr Ser Thr Asn
            20                  25                  30 ttc tcc ggc ctc acc ccc acg ccg aac tcc gcc agg atg aag gtt aaa     144
Phe Ser Gly Leu Thr Pro Thr Pro Asn Ser Ala Arg Met Lys Val Lys
        35                  40                  45 cca aac gct cag gcc cca ccc aag atc aac ggc aag aga gtc ggc ctc     192
Pro Asn Ala Gln Ala Pro Pro Lys Ile Asn Gly Lys Arg Val Gly Leu
    50                  55                  60 cct ggc tcg gtg gag atc ttg aag cct gat agc gag act tcg caa cca     240
Pro Gly Ser Val Glu Ile Leu Lys Pro Asp Ser Glu Thr Ser Gln Pro
65                  70                  75                  80
```

```
gca ccg agg acg ttc atc aac cag ctg cct gac tgg agc atg ctc ctc    288
Ala Pro Arg Thr Phe Ile Asn Gln Leu Pro Asp Trp Ser Met Leu Leu
            85                  90                  95 gcc gcc atc acg acc gtc ttc ttg gcg gct gag aag cag tgg atg atg    336
Ala Ala Ile Thr Thr Val Phe Leu Ala Ala Glu Lys Gln Trp Met Met
        100                 105                 110 ctc gac tgg aaa ccg agg cgt tct gac gtg att atg gat ccg ttt ggg    384
Leu Asp Trp Lys Pro Arg Arg Ser Asp Val Ile Met Asp Pro Phe Gly
        115                 120                 125 tta ggg agg atc gtt cag gat ggg ctt gtg ttc cgt cag aat ttt tct    432
Leu Gly Arg Ile Val Gln Asp Gly Leu Val Phe Arg Gln Asn Phe Ser
130                 135                 140 att cgg tct tat gag ata ggt gct gat cgc tct gcg tct ata gaa acg    480
Ile Arg Ser Tyr Glu Ile Gly Ala Asp Arg Ser Ala Ser Ile Glu Thr
145                 150                 155                 160 gtt atg aat cat tta cag gtactgatta tgattatgat tgtagtcgct           528
Val Met Asn His Leu Gln
                165 tgttgttact gggcaaactt aaatatgtat tgctcttatg ttgtgatag gaa acg      584
                                                        Glu Thr gca ctc aac cat gtt aag act gct ggg ctg ctt gga gat ggg ttt ggt    632
Ala Leu Asn His Val Lys Thr Ala Gly Leu Leu Gly Asp Gly Phe Gly
        170                 175                 180 tct act cct gag atg gtt aag aag aac ttg ata tgg gtt gtt act cgt    680
Ser Thr Pro Glu Met Val Lys Lys Asn Leu Ile Trp Val Val Thr Arg
185                 190                 195                 200 atg cag gtt gtc gtt gat aaa tat cct act tg gtaagctatt ctcaacaac    732
Met Gln Val Val Val Asp Lys Tyr Pro Thr Trp
                205                 210 tctgagaatc actgcttcct tgtgagtca tttgcttatt caaatatctg cctcatag g    791 gga gat gtt gtg gaa gta gat aca tgg gtg agc cag tct gga aag aac    839
Gly Asp Val Val Glu Val Asp Thr Trp Val Ser Gln Ser Gly Lys Asn
            215                 220                 225 ggt atg cgt cgt gat tgg cta gtt cga gat ggc aat act gga gag att    887
Gly Met Arg Arg Asp Trp Leu Val Arg Asp Gly Asn Thr Gly Glu Ile
        230                 235                 240 tta aca aga gca tca ag gttagatttt atttttggt ttacttgggt             934
Leu Thr Arg Ala Ser Ser
245 tagatatctg ataattgagt tataatcatc tccgtgttgt gtaaactatt cttttgcag    994 t gtg tgg gtg atg atg aat aaa ctg aca aga aga tta tca aag att cct   1043
  Val Trp Val Met Met Asn Lys Leu Thr Arg Arg Leu Ser Lys Ile Pro
      250                 255                 260                 265 gaa gag gtt cga ggg gag ata gag cct tac ttt gtt aac tca gac cca    1091
Glu Glu Val Arg Gly Glu Ile Glu Pro Tyr Phe Val Asn Ser Asp Pro
            270                 275                 280 gtc ctt gcc gag gac agc aga aag tta aca aaa ctt gat gac aaa act    1139
Val Leu Ala Glu Asp Ser Arg Lys Leu Thr Lys Leu Asp Asp Lys Thr
        285                 290                 295 gct gtc tat gtt cgt tct ggt ctc act gtaagtacaa atacttcact          1186
Ala Val Tyr Val Arg Ser Gly Leu Thr
        300                 305 ctatgtttca acaaagcctg taaattttg agtctcttac aggtttggta atgaactttt    1246 tgcag ccg cgt tgg agt gac ttg gat gtt aac cag cac gtt aac aat gtg   1296
      Pro Arg Trp Ser Asp Leu Asp Val Asn Gln His Val Asn Asn Val
          310                 315                 320 aag tac atc ggg tgg ata ctg gag agt gct cca gtg ggg atg atg gag    1344
Lys Tyr Ile Gly Trp Ile Leu Glu Ser Ala Pro Val Gly Met Met Glu
```

```
                        325                     330                     335
agt cag aag ctg aaa agc atg act ctg gag tat cgc agg gag tgt ggg            1392
Ser Gln Lys Leu Lys Ser Met Thr Leu Glu Tyr Arg Arg Glu Cys Gly
            340                     345                     350 aga gac agt gtg ctc cag tcc ctc acc gcg gtt tcg ggc tgc gat atc            1440
Arg Asp Ser Val Leu Gln Ser Leu Thr Ala Val Ser Gly Cys Asp Ile
    355                     360                     365 ggt agc ctc ggg aca gcc ggt gaa gtg gaa tgt cag cat ctg ctc aga            1488
Gly Ser Leu Gly Thr Ala Gly Glu Val Glu Cys Gln His Leu Leu Arg
370                     375                     380                     385 ctc cag gat gga gcc gaa gtg gtg aga gga aga aca gag tgg agt tcc            1536
Leu Gln Asp Gly Ala Glu Val Val Arg Gly Arg Thr Glu Trp Ser Ser
            390                     395                     400 aaa aca tca aca aca act tgg gac atc aca ccg tga                            1572
Lys Thr Ser Thr Thr Thr Trp Asp Ile Thr Pro
            405                     410

<210> SEQ ID NO 8
<211> LENGTH: 412
<212> TYPE: PRT
<213> ORGANISM: Brassica napus

<400> SEQUENCE: 8

Met Val Ala Thr Ser Ala Thr Ser Ser Phe Phe Pro Leu Pro Ser Ser
1               5                   10                  15

Pro Leu Asp Pro Thr Ala Lys Thr Asn Lys Val Thr Thr Ser Thr Asn
            20                  25                  30

Phe Ser Gly Leu Thr Pro Thr Pro Asn Ser Ala Arg Met Lys Val Lys
        35                  40                  45

Pro Asn Ala Gln Ala Pro Pro Lys Ile Asn Gly Lys Arg Val Gly Leu
    50                  55                  60

Pro Gly Ser Val Glu Ile Leu Lys Pro Asp Ser Glu Thr Ser Gln Pro
65                  70                  75                  80

Ala Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Arg Arg Ser Asp Val Ile Met Asp Pro Phe Gly
        115                 120                 125

Leu Gly Arg Ile Val Gln Asp Gly Leu Val Phe Arg Gln Asn Phe Ser
    130                 135                 140

Ile Arg Ser Tyr Glu Ile Gly Ala Asp Arg Ser Ala Ser Ile Glu Thr
145                 150                 155                 160

Val Met Asn His Leu Gln Glu Thr Ala Leu Asn His Val Lys Thr Ala
                165                 170                 175

Gly Leu Leu Gly Asp Gly Phe Gly Ser Thr Pro Glu Met Val Lys Lys
            180                 185                 190

Asn Leu Ile Trp Val Val Thr Arg Met Gln Val Val Asp Lys Tyr
        195                 200                 205

Pro Thr Trp Gly Asp Val Val Glu Val Asp Thr Trp Val Ser Gln Ser
    210                 215                 220

Gly Lys Asn Gly Met Arg Arg Asp Trp Leu Val Arg Asp Gly Asn Thr
225                 230                 235                 240

Gly Glu Ile Leu Thr Arg Ala Ser Ser Val Trp Val Met Met Asn Lys
                245                 250                 255

Leu Thr Arg Arg Leu Ser Lys Ile Pro Glu Glu Val Arg Gly Glu Ile
```

260                 265                 270
Glu Pro Tyr Phe Val Asn Ser Asp Pro Val Leu Ala Glu Asp Ser Arg
            275                 280                 285

Lys Leu Thr Lys Leu Asp Asp Lys Thr Ala Val Tyr Val Arg Ser Gly
        290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Val Gly Met Met
                325                 330                 335

Glu Ser Gln Lys Leu Lys Ser Met Thr Leu Glu Tyr Arg Arg Glu Cys
            340                 345                 350

Gly Arg Asp Ser Val Leu Gln Ser Leu Thr Ala Val Ser Gly Cys Asp
        355                 360                 365

Ile Gly Ser Leu Gly Thr Ala Gly Glu Val Glu Cys Gln His Leu Leu
    370                 375                 380

Arg Leu Gln Asp Gly Ala Glu Val Val Arg Gly Arg Thr Glu Trp Ser
385                 390                 395                 400

Ser Lys Thr Ser Thr Thr Thr Trp Asp Ile Thr Pro
                405                 410

<210> SEQ ID NO 9
<211> LENGTH: 1770
<212> TYPE: DNA
<213> ORGANISM: Brassica napus
<220> FEATURE:
<221> NAME/KEY: CDS
<222> LOCATION: (1)..(504)
<220> FEATURE:
<221> NAME/KEY: mat_peptide
<222> LOCATION: (1)..(1767)
<223> OTHER INFORMATION: mature peptide starts at amino acid 91
<220> FEATURE:
<221> NAME/KEY: misc_feature
<222> LOCATION: (490)..(492)
<223> OTHER INFORMATION: conserved Met
<220> FEATURE:
<221> NAME/KEY: CDS
<222> LOCATION: (581)..(714)
<220> FEATURE:
<221> NAME/KEY: misc_feature
<222> LOCATION: (602)..(604)
<223> OTHER INFORMATION: conserved Lys
<220> FEATURE:
<221> NAME/KEY: misc_feature
<222> LOCATION: (674)..(676)
<223> OTHER INFORMATION: conserved Val
<220> FEATURE:
<221> NAME/KEY: CDS
<222> LOCATION: (945)..(1058)
<220> FEATURE:
<221> NAME/KEY: misc_feature
<222> LOCATION: (997)..(999)
<223> OTHER INFORMATION: conserved Met
<220> FEATURE:
<221> NAME/KEY: CDS
<222> LOCATION: (1190)..(1361)
<220> FEATURE:
<221> NAME/KEY: misc_feature
<222> LOCATION: (1227)..(1229)
<223> OTHER INFORMATION: conserved Ser
<220> FEATURE:
<221> NAME/KEY: CDS
<222> LOCATION: (1447)..(1767)
<220> FEATURE:
<221> NAME/KEY: misc_feature
<222> LOCATION: (1453)..(1455)
<223> OTHER INFORMATION: conserved Trp
<220> FEATURE:
<221> NAME/KEY: misc_feature

```
<222> LOCATION: (1471)..(1473)
<223> OTHER INFORMATION: conserved Asn
<220> FEATURE:
<221> NAME/KEY: misc_feature
<222> LOCATION: (1477)..(1479)
<223> OTHER INFORMATION: conserved His
<220> FEATURE:
<221> NAME/KEY: misc_feature
<222> LOCATION: (1582)..(1584)
<223> OTHER INFORMATION: conserved Cys

<400> SEQUENCE: 9
```

| | | | | | | | | | | | | | | | | |
|---|---|---|---|---|---|---|---|---|---|---|---|---|---|---|---|---|
| atg | gtg | gct | act | tcc | gct | acg | tcc | tcg | ttt | ttt | cat | gtt | cca | tct | tcc | 48 |
| Met | Val | Ala | Thr | Ser | Ala | Thr | Ser | Ser | Phe | Phe | His | Val | Pro | Ser | Ser | |
| 1 | | | | 5 | | | | | 10 | | | | | 15 | | |
| tcc | tct | ctt | gat | act | aat | ggg | aag | ggg | aac | aga | gtt | gcg | tcc | acg | aac | 96 |
| Ser | Ser | Leu | Asp | Thr | Asn | Gly | Lys | Gly | Asn | Arg | Val | Ala | Ser | Thr | Asn | |
| | | | 20 | | | | | 25 | | | | | 30 | | | |
| ttc | gct | gga | ctt | aac | tca | acg | cca | agc | tct | ggg | agg | atg | aag | gtt | aaa | 144 |
| Phe | Ala | Gly | Leu | Asn | Ser | Thr | Pro | Ser | Ser | Gly | Arg | Met | Lys | Val | Lys | |
| | | 35 | | | | | 40 | | | | | 45 | | | | |
| cca | aac | gct | cag | gct | cca | ccc | aag | atc | aac | ggg | aag | aaa | gct | aac | ttg | 192 |
| Pro | Asn | Ala | Gln | Ala | Pro | Pro | Lys | Ile | Asn | Gly | Lys | Lys | Ala | Asn | Leu | |
| 50 | | | | | 55 | | | | | 60 | | | | | | |
| cct | ggt | tct | gta | gag | ata | tca | aag | tct | gac | aac | gag | act | tcg | cag | ccc | 240 |
| Pro | Gly | Ser | Val | Glu | Ile | Ser | Lys | Ser | Asp | Asn | Glu | Thr | Ser | Gln | Pro | |
| 65 | | | | | 70 | | | | | 75 | | | | | 80 | |
| gca | ccc | gca | ccg | agg | acg | ttt | atc | aac | cag | ctg | cct | gac | tgg | agc | atg | 288 |
| Ala | Pro | Ala | Pro | Arg | Thr | Phe | Ile | Asn | Gln | Leu | Pro | Asp | Trp | Ser | Met | |
| | | | | 85 | | | | | 90 | | | | | 95 | | |
| ctt | ctc | gct | gcc | ata | aca | acc | att | ttc | ttg | gcg | gct | gag | aaa | cag | tgg | 336 |
| Leu | Leu | Ala | Ala | Ile | Thr | Thr | Ile | Phe | Leu | Ala | Ala | Glu | Lys | Gln | Trp | |
| | | | 100 | | | | | 105 | | | | | 110 | | | |
| atg | atg | ctt | gac | tgg | aaa | ccc | agg | cgt | tct | gat | atg | att | atg | gat | cct | 384 |
| Met | Met | Leu | Asp | Trp | Lys | Pro | Arg | Arg | Ser | Asp | Met | Ile | Met | Asp | Pro | |
| | | 115 | | | | | 120 | | | | | 125 | | | | |
| ttc | ggt | tta | ggg | aga | atc | gtt | cag | gat | ggt | ctt | gtc | ttt | cgt | cag | aat | 432 |
| Phe | Gly | Leu | Gly | Arg | Ile | Val | Gln | Asp | Gly | Leu | Val | Phe | Arg | Gln | Asn | |
| 130 | | | | | 135 | | | | | 140 | | | | | | |
| ttc | tcc | att | agg | tct | tat | gag | ata | ggt | gct | gat | cgc | tct | gcg | tct | ata | 480 |
| Phe | Ser | Ile | Arg | Ser | Tyr | Glu | Ile | Gly | Ala | Asp | Arg | Ser | Ala | Ser | Ile | |
| 145 | | | | | 150 | | | | | 155 | | | | | 160 | |

| | | | | | | |
|---|---|---|---|---|---|---|
| gaa act gtt atg aat cat tta cag gtaggtacta ctttgattgt tatcacactt | | | | | | 534 |
| Glu Thr Val Met Asn His Leu Gln | | | | | | |
| 165 | | | | | | |

| | |
|---|---|
| gtcaatagat atatgctc atgacaagct cttatgctaa tgacag gaa acg gcc | 589 |
| Glu Thr Ala | |
| 170 | |

| | | | | | | | | | | | | | |
|---|---|---|---|---|---|---|---|---|---|---|---|---|---|
| cta | aac | cat | gtg | aag | tct | gcc | gga | ctg | ctg | gaa | aat | ggg | ttt | ggt | tct | 637 |
| Leu | Asn | His | Val | Lys | Ser | Ala | Gly | Leu | Leu | Glu | Asn | Gly | Phe | Gly | Ser | |
| | | | 175 | | | | | 180 | | | | | 185 | | | |
| act | ccc | gag | atg | ttt | aag | aag | aac | ttg | ata | tgg | gtc | gtt | gct | cgt | atg | 685 |
| Thr | Pro | Glu | Met | Phe | Lys | Lys | Asn | Leu | Ile | Trp | Val | Val | Ala | Arg | Met | |
| | | 190 | | | | | 195 | | | | | 200 | | | | |

| | |
|---|---|
| cag gtt gtc gtt gat aaa tat cct act tg gtaagccatt gtcagtctta | 734 |
| Gln Val Val Val Asp Lys Tyr Pro Thr Trp | |
| 205 210 | |

| | |
|---|---|
| ccacttaact taaaatcatt atgctactgt ctctgagaat ccctggttct cgttgtgagt | 794 |
| tatccaaatt atcttgcata aacttgagta tgcaagttca tgctctcact tgctcatgtg | 854 |
| actaggacat tttgcaccct tagattacat gatgtgcttg catattacag tgtgcataga | 914 |

```
tcattactta ttcaaatatc tgactaacag g gga gat gtt gtg gaa gtg gat      966
                                  Gly Asp Val Val Glu Val Asp
                                  215                 220 aca tgg gtt agt cag tct gga aag aat ggt atg cgt cgt gat tgg ctg    1014
Thr Trp Val Ser Gln Ser Gly Lys Asn Gly Met Arg Arg Asp Trp Leu
            225                 230                 235 gtt cgg gat tgc aat act gga gaa att gta acg cga gca tca ag         1058
Val Arg Asp Cys Asn Thr Gly Glu Ile Val Thr Arg Ala Ser Ser
            240                 245                 250 gtcagagttc ttatgttttg gtttactgac tccagctatt atcattttgc tctctgtttg  1118
tattgtttgc tctgccatta gtttgataat agagacttta tatatgtatg gcaattttct  1178 tcttttgca g t ttg tgg gtg atg atg aat aaa ctc aca agg aga ttg      1226
              Leu Trp Val Met Met Asn Lys Leu Thr Arg Arg Leu
                               255                 260 tca aag att cct gaa gag gtt cga ggg gaa ata gag cct tat ttt gtg    1274
Ser Lys Ile Pro Glu Glu Val Arg Gly Glu Ile Glu Pro Tyr Phe Val
            265                 270                 275 aac tct gat cct gtc att gcc gaa gac agc aga aag tta acc aaa ctt    1322
Asn Ser Asp Pro Val Ile Ala Glu Asp Ser Arg Lys Leu Thr Lys Leu
280                 285                 290                 295 gat gac aag act gct gac tat gtt cgt tcg ggt ctc act gtaagtaccc     1371
Asp Asp Lys Thr Ala Asp Tyr Val Arg Ser Gly Leu Thr
                300                 305 taccttttcaa caacaagctt gtcaaaactc tcgaggttgg ttcttatgga ttggtaatga 1431 aactttttta ttcag ccg agg tgg agt gac ttg gat gtt aac cag cat gtt  1482
                 Pro Arg Trp Ser Asp Leu Asp Val Asn Gln His Val
                                310                 315                 320 aac aat gta aag tac atc ggg tgg ata ctg gag agt gct cca gca ggg    1530
Asn Asn Val Lys Tyr Ile Gly Trp Ile Leu Glu Ser Ala Pro Ala Gly
                325                 330                 335 atg ctg gag agt cag aag ctg aaa agc atg act ctg gag tat cgc agg    1578
Met Leu Glu Ser Gln Lys Leu Lys Ser Met Thr Leu Glu Tyr Arg Arg
                340                 345                 350 gag tgc ggg aga gac agt gtg ctt cag tct ctc acc gcg gtc tct gga    1626
Glu Cys Gly Arg Asp Ser Val Leu Gln Ser Leu Thr Ala Val Ser Gly
                355                 360                 365 tgt gat gtc ggt aac ctc ggg aca gcc ggg gaa gtg gag tgt cag cat    1674
Cys Asp Val Gly Asn Leu Gly Thr Ala Gly Glu Val Glu Cys Gln His
        370                 375                 380 ttg ctt cgt ctc cag gat gga gct gaa gtg gtg aga gga aga aca gag    1722
Leu Leu Arg Leu Gln Asp Gly Ala Glu Val Val Arg Gly Arg Thr Glu
385                 390                 395                 400 tgg agt tcc aag aca gaa gca aca act tgg gac act gct aca tcg taa   1770
Trp Ser Ser Lys Thr Glu Ala Thr Thr Trp Asp Thr Ala Thr Ser
                405                 410                 415

<210> SEQ ID NO 10
<211> LENGTH: 415
<212> TYPE: PRT
<213> ORGANISM: Brassica napus

<400> SEQUENCE: 10

Met Val Ala Thr Ser Ala Thr Ser Ser Phe Phe His Val Pro Ser Ser
1               5                   10                  15

Ser Ser Leu Asp Thr Asn Gly Lys Gly Asn Arg Val Ala Ser Thr Asn
            20                  25                  30

Phe Ala Gly Leu Asn Ser Thr Pro Ser Ser Gly Arg Met Lys Val Lys
        35                  40                  45
```

```
Pro Asn Ala Gln Ala Pro Pro Lys Ile Asn Gly Lys Lys Ala Asn Leu
    50                  55                  60

Pro Gly Ser Val Glu Ile Ser Lys Ser Asp Asn Glu Thr Ser Gln Pro
65                  70                  75                  80

Ala Pro Ala Pro Arg Thr Phe Ile Asn Gln Leu Pro Asp Trp Ser Met
                85                  90                  95

Leu Leu Ala Ala Ile Thr Thr Ile Phe Leu Ala Ala Glu Lys Gln Trp
            100                 105                 110

Met Met Leu Asp Trp Lys Pro Arg Arg Ser Asp Met Ile Met Asp Pro
        115                 120                 125

Phe Gly Leu Gly Arg Ile Val Gln Asp Gly Leu Val Phe Arg Gln Asn
130                 135                 140

Phe Ser Ile Arg Ser Tyr Glu Ile Gly Ala Asp Arg Ser Ala Ser Ile
145                 150                 155                 160

Glu Thr Val Met Asn His Leu Gln Glu Thr Ala Leu Asn His Val Lys
                165                 170                 175

Ser Ala Gly Leu Leu Glu Asn Gly Phe Gly Ser Thr Pro Glu Met Phe
            180                 185                 190

Lys Lys Asn Leu Ile Trp Val Val Ala Arg Met Gln Val Val Val Asp
        195                 200                 205

Lys Tyr Pro Thr Trp Gly Asp Val Val Glu Val Asp Thr Trp Val Ser
    210                 215                 220

Gln Ser Gly Lys Asn Gly Met Arg Arg Asp Trp Leu Val Arg Asp Cys
225                 230                 235                 240

Asn Thr Gly Glu Ile Val Thr Arg Ala Ser Ser Leu Trp Val Met Met
                245                 250                 255

Asn Lys Leu Thr Arg Arg Leu Ser Lys Ile Pro Glu Glu Val Arg Gly
            260                 265                 270

Glu Ile Glu Pro Tyr Phe Val Asn Ser Asp Pro Val Ile Ala Glu Asp
        275                 280                 285

Ser Arg Lys Leu Thr Lys Leu Asp Asp Lys Thr Ala Asp Tyr Val Arg
290                 295                 300

Ser Gly Leu Thr Pro Arg Trp Ser Asp Leu Asp Val Asn Gln His Val
305                 310                 315                 320

Asn Asn Val Lys Tyr Ile Gly Trp Ile Leu Glu Ser Ala Pro Ala Gly
                325                 330                 335

Met Leu Glu Ser Gln Lys Leu Lys Ser Met Thr Leu Glu Tyr Arg Arg
            340                 345                 350

Glu Cys Gly Arg Asp Ser Val Leu Gln Ser Leu Thr Ala Val Ser Gly
        355                 360                 365

Cys Asp Val Gly Asn Leu Gly Thr Ala Gly Glu Val Glu Cys Gln His
    370                 375                 380

Leu Leu Arg Leu Gln Asp Gly Ala Glu Val Val Arg Gly Arg Thr Glu
385                 390                 395                 400

Trp Ser Ser Lys Thr Glu Ala Thr Thr Trp Asp Thr Ala Thr Ser
                405                 410                 415

<210> SEQ ID NO 11
<211> LENGTH: 1891
<212> TYPE: DNA
<213> ORGANISM: Brassica napus
<220> FEATURE:
<221> NAME/KEY: CDS
<222> LOCATION: (1)..(507)
<220> FEATURE:
<221> NAME/KEY: mat_peptide
```

-continued

```
<222> LOCATION: (1)..(1888)
<223> OTHER INFORMATION: mature peptide starts at amino acid 92
<220> FEATURE:
<221> NAME/KEY: misc_feature
<222> LOCATION: (493)..(495)
<223> OTHER INFORMATION: conserved Met
<220> FEATURE:
<221> NAME/KEY: CDS
<222> LOCATION: (930)..(1063)
<220> FEATURE:
<221> NAME/KEY: misc_feature
<222> LOCATION: (951)..(953)
<223> OTHER INFORMATION: conserved Lys
<220> FEATURE:
<221> NAME/KEY: misc_feature
<222> LOCATION: (1023)..(1025)
<223> OTHER INFORMATION: conserved Val
<220> FEATURE:
<221> NAME/KEY: CDS
<222> LOCATION: (1138)..(1251)
<220> FEATURE:
<221> NAME/KEY: misc_feature
<222> LOCATION: (1190)..(1192)
<223> OTHER INFORMATION: conserved Met
<220> FEATURE:
<221> NAME/KEY: CDS
<222> LOCATION: (1324)..(1495)
<220> FEATURE:
<221> NAME/KEY: misc_feature
<222> LOCATION: (1361)..(1363)
<223> OTHER INFORMATION: conserved Ser
<220> FEATURE:
<221> NAME/KEY: CDS
<222> LOCATION: (1571)..(1888)
<220> FEATURE:
<221> NAME/KEY: misc_feature
<222> LOCATION: (1577)..(1579)
<223> OTHER INFORMATION: conserved Trp
<220> FEATURE:
<221> NAME/KEY: misc_feature
<222> LOCATION: (1595)..(1597)
<223> OTHER INFORMATION: conserved Asn
<220> FEATURE:
<221> NAME/KEY: misc_feature
<222> LOCATION: (1601)..(1603)
<223> OTHER INFORMATION: conserved His
<220> FEATURE:
<221> NAME/KEY: misc_feature
<222> LOCATION: (1706)..(1708)
<223> OTHER INFORMATION: conserved Cys

<400> SEQUENCE: 11 atg gtg gcc acc tct gct aca tcc tca ttc ttc cct ctc cca tct tcc      48
Met Val Ala Thr Ser Ala Thr Ser Ser Phe Phe Pro Leu Pro Ser Ser
1               5                   10                  15 tct ctc gac cct aat ggc aaa acc aac aaa ctc acc tcc acc aac ttc      96
Ser Leu Asp Pro Asn Gly Lys Thr Asn Lys Leu Thr Ser Thr Asn Phe
            20                  25                  30 tct gga ctc aac ccc ata cca aac tct tcc ggc agg tta aag gtc aaa     144
Ser Gly Leu Asn Pro Ile Pro Asn Ser Ser Gly Arg Leu Lys Val Lys
        35                  40                  45 cca aac gcc caa gct cca tcc aag atc aac ggc aat aat gtc tcc ttg     192
Pro Asn Ala Gln Ala Pro Ser Lys Ile Asn Gly Asn Asn Val Ser Leu
    50                  55                  60 cca ggc tca gta cac atc gta aag act gat aat aac cac gat ctc tcg     240
Pro Gly Ser Val His Ile Val Lys Thr Asp Asn Asn His Asp Leu Ser
65                  70                  75                  80 caa caa cac gca ccc aga acg ttc atc aac cag cta cct gac tgg agc     288
Gln Gln His Ala Pro Arg Thr Phe Ile Asn Gln Leu Pro Asp Trp Ser
                85                  90                  95 atg ctt ctc gcc gcc atc aca acg gtc ttc tta gct gct gag aaa cag     336
Met Leu Leu Ala Ala Ile Thr Thr Val Phe Leu Ala Ala Glu Lys Gln
```

```
              100                 105                 110
tgg atg atg ctt gac tcg aaa ccg agg cgt tct gat atg att atg gat    384
Trp Met Met Leu Asp Ser Lys Pro Arg Arg Ser Asp Met Ile Met Asp
        115                 120                 125 ccg ttc ggg tta ggg agg atc gtt cag gat ggg ctt gtg tac cgt cag    432
Pro Phe Gly Leu Gly Arg Ile Val Gln Asp Gly Leu Val Tyr Arg Gln
130                 135                 140 aac ttc gat atc agg tct tat gaa ata ggt gct gat cgc tct gcg tct    480
Asn Phe Asp Ile Arg Ser Tyr Glu Ile Gly Ala Asp Arg Ser Ala Ser
145                 150                 155                 160 ata gaa aca gtc atg aac cac tta cag gtatattaca atcacactcg          527
Ile Glu Thr Val Met Asn His Leu Gln
                165 attgatacta gagcttgaca tgttggtttt tatcttttta taaattgttt agtgacattt    587 tcaaacatat agataaggt tatttagata tttctaggtt cctacaaacc tacccagact    647 caaaccccgt ccggaaattt ataatattaa taccgaacag agttttattt taaaccaaaa    707 aatcagttga cccgcacggg atgttggttt ttatctattt tatacattgt ttaaggacat    767 ttttaaacat ataaatatag gttatttaga tatttctagg ttcctacgaa cctacccgga    827 aatttataat acccgaacat agtttaattt ttaaaccaaa aatccaatac ccgaaaaaac    887 caatctgtga tatgcatgat ctaactcttg tcctcgtgac ag gaa acg gct ctc     941
                                              Glu Thr Ala Leu
                                                          170 aac cat gtg aag tct gct gga ctg ctg gga gat ggg ttt ggt tct acc    989
Asn His Val Lys Ser Ala Gly Leu Leu Gly Asp Gly Phe Gly Ser Thr
        175                 180                 185 cct gag atg gtt aag aag aac ttg ata tgg gtc gtt act cgt atg cag   1037
Pro Glu Met Val Lys Lys Asn Leu Ile Trp Val Val Thr Arg Met Gln
190                 195                 200                 205 gtt gtc gtt gat aaa tat cct act tg  gtaagccctc ttagcactta          1083
Val Val Val Asp Lys Tyr Pro Thr Trp
                210 accttaaaac aatatgcatg aatcatttgc ttattcaaat gtctgcttca ccag g gga  1141
                                                              Gly
                                                              215 gat gtt gtt gaa gta gat aca tgg gtt agt aag tct ggg aag aat ggt   1189
Asp Val Val Glu Val Asp Thr Trp Val Ser Lys Ser Gly Lys Asn Gly
                220                 225                 230 atg cgt cgt gat tgg cta gtt cgg gat tgt aat act gga gaa att tta   1237
Met Arg Arg Asp Trp Leu Val Arg Asp Cys Asn Thr Gly Glu Ile Leu
        235                 240                 245 aca aga gca tca ag  gttagcttct ttttgtttac tccagctatt atctgattat   1291
Thr Arg Ala Ser Ser
250 tgagttataa ccatctctgt gttgcaaaac ag t gtg tgg gtg atg atg aat aaa  1345
                                  Val Trp Val Met Met Asn Lys
                                                          255 gtg aca agg aga tta tca aag ctt cct gaa gag gtt cga ggg gaa ata   1393
Val Thr Arg Arg Leu Ser Lys Leu Pro Glu Glu Val Arg Gly Glu Ile
260                 265                 270                 275 gag cct tac ttt gtg aac tct gac cct atc ctt gcc gag gac agc aga   1441
Glu Pro Tyr Phe Val Asn Ser Asp Pro Ile Leu Ala Glu Asp Ser Arg
            280                 285                 290 aag tta aca aaa cta gat gag aag act gct gac tat gtt cgc tct ggt   1489
Lys Leu Thr Lys Leu Asp Glu Lys Thr Ala Asp Tyr Val Arg Ser Gly
                295                 300                 305 ctc acc gtaagtataa atatttgttt ttatctttca gcaagtgaga ttctgatggg    1545
Leu Thr
```

```
Leu Thr tttggtgatt atctaactttt tgcag ccg aga tgg agt gac ttg gat gtt aac    1597
                              Pro Arg Trp Ser Asp Leu Asp Val Asn
                              310             315 cag cat gtt aac aac gtg aag tac att ggt tgg ata ctc gag agt gct    1645
Gln His Val Asn Asn Val Lys Tyr Ile Gly Trp Ile Leu Glu Ser Ala
320                 325                 330 cca gtg gag atg atg gag aag cat aag ctg aaa agc atg act ctg gag    1693
Pro Val Glu Met Met Glu Lys His Lys Leu Lys Ser Met Thr Leu Glu
335                 340                 345                 350 tat agg agg gaa tgc ggg aga gac agt gtg ctt cag tct ctc acc gcg    1741
Tyr Arg Arg Glu Cys Gly Arg Asp Ser Val Leu Gln Ser Leu Thr Ala
                355                 360                 365 gtt tcg ggt tgc gat gtt ggt agc ctc ggg aca gct ggt gaa gtg gaa    1789
Val Ser Gly Cys Asp Val Gly Ser Leu Gly Thr Ala Gly Glu Val Glu
        370                 375                 380 tgt cag cat ttg ctt cga ctc cag gat gga gct gaa gtg gtg aag gga    1837
Cys Gln His Leu Leu Arg Leu Gln Asp Gly Ala Glu Val Val Lys Gly
385                 390                 395 cga aca gtg tgg agt tcc aaa aca cca tca aca act tgg gac act aca    1885
Arg Thr Val Trp Ser Ser Lys Thr Pro Ser Thr Thr Trp Asp Thr Thr
400                 405                 410 tcg taa                                                             1891
Ser
415

<210> SEQ ID NO 12
<211> LENGTH: 415
<212> TYPE: PRT
<213> ORGANISM: Brassica napus

<400> SEQUENCE: 12

Met Val Ala Thr Ser Ala Thr Ser Ser Phe Phe Pro Leu Pro Ser Ser
1               5                   10                  15

Ser Leu Asp Pro Asn Gly Lys Thr Asn Lys Leu Thr Ser Thr Asn Phe
            20                  25                  30

Ser Gly Leu Asn Pro Ile Pro Asn Ser Ser Gly Arg Leu Lys Val Lys
        35                  40                  45

Pro Asn Ala Gln Ala Pro Ser Lys Ile Asn Gly Asn Asn Val Ser Leu
    50                  55                  60

Pro Gly Ser Val His Ile Val Lys Thr Asp Asn Asn His Asp Leu Ser
65                  70                  75                  80

Gln Gln His Ala Pro Arg Thr Phe Ile Asn Gln Leu Pro Asp Trp Ser
                85                  90                  95

Met Leu Leu Ala Ala Ile Thr Thr Val Phe Leu Ala Ala Glu Lys Gln
            100                 105                 110

Trp Met Met Leu Asp Ser Lys Pro Arg Arg Ser Asp Met Ile Met Asp
        115                 120                 125

Pro Phe Gly Leu Gly Arg Ile Val Gln Asp Gly Leu Val Tyr Arg Gln
    130                 135                 140

Asn Phe Asp Ile Arg Ser Tyr Glu Ile Gly Ala Asp Arg Ser Ala Ser
145                 150                 155                 160

Ile Glu Thr Val Met Asn His Leu Gln Glu Thr Ala Leu Asn His Val
                165                 170                 175

Lys Ser Ala Gly Leu Leu Gly Asp Gly Phe Gly Ser Thr Pro Glu Met
            180                 185                 190

Val Lys Lys Asn Leu Ile Trp Val Val Thr Arg Met Gln Val Val Val
```

```
                195                 200                 205
Asp Lys Tyr Pro Thr Trp Gly Asp Val Glu Val Asp Thr Trp Val
    210                 215                 220

Ser Lys Ser Gly Lys Asn Gly Met Arg Arg Asp Trp Leu Val Arg Asp
225                 230                 235                 240

Cys Asn Thr Gly Glu Ile Leu Thr Arg Ala Ser Ser Val Trp Val Met
                245                 250                 255

Met Asn Lys Val Thr Arg Arg Leu Ser Lys Leu Pro Glu Glu Val Arg
            260                 265                 270

Gly Glu Ile Glu Pro Tyr Phe Val Asn Ser Asp Pro Ile Leu Ala Glu
        275                 280                 285

Asp Ser Arg Lys Leu Thr Lys Leu Asp Glu Lys Thr Ala Asp Tyr Val
    290                 295                 300

Arg Ser Gly Leu Thr Pro Arg Trp Ser Asp Leu Asp Val Asn Gln His
305                 310                 315                 320

Val Asn Asn Val Lys Tyr Ile Gly Trp Ile Leu Glu Ser Ala Pro Val
                325                 330                 335

Glu Met Met Glu Lys His Lys Leu Lys Ser Met Thr Leu Glu Tyr Arg
            340                 345                 350

Arg Glu Cys Gly Arg Asp Ser Val Leu Gln Ser Leu Thr Ala Val Ser
        355                 360                 365

Gly Cys Asp Val Gly Ser Leu Gly Thr Ala Gly Glu Val Glu Cys Gln
370                 375                 380

His Leu Leu Arg Leu Gln Asp Gly Ala Glu Val Val Lys Gly Arg Thr
385                 390                 395                 400

Val Trp Ser Ser Lys Thr Pro Ser Thr Thr Trp Asp Thr Thr Ser
                405                 410                 415

<210> SEQ ID NO 13
<211> LENGTH: 1560
<212> TYPE: DNA
<213> ORGANISM: Brassica napus
<220> FEATURE:
<221> NAME/KEY: CDS
<222> LOCATION: (1)..(501)
<220> FEATURE:
<221> NAME/KEY: mat_peptide
<222> LOCATION: (1)..(1557)
<223> OTHER INFORMATION: mature peptide starts at amino acid 90
<220> FEATURE:
<221> NAME/KEY: misc_feature
<222> LOCATION: (487)..(489)
<223> OTHER INFORMATION: conserved Met
<220> FEATURE:
<221> NAME/KEY: CDS
<222> LOCATION: (587)..(720)
<220> FEATURE:
<221> NAME/KEY: misc_feature
<222> LOCATION: (608)..(610)
<223> OTHER INFORMATION: conserved Lys
<220> FEATURE:
<221> NAME/KEY: misc_feature
<222> LOCATION: (680)..(682)
<223> OTHER INFORMATION: conserved Val
<220> FEATURE:
<221> NAME/KEY: CDS
<222> LOCATION: (795)..(908)
<220> FEATURE:
<221> NAME/KEY: misc_feature
<222> LOCATION: (847)..(849)
<223> OTHER INFORMATION: conserved Met
<220> FEATURE:
<221> NAME/KEY: CDS
<222> LOCATION: (978)..(1149)
<220> FEATURE:
```

```
<221> NAME/KEY: misc_feature
<222> LOCATION: (1015)..(1017)
<223> OTHER INFORMATION: conserved Ser
<220> FEATURE:
<221> NAME/KEY: CDS
<222> LOCATION: (1240)..(1557)
<220> FEATURE:
<221> NAME/KEY: misc_feature
<222> LOCATION: (1246)..(1248)
<223> OTHER INFORMATION: conserved Trp
<220> FEATURE:
<221> NAME/KEY: misc_feature
<222> LOCATION: (1264)..(1266)
<223> OTHER INFORMATION: conserved Asn
<220> FEATURE:
<221> NAME/KEY: misc_feature
<222> LOCATION: (1270)..(1272)
<223> OTHER INFORMATION: conserved His
<220> FEATURE:
<221> NAME/KEY: misc_feature
<222> LOCATION: (1375)..(1377)
<223> OTHER INFORMATION: conserved Cys

<400> SEQUENCE: 13 atg gtg gcc acc tca gct aca tcc tca ttc ttc cct ctc cca tct tcc      48
Met Val Ala Thr Ser Ala Thr Ser Ser Phe Phe Pro Leu Pro Ser Ser
1               5                   10                  15 cca ctc gac ccc acc gca aaa acc aac aaa gtc acc acc tcc acc aac      96
Pro Leu Asp Pro Thr Ala Lys Thr Asn Lys Val Thr Thr Ser Thr Asn
            20                  25                  30 ttc tcc ggc ctc tcc ccc act cca aac tcc tcc ggc agg atg aag gtt      144
Phe Ser Gly Leu Ser Pro Thr Pro Asn Ser Ser Gly Arg Met Lys Val
        35                  40                  45 aaa cca aac gct cag gcc cca ccc aag atc aac ggc aag aga gtc ggt      192
Lys Pro Asn Ala Gln Ala Pro Pro Lys Ile Asn Gly Lys Arg Val Gly
    50                  55                  60 ctc cct ggc tcg gtg aag cct gat aac gag acg tcc tca cag cat ccc      240
Leu Pro Gly Ser Val Lys Pro Asp Asn Glu Thr Ser Ser Gln His Pro
65                  70                  75                  80 gca gca ccg agg acg ttc atc aac cag ctg cct gac tgg agc atg ctt      288
Ala Ala Pro Arg Thr Phe Ile Asn Gln Leu Pro Asp Trp Ser Met Leu
                85                  90                  95 ctt gct gca ata aca acc gtc ttc ttg gcg gct gag aag cag tgg atg      336
Leu Ala Ala Ile Thr Thr Val Phe Leu Ala Ala Glu Lys Gln Trp Met
            100                 105                 110 atg ctt gac tgg aaa ccg agg cgc tct gac gtg att atg gat ccg ttt      384
Met Leu Asp Trp Lys Pro Arg Arg Ser Asp Val Ile Met Asp Pro Phe
        115                 120                 125 ggg tta ggg agg atc gtt cag gat ggg ctt gtg ttc cgt cag aat ttc      432
Gly Leu Gly Arg Ile Val Gln Asp Gly Leu Val Phe Arg Gln Asn Phe
    130                 135                 140 tct att cgg tct tat gag ata ggt gct gat cgc tct gcg tct ata gaa      480
Ser Ile Arg Ser Tyr Glu Ile Gly Ala Asp Arg Ser Ala Ser Ile Glu
145                 150                 155                 160 acg gtt atg aat cat tta cag gtactgatta tgattatgat tatgattgta         531
Thr Val Met Asn His Leu Gln
                165 gttgcttgtt gttactggac aaagttaata tgtattgctg ttatggttat gatag gaa     589
                                                              Glu acg gca ctc aac cat gtt aag act gct gga ctg ctt gga gat ggg ttt      637
Thr Ala Leu Asn His Val Lys Thr Ala Gly Leu Leu Gly Asp Gly Phe
        170                 175                 180 ggt tct act cct gag atg gtt aag aag aac ttg att tgg gtt gtt act      685
Gly Ser Thr Pro Glu Met Val Lys Lys Asn Leu Ile Trp Val Val Thr
    185                 190                 195                 200
```

```
cgt atg cag gtt gtc gtt gat aaa tat cct act tg  gtaagctatt              730
Arg Met Gln Val Val Val Asp Lys Tyr Pro Thr Trp
            205                     210 ctcaagcaac cctgagaatc actgcttcct ttgtcatttg cttattcaaa tatctgtctc      790 acag g gga gat gtt gtg gaa gta gat aca tgg gtg agc cag tct gga         837
      Gly Asp Val Val Glu Val Asp Thr Trp Val Ser Gln Ser Gly
              215                 220                 225 aag aac ggt atg cgt cgt gat tgg cta gtt cga gat ggc aat act gga        885
Lys Asn Gly Met Arg Arg Asp Trp Leu Val Arg Asp Gly Asn Thr Gly
            230                 235                 240 gaa att tta aca aga gca tca ag  gttagatttt tatttatcgg ttaggtatct       938
Glu Ile Leu Thr Arg Ala Ser Ser
            245 gaaaatttga gttactaatg caaaatatta tttttgcag t gtg tgg gtg atg atg       993
                                              Val Trp Val Met Met
                                                              255 aat aaa ctg aca aga aga tta tca aag att cct gaa gag gtt cga ggg       1041
Asn Lys Leu Thr Arg Arg Leu Ser Lys Ile Pro Glu Glu Val Arg Gly
            260                 265                 270 gag ata gag cct tac ttt gtt aat tca gac cca gtc ctt gct gag gac       1089
Glu Ile Glu Pro Tyr Phe Val Asn Ser Asp Pro Val Leu Ala Glu Asp
        275                 280                 285 agc aga aag tta act aaa ctt gat gac aag act gct gac tat gtt cgt       1137
Ser Arg Lys Leu Thr Lys Leu Asp Asp Lys Thr Ala Asp Tyr Val Arg
        290                 295                 300 tct ggt ctc act gtaagtatgc atactttctc tatgtttcat caaagcctgt           1189
Ser Gly Leu Thr
        305 aaacttctga gattcttaca gtttttattt ggtaatttaa acttttgcag ccg cgt        1245
                                                      Pro Arg tgg agt gac ttg gat gtt aac cag cac gtt aac aat gtg aag tac atc       1293
Trp Ser Asp Leu Asp Val Asn Gln His Val Asn Asn Val Lys Tyr Ile
310                 315                 320                 325 ggg tgg ata ctg gag agt gca cct gtg ggg atg atg gag agt cag aag       1341
Gly Trp Ile Leu Glu Ser Ala Pro Val Gly Met Met Glu Ser Gln Lys
            330                 335                 340 ctg aaa agc atg act ctg gag tat cgc agg gag tgc ggg agg gac agt       1389
Leu Lys Ser Met Thr Leu Glu Tyr Arg Arg Glu Cys Gly Arg Asp Ser
            345                 350                 355 gtg ctt cag tcc ctc acc gcg gtt tcg ggc tgc gat gtt ggt agt ctt       1437
Val Leu Gln Ser Leu Thr Ala Val Ser Gly Cys Asp Val Gly Ser Leu
            360                 365                 370 ggg aca gct ggt gaa gtg gaa tgt cag cac ctg ctc cgt ctc cag gat       1485
Gly Thr Ala Gly Glu Val Glu Cys Gln His Leu Leu Arg Leu Gln Asp
        375                 380                 385 gga gct gaa gtg gtg aga gga aga aca gag tgg agt tcc aaa aca tca       1533
Gly Ala Glu Val Val Arg Gly Arg Thr Glu Trp Ser Ser Lys Thr Ser
390                 395                 400                 405 aca aca act tgg gac att aca ccg tga                                   1560
Thr Thr Thr Trp Asp Ile Thr Pro
            410

<210> SEQ ID NO 14
<211> LENGTH: 413
<212> TYPE: PRT
<213> ORGANISM: Brassica napus

<400> SEQUENCE: 14

Met Val Ala Thr Ser Ala Thr Ser Ser Phe Phe Pro Leu Pro Ser Ser
```

```
            1               5                  10                 15
          Pro Leu Asp Pro Thr Ala Lys Thr Asn Lys Val Thr Thr Ser Thr Asn
                          20                  25                 30

Phe Ser Gly Leu Ser Pro Thr Pro Asn Ser Ser Gly Arg Met Lys Val
                          35                  40                 45

Lys Pro Asn Ala Gln Ala Pro Pro Lys Ile Asn Gly Lys Arg Val Gly
           50                              55                 60

Leu Pro Gly Ser Val Lys Pro Asp Asn Glu Thr Ser Ser Gln His Pro
           65                  70                  75                 80

Ala Ala Pro Arg Thr Phe Ile Asn Gln Leu Pro Asp Trp Ser Met Leu
                          85                  90                 95

Leu Ala Ala Ile Thr Thr Val Phe Leu Ala Ala Glu Lys Gln Trp Met
                          100                 105                110

Met Leu Asp Trp Lys Pro Arg Arg Ser Asp Val Ile Met Asp Pro Phe
                          115                 120                125

Gly Leu Gly Arg Ile Val Gln Asp Gly Leu Val Phe Arg Gln Asn Phe
                          130                 135                140

Ser Ile Arg Ser Tyr Glu Ile Gly Ala Asp Arg Ser Ala Ser Ile Glu
          145                 150                 155                160

Thr Val Met Asn His Leu Gln Glu Thr Ala Leu Asn His Val Lys Thr
                          165                 170                175

Ala Gly Leu Leu Gly Asp Gly Phe Gly Ser Thr Pro Glu Met Val Lys
                          180                 185                190

Lys Asn Leu Ile Trp Val Val Thr Arg Met Gln Val Val Asp Lys
                          195                 200                205

Tyr Pro Thr Trp Gly Asp Val Val Glu Val Asp Thr Trp Val Ser Gln
           210                 215                 220

Ser Gly Lys Asn Gly Met Arg Arg Asp Trp Leu Val Arg Asp Gly Asn
          225                 230                 235                240

Thr Gly Glu Ile Leu Thr Arg Ala Ser Ser Val Trp Val Met Met Asn
                          245                 250                255

Lys Leu Thr Arg Arg Leu Ser Lys Ile Pro Glu Glu Val Arg Gly Glu
                          260                 265                270

Ile Glu Pro Tyr Phe Val Asn Ser Asp Pro Val Leu Ala Glu Asp Ser
                          275                 280                285

Arg Lys Leu Thr Lys Leu Asp Asp Lys Thr Ala Asp Tyr Val Arg Ser
                          290                 295                300

Gly Leu Thr Pro Arg Trp Ser Asp Leu Asp Val Asn Gln His Val Asn
          305                 310                 315                320

Asn Val Lys Tyr Ile Gly Trp Ile Leu Glu Ser Ala Pro Val Gly Met
                          325                 330                335

Met Glu Ser Gln Lys Leu Lys Ser Met Thr Leu Glu Tyr Arg Arg Glu
                          340                 345                350

Cys Gly Arg Asp Ser Val Leu Gln Ser Leu Thr Ala Val Ser Gly Cys
                          355                 360                365

Asp Val Gly Ser Leu Gly Thr Ala Gly Glu Val Glu Cys Gln His Leu
                          370                 375                380

Leu Arg Leu Gln Asp Gly Ala Glu Val Val Arg Gly Arg Thr Glu Trp
          385                 390                 395                400

Ser Ser Lys Thr Ser Thr Thr Thr Trp Asp Ile Thr Pro
                          405                 410

<210> SEQ ID NO 15
```

```
<211> LENGTH: 1632
<212> TYPE: DNA
<213> ORGANISM: Brassica napus
<220> FEATURE:
<221> NAME/KEY: CDS
<222> LOCATION: (1)..(504)
<220> FEATURE:
<221> NAME/KEY: mat_peptide
<222> LOCATION: (1)..(1629)
<223> OTHER INFORMATION: mature peptide starts at amino acid 91
<220> FEATURE:
<221> NAME/KEY: misc_feature
<222> LOCATION: (490)..(492)
<223> OTHER INFORMATION: conserved Met
<220> FEATURE:
<221> NAME/KEY: CDS
<222> LOCATION: (584)..(717)
<220> FEATURE:
<221> NAME/KEY: misc_feature
<222> LOCATION: (605)..(607)
<223> OTHER INFORMATION: conserved Lys
<220> FEATURE:
<221> NAME/KEY: misc_feature
<222> LOCATION: (677)..(679)
<223> OTHER INFORMATION: conserved Val
<220> FEATURE:
<221> NAME/KEY: CDS
<222> LOCATION: (812)..(925)
<220> FEATURE:
<221> NAME/KEY: misc_feature
<222> LOCATION: (964)..(966)
<223> OTHER INFORMATION: conserved Met
<220> FEATURE:
<221> NAME/KEY: CDS
<222> LOCATION: (1059)..(1230)
<220> FEATURE:
<221> NAME/KEY: misc_feature
<222> LOCATION: (1096)..(1098)
<223> OTHER INFORMATION: conserved Ser
<220> FEATURE:
<221> NAME/KEY: CDS
<222> LOCATION: (1309)..(1629)
<220> FEATURE:
<221> NAME/KEY: misc_feature
<222> LOCATION: (1315)..(1317)
<223> OTHER INFORMATION: conserved Trp
<220> FEATURE:
<221> NAME/KEY: misc_feature
<222> LOCATION: (1333)..(1335)
<223> OTHER INFORMATION: conserved Asn
<220> FEATURE:
<221> NAME/KEY: misc_feature
<222> LOCATION: (1339)..(1341)
<223> OTHER INFORMATION: conserved His
<220> FEATURE:
<221> NAME/KEY: misc_feature
<222> LOCATION: (1444)..(1446)
<223> OTHER INFORMATION: conserved Cys

<400> SEQUENCE: 15 atg gtg gct act tgc gct acg tcg tcg ttt ttt cat gtt cca tct tct      48
Met Val Ala Thr Cys Ala Thr Ser Ser Phe Phe His Val Pro Ser Ser
 1               5                  10                  15 tcc tcg ctt gat acg aat ggg aag ggg aac aga gtt ggg tcc act aat      96
Ser Ser Leu Asp Thr Asn Gly Lys Gly Asn Arg Val Gly Ser Thr Asn
             20                  25                  30 ttt gct gga ctt aac tca acg cca agc tct ggg agg atg aag gtt aag     144
Phe Ala Gly Leu Asn Ser Thr Pro Ser Ser Gly Arg Met Lys Val Lys
         35                  40                  45 cca aac gct cag gct cca ccc aag atc aac ggg aag aaa gct aac ttg     192
Pro Asn Ala Gln Ala Pro Pro Lys Ile Asn Gly Lys Lys Ala Asn Leu
     50                  55                  60 cct ggc tct gta gag ata tca aag gct gac aac gag act tcg cag ccc     240
Pro Gly Ser Val Glu Ile Ser Lys Ala Asp Asn Glu Thr Ser Gln Pro
```

```
                  65                  70                  75                  80
gca cac gca ccg agg acg ttt atc aac cag ctg cct gac tgg agt atg              288
Ala His Ala Pro Arg Thr Phe Ile Asn Gln Leu Pro Asp Trp Ser Met
                        85                  90                  95 ctg ctt gct gct ata act acc att ttc ttg gca gcg gag aaa cag tgg              336
Leu Leu Ala Ala Ile Thr Thr Ile Phe Leu Ala Ala Glu Lys Gln Trp
                100                 105                 110 atg atg ctt gac tgg aaa ccg agg cgt tct gat atg att atg gat cct              384
Met Met Leu Asp Trp Lys Pro Arg Arg Ser Asp Met Ile Met Asp Pro
            115                 120                 125 ttt ggt tta ggg aga att gtt cag gat ggt ctt gtg ttc cgt cag aat              432
Phe Gly Leu Gly Arg Ile Val Gln Asp Gly Leu Val Phe Arg Gln Asn
        130                 135                 140 ttt tcc att agg tct tat gaa ata ggt gct gat cgc tct gcg tct ata              480
Phe Ser Ile Arg Ser Tyr Glu Ile Gly Ala Asp Arg Ser Ala Ser Ile
145                 150                 155                 160 gaa act gtc atg aat cat tta cag gtactgcttt gattgtggtt acactcacat             534
Glu Thr Val Met Asn His Leu Gln
                    165 gttgtcccaa tagatatatg ctcatgacaa gctcttatgc taatgacag gaa acg gcg            592
                                                        Glu Thr Ala
                                                                170 ctt aat cat gtg aag tct gcc gga ctg ctg gaa aat ggg ttt ggg tcc              640
Leu Asn His Val Lys Ser Ala Gly Leu Leu Glu Asn Gly Phe Gly Ser
            175                 180                 185 act cct gag atg ttt aag aag aat ttg ata tgg gtc gtt gct cgt atg              688
Thr Pro Glu Met Phe Lys Lys Asn Leu Ile Trp Val Val Ala Arg Met
        190                 195                 200 cag gtt gtc gtt gat aaa tat cct act tg gtaagccatt gttagtctta                 737
Gln Val Val Val Asp Lys Tyr Pro Thr Trp
    205                 210 gcacttgact taaaatcatt ttgcatatta cagtgtgcgt agatcatttg cttattcaaa            797
tatctgactc acag g gga gat gtt gtg gaa gtg gat act tgg gtt agt cag            848
                  Gly Asp Val Val Glu Val Asp Thr Trp Val Ser Gln
                            215                 220                 225 tct gga aag aat ggt atg cgt cgt gat tgg cta gtt cgg gat tgc aat              896
Ser Gly Lys Asn Gly Met Arg Arg Asp Trp Leu Val Arg Asp Cys Asn
            230                 235                 240 act gga gaa att gta acg cga gca tca ag gtcagagttc ttatattttg                 945
Thr Gly Glu Ile Val Thr Arg Ala Ser Ser
            245                 250 gtttactcca gctattatcg ttttgctctc tgtttgtatt gtttcctctg ccattagttt            1005
gataattgag tctttatagt tgtatatgta tggcaatttt cttcttttg cag t ttg              1062
                                                              Leu tgg gtg atg atg aat aaa ctc aca agg aga ttg tca aag att cct gaa              1110
Trp Val Met Met Asn Lys Leu Thr Arg Arg Leu Ser Lys Ile Pro Glu
        255                 260                 265 gag gtt cga ggg gaa ata gag cct tat ttt gtg aac tct gat cct gtc              1158
Glu Val Arg Gly Glu Ile Glu Pro Tyr Phe Val Asn Ser Asp Pro Val
    270                 275                 280 att gcc gaa gac agc aga aag tta aca aaa ctt gat gac aag act gct              1206
Ile Ala Glu Asp Ser Arg Lys Leu Thr Lys Leu Asp Asp Lys Thr Ala
285                 290                 295                 300 gac tat gtt cgt tct ggt ctc act gtaagtacct tacctttcga caagcctgtc             1260
Asp Tyr Val Arg Ser Gly Leu Thr
                305 aaaactcttg aggttctaat ggtttggtaa tgaacttttt tttggcag ccg agg tgg             1317
                                                    Pro Arg Trp
```

```
agt gac ttg gat gtt aac cag cat gtt aac aat gta aag tac att ggg        1365
Ser Asp Leu Asp Val Asn Gln His Val Asn Asn Val Lys Tyr Ile Gly
        315                 320                 325 tgg ata ctg gag agt gct cca gca ggg atg ctg gag agt cag aag ctg        1413
Trp Ile Leu Glu Ser Ala Pro Ala Gly Met Leu Glu Ser Gln Lys Leu
    330                 335                 340 aaa agc atg act ctg gag tat cgc agg gag tgc ggg aga gac agt gtg        1461
Lys Ser Met Thr Leu Glu Tyr Arg Arg Glu Cys Gly Arg Asp Ser Val
345                 350                 355 ctt cag tct ctc acc gca gtc tct gga tgt gat gtc ggt aac ctc ggg        1509
Leu Gln Ser Leu Thr Ala Val Ser Gly Cys Asp Val Gly Asn Leu Gly
    360                 365                 370                 375 aca gcc ggg gaa gtg gag tgt cag cat ttg ctt cga ctc cag gat gga        1557
Thr Ala Gly Glu Val Glu Cys Gln His Leu Leu Arg Leu Gln Asp Gly
                380                 385                 390 gct gaa gtg gtg aga gga aga aca gag tgg agc tcc aag aca gga gca        1605
Ala Glu Val Val Arg Gly Arg Thr Glu Trp Ser Ser Lys Thr Gly Ala
            395                 400                 405 aca act tgg gac act act aca tcg taa                                    1632
Thr Thr Trp Asp Thr Thr Thr Ser
        410                 415

<210> SEQ ID NO 16
<211> LENGTH: 415
<212> TYPE: PRT
<213> ORGANISM: Brassica napus

<400> SEQUENCE: 16

Met Val Ala Thr Cys Ala Thr Ser Ser Phe Phe His Val Pro Ser Ser
1               5                   10                  15

Ser Ser Leu Asp Thr Asn Gly Lys Gly Asn Arg Val Gly Ser Thr Asn
            20                  25                  30

Phe Ala Gly Leu Asn Ser Thr Pro Ser Ser Gly Arg Met Lys Val Lys
        35                  40                  45

Pro Asn Ala Gln Ala Pro Pro Lys Ile Asn Gly Lys Lys Ala Asn Leu
    50                  55                  60

Pro Gly Ser Val Glu Ile Ser Lys Ala Asp Asn Glu Thr Ser Gln Pro
65                  70                  75                  80

Ala His Ala Pro Arg Thr Phe Ile Asn Gln Leu Pro Asp Trp Ser Met
                85                  90                  95

Leu Leu Ala Ala Ile Thr Thr Ile Phe Leu Ala Ala Glu Lys Gln Trp
            100                 105                 110

Met Met Leu Asp Trp Lys Pro Arg Arg Ser Asp Met Ile Met Asp Pro
        115                 120                 125

Phe Gly Leu Gly Arg Ile Val Gln Asp Gly Leu Val Phe Arg Gln Asn
    130                 135                 140

Phe Ser Ile Arg Ser Tyr Glu Ile Gly Ala Asp Arg Ser Ala Ser Ile
145                 150                 155                 160

Glu Thr Val Met Asn His Leu Gln Glu Thr Ala Leu Asn His Val Lys
                165                 170                 175

Ser Ala Gly Leu Leu Glu Asn Gly Phe Gly Ser Thr Pro Glu Met Phe
            180                 185                 190

Lys Lys Asn Leu Ile Trp Val Val Ala Arg Met Gln Val Val Val Asp
        195                 200                 205

Lys Tyr Pro Thr Trp Gly Asp Val Val Glu Val Asp Thr Trp Val Ser
    210                 215                 220
```

-continued

```
Gln Ser Gly Lys Asn Gly Met Arg Arg Asp Trp Leu Val Arg Asp Cys
225                 230                 235                 240

Asn Thr Gly Glu Ile Val Thr Arg Ala Ser Ser Leu Trp Val Met Met
            245                 250                 255

Asn Lys Leu Thr Arg Arg Leu Ser Lys Ile Pro Glu Glu Val Arg Gly
        260                 265                 270

Glu Ile Glu Pro Tyr Phe Val Asn Ser Asp Pro Val Ile Ala Glu Asp
    275                 280                 285

Ser Arg Lys Leu Thr Lys Leu Asp Asp Lys Thr Ala Asp Tyr Val Arg
290                 295                 300

Ser Gly Leu Thr Pro Arg Trp Ser Asp Leu Asp Val Asn Gln His Val
305                 310                 315                 320

Asn Asn Val Lys Tyr Ile Gly Trp Ile Leu Glu Ser Ala Pro Ala Gly
            325                 330                 335

Met Leu Glu Ser Gln Lys Leu Lys Ser Met Thr Leu Glu Tyr Arg Arg
        340                 345                 350

Glu Cys Gly Arg Asp Ser Val Leu Gln Ser Leu Thr Ala Val Ser Gly
    355                 360                 365

Cys Asp Val Gly Asn Leu Gly Thr Ala Gly Val Glu Cys Gln His
370                 375                 380

Leu Leu Arg Leu Gln Asp Gly Ala Glu Val Val Arg Gly Arg Thr Glu
385                 390                 395                 400

Trp Ser Ser Lys Thr Gly Ala Thr Thr Trp Asp Thr Thr Ser
                405                 410                 415

<210> SEQ ID NO 17
<211> LENGTH: 1715
<212> TYPE: DNA
<213> ORGANISM: Brassica napus
<220> FEATURE:
<221> NAME/KEY: CDS
<222> LOCATION: (1)..(507)
<220> FEATURE:
<221> NAME/KEY: mat_peptide
<222> LOCATION: (1)..(1712)
<223> OTHER INFORMATION: mature peptide starts at amino acid 92
<220> FEATURE:
<221> NAME/KEY: misc_feature
<222> LOCATION: (493)..(495)
<223> OTHER INFORMATION: conserved Met
<220> FEATURE:
<221> NAME/KEY: CDS
<222> LOCATION: (740)..(873)
<220> FEATURE:
<221> NAME/KEY: misc_feature
<222> LOCATION: (761)..(763)
<223> OTHER INFORMATION: conserved Lys
<220> FEATURE:
<221> NAME/KEY: misc_feature
<222> LOCATION: (833)..(835)
<223> OTHER INFORMATION: conserved Val
<220> FEATURE:
<221> NAME/KEY: CDS
<222> LOCATION: (947)..(1060)
<220> FEATURE:
<221> NAME/KEY: misc_feature
<222> LOCATION: (999)..(1001)
<223> OTHER INFORMATION: conserved Met
<220> FEATURE:
<221> NAME/KEY: CDS
<222> LOCATION: (1139)..(1310)
<220> FEATURE:
<221> NAME/KEY: misc_feature
<222> LOCATION: (1176)..(1178)
<223> OTHER INFORMATION: conserved Ser
<220> FEATURE:
```

```
<221> NAME/KEY: CDS
<222> LOCATION: (1395)..(1712)
<220> FEATURE:
<221> NAME/KEY: misc_feature
<222> LOCATION: (1401)..(1403)
<223> OTHER INFORMATION: conserved Trp
<220> FEATURE:
<221> NAME/KEY: misc_feature
<222> LOCATION: (1419)..(1421)
<223> OTHER INFORMATION: conserved Asn
<220> FEATURE:
<221> NAME/KEY: misc_feature
<222> LOCATION: (1425)..(1427)
<223> OTHER INFORMATION: conserved His
<220> FEATURE:
<221> NAME/KEY: misc_feature
<222> LOCATION: (1530)..(1532)
<223> OTHER INFORMATION: conserved Cys

<400> SEQUENCE: 17 atg gtg gcc acc tct gct aca tcc tca ttc ttc cct ctc cca tct tcc      48
Met Val Ala Thr Ser Ala Thr Ser Ser Phe Phe Pro Leu Pro Ser Ser
1               5                   10                  15 tct ctc gac ccc aat ggc aaa acc aac aaa gcc acc tcc acc aac ttc      96
Ser Leu Asp Pro Asn Gly Lys Thr Asn Lys Ala Thr Ser Thr Asn Phe
            20                  25                  30 tcc gga ctc aac ccc aca cca aac tct tcc ggc agg tta aag gtc aaa     144
Ser Gly Leu Asn Pro Thr Pro Asn Ser Ser Gly Arg Leu Lys Val Lys
        35                  40                  45 cca aac gct cag gct cca tcc aag atc aac ggc aag aaa gtc tcc ttg     192
Pro Asn Ala Gln Ala Pro Ser Lys Ile Asn Gly Lys Lys Val Ser Leu
50                  55                  60 cca ggc tca gta cac atc gta aag act gat aat aac cac gat ctc tcg     240
Pro Gly Ser Val His Ile Val Lys Thr Asp Asn Asn His Asp Leu Ser
65                  70                  75                  80 caa caa aac gca ccc aga acg ttc atc aac cag cta cct gac tgg agc     288
Gln Gln Asn Ala Pro Arg Thr Phe Ile Asn Gln Leu Pro Asp Trp Ser
                85                  90                  95 atg ctt ctc gcc gcc atc aca acg gtc ttc tta gca gct gag aag cag     336
Met Leu Leu Ala Ala Ile Thr Thr Val Phe Leu Ala Ala Glu Lys Gln
            100                 105                 110 tgg atg atg ctt gat act aaa ccg aga cgc tcc gac atg att atg gat     384
Trp Met Met Leu Asp Thr Lys Pro Arg Arg Ser Asp Met Ile Met Asp
        115                 120                 125 ccg ttt ggg tta ggg aga atc gtt cag gat ggg ctt gtg tac cgt cag     432
Pro Phe Gly Leu Gly Arg Ile Val Gln Asp Gly Leu Val Tyr Arg Gln
130                 135                 140 aat ttc gat atc agg tct tat gaa ata ggt gct gat cgc tct gca tct     480
Asn Phe Asp Ile Arg Ser Tyr Glu Ile Gly Ala Asp Arg Ser Ala Ser
145                 150                 155                 160 ata gaa act gtc atg aat cac tta cag gtatattaca atcacactcg           527
Ile Glu Thr Val Met Asn His Leu Gln
                165 tttgatacta tagcttgacc cgcactgatg ttggttttta tatttttata aattgtttag    587 tgacatatag ataggtta tttagatatt tctaggttcc tacgaaccta cccggactca     647 aaccctgtcc gtaaaattga gtttaatttt aaaccaaaaa aatccgatac ccgaaaaaac    707 cgatctgtat ctaactcttg tcctcatgac ag gaa acg gct ctc aac cat gtg      760
                                   Glu Thr Ala Leu Asn His Val
                                   170                 175 aag tct gca gga ctg ctg gga gat ggg ttt ggt tct aca cct gag atg     808
Lys Ser Ala Gly Leu Leu Gly Asp Gly Phe Gly Ser Thr Pro Glu Met
            180                 185                 190
```

```
gtt aag aag aac ttg ata tgg gtt gtt act cgt atg cag gtt gta gtt     856
Val Lys Lys Asn Leu Ile Trp Val Val Thr Arg Met Gln Val Val Val
        195                 200                 205 gat aaa tat cct act tg gtaagctctc ttgccactta accttaaaca              903
Asp Lys Tyr Pro Thr Trp
    210 atatgcatga atcatttgct tattcaaatg tctgtttcac cag g gga gat gtt gtt    959
                                                  Gly Asp Val Val
                                                              215 gaa gta gat aca tgg gtc agt aag tct ggg aag aat ggt atg cgt cgt     1007
Glu Val Asp Thr Trp Val Ser Lys Ser Gly Lys Asn Gly Met Arg Arg
        220                 225                 230 gat tgg cta gtt cgt gat tgc aat act gga gaa atc tta aca cgc gca     1055
Asp Trp Leu Val Arg Asp Cys Asn Thr Gly Glu Ile Leu Thr Arg Ala
235                 240                 245                 250 tca ag gttagcttta ttttgttttt gtttactcca gctattatct gattattgag       1110
Ser Ser ttataaccat ctctatgtta caaaacag t gtg tgg gtg atg atg aat aaa ctg    1163
                                 Val Trp Val Met Met Asn Lys Leu
                                                 255             260 aca agg aga tta tca aag ctt cct gaa gag gtt cga ggg gaa ata gag     1211
Thr Arg Arg Leu Ser Lys Leu Pro Glu Glu Val Arg Gly Glu Ile Glu
                265                 270                 275 cct tac ttt gtg aac tct gac cca atc ctt gcc gag gac agc aga aag     1259
Pro Tyr Phe Val Asn Ser Asp Pro Ile Leu Ala Glu Asp Ser Arg Lys
        280                 285                 290 tta aca aag cta gat gac aag act gct gac tat gtt cgc tct ggt ctc     1307
Leu Thr Lys Leu Asp Asp Lys Thr Ala Asp Tyr Val Arg Ser Gly Leu
        295                 300                 305 acc gtaagtataa atattcaact ctttatcttt tagcgtgtaa aactcttgag          1360
Thr agattcttat gagtttggtg atgaactttt gcag ccg aga tgg agt gac ttg gat   1415
                                      Pro Arg Trp Ser Asp Leu Asp
                                              310                 315 gtt aac cag cat gtt aac aac gtg aag tac att ggt tgg ata ctc gag     1463
Val Asn Gln His Val Asn Asn Val Lys Tyr Ile Gly Trp Ile Leu Glu
        320                 325                 330 agt gct cca gta gag atg atg gag aag cat aag ctg aaa agc atg act     1511
Ser Ala Pro Val Glu Met Met Glu Lys His Lys Leu Lys Ser Met Thr
        335                 340                 345 ctg gag tat agg agg gaa tgc ggg aga gac agt gtg ctt cag tct ctc     1559
Leu Glu Tyr Arg Arg Glu Cys Gly Arg Asp Ser Val Leu Gln Ser Leu
350                 355                 360 acc gcg gtt tcg gga tgc gat gtt ggt agc ctc ggg aca gct ggt gaa     1607
Thr Ala Val Ser Gly Cys Asp Val Gly Ser Leu Gly Thr Ala Gly Glu
365                 370                 375                 380 gtg gaa tgt cag cat ttg ctt cga cac cag gat gga gct gaa gtg gtg     1655
Val Glu Cys Gln His Leu Leu Arg His Gln Asp Gly Ala Glu Val Val
                385                 390                 395 aag gga cga aca gtg tgg agt tcg aaa aca cca tca acg act tgg gac     1703
Lys Gly Arg Thr Val Trp Ser Ser Lys Thr Pro Ser Thr Thr Trp Asp
        400                 405                 410 act aca tcg taa                                                     1715
Thr Thr Ser
        415

<210> SEQ ID NO 18
<211> LENGTH: 415
<212> TYPE: PRT
<213> ORGANISM: Brassica napus
```

<400> SEQUENCE: 18

```
Met Val Ala Thr Ser Ala Thr Ser Ser Phe Phe Pro Leu Pro Ser Ser
1               5                   10                  15

Ser Leu Asp Pro Asn Gly Lys Thr Asn Lys Ala Thr Ser Thr Asn Phe
            20                  25                  30

Ser Gly Leu Asn Pro Thr Pro Asn Ser Ser Gly Arg Leu Lys Val Lys
        35                  40                  45

Pro Asn Ala Gln Ala Pro Ser Lys Ile Asn Gly Lys Lys Val Ser Leu
    50                  55                  60

Pro Gly Ser Val His Ile Val Lys Thr Asp Asn Asn His Asp Leu Ser
65              70                  75                  80

Gln Gln Asn Ala Pro Arg Thr Phe Ile Asn Gln Leu Pro Asp Trp Ser
                85                  90                  95

Met Leu Leu Ala Ala Ile Thr Thr Val Phe Leu Ala Ala Glu Lys Gln
            100                 105                 110

Trp Met Met Leu Asp Thr Lys Pro Arg Arg Ser Asp Met Ile Met Asp
        115                 120                 125

Pro Phe Gly Leu Gly Arg Ile Val Gln Asp Gly Leu Val Tyr Arg Gln
    130                 135                 140

Asn Phe Asp Ile Arg Ser Tyr Glu Ile Gly Ala Asp Arg Ser Ala Ser
145                 150                 155                 160

Ile Glu Thr Val Met Asn His Leu Gln Glu Thr Ala Leu Asn His Val
                165                 170                 175

Lys Ser Ala Gly Leu Leu Gly Asp Gly Phe Gly Ser Thr Pro Glu Met
            180                 185                 190

Val Lys Lys Asn Leu Ile Trp Val Val Thr Arg Met Gln Val Val Val
        195                 200                 205

Asp Lys Tyr Pro Thr Trp Gly Asp Val Val Glu Val Asp Thr Trp Val
    210                 215                 220

Ser Lys Ser Gly Lys Asn Gly Met Arg Arg Asp Trp Leu Val Arg Asp
225                 230                 235                 240

Cys Asn Thr Gly Glu Ile Leu Thr Arg Ala Ser Ser Val Trp Val Met
                245                 250                 255

Met Asn Lys Leu Thr Arg Arg Leu Ser Lys Leu Pro Glu Glu Val Arg
            260                 265                 270

Gly Glu Ile Glu Pro Tyr Phe Val Asn Ser Asp Pro Ile Leu Ala Glu
        275                 280                 285

Asp Ser Arg Lys Leu Thr Lys Leu Asp Asp Lys Thr Ala Asp Tyr Val
    290                 295                 300

Arg Ser Gly Leu Thr Pro Arg Trp Ser Asp Leu Asp Val Asn Gln His
305                 310                 315                 320

Val Asn Asn Val Lys Tyr Ile Gly Trp Ile Leu Glu Ser Ala Pro Val
                325                 330                 335

Glu Met Met Glu Lys His Lys Leu Lys Ser Met Thr Leu Glu Tyr Arg
            340                 345                 350

Arg Glu Cys Gly Arg Asp Ser Val Leu Gln Ser Leu Thr Ala Val Ser
        355                 360                 365

Gly Cys Asp Val Gly Ser Leu Gly Thr Ala Gly Glu Val Glu Cys Gln
    370                 375                 380

His Leu Leu Arg His Gln Asp Gly Ala Glu Val Val Lys Gly Arg Thr
385                 390                 395                 400

Val Trp Ser Ser Lys Thr Pro Ser Thr Thr Trp Asp Thr Thr Ser
```

```
<210> SEQ ID NO 19
<211> LENGTH: 1572
<212> TYPE: DNA
<213> ORGANISM: Brassica napus
<220> FEATURE:
<221> NAME/KEY: CDS
<222> LOCATION: (1)..(498)
<220> FEATURE:
<221> NAME/KEY: mat_peptide
<222> LOCATION: (1)..(1569)
<223> OTHER INFORMATION: mature peptide starts at amino acid 89
<220> FEATURE:
<221> NAME/KEY: misc_feature
<222> LOCATION: (484)..(486)
<223> OTHER INFORMATION: conserved Met
<220> FEATURE:
<221> NAME/KEY: CDS
<222> LOCATION: (579)..(712)
<220> FEATURE:
<221> NAME/KEY: misc_feature
<222> LOCATION: (600)..(602)
<223> OTHER INFORMATION: conserved Lys
<220> FEATURE:
<221> NAME/KEY: misc_feature
<222> LOCATION: (672)..(674)
<223> OTHER INFORMATION: conserved Val
<220> FEATURE:
<221> NAME/KEY: CDS
<222> LOCATION: (791)..(904)
<220> FEATURE:
<221> NAME/KEY: misc_feature
<222> LOCATION: (848)..(850)
<223> OTHER INFORMATION: conserved Met
<220> FEATURE:
<221> NAME/KEY: CDS
<222> LOCATION: (995)..(1166)
<220> FEATURE:
<221> NAME/KEY: misc_feature
<222> LOCATION: (1032)..(1034)
<223> OTHER INFORMATION: conserved Ser
<220> FEATURE:
<221> NAME/KEY: CDS
<222> LOCATION: (1252)..(1569)
<220> FEATURE:
<221> NAME/KEY: misc_feature
<222> LOCATION: (1258)..(1260)
<223> OTHER INFORMATION: conserved Trp
<220> FEATURE:
<221> NAME/KEY: misc_feature
<222> LOCATION: (1276)..(1278)
<223> OTHER INFORMATION: conserved Asn
<220> FEATURE:
<221> NAME/KEY: misc_feature
<222> LOCATION: (1282)..(1284)
<223> OTHER INFORMATION: conserved His
<220> FEATURE:
<221> NAME/KEY: misc_feature
<222> LOCATION: (1387)..(1389)
<223> OTHER INFORMATION: conserved Cys

<400> SEQUENCE: 19 atg gtg gcc acc tca gct aca tcc tca ttc ttc cct ctc cca tct tcc      48
Met Val Ala Thr Ser Ala Thr Ser Ser Phe Phe Pro Leu Pro Ser Ser
 1               5                  10                  15 ccc ctc gac ccc acc gca aaa acc aac aaa gtc acc acc tcc acc aac      96
Pro Leu Asp Pro Thr Ala Lys Thr Asn Lys Val Thr Thr Ser Thr Asn
             20                  25                  30 ttc tcc ggc ctc aca ccc acg ccg aac tcc gcc agg atg aag gtt aaa     144
Phe Ser Gly Leu Thr Pro Thr Pro Asn Ser Ala Arg Met Lys Val Lys
         35                  40                  45 cca aac gct cag gcc cca ccc aag atc aac ggc aag aga gtc ggc ctc     192
Pro Asn Ala Gln Ala Pro Pro Lys Ile Asn Gly Lys Arg Val Gly Leu
```

```
                  50                  55                  60
cct ggc tcg gtg gag atc ttg aag cct gat agc gag act tcg caa cca     240
Pro Gly Ser Val Glu Ile Leu Lys Pro Asp Ser Glu Thr Ser Gln Pro
 65                  70                  75                  80 gca ccg agg acg ttc atc aac cag ctg cct gac tgg agc atg ctc ctc     288
Ala Pro Arg Thr Phe Ile Asn Gln Leu Pro Asp Trp Ser Met Leu Leu
                 85                  90                  95 gcc gcc atc acg acc gtc ttc ttg gcg gct gag aag cag tgg atg atg     336
Ala Ala Ile Thr Thr Val Phe Leu Ala Ala Glu Lys Gln Trp Met Met
            100                 105                 110 ctc gac tgg aaa ccg agg cgt tct gac gtg att atg gat ccg ttt ggg     384
Leu Asp Trp Lys Pro Arg Arg Ser Asp Val Ile Met Asp Pro Phe Gly
        115                 120                 125 tta ggg agg atc gtt cag gat ggg ctt gtg ttc cgt cag aat ttt tct     432
Leu Gly Arg Ile Val Gln Asp Gly Leu Val Phe Arg Gln Asn Phe Ser
    130                 135                 140 att cgg tct tat gag ata ggt gct gat cgc tct gcg tct ata gaa acg     480
Ile Arg Ser Tyr Glu Ile Gly Ala Asp Arg Ser Ala Ser Ile Glu Thr
145                 150                 155                 160 gtt atg aat cat tta cag gtactgatta tgattatgat tgtagtcgct            528
Val Met Asn His Leu Gln
                165 tgttgttact ggacaaactt aaatatgtat tgctcttatg gttgtgatag gaa acg      584
                                                         Glu Thr gca ctc aac cat gtt aag act gct ggg ctg ctt gga gat ggg ttt ggt     632
Ala Leu Asn His Val Lys Thr Ala Gly Leu Leu Gly Asp Gly Phe Gly
        170                 175                 180 tct act cct gag atg gtt aag aag aac ttg ata tgg gtt gtt act cgt     680
Ser Thr Pro Glu Met Val Lys Lys Asn Leu Ile Trp Val Val Thr Arg
185                 190                 195                 200 atg cag gtt gtc gtt gat aaa tat cct act tg gtaagctatt ctcaacaac     732
Met Gln Val Val Val Asp Lys Tyr Pro Thr Trp
                205                 210 tctgagaatc actgcttcct tgtgagtca tttgcttatt caaatatctg cctcatag g    791 gga gat gtt gtg gaa gta gat aca tgg gtg agc cag tct gga aag aac     839
Gly Asp Val Val Glu Val Asp Thr Trp Val Ser Gln Ser Gly Lys Asn
            215                 220                 225 ggt atg cgt cgt gat tgg ctt gtt cgg gat ggc aat act gga gag att     887
Gly Met Arg Arg Asp Trp Leu Val Arg Asp Gly Asn Thr Gly Glu Ile
        230                 235                 240 tta aca aga gca tca ag gttagatttt attttttggt ttacttgggt             934
Leu Thr Arg Ala Ser Ser
    245 tagatatctg ataattgagt tataatcatc tccgtgttgt gtaaactatt cttttgcag    994 t gtg tgg gtg atg atg aat aaa ctg aca aga aga tta tca aag att cct   1043
  Val Trp Val Met Met Asn Lys Leu Thr Arg Arg Leu Ser Lys Ile Pro
   250                 255                 260                 265 gaa gag gtt cga ggg gag ata gag cct tac ttt gtt aac tca gac cca     1091
Glu Glu Val Arg Gly Glu Ile Glu Pro Tyr Phe Val Asn Ser Asp Pro
                270                 275                 280 gtc ctt gcc gag gac agc aga aag tta aca aaa ctt gat gac aaa act     1139
Val Leu Ala Glu Asp Ser Arg Lys Leu Thr Lys Leu Asp Asp Lys Thr
            285                 290                 295 gct gtc tat gtt cgt tct ggt ctc act gtaagtacaa atacttcact           1186
Ala Val Tyr Val Arg Ser Gly Leu Thr
        300                 305 ctatgtttca acaaagcctg taaatttttg agtctcttac aggtttggta atgaactttt   1246
```

```
tgcag ccg cgt tgg agt gac ttg gat gtt aac cag cac gtt aac aat gtg   1296
      Pro Arg Trp Ser Asp Leu Asp Val Asn Gln His Val Asn Asn Val
              310                 315                 320 aag tac atc ggg tgg ata ctg gag agt gct cca gtg ggg atg atg gag   1344
Lys Tyr Ile Gly Trp Ile Leu Glu Ser Ala Pro Val Gly Met Met Glu
            325                 330                 335 agt cag aag ctg aaa agc atg act ctg gag tat cgc agg gag tgt ggg   1392
Ser Gln Lys Leu Lys Ser Met Thr Leu Glu Tyr Arg Arg Glu Cys Gly
        340                 345                 350 aga gac agt gtg ctc cag tcc ctc acc gcg gtt tcg ggc tgc gat atc   1440
Arg Asp Ser Val Leu Gln Ser Leu Thr Ala Val Ser Gly Cys Asp Ile
    355                 360                 365 ggt agc ctc ggg aca gcc ggt gaa gtg gaa tgt cag cat ctg ctc aga   1488
Gly Ser Leu Gly Thr Ala Gly Glu Val Glu Cys Gln His Leu Leu Arg
370                 375                 380                 385 ctc cag gat gga gcc gaa gtg gtg aga gga aga aca gag tgg agt tcc   1536
Leu Gln Asp Gly Ala Glu Val Val Arg Gly Arg Thr Glu Trp Ser Ser
                390                 395                 400 aaa aca tca aca aca act tgg gac atc aca ccg tga                    1572
Lys Thr Ser Thr Thr Thr Trp Asp Ile Thr Pro
            405                 410

<210> SEQ ID NO 20
<211> LENGTH: 412
<212> TYPE: PRT
<213> ORGANISM: Brassica napus

<400> SEQUENCE: 20

Met Val Ala Thr Ser Ala Thr Ser Ser Phe Phe Pro Leu Pro Ser Ser
1               5                   10                  15

Pro Leu Asp Pro Thr Ala Lys Thr Asn Lys Val Thr Thr Ser Thr Asn
            20                  25                  30

Phe Ser Gly Leu Thr Pro Thr Pro Asn Ser Ala Arg Met Lys Val Lys
        35                  40                  45

Pro Asn Ala Gln Ala Pro Lys Ile Asn Gly Lys Arg Val Gly Leu
    50                  55                  60

Pro Gly Ser Val Glu Ile Leu Lys Pro Asp Ser Glu Thr Ser Gln Pro
65                  70                  75                  80

Ala Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Arg Arg Ser Asp Val Ile Met Asp Pro Phe Gly
        115                 120                 125

Leu Gly Arg Ile Val Gln Asp Gly Leu Val Phe Arg Gln Asn Phe Ser
    130                 135                 140

Ile Arg Ser Tyr Glu Ile Gly Ala Asp Arg Ser Ala Ser Ile Glu Thr
145                 150                 155                 160

Val Met Asn His Leu Gln Glu Thr Ala Leu Asn His Val Lys Thr Ala
                165                 170                 175

Gly Leu Leu Gly Asp Gly Phe Gly Ser Thr Pro Glu Met Val Lys Lys
            180                 185                 190

Asn Leu Ile Trp Val Val Thr Arg Met Gln Val Val Asp Lys Tyr
        195                 200                 205

Pro Thr Trp Gly Asp Val Val Glu Val Asp Thr Trp Val Ser Gln Ser
    210                 215                 220

Gly Lys Asn Gly Met Arg Arg Asp Trp Leu Val Arg Asp Gly Asn Thr
```

```
            225                 230                 235                 240
Gly Glu Ile Leu Thr Arg Ala Ser Ser Val Trp Val Met Met Asn Lys
                245                 250                 255
Leu Thr Arg Arg Leu Ser Lys Ile Pro Glu Glu Val Arg Gly Glu Ile
                260                 265                 270
Glu Pro Tyr Phe Val Asn Ser Asp Pro Val Leu Ala Glu Asp Ser Arg
                275                 280                 285
Lys Leu Thr Lys Leu Asp Asp Lys Thr Ala Val Tyr Val Arg Ser Gly
            290                 295                 300
Leu Thr Pro Arg Trp Ser Asp Leu Asp Val Asn Gln His Val Asn Asn
305                 310                 315                 320
Val Lys Tyr Ile Gly Trp Ile Leu Glu Ser Ala Pro Val Gly Met Met
                325                 330                 335
Glu Ser Gln Lys Leu Lys Ser Met Thr Leu Glu Tyr Arg Arg Glu Cys
                340                 345                 350
Gly Arg Asp Ser Val Leu Gln Ser Leu Thr Ala Val Ser Gly Cys Asp
                355                 360                 365
Ile Gly Ser Leu Gly Thr Ala Gly Glu Val Glu Cys Gln His Leu Leu
            370                 375                 380
Arg Leu Gln Asp Gly Ala Glu Val Val Arg Gly Arg Thr Glu Trp Ser
385                 390                 395                 400
Ser Lys Thr Ser Thr Thr Thr Trp Asp Ile Thr Pro
                405                 410

<210> SEQ ID NO 21
<211> LENGTH: 1770
<212> TYPE: DNA
<213> ORGANISM: Brassica napus
<220> FEATURE:
<221> NAME/KEY: CDS
<222> LOCATION: (1)..(504)
<220> FEATURE:
<221> NAME/KEY: mat_peptide
<222> LOCATION: (1)..(1767)
<223> OTHER INFORMATION: mature peptide starts at amino acid 91
<220> FEATURE:
<221> NAME/KEY: misc_feature
<222> LOCATION: (490)..(492)
<223> OTHER INFORMATION: conserved Met
<220> FEATURE:
<221> NAME/KEY: CDS
<222> LOCATION: (581)..(714)
<220> FEATURE:
<221> NAME/KEY: misc_feature
<222> LOCATION: (602)..(604)
<223> OTHER INFORMATION: conserved Lys
<220> FEATURE:
<221> NAME/KEY: misc_feature
<222> LOCATION: (674)..(676)
<223> OTHER INFORMATION: conserved Val
<220> FEATURE:
<221> NAME/KEY: CDS
<222> LOCATION: (945)..(1058)
<220> FEATURE:
<221> NAME/KEY: misc_feature
<222> LOCATION: (997)..(999)
<223> OTHER INFORMATION: conserved Met
<220> FEATURE:
<221> NAME/KEY: CDS
<222> LOCATION: (1190)..(1361)
<220> FEATURE:
<221> NAME/KEY: misc_feature
<222> LOCATION: (1227)..(1229)
<223> OTHER INFORMATION: conserved Ser
<220> FEATURE:
<221> NAME/KEY: CDS
<222> LOCATION: (1447)..(1767)
```

```
<220> FEATURE:
<221> NAME/KEY: misc_feature
<222> LOCATION: (1453)..(1455)
<223> OTHER INFORMATION: conserved Trp
<220> FEATURE:
<221> NAME/KEY: misc_feature
<222> LOCATION: (1471)..(1473)
<223> OTHER INFORMATION: conserved Asn
<220> FEATURE:
<221> NAME/KEY: misc_feature
<222> LOCATION: (1477)..(1479)
<223> OTHER INFORMATION: conserved His
<220> FEATURE:
<221> NAME/KEY: misc_feature
<222> LOCATION: (1582)..(1584)
<223> OTHER INFORMATION: conserved Cys

<400> SEQUENCE: 21 atg gtg gct act tcc gct acg tcc tcg ttt ttt cat gtt cca tct tcc      48
Met Val Ala Thr Ser Ala Thr Ser Ser Phe Phe His Val Pro Ser Ser
1               5                   10                  15 tcc tct ctt gat act aat ggg aag ggg aac aga gtt gcg tcc acg aac      96
Ser Ser Leu Asp Thr Asn Gly Lys Gly Asn Arg Val Ala Ser Thr Asn
            20                  25                  30 ttc gct gga ctt aac tca acg cca agc tct ggg agg atg aag gtt aaa     144
Phe Ala Gly Leu Asn Ser Thr Pro Ser Ser Gly Arg Met Lys Val Lys
        35                  40                  45 cca aac gct cag gct cca ccc aag atc aac ggg aag aaa gct aac ttg     192
Pro Asn Ala Gln Ala Pro Pro Lys Ile Asn Gly Lys Lys Ala Asn Leu
50                  55                  60 cct ggt tct gta gag ata tca aag tct gac aac gag act tcg cag ccc     240
Pro Gly Ser Val Glu Ile Ser Lys Ser Asp Asn Glu Thr Ser Gln Pro
65                  70                  75                  80 gca ccc gca ccg agg acg ttt atc aac cag ctg cct gac tgg agc atg     288
Ala Pro Ala Pro Arg Thr Phe Ile Asn Gln Leu Pro Asp Trp Ser Met
                85                  90                  95 ctt ctc gct gcc ata aca acc att ttc ttg gcg gct gag aaa cag tgg     336
Leu Leu Ala Ala Ile Thr Thr Ile Phe Leu Ala Ala Glu Lys Gln Trp
            100                 105                 110 atg atg ctt gac tgg aaa ccc agg cgt tct gat atg att atg gat cct     384
Met Met Leu Asp Trp Lys Pro Arg Arg Ser Asp Met Ile Met Asp Pro
        115                 120                 125 ttc ggt tta ggg aga atc gtt cag gat ggt ctt gtc ttt cgt cag aat     432
Phe Gly Leu Gly Arg Ile Val Gln Asp Gly Leu Val Phe Arg Gln Asn
130                 135                 140 ttc tcc att agg tct tat gag ata ggt gct gat cgc tct gcg tct ata     480
Phe Ser Ile Arg Ser Tyr Glu Ile Gly Ala Asp Arg Ser Ala Ser Ile
145                 150                 155                 160 gaa act gtt atg aat cat tta cag gtaggtacta ctttgattgt tatcacactt    534
Glu Thr Val Met Asn His Leu Gln
                165 gtcaatagat atatgctc atgacaagct cttatgctaa tgacag gaa acg gcc        589
                                                 Glu Thr Ala
                                                         170 cta aac cat gtg aag tct gcc gga ctg ctg gaa aat ggg ttt ggt tct     637
Leu Asn His Val Lys Ser Ala Gly Leu Leu Glu Asn Gly Phe Gly Ser
            175                 180                 185 act ccc gag atg ttt aag aag aac ttg ata tgg gtc gtt gct cgt atg     685
Thr Pro Glu Met Phe Lys Lys Asn Leu Ile Trp Val Val Ala Arg Met
        190                 195                 200 cag gtt gtc gtt gat aaa tat cct act tg gtaagccatt gtcagtctta        734
Gln Val Val Val Asp Lys Tyr Pro Thr Trp
205                 210
```

```
ccacttaact taaaatcatt atgctactgt ctctgagaat ccctggttct cgttgtgagt    794
tatccaaatt atcttgcata aacttgagta tgcaagttca tgctctcact tgctcatgtg    854
actaggacat tttgcaccct tagattacat gatgtgcttg catattacag tgtgcataga    914
tcattactta ttcaaatatc tgactaacag g gga gat gtt gtg gaa gtg gat      966
                                   Gly Asp Val Val Glu Val Asp
                                   215                 220 aca tgg gtt agt cag tct gga aag aat ggt atg cgt cgt gat tgg ctg     1014
Thr Trp Val Ser Gln Ser Gly Lys Asn Gly Met Arg Arg Asp Trp Leu
            225                 230                 235 gtt cgg gat tgc aat act gga gaa att gta acg cga gca tca ag          1058
Val Arg Asp Cys Asn Thr Gly Glu Ile Val Thr Arg Ala Ser Ser
        240                 245                 250 gtcagagttc ttatgttttg gtttactgac tccagctatt atcatttgc tctctgtttg    1118 tattgtttgc tctgccatta gtttgataat agagacttta tatatgtatg caattttct    1178 tcttttgca g t ttg tgg gtg atg atg aat aaa ctc aca agg aga ttg       1226
              Leu Trp Val Met Met Asn Lys Leu Thr Arg Arg Leu
                      255                 260 tca aag att cct gaa gag gtt cga ggg gaa ata gag cct tat ttt gtg     1274
Ser Lys Ile Pro Glu Glu Val Arg Gly Glu Ile Glu Pro Tyr Phe Val
    265                 270                 275 aac tct gat cct gtc att gcc gaa gac agc aga aag tta acc aaa ctt     1322
Asn Ser Asp Pro Val Ile Ala Glu Asp Ser Arg Lys Leu Thr Lys Leu
280                 285                 290                 295 gat gac aag act gct gac tat gtt cgt tcg ggt ctc act gtaagtaccc      1371
Asp Asp Lys Thr Ala Asp Tyr Val Arg Ser Gly Leu Thr
                300                 305 tacctttcaa caacaagctt gtcaaaactc tcgaggttgg ttcttatgga ttggtaatga   1431
aactttttta ttcag ccg agg tgg agt gac ttg gat gtt aac cag cat gtt   1482
                Pro Arg Trp Ser Asp Leu Asp Val Asn Gln His Val
                    310                 315                 320 aac aat gta aag tac atc ggg tgg ata ctg gag agt gct cca gca ggg     1530
Asn Asn Val Lys Tyr Ile Gly Trp Ile Leu Glu Ser Ala Pro Ala Gly
            325                 330                 335 atg ctg gag agt cag aag ctg aaa agc atg act ctg gag tat cgc agg     1578
Met Leu Glu Ser Gln Lys Leu Lys Ser Met Thr Leu Glu Tyr Arg Arg
        340                 345                 350 gag tgc ggg aga gac agt gtg ctt cag tct ctc acc gcg gtc tct gga     1626
Glu Cys Gly Arg Asp Ser Val Leu Gln Ser Leu Thr Ala Val Ser Gly
    355                 360                 365 tgt gat gtc ggt aac ctc ggg aca gcc ggg gaa gtg gag tgt cag cat     1674
Cys Asp Val Gly Asn Leu Gly Thr Ala Gly Glu Val Glu Cys Gln His
370                 375                 380 ttg ctt cgt ctc cag gat gga gct gaa gtg gtg aga gga aga aca gag     1722
Leu Leu Arg Leu Gln Asp Gly Ala Glu Val Val Arg Gly Arg Thr Glu
385                 390                 395                 400 tgg agt tcc aag aca gaa gca aca act tgg gac act gct aca tcg taa     1770
Trp Ser Ser Lys Thr Glu Ala Thr Thr Trp Asp Thr Ala Thr Ser
                405                 410                 415

<210> SEQ ID NO 22
<211> LENGTH: 415
<212> TYPE: PRT
<213> ORGANISM: Brassica napus

<400> SEQUENCE: 22

Met Val Ala Thr Ser Ala Thr Ser Ser Phe Phe His Val Pro Ser Ser
1               5                   10                  15
```

```
Ser Ser Leu Asp Thr Asn Gly Lys Gly Asn Arg Val Ala Ser Thr Asn
         20                  25                  30

Phe Ala Gly Leu Asn Ser Thr Pro Ser Gly Arg Met Lys Val Lys
         35                  40                  45

Pro Asn Ala Gln Ala Pro Pro Lys Ile Asn Gly Lys Lys Ala Asn Leu
 50                  55                  60

Pro Gly Ser Val Glu Ile Ser Lys Ser Asp Asn Glu Thr Ser Gln Pro
 65                  70                  75                  80

Ala Pro Ala Pro Arg Thr Phe Ile Asn Gln Leu Pro Asp Trp Ser Met
                 85                  90                  95

Leu Leu Ala Ala Ile Thr Thr Ile Phe Leu Ala Ala Glu Lys Gln Trp
                100                 105                 110

Met Met Leu Asp Trp Lys Pro Arg Arg Ser Asp Met Ile Met Asp Pro
         115                 120                 125

Phe Gly Leu Gly Arg Ile Val Gln Asp Gly Leu Val Phe Arg Gln Asn
         130                 135                 140

Phe Ser Ile Arg Ser Tyr Glu Ile Gly Ala Asp Arg Ser Ala Ser Ile
145                 150                 155                 160

Glu Thr Val Met Asn His Leu Gln Glu Thr Ala Leu Asn His Val Lys
                165                 170                 175

Ser Ala Gly Leu Leu Glu Asn Gly Phe Gly Ser Thr Pro Glu Met Phe
         180                 185                 190

Lys Lys Asn Leu Ile Trp Val Ala Arg Met Gln Val Val Val Asp
         195                 200                 205

Lys Tyr Pro Thr Trp Gly Asp Val Val Glu Val Asp Thr Trp Val Ser
210                 215                 220

Gln Ser Gly Lys Asn Gly Met Arg Arg Asp Trp Leu Val Arg Asp Cys
225                 230                 235                 240

Asn Thr Gly Glu Ile Val Thr Arg Ala Ser Ser Leu Trp Val Met Met
                245                 250                 255

Asn Lys Leu Thr Arg Arg Leu Ser Lys Ile Pro Glu Glu Val Arg Gly
         260                 265                 270

Glu Ile Glu Pro Tyr Phe Val Asn Ser Asp Pro Val Ile Ala Glu Asp
         275                 280                 285

Ser Arg Lys Leu Thr Lys Leu Asp Asp Lys Thr Ala Asp Tyr Val Arg
 290                 295                 300

Ser Gly Leu Thr Pro Arg Trp Ser Asp Leu Asp Val Asn Gln His Val
305                 310                 315                 320

Asn Asn Val Lys Tyr Ile Gly Trp Ile Leu Glu Ser Ala Pro Ala Gly
                325                 330                 335

Met Leu Glu Ser Gln Lys Leu Lys Ser Met Thr Leu Glu Tyr Arg Arg
         340                 345                 350

Glu Cys Gly Arg Asp Ser Val Leu Gln Ser Leu Thr Ala Val Ser Gly
         355                 360                 365

Cys Asp Val Gly Asn Leu Gly Thr Ala Gly Glu Val Glu Cys Gln His
 370                 375                 380

Leu Leu Arg Leu Gln Asp Gly Ala Glu Val Val Arg Gly Arg Thr Glu
385                 390                 395                 400

Trp Ser Ser Lys Thr Glu Ala Thr Thr Trp Asp Thr Ala Thr Ser
                405                 410                 415

<210> SEQ ID NO 23
<211> LENGTH: 1892
<212> TYPE: DNA
```

```
<213> ORGANISM: Brassica napus
<220> FEATURE:
<221> NAME/KEY: CDS
<222> LOCATION: (1)..(507)
<220> FEATURE:
<221> NAME/KEY: mat_peptide
<222> LOCATION: (1)..(1889)
<223> OTHER INFORMATION: mature peptide starts at amino acid 92
<220> FEATURE:
<221> NAME/KEY: misc_feature
<222> LOCATION: (493)..(495)
<223> OTHER INFORMATION: conserved Met
<220> FEATURE:
<221> NAME/KEY: CDS
<222> LOCATION: (931)..(1064)
<220> FEATURE:
<221> NAME/KEY: misc_feature
<222> LOCATION: (952)..(954)
<223> OTHER INFORMATION: conserved Lys
<220> FEATURE:
<221> NAME/KEY: misc_feature
<222> LOCATION: (1024)..(1026)
<223> OTHER INFORMATION: conserved Val
<220> FEATURE:
<221> NAME/KEY: CDS
<222> LOCATION: (1139)..(1252)
<220> FEATURE:
<221> NAME/KEY: misc_feature
<222> LOCATION: (1191)..(1193)
<223> OTHER INFORMATION: conserved Met
<220> FEATURE:
<221> NAME/KEY: CDS
<222> LOCATION: (1325)..(1496)
<220> FEATURE:
<221> NAME/KEY: misc_feature
<222> LOCATION: (1362)..(1364)
<223> OTHER INFORMATION: conserved Ser
<220> FEATURE:
<221> NAME/KEY: CDS
<222> LOCATION: (1572)..(1889)
<220> FEATURE:
<221> NAME/KEY: misc_feature
<222> LOCATION: (1578)..(1580)
<223> OTHER INFORMATION: conserved Trp
<220> FEATURE:
<221> NAME/KEY: misc_feature
<222> LOCATION: (1596)..(1598)
<223> OTHER INFORMATION: conserved Asn
<220> FEATURE:
<221> NAME/KEY: misc_feature
<222> LOCATION: (1602)..(1604)
<223> OTHER INFORMATION: conserved His
<220> FEATURE:
<221> NAME/KEY: misc_feature
<222> LOCATION: (1707)..(1709)
<223> OTHER INFORMATION: conserved Cys

<400> SEQUENCE: 23 atg gtg gcc acc tct gct aca tcc tca ttc ttc cct ctc cca tct tcc      48
Met Val Ala Thr Ser Ala Thr Ser Ser Phe Phe Pro Leu Pro Ser Ser
1               5                   10                  15 tct ctc gac cct aat ggc aaa acc aac aaa ctc acc tcc acc aac ttc      96
Ser Leu Asp Pro Asn Gly Lys Thr Asn Lys Leu Thr Ser Thr Asn Phe
            20                  25                  30 tct gga ctc aac ccc ata cca aac tct tcc ggc agg tta aag gtc aaa     144
Ser Gly Leu Asn Pro Ile Pro Asn Ser Ser Gly Arg Leu Lys Val Lys
        35                  40                  45 cca aac gcc caa gct cca tcc aag atc aac ggc aat aat gtc tcc ttg     192
Pro Asn Ala Gln Ala Pro Ser Lys Ile Asn Gly Asn Asn Val Ser Leu
    50                  55                  60 cca ggc tca gta cac atc gta aag act gat aat aac cac gat ctc tcg     240
Pro Gly Ser Val His Ile Val Lys Thr Asp Asn Asn His Asp Leu Ser
65                  70                  75                  80
```

| | |
|---|---|
| caa caa cac gca ccc aga acg ttc atc aac cag cta cct gac tgg agc<br>Gln Gln His Ala Pro Arg Thr Phe Ile Asn Gln Leu Pro Asp Trp Ser<br>             85                     90                     95 | 288 |
| atg ctt ctc gcc gcc atc aca acg gtc ttc tta gct gct gag aaa cag<br>Met Leu Leu Ala Ala Ile Thr Thr Val Phe Leu Ala Ala Glu Lys Gln<br>            100                 105               110 | 336 |
| tgg atg atg ctt gac tcg aaa ccg agg cgt tct gat atg att atg gat<br>Trp Met Met Leu Asp Ser Lys Pro Arg Arg Ser Asp Met Ile Met Asp<br>        115                 120               125 | 384 |
| ccg ttc ggg tta ggg agg atc gtt cag gat ggg ctt gtg tac cgt cag<br>Pro Phe Gly Leu Gly Arg Ile Val Gln Asp Gly Leu Val Tyr Arg Gln<br>130               135               140 | 432 |
| aac ttc gat atc agg tct tat gaa ata ggt gct gat cgc tct gcg tct<br>Asn Phe Asp Ile Arg Ser Tyr Glu Ile Gly Ala Asp Arg Ser Ala Ser<br>145               150               155               160 | 480 |
| ata gaa aca gtc atg aac cac tta cag gtatattaca atcacactcg<br>Ile Glu Thr Val Met Asn His Leu Gln<br>            165 | 527 |
| attgatacta gagcttgaca tgttggtttt tatcttttta taaattgttt agtgacattt | 587 |
| tcaaacatat agatataggt tatttagata tttctaggtt cctacaaacc tacccagact | 647 |
| caaaccccgt ccggaaattt ataatattaa taccgaacag agttttattt taaaccaaaa | 707 |
| aatcagttga cccgcacggg atgttggttt ttatctattt tatacattgt ttaaggacat | 767 |
| ttttaaacat ataaatatag gttatttaga tatttctagg ttcctacgaa cctacccgga | 827 |
| aatttataat acccgaacat agtttaattt taaaccaaa aaatccaata cccgaaaaaa | 887 |
| ccaatctgtg atatgcatga tctaactctt gtcctcgtga cag gaa acg gct ctc<br>                                                                                              Glu Thr Ala Leu<br>                                                                                                         170 | 942 |
| aac cat gtg aag tct gct gga ctg ctg gga gat ggg ttt ggt tct acc<br>Asn His Val Lys Ser Ala Gly Leu Leu Gly Asp Gly Phe Gly Ser Thr<br>            175                 180                 185 | 990 |
| cct gag atg gtt aag aag aac ttg ata tgg gtc gtt act cgt atg cag<br>Pro Glu Met Val Lys Lys Asn Leu Ile Trp Val Val Thr Arg Met Gln<br>190               195               200               205 | 1038 |
| gtt gtc gtt gat aaa tat cct act tg  gtaagccctc ttagcactta<br>Val Val Val Asp Lys Tyr Pro Thr Trp<br>               210 | 1084 |
| accttaaaac aatatgcatg aatcatttgc ttattcaaat gtctgcttca ccag g gga<br>                                                                                                                                                                        Gly<br>                                                                                                                                                                               215 | 1142 |
| gat gtt gtt gaa gta gat aca tgg gtt agt aag tct ggg aag aat ggt<br>Asp Val Val Glu Val Asp Thr Trp Val Ser Lys Ser Gly Lys Asn Gly<br>                     220                 225                 230 | 1190 |
| atg cgt cgt gat tgg ctt gtt cgg gat tgt aat act gga gaa att tta<br>Met Arg Arg Asp Trp Leu Val Arg Asp Cys Asn Thr Gly Glu Ile Leu<br>            235                 240                 245 | 1238 |
| aca aga gca tca ag  gttagcttct ttttgtttac tccagctatt atctgattat<br>Thr Arg Ala Ser Ser<br>             250 | 1292 |
| tgagttataa ccatctctgt gttgcaaaac ag t gtg tgg gtg atg atg aat aaa<br>                                                                          Val Trp Val Met Met Asn Lys<br>                                                                                                255 | 1346 |
| gtg aca agg aga tta tca aag ctt cct gaa gag gtt cga ggg gaa ata<br>Val Thr Arg Arg Leu Ser Lys Leu Pro Glu Glu Val Arg Gly Glu Ile<br>260               265               270                 275 | 1394 |
| gag cct tac ttt gtg aac tct gac cct atc ctt gcc gag gac agc aga<br>Glu Pro Tyr Phe Val Asn Ser Asp Pro Ile Leu Ala Glu Asp Ser Arg<br>            280                 285                 290 | 1442 |

```
aag tta aca aaa cta gat gag aag act gct gac tat gtt cgc tct ggt    1490
Lys Leu Thr Lys Leu Asp Glu Lys Thr Ala Asp Tyr Val Arg Ser Gly
            295                 300                 305 ctc acc gtaagtataaa atatttgttt ttatctttca gcaagtgaga ttctgatggg    1546
Leu Thr tttggtgatt atctaacttt tgcag ccg aga tgg agt gac ttg gat gtt aac    1598
                              Pro Arg Trp Ser Asp Leu Asp Val Asn
                              310                 315 cag cat gtt aac aac gtg aag tac att ggt tgg ata ctc gag agt gct    1646
Gln His Val Asn Asn Val Lys Tyr Ile Gly Trp Ile Leu Glu Ser Ala
        320                 325                 330 cca gtg gag atg atg gag aag cat aag ctg aaa agc atg act ctg gag    1694
Pro Val Glu Met Met Glu Lys His Lys Leu Lys Ser Met Thr Leu Glu
335                 340                 345                 350 tat agg agg gaa tgc ggg aga gac agt gtg ctt cag tct ctc acc gcg    1742
Tyr Arg Arg Glu Cys Gly Arg Asp Ser Val Leu Gln Ser Leu Thr Ala
                355                 360                 365 gtt tcg ggt tgc gat gtt ggt agc ctc ggg aca gct ggt gaa gtg gaa    1790
Val Ser Gly Cys Asp Val Gly Ser Leu Gly Thr Ala Gly Glu Val Glu
            370                 375                 380 tgt cag cat ttg ctt cga ctc cag gat gga gct gaa gtg gtg aag gga    1838
Cys Gln His Leu Leu Arg Leu Gln Asp Gly Ala Glu Val Val Lys Gly
                385                 390                 395 cga aca gtg tgg agt tcc aaa aca cca tca aca act tgg gac act aca    1886
Arg Thr Val Trp Ser Ser Lys Thr Pro Ser Thr Thr Trp Asp Thr Thr
    400                 405                 410 tcg taa                                                            1892
Ser
415

<210> SEQ ID NO 24
<211> LENGTH: 415
<212> TYPE: PRT
<213> ORGANISM: Brassica napus

<400> SEQUENCE: 24

Met Val Ala Thr Ser Ala Thr Ser Ser Phe Phe Pro Leu Pro Ser Ser
1               5                   10                  15

Ser Leu Asp Pro Asn Gly Lys Thr Asn Lys Leu Thr Ser Thr Asn Phe
            20                  25                  30

Ser Gly Leu Asn Pro Ile Pro Asn Ser Ser Gly Arg Leu Lys Val Lys
        35                  40                  45

Pro Asn Ala Gln Ala Pro Ser Lys Ile Asn Gly Asn Asn Val Ser Leu
    50                  55                  60

Pro Gly Ser Val His Ile Val Lys Thr Asp Asn Asn His Asp Leu Ser
65                  70                  75                  80

Gln Gln His Ala Pro Arg Thr Phe Ile Asn Gln Leu Pro Asp Trp Ser
                85                  90                  95

Met Leu Leu Ala Ala Ile Thr Thr Val Phe Leu Ala Ala Glu Lys Gln
            100                 105                 110

Trp Met Met Leu Asp Ser Lys Pro Arg Arg Ser Asp Met Ile Met Asp
        115                 120                 125

Pro Phe Gly Leu Gly Arg Ile Val Gln Asp Gly Leu Val Tyr Arg Gln
    130                 135                 140

Asn Phe Asp Ile Arg Ser Tyr Glu Ile Gly Ala Asp Arg Ser Ala Ser
145                 150                 155                 160

Ile Glu Thr Val Met Asn His Leu Gln Glu Thr Ala Leu Asn His Val
```

|   |   |   |   | 165 |   |   |   | 170 |   |   |   | 175 |   |   |
|---|---|---|---|---|---|---|---|---|---|---|---|---|---|---|

Lys Ser Ala Gly Leu Leu Gly Asp Gly Phe Gly Ser Thr Pro Glu Met
            180                 185                 190

Val Lys Lys Asn Leu Ile Trp Val Val Thr Arg Met Gln Val Val
            195                 200                 205

Asp Lys Tyr Pro Thr Trp Gly Asp Val Val Glu Val Asp Thr Trp Val
            210                 215                 220

Ser Lys Ser Gly Lys Asn Gly Met Arg Arg Asp Trp Leu Val Arg Asp
225                 230                 235                 240

Cys Asn Thr Gly Glu Ile Leu Thr Arg Ala Ser Ser Val Trp Val Met
            245                 250                 255

Met Asn Lys Val Thr Arg Arg Leu Ser Lys Leu Pro Glu Glu Val Arg
            260                 265                 270

Gly Glu Ile Glu Pro Tyr Phe Val Asn Ser Asp Pro Ile Leu Ala Glu
            275                 280                 285

Asp Ser Arg Lys Leu Thr Lys Leu Asp Glu Lys Thr Ala Asp Tyr Val
            290                 295                 300

Arg Ser Gly Leu Thr Pro Arg Trp Ser Asp Leu Asp Val Asn Gln His
305                 310                 315                 320

Val Asn Asn Val Lys Tyr Ile Gly Trp Ile Leu Glu Ser Ala Pro Val
            325                 330                 335

Glu Met Glu Lys His Lys Leu Lys Ser Met Thr Leu Glu Tyr Arg
            340                 345                 350

Arg Glu Cys Gly Arg Asp Ser Val Leu Gln Ser Leu Thr Ala Val Ser
            355                 360                 365

Gly Cys Asp Val Gly Ser Leu Gly Thr Ala Gly Glu Val Glu Cys Gln
            370                 375                 380

His Leu Leu Arg Leu Gln Asp Gly Ala Glu Val Val Lys Gly Arg Thr
385                 390                 395                 400

Val Trp Ser Ser Lys Thr Pro Ser Thr Thr Trp Asp Thr Thr Ser
            405                 410                 415

<210> SEQ ID NO 25
<211> LENGTH: 487
<212> TYPE: DNA
<213> ORGANISM: Artificial Sequence
<220> FEATURE:
<223> OTHER INFORMATION: 5' AtFATB1 probe

<400> SEQUENCE: 25

```
gaactttcat caaccagtta cctgactgga gcatgcttct tgctgctata actacgattt    60
tcttagcggc tgagaaacag tggatgatgc ttgattggaa acctaggcgt tctgacatgc   120
tggtggatcc ttttggtata gggagaattg ttcaggatgg ccttgtgttc cgtcagaatt   180
tttctattag gtcatatgaa ataggtgctg atcgctctgc atctatagaa accgtcatga   240
atcatctgca ggtaccatttt gattatgatt acggttacct gttgtcactg gtttaattga   300
tatgtatgaa caagctctta tgctcatgac aggaaacggc gcttaatcat gttaagactg   360
ctggattgct tggagatggg tttggctcta cacctgagat gtttaagaag gacttgatat   420
gggttgtcac tcgtatgcag gttgtggttg ataaatatcc tacttggtaa gctatcctct   480
tgcataa                                                             487
```

<210> SEQ ID NO 26
<211> LENGTH: 22
<212> TYPE: DNA

```
<213> ORGANISM: Artificial Sequence
<220> FEATURE:
<223> OTHER INFORMATION: oligonucleotide primer KVA05-14

<400> SEQUENCE: 26
gaactttcat caaccagtta cc                                              22

<210> SEQ ID NO 27
<211> LENGTH: 22
<212> TYPE: DNA
<213> ORGANISM: Artificial Sequence
<220> FEATURE:
<223> OTHER INFORMATION: oligonucleotide primer KVA05-15

<400> SEQUENCE: 27
ttatgcaaga ggatagctta cc                                              22

<210> SEQ ID NO 28
<211> LENGTH: 352
<212> TYPE: DNA
<213> ORGANISM: Artificial Sequence
<220> FEATURE:
<223> OTHER INFORMATION: 3' AtFATB1 probe

<400> SEQUENCE: 28
cagtgtgtgg gtgatgatga ataaactgac aaggagattg tcaaagattc ctgaagaggt     60
tcgaggggaa atagagcctt attttgtgaa ttctgatcct gtccttgccg aggacagcag    120
aaagttaaca aaaattgatg acaagactgc tgactatgtt cgatctggtc tcactgtaag    180
tatctagtat ttactgctgt atgtttcaac aaacctttga ccagcttgta agactctcta    240
atggcttggt aatgaacatt ttcagcctcg atggagtgac ctagatgtta accagcatgt    300
gaataatgta aagtacattg ggtggatcct ggagagtgct ccagtgggaa ta            352

<210> SEQ ID NO 29
<211> LENGTH: 20
<212> TYPE: DNA
<213> ORGANISM: Artificial Sequence
<220> FEATURE:
<223> OTHER INFORMATION: oligonucleotide primer KVA05-16

<400> SEQUENCE: 29
cagtgtgtgg gtgatgatga                                                 20

<210> SEQ ID NO 30
<211> LENGTH: 20
<212> TYPE: DNA
<213> ORGANISM: Artificial Sequence
<220> FEATURE:
<223> OTHER INFORMATION: oligonucleotide primer KVA05-17

<400> SEQUENCE: 30
tattcccact ggagcactct                                                 20

<210> SEQ ID NO 31
<211> LENGTH: 21
<212> TYPE: DNA
<213> ORGANISM: Artificial Sequence
<220> FEATURE:
<223> OTHER INFORMATION: Forward primer for detection of FATB-A1 (SOSR)

<400> SEQUENCE: 31
ctgataacga gacgtcctca c                                               21
```

```
<210> SEQ ID NO 32
<211> LENGTH: 20
<212> TYPE: DNA
<213> ORGANISM: Artificial Sequence
<220> FEATURE:
<223> OTHER INFORMATION: reverse primer for detection of FATB-A1 (SORS)

<400> SEQUENCE: 32
catcctggag acggagcagg                                              20

<210> SEQ ID NO 33
<211> LENGTH: 21
<212> TYPE: DNA
<213> ORGANISM: Artificial Sequence
<220> FEATURE:
<223> OTHER INFORMATION: Forward primer for detection of FATB-A2 (SOSR)

<400> SEQUENCE: 33
ctgcctgact ggagtatgct g                                            21

<210> SEQ ID NO 34
<211> LENGTH: 21
<212> TYPE: DNA
<213> ORGANISM: Artificial Sequence
<220> FEATURE:
<223> OTHER INFORMATION: Reverse primer for detection of FATB-A2 (SOSR)

<400> SEQUENCE: 34
gttgttgctc ctgtcttgga g                                            21

<210> SEQ ID NO 35
<211> LENGTH: 21
<212> TYPE: DNA
<213> ORGANISM: Artificial Sequence
<220> FEATURE:
<223> OTHER INFORMATION: forward primer for detection of FATB-A3 (SOSR)

<400> SEQUENCE: 35
gcagtggatg atgcttgata c                                            21

<210> SEQ ID NO 36
<211> LENGTH: 21
<212> TYPE: DNA
<213> ORGANISM: Artificial Sequence
<220> FEATURE:
<223> OTHER INFORMATION: reverse primer for detection of FATB-A3 (SOSR)

<400> SEQUENCE: 36
caagtcgttg atggtgtttt c                                            21

<210> SEQ ID NO 37
<211> LENGTH: 21
<212> TYPE: DNA
<213> ORGANISM: Artificial Sequence
<220> FEATURE:
<223> OTHER INFORMATION: Forward primer for detection of FATB-C1 (SOSR)

<400> SEQUENCE: 37
ctgcctgact ggagcatgct c                                            21

<210> SEQ ID NO 38
<211> LENGTH: 21
<212> TYPE: DNA
<213> ORGANISM: Artificial Sequence
<220> FEATURE:
<223> OTHER INFORMATION: reverse primer for detection of FATB-C1 (SOSR)
```

-continued

<400> SEQUENCE: 38
gttcttcctc tcaccacttc g                                              21

<210> SEQ ID NO 39
<211> LENGTH: 21
<212> TYPE: DNA
<213> ORGANISM: Artificial Sequence
<220> FEATURE:
<223> OTHER INFORMATION: Forward primer for detection of FATB-C2 (SOSR)

<400> SEQUENCE: 39
atcgttcagg atggtcttgt c                                              21

<210> SEQ ID NO 40
<211> LENGTH: 21
<212> TYPE: DNA
<213> ORGANISM: Artificial Sequence
<220> FEATURE:
<223> OTHER INFORMATION: Reverse primer for detection of FATB-C2 (SOSR)

<400> SEQUENCE: 40
gcagtcttgt catcaagttt g                                              21

<210> SEQ ID NO 41
<211> LENGTH: 21
<212> TYPE: DNA
<213> ORGANISM: Artificial Sequence
<220> FEATURE:
<223> OTHER INFORMATION: Forward primer for detection of FATB-C3 (SOSR)

<400> SEQUENCE: 41
acagtggatg atgcttgact c                                              21

<210> SEQ ID NO 42
<211> LENGTH: 21
<212> TYPE: DNA
<213> ORGANISM: Artificial Sequence
<220> FEATURE:
<223> OTHER INFORMATION: Reverse primer for detection of FATB-C3 (SOSR)

<400> SEQUENCE: 42
cgaacatagt cagcagtctt c                                              21

<210> SEQ ID NO 43
<211> LENGTH: 21
<212> TYPE: DNA
<213> ORGANISM: Artificial Sequence
<220> FEATURE:
<223> OTHER INFORMATION: Reverse primer for detection of deletion
      mutation in FATB-A1

<400> SEQUENCE: 43
cagtcttaac atggttgagt g                                              21

<210> SEQ ID NO 44
<211> LENGTH: 21
<212> TYPE: DNA
<213> ORGANISM: Artificial Sequence
<220> FEATURE:
<223> OTHER INFORMATION: Forward primer for detection of deletion
      mutation in FATB-A2

<400> SEQUENCE: 44
catgttccat cttcttcctc g                                              21

<210> SEQ ID NO 45
<211> LENGTH: 21
<212> TYPE: DNA
<213> ORGANISM: Artificial Sequence
<220> FEATURE:
<223> OTHER INFORMATION: Reverse primer for detection of deletion
      mutation in FATB-A2

<400> SEQUENCE: 45
tattgggaca acatgtgagt g                                             21

<210> SEQ ID NO 46
<211> LENGTH: 21
<212> TYPE: DNA
<213> ORGANISM: Artificial Sequence
<220> FEATURE:
<223> OTHER INFORMATION: Reverse primer for detection of deletion
      mutation in FATB-A3

<400> SEQUENCE: 46
ttcttcttaa ccatctcagg t                                             21

<210> SEQ ID NO 47
<211> LENGTH: 21
<212> TYPE: DNA
<213> ORGANISM: Artificial Sequence
<220> FEATURE:
<223> OTHER INFORMATION: Reverse primer for detection of deletion
      mutation in FATB-C1

<400> SEQUENCE: 47
ccaaacccat ctccaagcag c                                             21

<210> SEQ ID NO 48
<211> LENGTH: 21
<212> TYPE: DNA
<213> ORGANISM: Artificial Sequence
<220> FEATURE:
<223> OTHER INFORMATION: Reverse primer for detection of deletion
      mutation in FATB-C2

<400> SEQUENCE: 48
taactcacaa cgagaaccag g                                             21

<210> SEQ ID NO 49
<211> LENGTH: 21
<212> TYPE: DNA
<213> ORGANISM: Artificial Sequence
<220> FEATURE:
<223> OTHER INFORMATION: reverse primer for detection of deletion
      mutation in FATB-C3

<400> SEQUENCE: 49
ctttgataat ctccttgtca c                                             21

<210> SEQ ID NO 50
<211> LENGTH: 22
<212> TYPE: DNA
<213> ORGANISM: Artificial Sequence
<220> FEATURE:
<223> OTHER INFORMATION: Forward oligonucleotide for detection of
      FATB-A1-EMS05

<400> SEQUENCE: 50
ggcggctgag aagcagtgaa ta                                            22

<210> SEQ ID NO 51

```
<211> LENGTH: 22
<212> TYPE: DNA
<213> ORGANISM: Artificial Sequence
<220> FEATURE:
<223> OTHER INFORMATION: Forward oligonucleotide for detection of
      FATB-A1

<400> SEQUENCE: 51
ggcggctgag aagcagtgga tg                                              22

<210> SEQ ID NO 52
<211> LENGTH: 19
<212> TYPE: DNA
<213> ORGANISM: Artificial Sequence
<220> FEATURE:
<223> OTHER INFORMATION: Reverse oligonucleotide for detection of
      FATB-A1-EMS05 and -A1

<400> SEQUENCE: 52
ggactgaagc acactgtcc                                                  19

<210> SEQ ID NO 53
<211> LENGTH: 21
<212> TYPE: DNA
<213> ORGANISM: Artificial Sequence
<220> FEATURE:
<223> OTHER INFORMATION: Forward oligonucleotide for detection of
      FATB-A1-EMS06

<400> SEQUENCE: 53
cagtggatga tgcttgactg a                                               21

<210> SEQ ID NO 54
<211> LENGTH: 21
<212> TYPE: DNA
<213> ORGANISM: Artificial Sequence
<220> FEATURE:
<223> OTHER INFORMATION: Forward oligonucleotide for detection of
      FATB-A1

<400> SEQUENCE: 54
cagtggatga tgcttgactg g                                               21

<210> SEQ ID NO 55
<211> LENGTH: 20
<212> TYPE: DNA
<213> ORGANISM: Artificial Sequence
<220> FEATURE:
<223> OTHER INFORMATION: Reverse oligonucleotide for detection of
      FATB-A1-EMS06 and -A1

<400> SEQUENCE: 55
gcatacgagt aacaacccaa                                                 20

<210> SEQ ID NO 56
<211> LENGTH: 20
<212> TYPE: DNA
<213> ORGANISM: Artificial Sequence
<220> FEATURE:
<223> OTHER INFORMATION: Reverse oligonucleotide for detection of
      FATB-A2-EMS05

<400> SEQUENCE: 56
agcagcaagc agcatacttc                                                 20

<210> SEQ ID NO 57
<211> LENGTH: 20
```

```
-continued

<212> TYPE: DNA
<213> ORGANISM: Artificial Sequence
<220> FEATURE:
<223> OTHER INFORMATION: Reverse oligonucleotide for detection of
      FATB-A2

<400> SEQUENCE: 57
tagcagcaag cagcatactc                                             20

<210> SEQ ID NO 58
<211> LENGTH: 21
<212> TYPE: DNA
<213> ORGANISM: Artificial Sequence
<220> FEATURE:
<223> OTHER INFORMATION: Forward oligonucleotide for detection of
      FATB-A2-EMS05 and -A2

<400> SEQUENCE: 58
gagttgggtc cactaattttt g                                          21

<210> SEQ ID NO 59
<211> LENGTH: 21
<212> TYPE: DNA
<213> ORGANISM: Artificial Sequence
<220> FEATURE:
<223> OTHER INFORMATION: Reverse oligonucleotide for detection of
      FATB-A2-EMS01

<400> SEQUENCE: 59
gagttgggtc cactaattttt g                                          21

<210> SEQ ID NO 60
<211> LENGTH: 20
<212> TYPE: DNA
<213> ORGANISM: Artificial Sequence
<220> FEATURE:
<223> OTHER INFORMATION: Reverse oligonucleotide for detection of
      FATB-A2

<400> SEQUENCE: 60
cggaacacaa gaccatccta                                             20

<210> SEQ ID NO 61
<211> LENGTH: 20
<212> TYPE: DNA
<213> ORGANISM: Artificial Sequence
<220> FEATURE:
<223> OTHER INFORMATION: Forward oligonucleotide for detection of
      FATB-A2-EMS01 and -A2

<400> SEQUENCE: 61
cggaacacaa gaccatcctg                                             20

<210> SEQ ID NO 62
<211> LENGTH: 20
<212> TYPE: DNA
<213> ORGANISM: Artificial Sequence
<220> FEATURE:
<223> OTHER INFORMATION: Reverse oligonucleotide for detection of
      FATB-A3-EMS01

<400> SEQUENCE: 62
tatttatcaa ctacaaccta                                             20

<210> SEQ ID NO 63
<211> LENGTH: 20
<212> TYPE: DNA
```

```
<213> ORGANISM: Artificial Sequence
<220> FEATURE:
<223> OTHER INFORMATION: Reverse oligonucleotide for detection of
      FATB-A3

<400> SEQUENCE: 63
tatttatcaa ctacaacctg                                             20

<210> SEQ ID NO 64
<211> LENGTH: 21
<212> TYPE: DNA
<213> ORGANISM: Artificial Sequence
<220> FEATURE:
<223> OTHER INFORMATION: Forward oligonucleotide for detection of
      FATB-A3-EMS01 and -A3

<400> SEQUENCE: 64
caatggcaaa accaacaaag c                                           21

<210> SEQ ID NO 65
<211> LENGTH: 21
<212> TYPE: DNA
<213> ORGANISM: Artificial Sequence
<220> FEATURE:
<223> OTHER INFORMATION: Forward oligonucleotide for detection of
      FATB-C1-EMS05

<400> SEQUENCE: 65
gttaagaaga acttgatatg a                                           21

<210> SEQ ID NO 66
<211> LENGTH: 21
<212> TYPE: DNA
<213> ORGANISM: Artificial Sequence
<220> FEATURE:
<223> OTHER INFORMATION: Forward oligonucleotide for detection of
      FATB-C1

<400> SEQUENCE: 66
gttaagaaga acttgatatg g                                           21

<210> SEQ ID NO 67
<211> LENGTH: 21
<212> TYPE: DNA
<213> ORGANISM: Artificial Sequence
<220> FEATURE:
<223> OTHER INFORMATION: Reverse oligonucleotide for detection of
      FATB-C1-EMS05, -C1-EMS04, and -C1

<400> SEQUENCE: 67
gttcttcctc tcaccacttc g                                           21

<210> SEQ ID NO 68
<211> LENGTH: 20
<212> TYPE: DNA
<213> ORGANISM: Artificial Sequence
<220> FEATURE:
<223> OTHER INFORMATION: Forward oligonucleotide for detection of
      FATB-C1-EMS04

<400> SEQUENCE: 68
cggttatgaa tcatttacaa                                             20

<210> SEQ ID NO 69
<211> LENGTH: 20
<212> TYPE: DNA
<213> ORGANISM: Artificial Sequence
<220> FEATURE:
```

```
<223> OTHER INFORMATION: Forward oligonucleotide for detection of
      FATB-C1

<400> SEQUENCE: 69
cggttatgaa tcatttacag                                              20

<210> SEQ ID NO 70
<211> LENGTH: 20
<212> TYPE: DNA
<213> ORGANISM: Artificial Sequence
<220> FEATURE:
<223> OTHER INFORMATION: Forward oligonucleotide for detection of
      FATB-C2-EMS02

<400> SEQUENCE: 70
gtctgacaac gagacttcgt                                              20

<210> SEQ ID NO 71
<211> LENGTH: 20
<212> TYPE: DNA
<213> ORGANISM: Artificial Sequence
<220> FEATURE:
<223> OTHER INFORMATION: Forward oligonucleotide for detection of
      FATB-C2

<400> SEQUENCE: 71
gtctgacaac gagacttcgc                                              20

<210> SEQ ID NO 72
<211> LENGTH: 20
<212> TYPE: DNA
<213> ORGANISM: Artificial Sequence
<220> FEATURE:
<223> OTHER INFORMATION: Reverse oligonucleotide for detection of
      FATB-C2-EMS02 and -C2

<400> SEQUENCE: 72
cagtattgca atcccgaacc                                              20

<210> SEQ ID NO 73
<211> LENGTH: 20
<212> TYPE: DNA
<213> ORGANISM: Artificial Sequence
<220> FEATURE:
<223> OTHER INFORMATION: Forward oligonucleotide for detection of
      FATB-C2-EMS03

<400> SEQUENCE: 73
tggcggctga gaaacagtga                                              20

<210> SEQ ID NO 74
<211> LENGTH: 20
<212> TYPE: DNA
<213> ORGANISM: Artificial Sequence
<220> FEATURE:
<223> OTHER INFORMATION: Forward oligonucleotide for detection of
      FATB-C2

<400> SEQUENCE: 74
tggcggctga gaaacagtgg                                              20

<210> SEQ ID NO 75
<211> LENGTH: 21
<212> TYPE: DNA
<213> ORGANISM: Artificial Sequence
<220> FEATURE:
<223> OTHER INFORMATION: Reverse oligonucleotide for detection of
```

FATB-C2-EMS03 and -C2

<400> SEQUENCE: 75
agggtactta cagtgagacc c                                              21

<210> SEQ ID NO 76
<211> LENGTH: 21
<212> TYPE: DNA
<213> ORGANISM: Artificial Sequence
<220> FEATURE:
<223> OTHER INFORMATION: Forward oligonucleotide for detection of
      FATB-C3-EMS02

<400> SEQUENCE: 76
cagtcatgaa ccacttacag a                                              21

<210> SEQ ID NO 77
<211> LENGTH: 21
<212> TYPE: DNA
<213> ORGANISM: Artificial Sequence
<220> FEATURE:
<223> OTHER INFORMATION: Forward oligonucleotide for detection of
      FATB-C3

<400> SEQUENCE: 77
cagtcatgaa ccacttacag g                                              21

<210> SEQ ID NO 78
<211> LENGTH: 20
<212> TYPE: DNA
<213> ORGANISM: Artificial Sequence
<220> FEATURE:
<223> OTHER INFORMATION: Reverse oligonucleotide for detection of
      FATB-C3-EMS02 and -C3

<400> SEQUENCE: 78
caacctgcat acgagtaacg                                                20

<210> SEQ ID NO 79
<211> LENGTH: 2864
<212> TYPE: DNA
<213> ORGANISM: Arabidopsis thaliana
<220> FEATURE:
<221> NAME/KEY: CDS
<222> LOCATION: (501)..(998)
<220> FEATURE:
<221> NAME/KEY: mat_peptide
<222> LOCATION: (501)..(2361)
<223> OTHER INFORMATION: mature peptide starts at amino acid 89
<220> FEATURE:
<221> NAME/KEY: misc_feature
<222> LOCATION: (984)..(986)
<223> OTHER INFORMATION: conserved Met
<220> FEATURE:
<221> NAME/KEY: CDS
<222> LOCATION: (1080)..(1213)
<220> FEATURE:
<221> NAME/KEY: misc_feature
<222> LOCATION: (1101)..(1103)
<223> OTHER INFORMATION: conserved Lys
<220> FEATURE:
<221> NAME/KEY: misc_feature
<222> LOCATION: (1173)..(1175)
<223> OTHER INFORMATION: conserved Val
<220> FEATURE:
<221> NAME/KEY: CDS
<222> LOCATION: (1441)..(1554)
<220> FEATURE:
<221> NAME/KEY: misc_feature
<222> LOCATION: (1493)..(1495)
<223> OTHER INFORMATION: conserved Met -continued

```
<220> FEATURE:
<221> NAME/KEY: CDS
<222> LOCATION: (1782)..(1953)
<220> FEATURE:
<221> NAME/KEY: misc_feature
<222> LOCATION: (1819)..(1821)
<223> OTHER INFORMATION: conserved Ser
<220> FEATURE:
<221> NAME/KEY: CDS
<222> LOCATION: (2044)..(2361)
<220> FEATURE:
<221> NAME/KEY: misc_feature
<222> LOCATION: (2050)..(2052)
<223> OTHER INFORMATION: conserved Trp
<220> FEATURE:
<221> NAME/KEY: misc_feature
<222> LOCATION: (2068)..(2070)
<223> OTHER INFORMATION: conserved Asn
<220> FEATURE:
<221> NAME/KEY: misc_feature
<222> LOCATION: (2074)..(2076)
<223> OTHER INFORMATION: conserved His
<220> FEATURE:
<221> NAME/KEY: misc_feature
<222> LOCATION: (2179)..(2181)
<223> OTHER INFORMATION: conserved Cys

<400> SEQUENCE: 79
acaagttttt gttttctttt tgcgtttcta cgatctggtt ttaccggctt tagctttttc      60
tcgcttctgt tctttgttgt tttgtatttc agatctggtg ttttttttct tacctgcatc     120
aaattggttt ctaccaaaac ttcggaaacc tcttttggca aatgttgaat ctttgaatac     180
aatgacgatt tacataatag tctcagtggc cgaactggat tatcttacaa tttacgcaat     240
aacaaaaagt ttttttttt tttttttttt tgtgtgtgtg tgtggtgtgt tgaagatttt      300
tagtgtttgt ttacttcgtt tatggaagtc cttttcctct tctgccattt ttgtagttaa     360
ctacaaatta tacctacttt aggaagatcc tcctgctagt agctaaaaga tgtagcattt     420
attttattat cactcacttg agctaacttt tttcgatctt tatttggtgg cagtgtcttt     480
gaacgcttca tctcctcgtc atg gtg gcc acc tct gct acg tcg tca ttc ttt     533
               Met Val Ala Thr Ser Ala Thr Ser Ser Phe Phe
                 1               5                  10 cct gta cca tct tct tca ctt gat cct aat gga aaa ggc aat aag att       581
Pro Val Pro Ser Ser Ser Leu Asp Pro Asn Gly Lys Gly Asn Lys Ile
        15                  20                  25 ggg tct acg aat ctt gct gga ctc aat tct gca cct aac tct ggt agg       629
Gly Ser Thr Asn Leu Ala Gly Leu Asn Ser Ala Pro Asn Ser Gly Arg
    30                  35                  40 atg aag gtt aaa cca aac gct cag gct cca cct aag att aat ggg aaa       677
Met Lys Val Lys Pro Asn Ala Gln Ala Pro Pro Lys Ile Asn Gly Lys
 45                  50                  55 aag gtt ggt ttg cct ggt tct gta gat att gta agg act gat acc gag       725
Lys Val Gly Leu Pro Gly Ser Val Asp Ile Val Arg Thr Asp Thr Glu
 60                  65                  70                  75 acc tca tca cac cct gcg ccg aga act ttc atc aac cag tta cct gac       773
Thr Ser Ser His Pro Ala Pro Arg Thr Phe Ile Asn Gln Leu Pro Asp
            80                  85                  90 tgg agc atg ctt ctt gct gct ata act acg att ttc tta gcg gct gag       821
Trp Ser Met Leu Leu Ala Ala Ile Thr Thr Ile Phe Leu Ala Ala Glu
        95                 100                 105 aaa cag tgg atg atg ctt gat tgg aaa cct agg cgt tct gac atg ctg       869
Lys Gln Trp Met Met Leu Asp Trp Lys Pro Arg Arg Ser Asp Met Leu
    110                 115                 120 gtg gat cct ttt ggt ata ggg aga att gtt cag gat ggc ctt gtg ttc       917
Val Asp Pro Phe Gly Ile Gly Arg Ile Val Gln Asp Gly Leu Val Phe
```

|  |  |
|---|---|
| cgt cag aat ttt tct att agg tca tat gaa ata ggt gct gat cgc tct<br>Arg Gln Asn Phe Ser Ile Arg Ser Tyr Glu Ile Gly Ala Asp Arg Ser<br>140                145                150                155 | 965 |
| gca tct ata gaa acc gtc atg aat cat ctg cag gtaccatttg attatgatta<br>Ala Ser Ile Glu Thr Val Met Asn His Leu Gln<br>        160                165 | 1018 |
| cggttacctg ttgtcactgg tttaattgat atgtatgaac aagctcttat gctcatgaca | 1078 |
| g gaa acg gcg ctt aat cat gtt aag act gct gga ttg ctt gga gat ggg<br>  Glu Thr Ala Leu Asn His Val Lys Thr Ala Gly Leu Leu Gly Asp Gly<br>          170                175                180 | 1127 |
| ttt ggc tct aca cct gag atg ttt aag aag aac ttg ata tgg gtt gtc<br>Phe Gly Ser Thr Pro Glu Met Phe Lys Lys Asn Leu Ile Trp Val Val<br>        185                190                195 | 1175 |
| act cgt atg cag gtt gtg gtt gat aaa tat cct act tg gtaagctatc<br>Thr Arg Met Gln Val Val Val Asp Lys Tyr Pro Thr Trp<br>200                205                210 | 1223 |
| ctcttgcata aacctggttc tgcaggttca tgctctcact cttttaacc aggtttggga | 1283 |
| aaaatgatgt gtatttcgtt ttttcagttg atactgcttt tacagtacga gatatatgct | 1343 |
| catatgacta atgacttctt gcaccctgaa ttatatgctc tgcatgcata ttatattgca | 1403 |
| tcataactca tttgcttatt caatatatgc ctcacag g gga gat gtt gtt gaa<br>                                    Gly Asp Val Val Glu<br>                                            215 | 1456 |
| gta gac acc tgg gtc agt cag tct gga aag aat ggt atg cgt cgt gat<br>Val Asp Thr Trp Val Ser Gln Ser Gly Lys Asn Gly Met Arg Arg Asp<br>          220                225                230 | 1504 |
| tgg cta gtt cgg gac tgt aat act gga gaa acc tta aca cga gca tca<br>Trp Leu Val Arg Asp Cys Asn Thr Gly Glu Thr Leu Thr Arg Ala Ser<br>        235                240                245 | 1552 |
| ag gttagatttt cttttggtat atttataagt tattctcatt ttcttcatct<br>Ser | 1604 |
| gatcattcat tggtctttct gatgaagata cctgatgtct ttactctctt tttatagtgt | 1664 |
| ttgctctatc atcaattaaa caaaaaacta cacaagttta tgtaatgaat aattaggaat | 1724 |
| tttttggtct catgggttag ctatttgaca gatgtattgc aaaatattat cttgcag t | 1782 |
| gtg tgg gtg atg atg aat aaa ctg aca agg aga ttg tca aag att cct<br>Val Trp Val Met Met Asn Lys Leu Thr Arg Arg Leu Ser Lys Ile Pro<br>250                255                260                265 | 1830 |
| gaa gag gtt cga ggg gaa ata gag cct tat ttt gtg aat tct gat cct<br>Glu Glu Val Arg Gly Glu Ile Glu Pro Tyr Phe Val Asn Ser Asp Pro<br>          270                275                280 | 1878 |
| gtc ctt gcc gag gac agc aga aag tta aca aaa att gat gac aag act<br>Val Leu Ala Glu Asp Ser Arg Lys Leu Thr Lys Ile Asp Asp Lys Thr<br>        285                290                295 | 1926 |
| gct gac tat gtt cga tct ggt ctc act gtaagtatct agtatttact<br>Ala Asp Tyr Val Arg Ser Gly Leu Thr<br>          300                305 | 1973 |
| gctgtatgtt tcaacaaacc tttgaccagc ttgtaagact ctctaatggc ttggtaatga | 2033 |
| acatttcag cct cga tgg agt gac cta gat gtt aac cag cat gtg aat<br>         Pro Arg Trp Ser Asp Leu Asp Val Asn Gln His Val Asn<br>                  310                315 | 2082 |
| aat gta aag tac att ggg tgg atc ctg gag agt gct cca gtg gga ata<br>Asn Val Lys Tyr Ile Gly Trp Ile Leu Glu Ser Ala Pro Val Gly Ile<br>320                325                330                335 | 2130 |
| atg gag agg cag aag ctg aaa agc atg act ctg gag tat cgg agg gaa<br>Met Glu Arg Gln Lys Leu Lys Ser Met Thr Leu Glu Tyr Arg Arg Glu | 2178 |

```
                340                 345                 350
tgc ggg aga gac agt gtg ctt cag tcc ctc act gca gtt acg ggt tgc    2226
Cys Gly Arg Asp Ser Val Leu Gln Ser Leu Thr Ala Val Thr Gly Cys
        355                 360                 365 gat atc ggt aac ctg gca aca gcg ggg gat gtg gaa tgt cag cat ttg    2274
Asp Ile Gly Asn Leu Ala Thr Ala Gly Asp Val Glu Cys Gln His Leu
    370                 375                 380 ctc cga ctc cag gat gga gcg gaa gtg gtg aga gga aga aca gag tgg    2322
Leu Arg Leu Gln Asp Gly Ala Glu Val Val Arg Gly Arg Thr Glu Trp
385                 390                 395 agt agt aaa aca cca aca aca act tgg gga act gca ccg taagaaaaag    2371
Ser Ser Lys Thr Pro Thr Thr Thr Trp Gly Thr Ala Pro
400                 405                 410 aaaacacaac aacaatggct catttgaatc cccttgtaac tatatctgct actaccacct    2431
tgcttgcttg caaccaccac caccaccacc accatttcat gtcctcctcc tcacaaaagt    2491
ttcggccacc aacccttgt atatttcttt ttttggttct tcttctttt ttattcgatg       2551 gagatttatt atatttattt aatctttcta tttatttttt tgcttaatgg gaatgggtg      2611 tcgtgtatca ttacgaattc tgatgttatg taacccatgt gccagcggaa gacaaaggca    2671
tcaactctct cttatcctaa atttattgta ctttgttgag ttttgtagtt gtttccagct     2731
aaacaagcac gtggacgatc cttgtaatga atttgtatga atgtgatgcc ttgtacctgt    2791
aaatttgatt gaaaggctat ttaataaaca cgaacaacca aaacggtttg tccaaacaat    2851
aaagccatcg cat                                                      2864
```

<210> SEQ ID NO 80
<211> LENGTH: 412
<212> TYPE: PRT
<213> ORGANISM: Arabidopsis thaliana

<400> SEQUENCE: 80

Met Val Ala Thr Ser Ala Thr Ser Ser Phe Phe Pro Val Pro Ser Ser
1               5                   10                  15

Ser Leu Asp Pro Asn Gly Lys Gly Asn Lys Ile Gly Ser Thr Asn Leu
            20                  25                  30

Ala Gly Leu Asn Ser Ala Pro Asn Ser Gly Arg Met Lys Val Lys Pro
        35                  40                  45

Asn Ala Gln Ala Pro Pro Lys Ile Asn Gly Lys Lys Val Gly Leu Pro
    50                  55                  60

Gly Ser Val Asp Ile Val Arg Thr Asp Thr Glu Thr Ser Ser His Pro
65                  70                  75                  80

Ala Pro Arg Thr Phe Ile Asn Gln Leu Pro Asp Trp Ser Met Leu Leu
                85                  90                  95

Ala Ala Ile Thr Thr Ile Phe Leu Ala Ala Glu Lys Gln Trp Met Met
            100                 105                 110

Leu Asp Trp Lys Pro Arg Arg Ser Asp Met Leu Val Asp Pro Phe Gly
        115                 120                 125

Ile Gly Arg Ile Val Gln Asp Gly Leu Val Phe Arg Gln Asn Phe Ser
    130                 135                 140

Ile Arg Ser Tyr Glu Ile Gly Ala Asp Arg Ser Ala Ser Ile Glu Thr
145                 150                 155                 160

Val Met Asn His Leu Gln Glu Thr Ala Leu Asn His Val Lys Thr Ala
                165                 170                 175

Gly Leu Leu Gly Asp Gly Phe Gly Ser Thr Pro Glu Met Phe Lys Lys
            180                 185                 190

```
Asn Leu Ile Trp Val Thr Arg Met Gln Val Val Asp Lys Tyr
        195                 200                 205

Pro Thr Trp Gly Asp Val Val Glu Val Asp Thr Trp Val Ser Gln Ser
210                 215                 220

Gly Lys Asn Gly Met Arg Arg Asp Trp Leu Val Arg Asp Cys Asn Thr
225                 230                 235                 240

Gly Glu Thr Leu Thr Arg Ala Ser Ser Val Trp Val Met Met Asn Lys
                245                 250                 255

Leu Thr Arg Arg Leu Ser Lys Ile Pro Glu Glu Val Arg Gly Glu Ile
                260                 265                 270

Glu Pro Tyr Phe Val Asn Ser Asp Pro Val Leu Ala Glu Asp Ser Arg
                275                 280                 285

Lys Leu Thr Lys Ile Asp Asp Lys Thr Ala Asp Tyr Val Arg Ser Gly
        290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Val Gly Ile Met
                325                 330                 335

Glu Arg Gln Lys Leu Lys Ser Met Thr Leu Glu Tyr Arg Arg Glu Cys
                340                 345                 350

Gly Arg Asp Ser Val Leu Gln Ser Leu Thr Ala Val Thr Gly Cys Asp
                355                 360                 365

Ile Gly Asn Leu Ala Thr Ala Gly Asp Val Glu Cys Gln His Leu Leu
        370                 375                 380

Arg Leu Gln Asp Gly Ala Glu Val Val Arg Gly Arg Thr Glu Trp Ser
385                 390                 395                 400

Ser Lys Thr Pro Thr Thr Thr Trp Gly Thr Ala Pro
                405                 410

<210> SEQ ID NO 81
<211> LENGTH: 28
<212> TYPE: DNA
<213> ORGANISM: Artificial Sequence
<220> FEATURE:
<223> OTHER INFORMATION: oligonucleotide for detection of FATB-A1-EMS05

<400> SEQUENCE: 81
gcgcctcggt ttccagtcaa gcatcatc                                        28

<210> SEQ ID NO 82
<211> LENGTH: 16
<212> TYPE: DNA
<213> ORGANISM: Artificial Sequence
<220> FEATURE:
<223> OTHER INFORMATION: oligonucleotide for detection of FATB-A1-EMS05

<400> SEQUENCE: 82
tcactgcttc tcagcc                                                     16

<210> SEQ ID NO 83
<211> LENGTH: 32
<212> TYPE: DNA
<213> ORGANISM: Artificial Sequence
<220> FEATURE:
<223> OTHER INFORMATION: oligonucleotide for detection of FATB-A1-EMS06

<400> SEQUENCE: 83
gatccataat cacgtcagag cgcctcggtt tc                                   32
```

```
<210> SEQ ID NO 84
<211> LENGTH: 17
<212> TYPE: DNA
<213> ORGANISM: Artificial Sequence
<220> FEATURE:
<223> OTHER INFORMATION: oligonucleotide for detection of FATB-A1-EMS06

<400> SEQUENCE: 84
tcagtcaagc atcatcc                                                    17

<210> SEQ ID NO 85
<211> LENGTH: 40
<212> TYPE: DNA
<213> ORGANISM: Artificial Sequence
<220> FEATURE:
<223> OTHER INFORMATION: oligonucleotide for detection of FATB-A2-EMS01

<400> SEQUENCE: 85
acctaatgga aaaattctga cggaacacaa gaccatcctt                           40

<210> SEQ ID NO 86
<211> LENGTH: 20
<212> TYPE: DNA
<213> ORGANISM: Artificial Sequence
<220> FEATURE:
<223> OTHER INFORMATION: oligonucleotide for detection of FATB-A2-EMS01

<400> SEQUENCE: 86
aaacaattct ccctaaacca                                                 20

<210> SEQ ID NO 87
<211> LENGTH: 40
<212> TYPE: DNA
<213> ORGANISM: Artificial Sequence
<220> FEATURE:
<223> OTHER INFORMATION: oligonucleotide for detection of FATB-A2-EMS05

<400> SEQUENCE: 87
tgccaagaaa atggtagtta tagcagcaag cagcatactc                           40

<210> SEQ ID NO 88
<211> LENGTH: 14
<212> TYPE: DNA
<213> ORGANISM: Artificial Sequence
<220> FEATURE:
<223> OTHER INFORMATION: oligonucleotide for detection of FATB-A2-EMS05

<400> SEQUENCE: 88
tcagtcaggc agct                                                       14

<210> SEQ ID NO 89
<211> LENGTH: 41
<212> TYPE: DNA
<213> ORGANISM: Artificial Sequence
<220> FEATURE:
<223> OTHER INFORMATION: oligonucleotide for detection of FATB-A3-EMS01

<400> SEQUENCE: 89
aagagagctt accaagtagg atatttatca actacaacct t                         41

<210> SEQ ID NO 90
<211> LENGTH: 18
<212> TYPE: DNA
<213> ORGANISM: Artificial Sequence
<220> FEATURE:
<223> OTHER INFORMATION: oligonucleotide for detection of FATB-A3-EMS01
```

<400> SEQUENCE: 90
acatacgagt aacaaccc                                                    18

<210> SEQ ID NO 91
<211> LENGTH: 43
<212> TYPE: DNA
<213> ORGANISM: Artificial Sequence
<220> FEATURE:
<223> OTHER INFORMATION: oligonucleotide for detection of FATB-C1-EMS04

<400> SEQUENCE: 91
ccagtaacaa caagcgacta caatcataat cataatcagt acc                        43

<210> SEQ ID NO 92
<211> LENGTH: 23
<212> TYPE: DNA
<213> ORGANISM: Artificial Sequence
<220> FEATURE:
<223> OTHER INFORMATION: oligonucleotide for detection of FATB-C1-EMS04

<400> SEQUENCE: 92
ttgtaaatga ttcataaccg ttt                                              23

<210> SEQ ID NO 93
<211> LENGTH: 41
<212> TYPE: DNA
<213> ORGANISM: Artificial Sequence
<220> FEATURE:
<223> OTHER INFORMATION: oligonucleotide for detection of FATB-C1-EMS05

<400> SEQUENCE: 93
taggatattt atcaacgaca acctgcatac gagtaacaac c                          41

<210> SEQ ID NO 94
<211> LENGTH: 23
<212> TYPE: DNA
<213> ORGANISM: Artificial Sequence
<220> FEATURE:
<223> OTHER INFORMATION: oligonucleotide for detection of FATB-C1-EMS05

<400> SEQUENCE: 94
tcatatcaag ttcttcttaa cca                                              23

<210> SEQ ID NO 95
<211> LENGTH: 43
<212> TYPE: DNA
<213> ORGANISM: Artificial Sequence
<220> FEATURE:
<223> OTHER INFORMATION: oligonucleotide for detection of FATB-C2-EMS02

<400> SEQUENCE: 95
cctggttctg tagagatatc aaagtctgac aacgagactt cgc                        43

<210> SEQ ID NO 96
<211> LENGTH: 12
<212> TYPE: DNA
<213> ORGANISM: Artificial Sequence
<220> FEATURE:
<223> OTHER INFORMATION: oligonucleotide for detection of FATB-C2-EMS02

<400> SEQUENCE: 96
tagcccgcac cc                                                          12

<210> SEQ ID NO 97

```
<211> LENGTH: 31
<212> TYPE: DNA
<213> ORGANISM: Artificial Sequence
<220> FEATURE:
<223> OTHER INFORMATION: oligonucleotide for detection of FATB-C2-EMS03

<400> SEQUENCE: 97
agaacgcctg ggtttccagt caagcatcat c                              31

<210> SEQ ID NO 98
<211> LENGTH: 16
<212> TYPE: DNA
<213> ORGANISM: Artificial Sequence
<220> FEATURE:
<223> OTHER INFORMATION: oligonucleotide for detection of FATB-C2-EMS03

<400> SEQUENCE: 98
tcactgtttc tcagcc                                               16

<210> SEQ ID NO 99
<211> LENGTH: 40
<212> TYPE: DNA
<213> ORGANISM: Artificial Sequence
<220> FEATURE:
<223> OTHER INFORMATION: oligonucleotide for detection of FATB-C3-EMS02

<400> SEQUENCE: 99
cgctctgcgt ctatagaaac agtcatgaac cacttacagt                     40

<210> SEQ ID NO 100
<211> LENGTH: 24
<212> TYPE: DNA
<213> ORGANISM: Artificial Sequence
<220> FEATURE:
<223> OTHER INFORMATION: oligonucleotide for detection of FATB-C3-EMS02

<400> SEQUENCE: 100
atatattaca atcacactcg attg                                      24

<210> SEQ ID NO 101
<211> LENGTH: 26
<212> TYPE: DNA
<213> ORGANISM: Artificial Sequence
<220> FEATURE:
<223> OTHER INFORMATION: oligonucleotide for detection of ENDO1

<400> SEQUENCE: 101
tgaggagcgt ggtggtccca cacctt                                    26

<210> SEQ ID NO 102
<211> LENGTH: 13
<212> TYPE: DNA
<213> ORGANISM: Artificial Sequence
<220> FEATURE:
<223> OTHER INFORMATION: oligonucleotide for detection of ENDO1

<400> SEQUENCE: 102
cgatgcgacc agc                                                  13

<210> SEQ ID NO 103
<211> LENGTH: 6
<212> TYPE: PRT
<213> ORGANISM: Artificial Sequence
<220> FEATURE:
```

-continued

```
<223> OTHER INFORMATION: N-terminal amino acids of mature FATB protein

<400> SEQUENCE: 1

Leu Pro Asp Trp Ser Met
1               5
```

BRASSICA PLANT COMPRISING MUTANT FATTY ACYL-ACP THIOESTERASE ALLELES

CROSS-REFERENCE TO RELATED APPLICATIONS

This application is the U.S. National Stage filing of International Application No. PCT/EP2008/005551, filed Jul. 7, 2008, which claims priority to EP 07075568.1, filed Jul. 9, 2007 and U.S. Patent Application No. 60/958,945, filed Jul. 10, 2007, the disclosures of each of which are hereby incorporated by reference.

FIELD OF THE INVENTION

This invention relates to the field of agricultural products, especially crop plants comprising novel seed lipid compositions. Provided are both wild type and mutant nucleic acid molecules encoding *Brassica* fatty acyl-acyl carrier protein (ACP) thioesterase B proteins (FATB) and the proteins as such. Also provided are *Brassica* plants, tissue and seeds comprising at least three mutant fatB alleles (of at least three different FATB protein-encoding *Brassica* genes) in their genome, whereby the seed oil fatty acid composition or profile is significantly altered. In addition, methods for generating *Brassica* plants which produce seeds comprising seed oil having reduced levels of saturated fatty acids are provided herein, as is seed oil obtainable from such seeds. Such seed oil requires no further mixing or modification and may be labeled as "low in saturates" or as containing "no saturates" according to the Food and Drug Administration (FDA) of the United States Department of Health and Human Services (HHS). Further provided are detection tools (kits) and methods for detecting the presence of one or more mutant fatB and/or wild type FATB alleles in *Brassica* plants, tissue(s) or seeds, as well as methods for transferring one or more mutant fatB and/or wild type FATB alleles to other *Brassica* plants and methods for combining different fatB and/or FATB alleles in plants. In particular, methods for combining a suitable number of mutant fatB alleles, which encode non-functional FATB proteins and/or FATB proteins having significantly reduced activity in vivo in such a way as to significantly reduce the relative amount of total saturated fatty acids and/or of specific saturated fatty acids which accumulate in *Brassica* seed oil. In addition uses of the plants, or parts thereof, and/or progeny thereof, seeds and seed oils and the methods and/or kits of the invention are provided.

BACKGROUND OF THE INVENTION

Vegetable oils are increasingly important economically because they are widely used in human and animal diets and in many industrial applications. However, the fatty acid composition of these oils is often not optimal for many of these uses. Because specialty oils with particular fatty acid composition are needed for both nutritional and industrial purposes, there is considerable interest in modifying oil composition by plant-breeding and/or by new molecular tools of plant biotechnology (see for example Scarth and Tang, 2006, Crop Science 46:1225-1236, for the modification of *Brassica* oil).

The specific performance and health attributes of edible oils are determined largely by their fatty acid composition. Most vegetable oils derived from commercial plant varieties are composed primarily of palmitic (16:0), stearic (18:0), oleic (18:1), linoleic (18:2) and linolenic (18:3) acids. Palmitic and stearic acids are, respectively, 16 and 18 carbon-long, saturated fatty acids. Oleic, linoleic, and linolenic acids are 18-carbon-long, unsaturated fatty acids containing one, two, and three double bonds, respectively. Oleic acid is referred to as a mono-unsaturated fatty acid, while linoleic and linolenic acids are referred to as poly-unsaturated fatty acids.

*Brassica* oilseed species, like *Brassica napus* (*B. napus*) and *Brassica juncea* (*B. juncea*), commonly known as rapeseed and mustard, are now the second largest oilseed crop after soybean (FAO, 2005; Raymer (2002) In J. Janick and A. Whipkey (ed.) Trends in new crops and new uses. ASHS Press, Alexandria, Va. Raymer, p. 122-126). Rapeseed oil produced by traditional *Brassica* oilseed cultivars (*B. napus*, *B. rapa*, and *B. juncea*) (Shahidi (1990) In Shahidi (ed.) Canola and rapeseed: Production, chemistry, nutrition, and processing technology. Van Nostrand Reinhold, New York, p. 3-13; Sovero (1993) In J. Janick and J. E. Simon (ed.) New crops. John Wiley & Sons, New York, p. 302-307), typically had a fatty acid composition of 5% palmitic acid (C16:0), 1% stearic acid (C18:0), 15% oleic acid (C18:1), 14% linoleic acid (C18:2), 9% linolenic acid (C18:3), and 45% erucic acid (C22:1) by weight based upon the total fatty acid content (called herein after wt %) (Ackman (1990) In Shahidi (ed.) Canola and rapeseed: Production, chemistry, nutrition, and processing technology. Van Nostrand Reinhold, New York, p. 81-98). Erucic acid is a nutritionally undesirable fatty acid and has been reduced to very low levels in *Brassica* oil for edible uses. The typical relative amount of saturated fatty acids based on the total fatty acids in the seed oil is between about 6.5% and 7.5%, whereby the majority is palmitic acid and stearic acid.

In Canada, plant scientists focused their efforts on creating so-called "double-low" varieties which were low in erucic acid in the seed oil and low in glucosinolates in the solid meal remaining after oil extraction (i.e., an erucic acid content of less than 2 wt % and a glucosinolate content of less than 30 micromoles per gram of the oil-free meal). These higher quality forms of rape developed in Canada are known as canola. Canola oil is characterized by a relatively low level of saturated fatty acids (on average about 7 wt %), a relatively high level of mono-unsaturated fatty acids (about 61 wt %) and an intermediate level of poly-unsaturated fatty acids (about 32 wt %), with a good balance between linoleic acid, i.e., an omega-6 fatty acid (about 21 wt %), and alpha-linolenic acid, i.e., an omega-3 fatty acids (about 11 wt %).

A major reason for the current interest in dietary fat relates to the evidence linking high fat intakes, especially saturated fat, to coronary heart disease. High levels of blood cholesterol, in particular the "bad" (low-density lipoprotein or LDL) cholesterol, constitute a major risk factor in coronary heart disease. Several studies suggest that diets high in mono-unsaturated fat and low in saturated fat may reduce the "bad" (low-density lipoprotein or LDL) cholesterol while maintaining the "good" (high-density lipoprotein or HDL) cholesterol (Nicolosi and Rogers, 1997, Med. Sci. Sports Exerc. 29:1422-1428).

Nutrition recommendations in North America and Europe call for a reduction in total fat intake to 30% or less and a reduction in saturated fat intake to less than 10% of total energy (21 C.F.R. 101.75 (b) (3)) (as compared to a saturated fat intake of about 15% to 20% of total caloric consumption in most industrialized nations). To facilitate consumer awareness, current labeling guidelines issued by the Food and Drug Administration (FDA) of the United States Department of Health and Human Services (HHS) now require total saturated fatty acid levels be 1 g or less of saturated fatty acids per reference amount customarily consumed and not more than 15 percent of calories from saturated fatty acids to receive the "low saturated fat" or "low sat" label (21 C.F.R. 101.62 (c)(2)) and less than 0.5 g of saturated fat and less than 0.5 g trans fatty acid (a type of unsaturated fatty acid produced by (partial) hydrogenation of plant oils and considered unhealthy as it increases the risk of coronary heart disease, despite being unsaturated) per reference amount customarily consumed and per labeled serving to receive the "no (or zero) saturated fat" or "no (or zero) sat" label (21 C.F.R. 101.62 (c) (1)). This means that the total saturated fatty acid content (the weight percentage of saturated fatty acids based on the total amount of fatty acids in the oil), i.e. the sum of the lauric acid (C12:0; dodecanoic acid), myristic acid (C14:0; tetradecanoic acid), palmitic acid (C16:0; hexadecanoic acid), stearic acid (C18:0; octadecanopic acid), archidic acid (C20:0; eicosanoic acid), behenic acid (C22:0; docosanoic acid), and lignoceric acid (C24:0; tetracosanoic acid) content, of plant oils needs to be less than 7 wt % to receive the "low sat" label and less than 3.5 wt % to receive the "no sat" label, (based on a reference amount of 15 ml or 14 g oil—21 C.F.R. 101.12).

Canola oil contains only about 7 wt % saturated fatty acids, as compared to the level of saturated fatty acids in other commonly used edible vegetable oils such as safflower oil (8 wt %), flaxseed oil (9 wt %), sunflower oil (12 wt %), corn oil (13 wt %), olive oil (15 wt %), soybean oil (15 wt %), peanut oil (19 wt %), cottonseed oil (27 wt %), palm oil (51 wt %), and coconut oil (91 wt %) (Source POS Pilot Plant Corporation). Various approaches were used to try to further decrease this level of saturated fatty acids.

Modification of vegetable oils may be effected chemically: U.S. Pat. No. 4,948,811 describes triglyceride salad/cooking oil compositions wherein the fatty acid content of the triglyceride of the oil comprises less than about 3 wt % saturated fatty acids obtained by chemical reaction or by physical separation of the saturates. However, chemical modification of vegetable oils to decrease the level of saturated fatty acids is not only more expensive than extraction of vegetable oil from Brassica oilseed plants (or any other oilseed plant) modified to provide an improved edible endogenous vegetable oil as presently disclosed, but might also not be a desired way of improving healthiness of oils for human consumption due to the potential inadvertent presence of residues from the chemical products used and of putative side products.

Another possibility of modifying fatty acid composition is by using genetic engineering. For example, US Patent Application No. 2004/0132189 describes the reduction of the level of saturated fatty acids in Brassica lines co-expressing Cuphea pullcherima beta-ketoacyl-acyl carrier protein synthase I and IV sequences as well as a safflower delta-9 desaturase to about 3 wt % and below 3.4 wt % as compared to a level of saturated fatty acids in non-transformed control lines of about 6.0 wt %. WO06/042049 describes Brassica plants with "no saturate" or reduced saturate levels of fatty acids in their seeds expressing a delta-9 desaturase gene. However, disadvantages of transgenic approaches for commercialization are the needs for regulatory approval and the varying acceptance in different parts of the world.

The fatty acid composition of vegetable oils can also be modified through traditional breeding techniques. These techniques utilize existing germplasm as a source of naturally occurring mutations that affect fatty acid composition. For example, Raney et al. (1999, In Proc. 10th Int. Rapeseed Cong.: New horizons for an old crop, Canberra, Australia) describe breeding populations derived from interspecific crosses of B. napus with B. rapa and B. oleracea wherein the level of saturated fatty acids, expressed as the sum of myristic, palmitic, stearic, archidic, behenic, and lignoceric acid, was decreased to less than 6 wt % and wherein the level of saturated fatty acids, expressed as the sum of myristic, palmitic and stearic acid, was decreased to less than 5 wt %.

Attempts have been made to increase the pool of available mutations from which to select desired characteristics by using mutagens. For example, WO 91/15578 describes rape plants which upon self-pollination are capable of forming rapeseeds which yield oil having a saturated fatty acid content of no more than 4 wt % in the form of palmitic and stearic acid which can be formed by chemical mutagenesis followed by selection.

In plants, de novo fatty acid synthesis is located exclusively in the stroma of plastids, where the acyl chains are covalently bound to a soluble acyl carrier protein (ACP) during the extension cycles. Carbon chain elongation can be terminated by transferring the acyl group to glycerol-3-phosphate, thereby retaining it in the plastidial, "prokaryotic", lipid biosynthesis pathway. Alternatively, specific thioesterases can intercept the prokaryotic (plastidial) pathway by hydrolyzing the newly formed acyl-ACP into a free fatty acid and ACP. Subsequently, the free fatty acid exits the plastids and supplies the cytoplasmic "eukaryotic" lipid biosynthesis pathway. The latter is located in the endoplasmic reticulum and is responsible for the formation of phospholipids, triglycerides, and other neutral lipids. Therefore, by hydrolyzing acyl-ACP and releasing the fatty acid, acyl-ACP thioesterases catalyze the first committed step in the eukaryotic lipid biosynthesis pathway in plant cells and play a crucial role in the distribution of de novo synthesized acyl groups between the two pathways (Löhden and Frentzen, 1988, Planta 176:506-512; Browse and Somerville, 1991, Annu Rev Plant Physiol Plant Mol Biol 42: 467-506; Gibson et al., 1994, Plant Cell Environ 17: 627-637).

Jones et al. (1995, Plant cell 7:359-371) and Voelker et al. (1997, Plant Physiology 114, 669-677) describe two distinct but related thioesterase gene classes in higher plants, termed FATA and FATB. These two thioesterase classes can be distinguished by sequence comparison and/or by their substrate specificity/preference. The FATA thioesterases (also called class I thioesterases) show a clear preference for C18:1 acyl- or oleoyl-ACP with only minor activity toward C18:0 acyl- and C16:0 acyl-ACPs (i.e. the acyl preference is 18:1>>18:0>>16:0). In contrast, FATB members (also called class II thioesterases) prefer saturated acyl-ACP groups as substrate, and substrate chain length varying greatly from C8 to C18 acyl-ACP (Mayer and Shanklin, 2005, J. Biol. Chem. 280(5): 3621-3627). In addition, FATB members can be further subdivided into two functional groups. Some FATB enzymes are specific for saturated acyl-ACPs in the C8 to C14 range (medium-chain acyl-ACP preferring thioesterases) and are found in medium-chain-producing species, with expression restricted to medium-chain-producing tissues. Enzymes of a second FATB group preferring C14 to C18 acyl-ACPs (predominantly palmitoyl-ACP, e.g. enzymes with a preference of C16:0>C18:1>C18:0; long-chain acyl-ACP preferring thioesterases) are probably present in all major plant parts and are not restricted to medium-chain-producing species (Jones et al., 1995, Plant cell 7:359-371). Why plants have these different types of thioesterases and what their individual roles are is still largely unclear.

FATA genes were isolated from a number of plant species, including Brassica species. For example, U.S. Pat. No. 5,530, 186, No. 5,530,186, and No. 5,945,585 describe FATA genes from soybean; Hellyer et al. (1992, Plant Mol. Biol. 20:763-780) describe FATA enzymes from Brassica napus; Loader et al. (1993, Plant Mol. Biol. 23(4): 769-778) describe the isolation and characterization of two acyl-ACP thioesterase clones from a Brassica napus embryo cDNA library using oligonucleotides derived from *B. napus* oleoyl-ACP thioesterase protein sequence data; and Mandal et al. (2000, Bioch. Soc. Transactions 28(6): 967-968) describe the cloning of acyl-ACP thioesterase gene sequences from *B. juncea* that show a homology with the FATA genes from different species.

FATB genes encoding FATB enzymes specific for saturated acyl-ACPs in the C8 to C14 range (medium-chain acyl-ACP preferring thioesterases) were isolated from a number of medium-chain-producing plant species, as described in the references below:

WO91/16421 describes the isolation of a lauroyl (C12:0)-ACP-preferring thioesterase from California bay (*Umbellularia californica*), a C10:0 acyl-ACP-preferring thioesterase from camphor (*Cuphea hookeriana*) and a stearoyl (C18:0)-ACP-preferring thioesterase from safflower (*Carthamus tinctorius*) and the expression of the California bay thioesterase in *Brassica* seed, resulting in an increased level of laurate as compared to the level in non-transgenic *Brassica* seed.

WO92/20236 describes the isolation of C8:0 to C14:0 acyl-ACP-preferring thioesterases and the expression of a lauroyl (C12:0)-ACP-preferring thioesterase from California bay in *Arabidopsis* and *Brassica campestris*, resulting in increased levels of laurate.

Voelker et al. (1992, Science 257: 72-74) describe the expression of a FATB cDNA (Uc FATB1) encoding a lauroyl (C12:0)-ACP thioesterase from California bay, a species that accumulates capric (C10:0) and lauric acid (C12:0) in the seed oil, in seeds of *Arabidopsis thaliana*, which normally do not accumulate laurate, resulting in the accumulation of laurate in mature seeds. Voelker et al. (1996, Plant J. 9:229-241) describe the transformation of the same FATB transgene into *Brassica napus*, resulting in the accumulation of laurate to nearly 60 mol % of the triglyceride acyl groups.

Eccleston and Ohlrogge (1998, Plant cell 10:613-621) describe the expression of a C12:0 acyl-ACP thioesterase from *Umbellularia californica* in *Brassica napus* seeds leading to a seed oil containing 1.8 mol % to 59.6 mol % laurate (C12:0).

WO94/10288 describes the isolation of C8:0 to C10:0 acyl-ACP-preferring thioesterases.

Martini et al. (1995, In Proc. 9th Int. Rapeseed Cong, Cambridge, UK, p. 461-463) describe that two FATB genes from *Cuphea lanceolata*, separately transformed in *B. napus*, resulted in the accumulation of caprylic (C8:0) and capric acid (C10:0) in *Brassica* seed oil at low levels.

Dehesh et al. (1996, Plant J. 9(2):167-172) describe the expression of a FATB cDNA (Ch FATB2) from the Mexican shrub *Cuphea hookeriana*, which accumulates up to 75 mol % caprylate (C8:0) and caprate (C10:0) in its seed oil, in seeds of transgenic canola, which normally does not accumulate these fatty acids, resulting in the accumulation of caprylate (C8:0), caprate (C10:0) and laurate (C12:0) up to 11, 27 and 2 mol %, respectively.

FATB genes encoding FATB enzymes specific for/preferring saturated acyl-ACPs in the C14 to C18 range (long-chain acyl-ACP preferring thioesterases) were isolated form a number of plant species:

WO95/13390 describes the isolation of palmitoyl (C16:0)-ACP thioesterase sequences from leek, mango, elm and camphor and their use in increasing and decreasing levels of saturated fatty acids in soybean and canola by genetic transformation.

Jones et al. (1995, Plant cell 7:259-371) describe the expression of a palmitoyl (C16:0)-ACP thioesterase cDNA from camphor (Ch FATB1) in transgenic *Brassica napus* plants resulting in an increase of palmitate (C16:0) levels from 6 mol % up to 35 mol %.

Voelker et al. (1997, Plant Physiol. 114:669-677) describe the expression of a C14:0 to C18:0 acyl-ACP thioesterase from nutmeg (*Myristica fragrans*), which accumulates predominantly myristate (14:0)-containing oil, in *Brassica napus* seeds, leading to a seed oil enriched in C14 to C18 saturates.

Voelker et al. (1997, Plant Physiol. 114:669-677) also describe the expression of a C10:0 and C16:0 acyl-ACP thioesterase from elm (*Ulmus americana*), which accumulates predominantly caprate (10:0)-containing oil, in *Brassica napus* seeds, leading to a seed oil enriched in C10 to C18 saturates, predominantly palmitate (C16:0), myristate (C14:0), and caprate (C10:0).

WO96/23892 describes myristoyl (C14:0)-ACP thioesterase sequences from *Cuphea palustris*, camphor and nutmeg and their use in the production of myristate in plant cells.

WO96/06936 describes soybean and canola palmitoyl (C16:0)-ACP thioesterase cDNAs and their use in increasing and decreasing levels of saturated fatty acids in soybean and canola by genetic transformation.

Dörmann et al. (2000, Plant Physiol 123:637-643) describe over-expression of a long chain acyl-ACP thioesterase cDNA from *Arabidopsis* (AtFATB1) under a seed-specific promoter in *Arabidopsis*, resulting in the accumulation of high amounts of palmitate (C16:0) in seeds (from 10 mol % in wild-type control to 38.6 mol %). Antisense expression of the *Arabidopsis* FATB1 cDNA under the cauliflower mosaic virus 35S promoter resulted in a strong reduction of seed palmitate content (from 11 mol % in wild-type control to 6 mol %) and flower palmitate content and only minor changes in leaf and root fatty acids.

Bonaventure et al. (2003, Plant Cell 15:1020-1033) describe that the palmitate (C16:0) content of glycerolipids of an *Arabidopsis* mutant with a T-DNA insertion in the FATB gene (in *Arabidopsis* two genes for FATA are present, but only a single gene for FATB; see Mekhedov et al. 2000, Plant Physiol. 122:389-402; and Beisson et al. 2003, Plant Physiol. 132: 681-697) was reduced by 42% in leaves, by 56% in flowers, by 48% in roots and by 56% in seeds. In addition, stearate (C18:0) was reduced by 50% in leaves and by 30% in seeds. The growth rate was significantly reduced in the mutant and mutant plants produced seeds with low viability, reduced germination and altered seed morphology, indicating that FATB is essential for plant growth and seed development.

Bonaventure et al. (2004, Plant Physiol 135:1269-1279) describe that the rate of fatty acid synthesis in leaves of the transgenic FATB knock-out mutant *Arabidopsis* plant increases by 40%, resulting in approximately the same amount of palmitate exported from the plastid as in wild type but an increase in oleate export of about 55%.

Pandian et al. (2004, poster abstract, 4th Int. Crop Sci. Cong.) reports the isolation of a full-length FATB gene sequences from *B. napus* (GenBank accession number DQ847275) and *B. juncea* (GenBank accession number DQ856315), the construction of an inverted repeat gene-silencing construct (under control of a seed-specific promoter) with a 740 bp conserved fragment of a part of the *B. napus* sequence which shared more than 90% sequence homology to FATB sequences of *B. juncea* and *Arabidopsis thaliana*, but less than 40% homology to the FATA genes of these three species, and its transformation into *Arabidopsis thaliana, B. napus* and *B. juncea*. The aim is to create transgenic plants with reduced palmitic acid content in the seed oil. The disclosure teaches nothing about the effect of this gene-silencing construct on the eventual seed oil composition (no results are disclosed) or about alternative methods for generating *Brassica* plants with low saturate seed oils.

Mayer and Shanklin (2005, J. Biol. Chem. 280(5): 3621-3627) describe a structural model of the *Arabidopsis* FATB protein wherein the N-terminal domain contains residues that affect specificity (see also Mayer and Shanklin, 2007, BMC Plant Biology 7(1):1-11) and the C-terminal domain contains catalytic residues.

Despite the fact that sequences of some FATB genes are available in the art, a need remains for fully understanding the genes and enzymes involved in the production and accumulation of saturated fatty acids in seed oil and in developing methods (especially non-transgenic methods) for reducing the relative amount of total saturated fatty acids and/or of specific saturated fatty acids in the seeds, without having a negative effect on the plants growth and development. To date, no (non-transgenic) *Brassica* crop plants are available in the art which produce seed oil containing significantly less than 7% saturated fatty acids. There remains, therefore, a need for tools and methods for developing such plants and oils as described hereinafter in the detailed description, the figures, the examples and the claims.

SUMMARY OF THE INVENTION

The inventors have found that *Brassica napus* plants comprise 6 different FATB genes and that the levels of saturated fatty acids in *Brassica* plants, particularly in the seed oil of said *Brassica* plants, can be controlled by controlling the number and/or types of FATB genes/alleles that are "functionally expressed" in seeds, i.e. that result in functional (biologically active) FATB protein. By combining a minimal number of mutant alleles of the six FATB genes ("fatB alleles"), while maintaining a minimal number of wild type FATB alleles, resulting in a minimal level of functional FATB protein, the level of saturated fatty acids in the seed oil can be modified and especially the relative amounts of saturated fatty acids (especially the amount of palmitic acid) are significantly reduced. It is thought that a minimal number of wild type FATB alleles is needed to maintain the production of a minimal amount of saturated fatty acids and/or of specific saturated fatty acids in specific tissues to assure a normal plant growth and seed development.

Thus, in a first aspect, the present invention provides in one embodiment a *Brassica* plant (and parts thereof, such as seeds) comprising at least three mutant FATB alleles in its genome, whereby the mutant FATB alleles are alleles of at least three different FATB genes selected from the group consisting of FATB-A1, FATB-A2, FATB-A3, FATB-C1, FATB-C2 and FATB-C3 and wherein the seeds of said plant produce a seed oil having equal to or less than 6 wt %, 5 wt %, 4 wt %, or 3.5 wt % (such as less than or equal to 3 wt %, 2 wt % or 1 wt %) saturated fatty acids based on the total amount of fatty acids in the seed oil.

In another aspect, the invention provides (isolated) nucleic acid sequences encoding wild type and/or mutant FATB proteins, as well as fragments thereof, and methods of using these nucleic acid sequences to modify the *Brassica* seed oil composition. Also provided are the proteins themselves and their use.

The invention further relates to a plurality of *Brassica* seeds, to *Brassica* plants and parts of plants comprising at least three (mutant) fatB alleles, and thus a significantly reduced amount of functional FATB proteins compared to seeds, plants and tissues comprising FATB alleles encoding the corresponding functional proteins. The plurality of seeds comprises seed oil with a modified relative amount and/or composition of saturated fatty acids. In one aspect, especially the amount of palmitic acid (C16:0) is significantly reduced compared to seed oil derived from seeds lacking the (at least three) mutant fatB alleles (i.e. comprising wild type FATB alleles instead).

In a further aspect, the invention relates to seed oil with a modified relative amount and/or composition of saturated fatty acids, which can be obtained by harvesting seeds from a *Brassica* plant according to the present invention and extracting the oil from the seeds or obtained by extraction from a plurality of *Brassica* seeds according to the present invention, and the use of the seed oil.

In a further aspect of the invention methods are provided for generating and selecting plants, plant parts and seeds containing at least three such mutant fatB alleles present at at least three different loci in the genome (i.e. at at least three different loci from at least three different FATB genes selected from the group consisting of FATB-A1, FATB-A2, FATB-A3, FATB-C1, FATB-C2 and FATB-C3), and to distinguish between the presence of mutant fatB alleles and wild type FATB alleles in a plant or plant part. Thus methods are provided (such as mutagenesis and/or marker assisted selection) for generating and/or identifying fatB alleles or plants or plant parts comprising such alleles and for combining a suitable number of fatB alleles and/or different types of fatB alleles in a single plant, whereby the saturated fatty acid levels of the seed oil of this plant are significantly reduced.

Methods are also provided for using the plants, plurality of seeds, plant parts, etc. of the invention, for obtaining "low saturate" or "no saturate" seed oil from crushed *Brassica* seeds. As used herein, "plant product" includes anything derived from a plant of the invention, including plant parts such as seeds, seed meal, seed cake, seed fats or oils.

BRIEF DESCRIPTION OF THE DRAWINGS

In FIG. 2-7 the exons are indicated with gray boxes, the introns by the horizontal lines in between the exons; the position of the mutations described in the Examples (named "EMSxx" according to their respective "FATB-Xx-EMSxx" name as described in the Examples) is indicated with vertical lines; the length and position of the FATB specific probes with SEQ ID NO:25 and 28 are indicated by vertical lines below the schematical representation of the FATB genes; the position of the FATB specific primers (named "ID xx" according to their respective SEQ ID NO: xx) are indicated by arrowheads; the scale bar indicates the length of the respective FATB genes.

Figure 1:
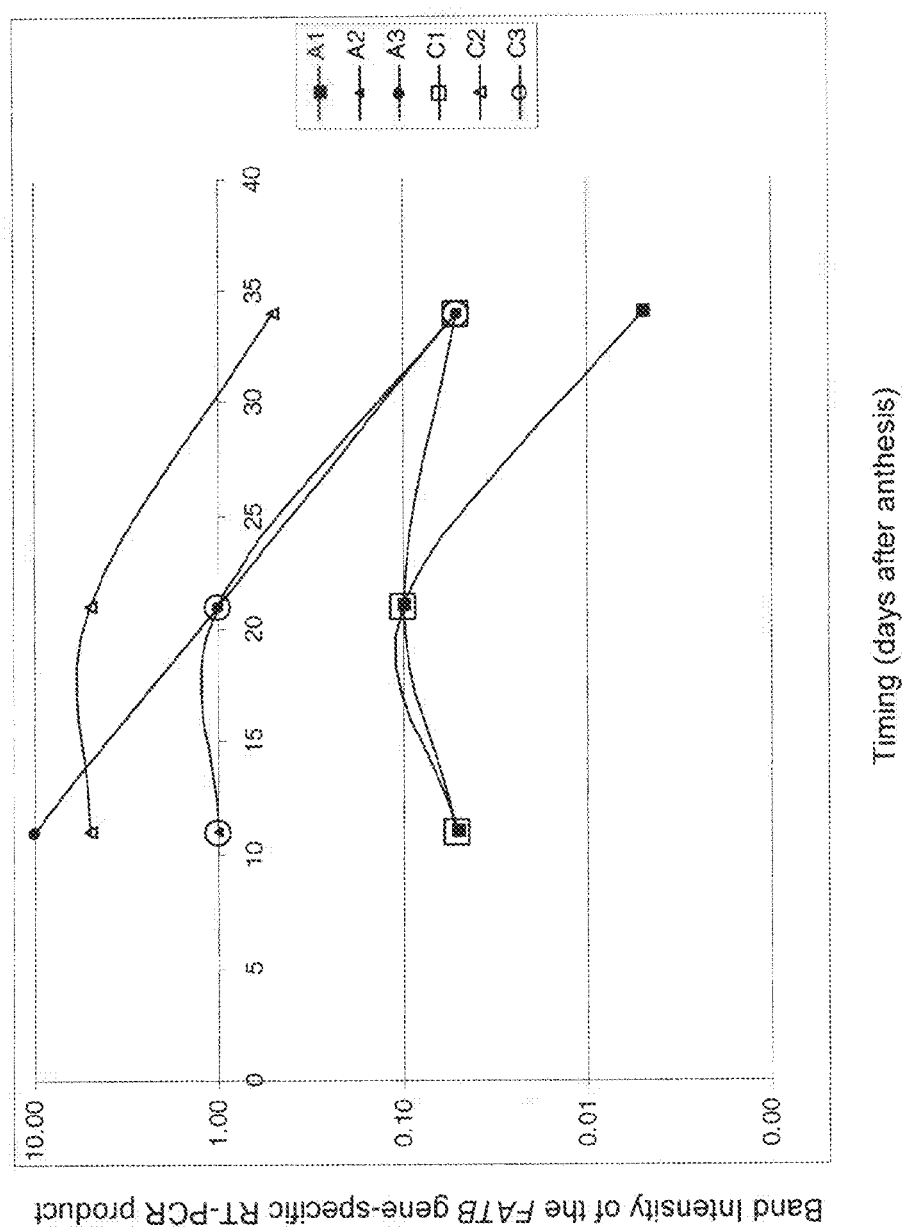
FIG. 1—Graph showing the results from the semi-quantitative RT-PCR of Example 3. The timing (11, 21 and 34 days after anthesis) (X-axis) and the level of expression of each FATB gene in seed (based on 10 ng RNA) expressed as the amount of genomic DNA (in ng) which generated a band intensity comparable with the band intensity of the FATB gene-specific RT-PCR product (Y-axis) is indicated.
Figure 2:
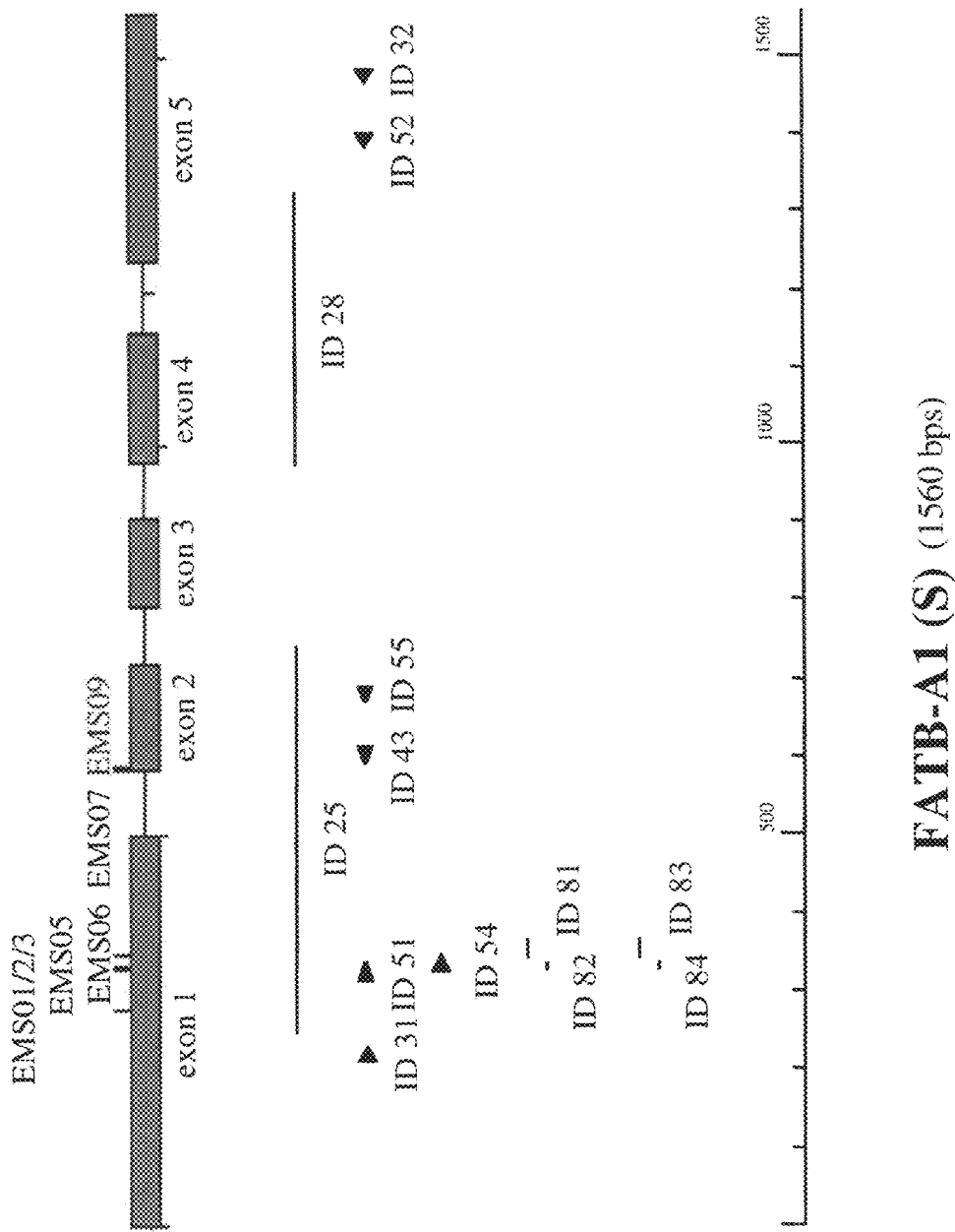
FIG. 2—Schematical representation of the FATB-A1 gene (with introns), encoding a wild-type FATB-A1 protein from spring oilseed rape (S) *Brassica napus*. (SEQ ID NO: 13)
Figure 3:
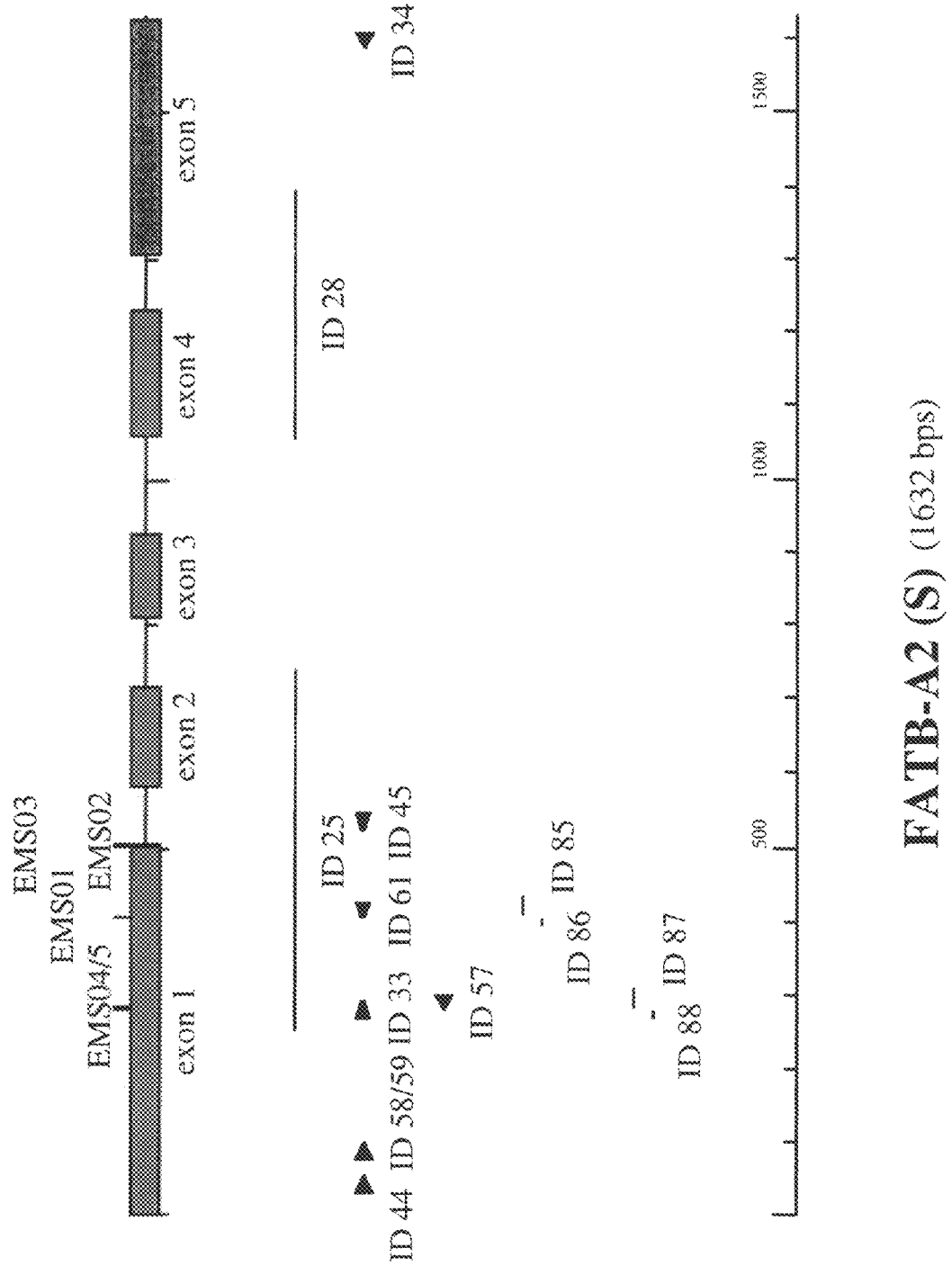
FIG. 3—Schematical representation of the FATB-A2 gene (with introns), encoding a wild-type FATB-A1 protein from spring oilseed rape (S) *Brassica napus*. (SEQ ID NO: 15)
Figure 4:
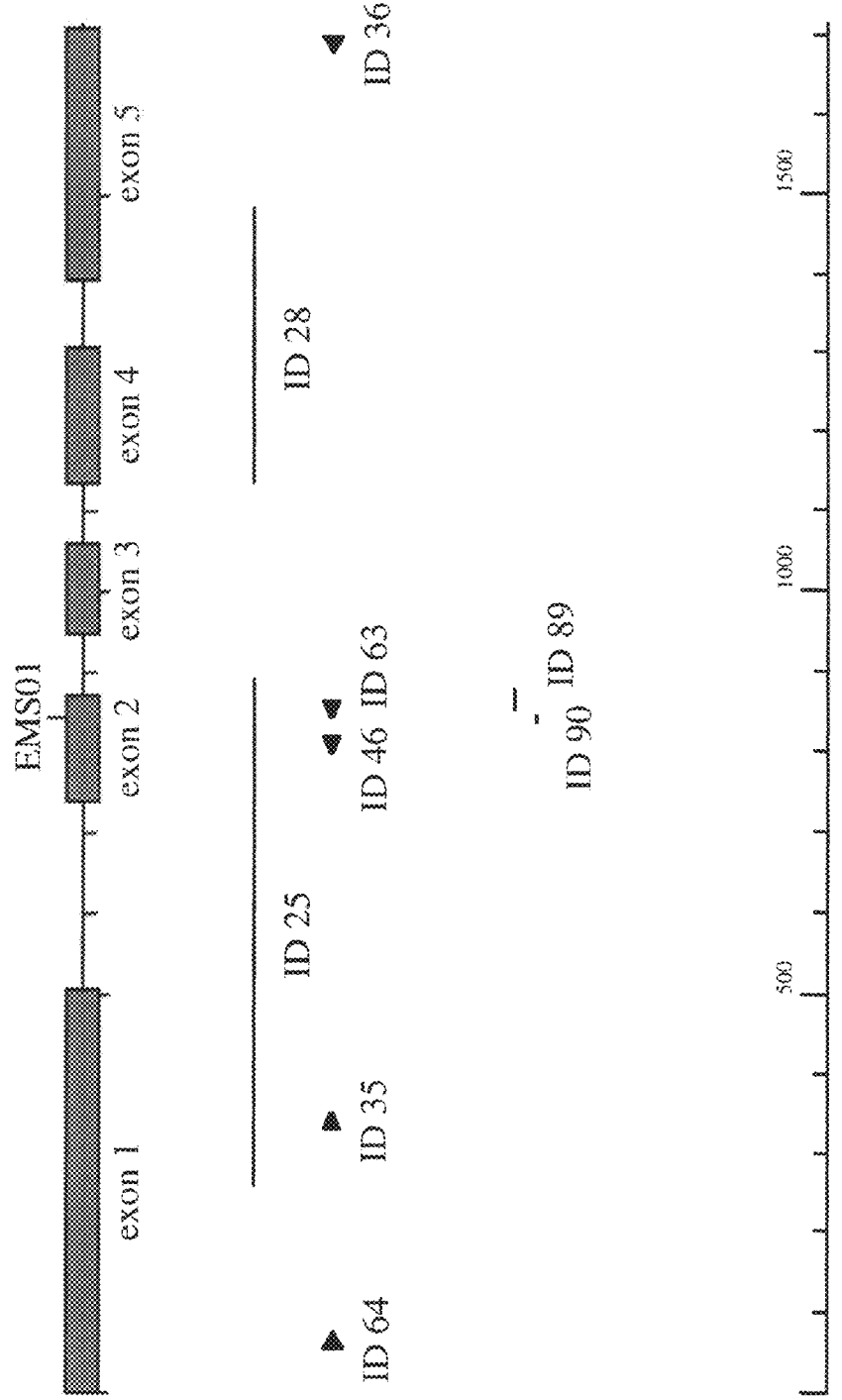
FIG. 4—Schematical representation of the FATB-A3 gene (with introns), encoding a wild-type FATB-A1 protein from spring oilseed rape (S) *Brassica napus*. (SEQ ID NO: 17)
Figure 5:
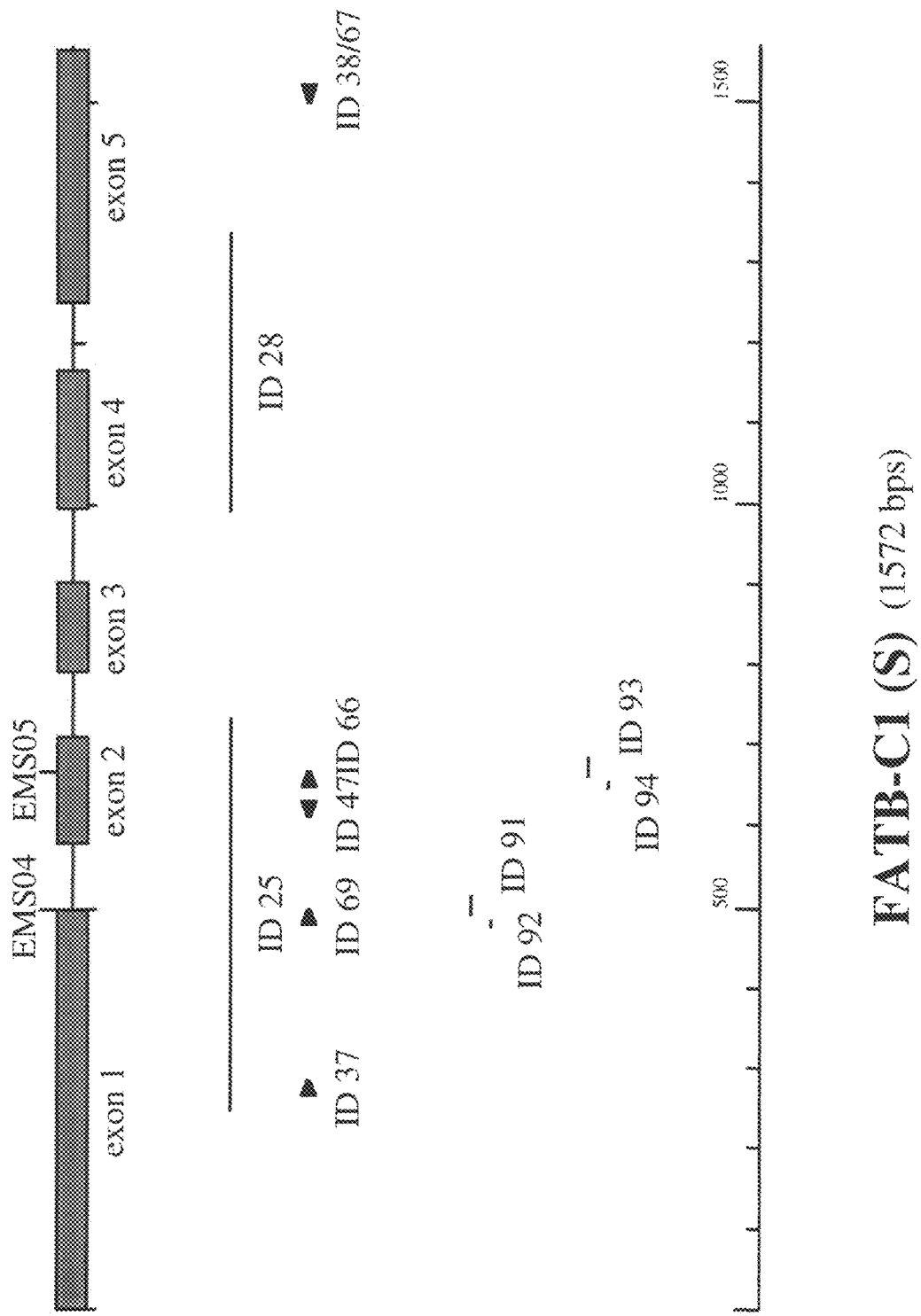
FIG. 5—Schematical representation of the FATB-C1 gene (with introns), encoding a wild-type FATB-A1 protein from spring oilseed rape (S) *Brassica napus*. (SEQ ID NO: 19)
Figure 6:
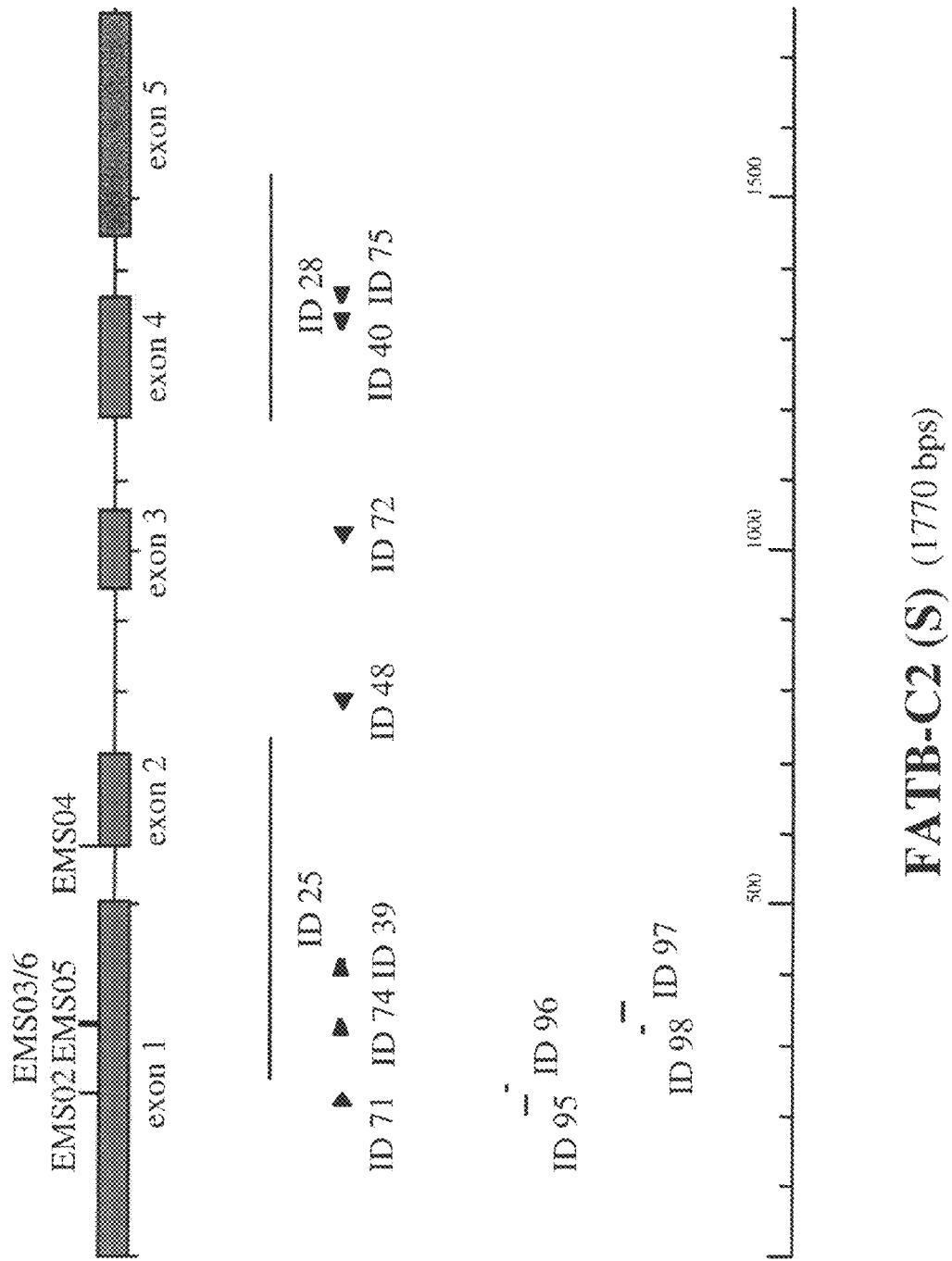
FIG. 6—Schematical representation of the FATB-C2 gene (with introns), encoding a wild-type FATB-A1 protein from spring oilseed rape (S) *Brassica napus*. (SEQ ID NO: 21)
Figure 7:
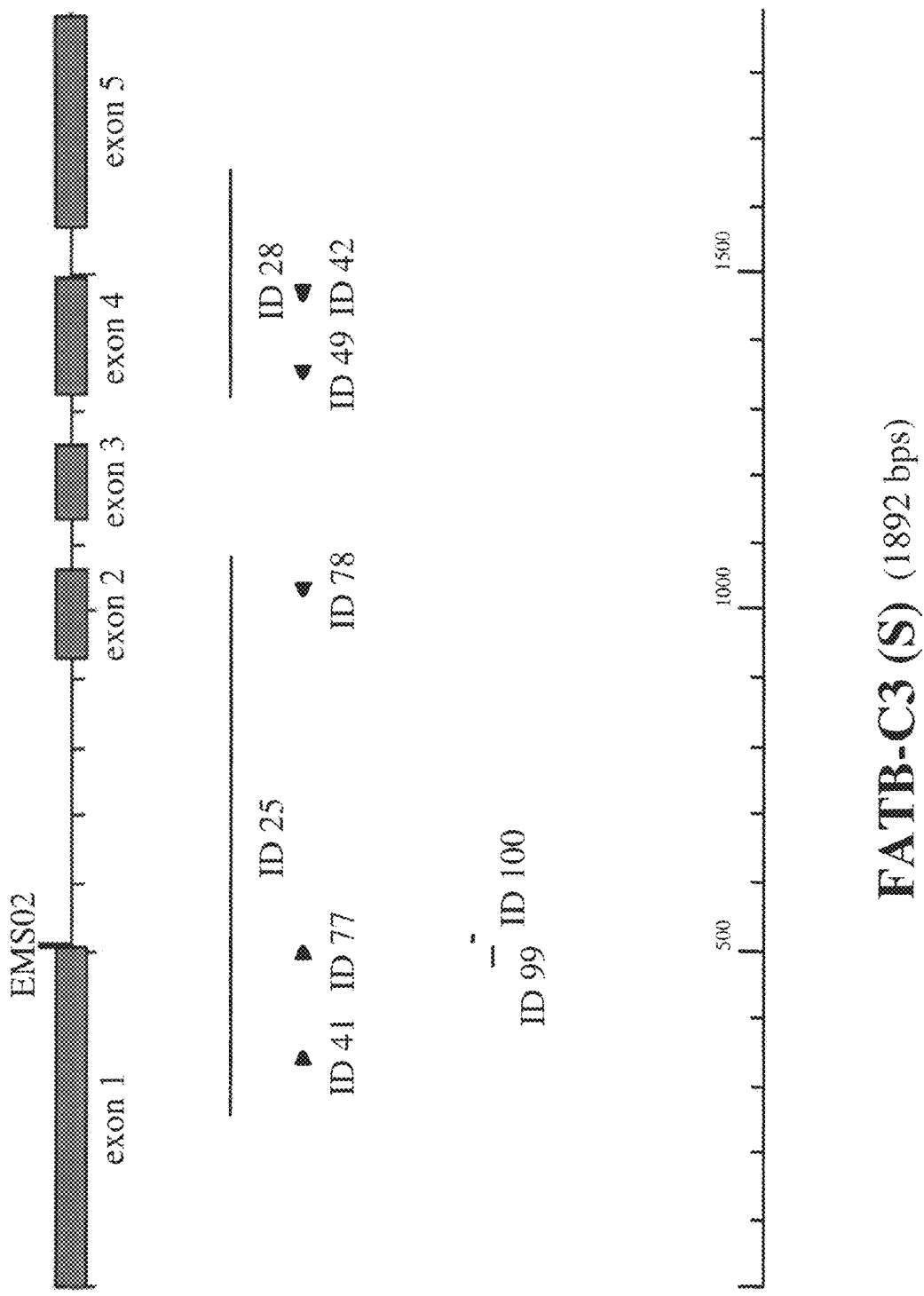
FIG. 7—Schematical representation of the FATB-C3 gene (with introns), encoding a wild-type FATB-A1 protein from spring oilseed rape (S) *Brassica napus*. (SEQ ID NO: 23)

The analysed *Brassica* plants were progeny plants of *Brassica* plants comprising three or four mutant FATB alleles, i.e. FATB-AX-EMSY or FATB-CX-EMSY alleles as indicated in Table 23, in heterozygous state as indicated. The mutant FATB alleles are referred to as 'aX-Y' and 'cX-Y' or as 'aX' and 'cX'; wild-type FATB alleles are referred to as 'AX' and 'CX').

GENERAL DEFINITIONS

"Low in saturates" or "low sats" oil refers herein to seed-derived oil containing (on average) less than 7 wt % of total saturated fatty acids based on the total wt % of fatty acids in the oil. The wt % saturated fatty acids of low sats seed oil can be equal to or less than 6 wt %, 5 wt %, 4 wt %, but above 3.5 wt % (e.g. 3.6 wt %).

"No saturates" or "no sats" oil refers herein to seed-derived oil containing (on average) less than 3.6 wt % of total saturated fatty acids based on the total wt % of fatty acids in the oil. The wt % saturated fatty acids of no sats seed oil can be equal to or less than 3.5 wt %, 3.0 wt %, 2.5 wt %, 2.0 wt %, 1.5 wt % or 1 wt %.

"Crop plant" refers to plant species cultivated as a crop, such as *Brassica napus* (AACC, 2n=38), *Brassica juncea* (AABB, 2n=36), *Brassica carinata* (BBCC, 2n=34), *Brassica rapa* (syn. *B. campestris*) (AA, 2n=20), *Brassica oleracea* (CC, 2n=18) or *Brassica nigra* (BB, 2n=16). The definition does not encompass weeds, such as *Arabidopsis thaliana*.

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence which is within a plant cell, e.g. an endogenous allele of a FATB gene present within the nuclear genome of a *Brassica* cell.

The term "gene" means a DNA sequence comprising a region (transcribed region), which is transcribed into an RNA molecule (e.g. a pre-mRNA, comprising intron sequences, which is then spliced into a mature mRNA) in a cell, operable linked to regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a 'transgene'), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional protein is produced; the term "not functionally expressed" to indicate that a protein with reduced or no functionality (biological activity) is produced or that no protein is produced (see also below).

The terms "protein" or "polypeptide" are used interchangeably and refer to molecules consisting of a chain of amino acids, without reference to a specific mode of action, size, 3-dimensional structure or origin. A "fragment" or "portion" of a FATB protein may thus still be referred to as a "protein". An "isolated protein" is used to refer to a protein which is no longer in its natural environment, for example in vitro or in a recombinant bacterial or plant host cell. An "enzyme" is a protein comprising enzymatic activity, such as functional FATB proteins, which are capable of hydrolyzing the substrate(s) fatty acyl-ACP into free fatty acids and ACP (EC number 3.1.2.).

The terms "target peptide" or "transit peptide" refer to amino acid sequences which target a protein to intracellular organelles such as plastids. Wild type FATB proteins comprise a plastid target peptide (or plastid transit peptide) at their N-terminal end.

"Mature protein" or "mature FATB protein" refers to a functional FATB enzyme without the plastid transit peptide. "Precursor protein" refers to the mature protein with its transit peptide.

The "FATB gene" refers herein to the nucleic acid sequence encoding a fatty acyl-ACP thioesterase type II protein (i.e. a FATB protein). A functional "FATB protein" has fatty acyl ACP thioesterase activity, i.e. it is capable of hydrolyzing fatty acyl-ACP substrates, preferably saturated fatty acyl-ACP substrates (e.g. palmitoyl-ACP; C16:0-ACP) into free fatty acid (e.g. C16:0) and ACP, which can be tested using a biological assay. To determine the function and/or the functionality of a specific FATB gene/protein, the bacterial expression system as described in Salas and Ohlrogge (2002, Archives of Biochemistry and Biophysics 403:25-34) or the agar-plate based colorimetric screen for thioesterase activity described in Mayer and Shanklin (2007, BMC Plant Biology 7(1):1-11) can, for example, be used. To determine the overall FATB activity in a plant or a plant tissue, assays for fatty acyl-ACP hydrolysis can be performed on plant extracts as described, for example, by Bonaventure et al. (2003, Plant Cell 15:1020-1033) and Eccleston and Ohlrogge (1998, Plant Cell 10: 613-622).

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as homeologous chromosomes (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found. For example, the "FATB-A1 locus" refers to the position on a chromosome of the A genome where the FATB-A1 gene (and two FATB-A1 alleles) is (are) found.

Whenever reference to a "plant" or "plants" according to the invention is made, it is understood that also plant parts (cells, tissues or organs, seeds, severed parts such as roots, leaves, flowers, pollen, etc.), progeny of the plants which retain the distinguishing characteristics of the parents (especially the seed oil composition), such as seed obtained by selfing or crossing, e.g. hybrid seed (obtained by crossing two inbred parental lines), hybrid plants and plant parts derived therefrom are encompassed herein, unless otherwise indicated.

A "molecular assay" (or test) refers to an assay that indicates (directly or indirectly) the presence or absence of one or more particular FATB alleles at one or more FATB loci (i.e. at one or more of the loci FATB-A1, FATB-A2, FATB-A3, FATB-C1, FATB-C2, and/or FATB-C3). In one embodiment it allows one to determine whether a particular (wild type or mutant) allele is homozygous or heterozygous at the locus in any individual plant.

As used herein, the term "wild type FATB" (e.g. wild type FATB-A1, FATB-A2, FATB-A3, FATB-C1, FATB-C2, or FATB-C3), means a naturally occurring allele found within Brassica plants, which encodes a functional FATB protein (e.g. a functional FATB-A1, FATB-A2, FATB-A3, FATB-C1, FATB-C2, or FATB-C3, respectively). In contrast, "mutant FATB" (e.g. mutant FATB-A1, FATB-A2, FATB-A3, FATB-C1, FATB-C2, or FATB-C3) refers to a FATB allele, which does not encode a functional FATB protein, i.e. a FATB allele encoding a non-functional FATB protein (e.g. a non-functional FATB-A1, FATB-A2, FATB-A3, FATB-C1, FATB-C2, or FATB-C3, respectively) or encoding no FATB protein. Such a "mutant FATB allele" is a wild-type FATB allele, which comprises one or more mutations in its nucleic acid sequence, whereby the mutation(s) preferably result in a significantly reduced (absolute or relative) amount of functional FATB protein in the cell in vivo. Mutant alleles of the FATB-protein-encoding nucleic acid sequences are designated as "fatB" (e.g. fatB-a1, fatB-a2, fatB-a3, fatB-c1, fatB-c2, or fatB-c3, respectively) herein. Mutant alleles can be either "natural mutant" alleles, which are mutant alleles found in nature (e.g. produced spontaneously without human application of mutagens) or "induced mutant" alleles, which are induced by human intervention, e.g. by mutagenesis.

A "significantly reduced amount of functional FATB protein" (e.g. functional FATB-A1, FATB-A2, FATB-A3, FATB-C1, FATB-C2 and/or FATB-C3 protein) refers to a reduction in the amount of a functional FATB protein produced by the cell comprising a mutant FATB allele by at least 30%, 40%, 50%, 60%, 70%, 80%, 90%, 95% or 100% (i.e. no functional protein is produced by the cell) as compared to the amount of the functional FATB protein produced by the cell not comprising the mutant FATB allele. This definition encompasses thus the production of a "non-functional" protein (e.g. truncated protein) having no biological activity in vivo, the reduction in the absolute amount of the functional protein (e.g. no functional protein being made due to the mutation in the gene), and/or the production of a protein with reduced biological activity, i.e. a "mal-functional" protein (such as a truncated protein or a protein produced by alternative mRNA splicing) compared to the activity of the wild type, functional protein. Likewise the term "mutant FATB protein" encompasses both a protein encoded by a mutant nucleic acid sequence ("fatB allele") whereby the mutation results in a significantly reduced and/or no FATB enzymatic activity in vivo, compared to the activity of the protein encoded by the non-mutant, wild type sequence ("FATB allele").

"Mutagenesis", as used herein, refers to the process in which plant cells (e.g., a Brassica seed or tissues, such as pollen, etc.) are contacted one or more times to a mutagenic agent, such as a chemical substance (such as ethylmethylsulfonate (EMS), ethylnitrosourea (ENU), etc.) or ionizing radiation (neutrons (such as in fast neutron mutagenesis, etc.), gamma rays (such as that supplied by a Cobalt 60 source), X-rays, etc.), or a combination of the foregoing. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, Brassica plants are regenerated from the treated cells using known techniques. For instance, the resulting Brassica seeds may be planted in accordance with conventional growing procedures and following self-pollination seed is formed on the plants. Alternatively, doubled haploid plantlets may be extracted to immediately form homozygous plants. Additional seed which is formed as a result of such self-pollination in the present or a subsequent generation may be harvested and screened for the presence of mutant FATB alleles. Several techniques are known to screen for specific mutant alleles, e.g., Deleteagene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant FATB alleles are described in the Examples below.

The term "ortholog" of a gene or protein refers herein to the homologous gene or protein found in another species, which has the same function as the gene or protein, but is (usually) diverged in sequence from the time point on when the species harbouring the genes diverged (i.e. the genes evolved from a common ancestor by speciation). Orthologs of the Brassica napus FATB genes may thus be identified in other plant species (e.g. Brassica juncea, etc.) based on both sequence comparisons (e.g. based on percentages sequence identity over the entire sequence or over specific domains) and/or functional analysis.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical" or "essentially similar", as used herein, refers to sequences, which, when optimally aligned as defined above, share at least a certain minimal percentage of sequence identity (as defined further below).

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 μg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1× SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

DETAILED DESCRIPTION

It was found by the inventors that Brassica napus (genome AACC, 2n=4x=38), which is an allotetraploid (amphidiploid) species containing essentially two diploid genomes (the A and the C genome) due to its origin from diploid ancestors, comprises a total of six FATB loci and FATB genes in its genome, three genes on the A genome (referred herein to as "FATB-A1", "FATB-A2" and "FATB-A3") and three genes on the C genome (referred herein to as "FATB-C1", "FATB-C2" and "FATB-C3"). The FATB-A1 gene is said to be "homeologous" to the FATB-C1 gene, FATB-A2 is homeologous to FATB-C2 and FATB-A3 is homeologous to FATB-C3, i.e. the "A genes" are found on the A genome and originate from the diploid ancestor B. rapa (AA), while the "C genes" are found on the C genome of B. napus and originate from the diploid ancestor B. oleracea (CC).

As in any diploid genome, two "alleles" can be present for each FATB gene at each FATB locus in the genome (one allele being the gene sequence found on one chromosome and the other on the homologous chromosome). The nucleotide sequence of these two alleles may be identical (homozygous) or different (heterozygous) in any given plant, although the number of different possible alleles existing for each FATB gene may be much larger than two in the species as a whole.

It was moreover found that plants comprising a mutation, which causes a significant reduction in the amount of functional FATB protein encoded by the wild type equivalent of the mutant fatB allele, in only one or two of these six FATB genes is not sufficient to significantly reduce the percentage (wt %) of saturated fatty acids in the seed oil of the plants. It is thought that at least three mutant fatB alleles, of three different FATB genes (selected from FATB-A1, FATB-A2, FATB-A3, FATB-C1, FATB-C2 and FATB-C3) need to be comprised in the plant in order to obtain plants which produce a low or no saturate seed oil.

Thus in one embodiment of the invention, plants comprising at least 3 mutant fatB alleles of three different FATB genes are provided herein, whereby the mutant fatB alleles result in a significantly reduced amount of functional FATB protein of the type encoded by the wild-type equivalent of these mutant alleles and thus an overall significantly reduced amount of the functional FATB proteins produced in the plant cells, specifically in the developing seeds, in vivo.

By combining sufficient copies of specific mutant fatB alleles with sufficient copies of specific wild type FATB alleles in one plant, it is possible to fine tune the amount and/or type of functional FATB proteins made, which in turn influences the export of (the amount and/or type of) free saturated fatty acids from the plastid and thus the fatty acid composition of the seed oil produced. The absolute and relative amount of each of the six FATB proteins can thus be tuned in such a way as to provide plants which produce sufficient FATB protein(s) for growth and development of the plant, while the desired amount and/or type of fatty acids is made and stored in the seed oil of these plants. Thus in one embodiment of the invention, plants and plant parts are provided comprising at least one functionally expressed FATB allele, selected from FATB-A1, FATB-A2, FATB-A3, FATB-C1, FATB-C2 and FATB-C3, which encodes a fully functional FATB protein, while the remaining alleles may be mutant fatB alleles.

Thus, in one aspect of the invention plants or plant parts comprising n-tuple mutant fatB alleles (of the 6 FATB genes) are provided, whereby n≤12, preferably n≤11 (e.g. n=10, 9 or 8), so that at least one allele produces a functional FATB protein.

In a further aspect of the invention homozygous FATB triple mutant- (n=6, i.e. homozygous for mutant alleles of three genes, selected from the 6 FATB genes), homozygous FATB quadruple mutant- (n=8) and/or homozygous FATB quintuple mutant- (n=10) plants or plant parts are provided, whereby the mutant alleles are selected from the genes FATB-A1, FATB-A2, FATB-A3, FATB-C1, FATB-C2 and FATB-C3.

Thus in one embodiment of the invention, homozygous FATB triple mutant plants are provided herein, wherein the genotype of the plant can be described as:
  fatB-a1/fatB-a1, fatB-a2/fatB-a2, fatB-a3/fatB-a3, FATB-C1/FATB-C1, FATB-C2/FATB-C2, FATB-C3/FATB-C3,
  fatB-a1/fatB-a1, fatB-a2/fatB-a2, FATB-A3/FATB-A3, fatB-c1/fatB-c1, FATB-C2/FATB-C2, FATB-C3/FATB-C3,
  fatB-a1/fatB-a1, fatB-a2/fatB-a2, FATB-A3/FATB-A3, FATB-C1/FATB-C1, fatB-c2/fatB-c2, FATB-C3/FATB-C3,
  fatB-a1/fatB-a1, fatB-a2/fatB-a2, FATB-A3/FATB-A3, FATB-C1/FATB-C1, FATB-C2/FATB-C2, fatB-c3/fatB-c3,
  fatB-a1/fatB-a1, FATB-A2/FATB-A2, fatB-a3/fatB-a3, fatB-c1/fatB-c1, FATB-C2/FATB-C2, FATB-C3/FATB-C3,
  fatB-a1/fatB-a1, FATB-A2/FATB-A2, fatB-a3/fatB-a3, FATB-C1/FATB-C1, fatB-c2/fatB-c2, FATB-C3/FATB-C3,
  fatB-a1/fatB-a1, FATB-A2/FATB-A2, fatB-a3/fatB-a3, FATB-C1/FATB-C1, FATB-C2/FATB-C2, fatB-c3/fatB-c3,
  fatB-a1/fatB-a1, FATB-A2/FATB-A2, FATB-A3/FATB-A3, fatB-c1/fatB-c1, fatB-c2/fatB-c2, FATB-C3/FATB-C3,
  fatB-a1/fatB-a1, FATB-A2/FATB-A2, FATB-A3/FATB-A3, fatB-c1/fatB-c1, FATB-C2/FATB-C2, fatB-c3/fatB-c3,
  fatB-a1/fatB-a1, FATB-A2/FATB-A2, FATB-A3/FATB-A3, FATB-C1/FATB-C1, fatB-c2/fatB-c2, fatB-c3/fatB-c3,
  FATB-A1/FATB-A1, fatB-a2/fatB-a2, fatB-a3/fatB-a3, fatB-c1/fatB-c1, FATB-C2/FATB-C2, FATB-C3/FATB-C3,
  FATB-A1/FATB-A1, fatB-a2/fatB-a2, fatB-a3/fatB-a3, FATB-C1/FATB-C1, fatB-c2/fatB-c2, FATB-C3/FATB-C3,
  FATB-A1/FATB-A1, fatB-a2/fatB-a2, fatB-a3/fatB-a3, FATB-C1/FATB-C1, FATB-C2/FATB-C2, fatB-c3/fatB-c3,
  FATB-A1/FATB-A1, fatB-a2/fatB-a2, FATB-A3/FATB-A3, fatB-c1/fatB-c1, fatB-c2/fatB-c2, FATB-C3/FATB-C3,
  FATB-A1/FATB-A1, fatB-a2/fatB-a2, FATB-A3/FATB-A3, fatB-c1/fatB-c1, FATB-C2/FATB-C2, fatB-c3/fatB-c3,
  FATB-A1/FATB-A1, fatB-a2/fatB-a2, FATB-A3/FATB-A3, FATB-C1/FATB-C1, fatB-c2/fatB-c2, fatB-c3/fatB-c3,
  FATB-A1/FATB-A1, FATB-A2/FATB-A2, fatB-a3/fatB-a3, fatB-c1/fatB-c1, fatB-c2/fatB-c2, FATB-C3/FATB-C3,
  FATB-A1/FATB-A1, FATB-A2/FATB-A2, fatB-a3/fatB-a3, fatB-c1/fatB-c1, FATB-C2/FATB-C2, fatB-c3/fatB-c3,
  FATB-A1/FATB-A1, FATB-A2/FATB-A2, fatB-a3/fatB-a3, FATB-C1/FATB-C1, fatB-c2/fatB-c2, fatB-c3/fatB-c3, or
  FATB-A1/FATB-A1, FATB-A2/FATB-A2, FATB-A3/FATB-A3, fatB-c1/fatB-c1, fatB-c2/fatB-c2, fatB-c3/fatB-c3.

In another embodiment of the invention, homozygous FATB quadruple mutant plants are provided herein, wherein the genotype of the plant can be described as:
  fatB-a1/fatB-a1, fatB-a2/fatB-a2, fatB-a3/fatB-a3, fatB-c1/fatB-c1, FATB-C2/FATB-C2, FATB-C3/FATB-C3,
  fatB-a1/fatB-a1, fatB-a2/fatB-a2, fatB-a3/fatB-a3, FATB-C1/FATB-C1, fatB-c2/fatB-c2, FATB-C3/FATB-C3,
  fatB-a1/fatB-a1, fatB-a2/fatB-a2, fatB-a3/fatB-a3, FATB-C1/FATB-C1, FATB-C2/FATB-C2, fatB-c3/fatB-c3,
  fatB-a1/fatB-a1, fatB-a2/fatB-a2, FATB-A3/FATB-A3, fatB-c1/fatB-c1, fatB-c2/fatB-c2, FATB-C3/FATB-C3,
  fatB-a1/fatB-a1, fatB-a2/fatB-a2, FATB-A3/FATB-A3, fatB-c1/fatB-c1, FATB-C2/FATB-C2, fatB-c3/fatB-c3,
  fatB-a1/fatB-a1, fatB-a2/fatB-a2, FATB-A3/FATB-A3, FATB-C1/FATB-C1, fatB-c2/fatB-c2, fatB-c3/fatB-c3,
  fatB-a1/fatB-a1, FATB-A2/FATB-A2, fatB-a3/fatB-a3, fatB-c1/fatB-c1, fatB-c2/fatB-c2, FATB-C3/FATB-C3,
  fatB-a1/fatB-a1, FATB-A2/FATB-A2, fatB-a3/fatB-a3, fatB-c1/fatB-c1, FATB-C2/FATB-C2, fatB-c3/fatB-c3,
  fatB-a1/fatB-a1, FATB-A2/FATB-A2, fatB-a3/fatB-a3, FATB-C1/FATB-C1, fatB-c2/fatB-c2, fatB-c3/fatB-c3,
  fatB-a1/fatB-a1, FATB-A2/FATB-A2, FATB-A3/FATB-A3, fatB-c1/fatB-c1, fatB-c2/fatB-c2, fatB-c3/fatB-c3,
  FATB-A1/FATB-A1, fatB-a2/fatB-a2, fatB-a3/fatB-a3, fatB-c1/fatB-c1, fatB-c2/fatB-c2, FATB-C3/FATB-C3,
  FATB-A1/FATB-A1, fatB-a2/fatB-a2, fatB-a3/fatB-a3, fatB-c1/fatB-c1, FATB-C2/FATB-C2, fatB-c3/fatB-c3,
  FATB-A1/FATB-A1, fatB-a2/fatB-a2, fatB-a3/fatB-a3, FATB-C1/FATB-C1, fatB-c2/fatB-c2, fatB-c3/fatB-c3,
  FATB-A1/FATB-A1, fatB-a2/fatB-a2, FATB-A3/FATB-A3, fatB-c1/fatB-c1, fatB-c2/fatB-c2, fatB-c3/fatB-c3, or
  FATB-A1/FATB-A1, FATB-A2/FATB-A2, fatB-a3/fatB-a3, fatB-c1/fatB-c1, fatB-c2/fatB-c2, fatB-c3/fatB-c3.

In yet another embodiment of the invention, homozygous FATB quintuple mutant plants are provided herein, wherein the genotype of the plant can be described as:

fatB-a1/fatB-a1, fatB-a2/fatB-a2, fatB-a3/fatB-a3, fatB-c1/fatB-c1, fatB-c2/fatB-c2, FATB-C3/FATB-C3, fatB-a1/fatB-a1, fatB-a2/fatB-a2, fatB-a3/fatB-a3, fatB-c1/fatB-c1, FATB-C2/FATB-C2, fatB-c3/fatB-c3, fatB-a1/fatB-a1, fatB-a2/fatB-a2, fatB-a3/fatB-a3, FATB-C1/FATB-C1, fatB-c2/fatB-c2, fatB-c3/fatB-c3, fatB-a1/fatB-a1, fatB-a2/fatB-a2, FATB-A3/FATB-A3, fatB-c1/fatB-c1, fatB-c2/fatB-c2, fatB-c3/fatB-c3, fatB-a1/fatB-a1, FATB-A2/FATB-A2, fatB-a3/fatB-a3, fatB-c1/fatB-c1, fatB-c2/fatB-c2, fatB-c3/fatB-c3, or FATB-A1/FATB-A1, fatB-a2/fatB-a2, fatB-a3/fatB-a3, fatB-c1/fatB-c1, fatB-c2/fatB-c2, fatB-c3/fatB-c3.

In a further aspect of the invention the homozygous FATB triple (n=6), quadruple (n=8) and/or quintuple (n=10) mutant plants or plant parts comprise a further mutant allele, wherein the mutant plants or plant parts are heterozygous for the additional mutant FATB allele (i.e., n=7, n=9, and n=11, respectively), and wherein the mutant allele is selected from the remaining wild-type FATB genes (i.e., FATB-A1, FATB-A2, FATB-A3, FATB-C1, FATB-C2 or FATB-C3 genes).

Thus in a further embodiment of the invention, homozygous FATB triple mutant plants comprising one further mutant FATB allele are provided herein, wherein the genotype of the plant can be described as:

fatB-a1/fatB-a1, fatB-a2/fatB-a2, fatB-a3/fatB-a3, fatB-c1/FATB-C1, FATB-C2/FATB-C2, FATB-C3/FATB-C3, fatB-a1/fatB-a1, fatB-a2/fatB-a2, fatB-a3/fatB-a3, FATB-C1/FATB-C1, fatB-c2/FATB-C2, FATB-C3/FATB-C3, fatB-a1/fatB-a1, fatB-a2/fatB-a2, fatB-a3/fatB-a3, FATB-C1/FATB-C1, FATB-C2/FATB-C2, fatB-c3/FATB-C3, fatB-a1/fatB-a1, fatB-a2/fatB-a2, fatB-a3/FATB-A3, fatB-c1/fatB-c1, FATB-C2/FATB-C2, FATB-C3/FATB-C3, fatB-a1/fatB-a1, fatB-a2/fatB-a2, FATB-A3/FATB-A3, fatB-c1/fatB-c1, fatB-c2/FATB-C2, FATB-C3/FATB-C3, fatB-a1/fatB-a1, fatB-a2/fatB-a2, FATB-A3/FATB-A3, fatB-c1/fatB-c1, FATB-C2/FATB-C2, fatB-c3/FATB-C3, fatB-a1/fatB-a1, fatB-a2/fatB-a2, FATB-A3/FATB-A3, FATB-C1/FATB-C1, fatB-c2/fatB-c2, FATB-C3/FATB-C3, fatB-a1/fatB-a1, fatB-a2/fatB-a2, FATB-A3/FATB-A3, fatB-c1/FATB-C1, fatB-c2/fatB-c2, FATB-C3/FATB-C3, fatB-a1/fatB-a1, fatB-a2/fatB-a2, FATB-A3/FATB-A3, FATB-C1/FATB-C1, fatB-c2/fatB-c2, FATB-C3/FATB-C3, fatB-a1/fatB-a1, fatB-a2/fatB-a2, FATB-A3/FATB-A3, FATB-C1/FATB-C1, FATB-C2/FATB-C2, fatB-c3/fatB-c3, fatB-a1/fatB-a1, fatB-a2/fatB-a2, FATB-A3/FATB-A3, fatB-c1/FATB-C1, FATB-C2/FATB-C2, fatB-c3/fatB-c3, fatB-a1/fatB-a1, fatB-a2/fatB-a2, FATB-A3/FATB-A3, FATB-C1/FATB-C1, fatB-c2/FATB-C2, fatB-c3/fatB-c3, fatB-a1/fatB-a1, fatB-a2/FATB-A2, fatB-a3/fatB-a3, fatB-c1/fatB-c1, FATB-C2/FATB-C2, FATB-C3/FATB-C3, fatB-a1/fatB-a1, FATB-A2/FATB-A2, fatB-a3/fatB-a3, fatB-c1/fatB-c1, fatB-c2/FATB-C2, FATB-C3/FATB-C3, fatB-a1/fatB-a1, FATB-A2/FATB-A2, fatB-a3/fatB-a3, fatB-c1/fatB-c1, FATB-C2/FATB-C2, fatB-c3/FATB-C3, fatB-a1/fatB-a1, fatB-a2/FATB-A2, fatB-a3/fatB-a3, FATB-C1/FATB-C1, fatB-c2/fatB-c2, FATB-C3/FATB-C3, fatB-a1/fatB-a1, FATB-A2/FATB-A2, fatB-a3/fatB-a3, fatB-c1/FATB-C1, fatB-c2/fatB-c2, FATB-C3/FATB-C3, fatB-a1/fatB-a1, FATB-A2/FATB-A2, fatB-a3/fatB-a3, FATB-C1/FATB-C1, fatB-c2/fatB-c2, FATB-C3/FATB-C3, fatB-a1/fatB-a1, fatB-a2/FATB-A2, fatB-a3/fatB-a3, FATB-C1/FATB-C1, FATB-C2/FATB-C2, fatB-c3/fatB-c3, fatB-a1/fatB-a1, FATB-A2/FATB-A2, fatB-a3/fatB-a3, fatB-c1/FATB-C1, FATB-C2/FATB-C2, fatB-c3/fatB-c3, fatB-a1/fatB-a1, FATB-A2/FATB-A2, fatB-a3/fatB-a3, FATB-C1/FATB-C1, fatB-c2/FATB-C2, fatB-c3/fatB-c3, fatB-a1/fatB-a1, fatB-a2/FATB-A2, FATB-A3/FATB-A3, fatB-c1/fatB-c1, fatB-c2/fatB-c2, FATB-C3/FATB-C3, fatB-a1/fatB-a1, FATB-A2/FATB-A2, fatB-a3/FATB-A3, fatB-c1/fatB-c1, fatB-c2/fatB-c2, FATB-C3/FATB-C3, fatB-a1/fatB-a1, FATB-A2/FATB-A2, FATB-A3/FATB-A3, fatB-c1/fatB-c1, fatB-c2/fatB-c2, fatB-c3/FATB-C3, fatB-a1/fatB-a1, FATB-A2/FATB-A2, FATB-A3/FATB-A3, fatB-c1/fatB-c1, FATB-C2/FATB-C2, fatB-c3/fatB-c3, fatB-a1/fatB-a1, FATB-A2/FATB-A2, fatB-a3/FATB-A3, fatB-c1/fatB-c1, FATB-C2/FATB-C2, fatB-c3/fatB-c3, fatB-a1/fatB-a1, FATB-A2/FATB-A2, FATB-A3/FATB-A3, fatB-c1/fatB-c1, FATB-C2/FATB-C2, fatB-c3/fatB-c3, fatB-a1/fatB-a1, fatB-a2/FATB-A2, FATB-A3/FATB-A3, FATB-C1/FATB-C1, fatB-c2/fatB-c2, fatB-c3/fatB-c3, fatB-a1/fatB-a1, FATB-A2/FATB-A2, fatB-a3/FATB-A3, FATB-C1/FATB-C1, fatB-c2/fatB-c2, fatB-c3/fatB-c3, fatB-a1/fatB-a1, FATB-A2/FATB-A2, FATB-A3/FATB-A3, fatB-c1/FATB-C1, fatB-c2/fatB-c2, fatB-c3/fatB-c3, fatB-a1/FATB-A1, fatB-a2/fatB-a2, fatB-a3/fatB-a3, fatB-c1/fatB-c1, FATB-C2/FATB-C2, FATB-C3/FATB-C3, FATB-A1/FATB-A1, fatB-a2/fatB-a2, fatB-a3/fatB-a3, fatB-c1/fatB-c1, fatB-c2/FATB-C2, FATB-C3/FATB-C3, FATB-A1/FATB-A1, fatB-a2/fatB-a2, fatB-a3/fatB-a3, fatB-c1/fatB-c1, FATB-C2/FATB-C2, fatB-c3/FATB-C3, fatB-a1/FATB-A1, fatB-a2/fatB-a2, fatB-a3/fatB-a3, FATB-C1/FATB-C1, fatB-c2/fatB-c2, FATB-C3/FATB-C3, FATB-A1/FATB-A1, fatB-a2/fatB-a2, fatB-a3/fatB-a3, fatB-c1/FATB-C1, fatB-c2/fatB-c2, FATB-C3/FATB-C3, FATB-A1/FATB-A1, fatB-a2/fatB-a2, fatB-a3/fatB-a3, FATB-C1/FATB-C1, fatB-c2/fatB-c2, FATB-C3/FATB-C3, fatB-a1/FATB-A1, fatB-a2/fatB-a2, fatB-a3/fatB-a3, FATB-C1/FATB-C1, FATB-C2/FATB-C2, fatB-c3/fatB-c3, FATB-A1/FATB-A1, fatB-a2/fatB-a2, fatB-a3/fatB-a3, fatB-c1/FATB-C1, FATB-C2/FATB-C2, fatB-c3, fatB-c3, FATB-A1/FATB-A1, fatB-a2/fatB-a2, fatB-a3/fatB-a3, FATB-C1/FATB-C1, fatB-c2/FATB-C2, fatB-c3/fatB-c3,
fatB-a1/FATB-A1, fatB-a2/fatB-a2, FATB-A3/FATB-A3, fatB-c1/fatB-c1, fatB-c2/fatB-c2, FATB-C3/FATB-C3,
FATB-A1/FATB-A1, fatB-a2/fatB-a2, fatB-a3/FATB-A3, fatB-c1/fatB-c1, fatB-c2/fatB-c2, FATB-C3/FATB-C3,
FATB-A1/FATB-A1, fatB-a2/fatB-a2, FATB-A3/FATB-A3, fatB-c1/fatB-c1, fatB-c2/fatB-c2, fatB-c3/FATB-C3,
fatB-a1/FATB-A1, fatB-a2/fatB-a2, FATB-A3/FATB-A3, fatB-c1/fatB-c1, FATB-C2/FATB-C2, fatB-c3/fatB-c3,
FATB-A1/FATB-A1, fatB-a2/fatB-a2, fatB-a3/FATB-A3, fatB-c1/fatB-c1, FATB-C2/FATB-C2, fatB-c3/fatB-c3,
FATB-A1/FATB-A1, fatB-a2/fatB-a2, FATB-A3/FATB-A3, fatB-c1/fatB-c1, FATB-C2/FATB-C2, fatB-c3/fatB-c3,
fatB-a1/FATB-A1, fatB-a2/fatB-a2, FATB-A3/FATB-A3, FATB-C1/FATB-C1, fatB-c2/fatB-c2, fatB-c3/fatB-c3,
FATB-A1/FATB-A1, fatB-a2/fatB-a2, fatB-a3/FATB-A3, FATB-C1/FATB-C1, fatB-c2/fatB-c2, fatB-c3/fatB-c3,
FATB-A1/FATB-A1, fatB-a2/fatB-a2, FATB-A3/FATB-A3, fatB-c1/FATB-C1, fatB-c2/fatB-c2, fatB-c3/fatB-c3,
fatB-a1/FATB-A1, FATB-A2/FATB-A2, fatB-a3/fatB-a3, fatB-c1/fatB-c1, fatB-c2/fatB-c2, FATB-C3/FATB-C3,
FATB-A1/FATB-A1, fatB-a2/FATB-A2, fatB-a3/fatB-a3, fatB-c1/fatB-c1, fatB-c2/fatB-c2, FATB-C3/FATB-C3,
FATB-A1/FATB-A1, FATB-A2/FATB-A2, fatB-a3/fatB-a3, fatB-c1/fatB-c1, fatB-c2/fatB-c2, fatB-c3/FATB-C3,
fatB-a1/FATB-A1, FATB-A2/FATB-A2, fatB-a3/fatB-a3, fatB-c1/fatB-c1, FATB-C2/FATB-C2, fatB-c3/fatB-c3,
FATB-A1/FATB-A1, fatB-a2/FATB-A2, fatB-a3/fatB-a3, fatB-c1/fatB-c1, FATB-C2/FATB-C2, fatB-c3/fatB-c3,
FATB-A1/FATB-A1, FATB-A2/FATB-A2, fatB-a3/fatB-a3, fatB-c1/fatB-c1, fatB-c2/FATB-C2, fatB-c3/fatB-c3,
fatB-a1/FATB-A1, FATB-A2/FATB-A2, fatB-a3/fatB-a3, FATB-C1/FATB-C1, fatB-c2/fatB-c2, fatB-c3/fatB-c3,
FATB-A1/FATB-A1, fatB-a2/FATB-A2, fatB-a3/fatB-a3, FATB-C1/FATB-C1, fatB-c2/fatB-c2, fatB-c3/fatB-c3,
FATB-A1/FATB-A1, FATB-A2/FATB-A2, fatB-a3/fatB-a3, fatB-c1/FATB-C1, fatB-c2/fatB-c2, fatB-c3/fatB-c3,
fatB-a1/FATB-A1, FATB-A2/FATB-A2, FATB-A3/FATB-A3, fatB-c1/fatB-c1, fatB-c2/fatB-c2, fatB-c3/fatB-c3,
FATB-A1/FATB-A1, fatB-a2/FATB-A2, FATB-A3/FATB-A3, fatB-c1/fatB-c1, fatB-c2/fatB-c2, fatB-c3/fatB-c3, or
FATB-A1/FATB-A1, FATB-A2/FATB-A2, fatB-a3/FATB-A3, fatB-c1/fatB-c1, fatB-c2/fatB-c2, fatB-c3/fatB-c3.

In still another embodiment of the invention, homozygous FATB quadruple mutant plants comprising one further mutant FATB allele are provided herein, wherein the genotype of the plant can be described as:
fatB-a1/fatB-a1, fatB-a2/fatB-a2, fatB-a3/fatB-a3, fatB-c1/fatB-c1, fatB-c2/FATB-C2, FATB-C3/FATB-C3,
fatB-a1/fatB-a1, fatB-a2/fatB-a2, fatB-a3/fatB-a3, fatB-c1/fatB-c1, FATB-C2/FATB-C2, fatB-c3/FATB-C3,
fatB-a1/fatB-a1, fatB-a2/fatB-a2, fatB-a3/fatB-a3, fatB-c1/FATB-C1, fatB-c2/fatB-c2, FATB-C3/FATB-C3,
fatB-a1/fatB-a1, fatB-a2/fatB-a2, fatB-a3/fatB-a3, FATB-C1/FATB-C1, fatB-c2/fatB-c2, fatB-c3/FATB-C3,
fatB-a1/fatB-a1, fatB-a2/fatB-a2, fatB-a3/fatB-a3, fatB-c1/FATB-C1, FATB-C2/FATB-C2, fatB-c3/fatB-c3,
fatB-a1/fatB-a1, fatB-a2/fatB-a2, fatB-a3/fatB-a3, FATB-C1/FATB-C1, fatB-c2/FATB-C2, fatB-c3/fatB-c3,
fatB-a1/fatB-a1, fatB-a2/fatB-a2, fatB-a3/FATB-A3, fatB-c1/fatB-c1, fatB-c2/fatB-c2, FATB-C3/FATB-C3,
fatB-a1/fatB-a1, fatB-a2, fatB-a2, FATB-A3/FATB-A3, fatB-c1/fatB-c1, fatB-c2/fatB-c2, fatB-c3/FATB-C3,
fatB-a1/fatB-a1, fatB-a2/fatB-a2, fatB-a3/FATB-A3, fatB-c1/fatB-c1, FATB-C2/FATB-C2, fatB-c3/fatB-c3,
fatB-a1/fatB-a1, fatB-a2/fatB-a2, FATB-A3/FATB-A3, fatB-c1/fatB-c1, fatB-c2/FATB-C2, fatB-c3/fatB-c3,
fatB-a1/fatB-a1, fatB-a2/fatB-a2, fatB-a3/FATB-A3, FATB-C1/FATB-C1, fatB-c2/fatB-c2, fatB-c3/fatB-c3,
fatB-a1/fatB-a1, fatB-a2/fatB-a2, FATB-A3/FATB-A3, fatB-c1/FATB-C1, fatB-c2/fatB-c2, fatB-c3/fatB-c3,
fatB-a1/fatB-a1, fatB-a2/FATB-A2, fatB-a3/fatB-a3, fatB-c1/fatB-c1, fatB-c2/fatB-c2, FATB-C3/FATB-C3,
fatB-a1/fatB-a1, FATB-A2/FATB-A2, fatB-a3/fatB-a3, fatB-c1/fatB-c1, fatB-c2/fatB-c2, fatB-c3/FATB-C3,
fatB-a1/fatB-a1, fatB-a2/FATB-A2, fatB-a3/fatB-a3, fatB-c1/fatB-c1, FATB-C2/FATB-C2, fatB-c3/fatB-c3,
fatB-a1/fatB-a1, FATB-A2/FATB-A2, fatB-a3/fatB-a3, fatB-c1/fatB-c1, FATB-C2/FATB-C2, fatB-c3/fatB-c3,
fatB-a1/fatB-a1, fatB-a2/FATB-A2, fatB-a3/fatB-a3, FATB-C1/FATB-C1, fatB-c2/fatB-c2, fatB-c3/fatB-c3,
fatB-a1/fatB-a1, FATB-A2/FATB-A2, fatB-a3/fatB-a3, FATB-C1/FATB-C1, fatB-c2/fatB-c2, fatB-c3/fatB-c3,
fatB-a1/fatB-a1, fatB-a2/FATB-A2, FATB-A3/FATB-A3, fatB-c1/fatB-c1, fatB-c2/fatB-c2, fatB-c3/fatB-c3,
fatB-a1/fatB-a1, FATB-A2/FATB-A2, fatB-a3/FATB-A3, fatB-c1/fatB-c1, fatB-c2/fatB-c2, fatB-c3/fatB-c3,
fatB-a1/FATB-A1, fatB-a2/fatB-a2, fatB-a3/fatB-a3, fatB-c1/fatB-c1, fatB-c2/fatB-c2, FATB-C3/FATB-C3,
FATB-A1/FATB-A1, fatB-a2/fatB-a2, fatB-a3/fatB-a3, fatB-c1/fatB-c1, fatB-c2/fatB-c2, fatB-c3/FATB-C3,
fatB-a1/FATB-A1, fatB-a2/fatB-a2, fatB-a3/fatB-a3, fatB-c1/fatB-c1, FATB-C2/FATB-C2, fatB-c3/fatB-c3,
FATB-A1/FATB-A1, fatB-a2/fatB-a2, fatB-a3/fatB-a3, fatB-c1/fatB-c1, fatB-c2/FATB-C2, fatB-c3/fatB-c3,
fatB-a1/FATB-A1, fatB-a2/fatB-a2, fatB-a3/fatB-a3, FATB-C1/FATB-C1, fatB-c2/fatB-c2, fatB-c3/fatB-c3,
FATB-A1/FATB-A1, fatB-a2/fatB-a2, fatB-a3/fatB-a3, fatB-c1/FATB-C1, fatB-c2/fatB-c2, fatB-c3/fatB-c3,
fatB-a1/FATB-A1, fatB-a2/fatB-a2, FATB-A3/FATB-A3, fatB-c1/fatB-c1, fatB-c2/fatB-c2, fatB-c3/fatB-c3,
FATB-A1/FATB-A1, fatB-a2/fatB-a2, fatB-a3/FATB-A3, fatB-c1/fatB-c1, fatB-c2/fatB-c2, fatB-c3/fatB-c3,
fatB-a1/FATB-A1, FATB-A2/FATB-A2, fatB-a3/fatB-a3, fatB-c1/fatB-c1, fatB-c2/fatB-c2, fatB-c3/fatB-c3, or
FATB-A1/FATB-A1, fatB-a2/FATB-A2, fatB-a3/fatB-a3, fatB-c1/fatB-c1, fatB-c2/fatB-c2, fatB-c3/fatB-c3.

In a further embodiment of the invention, homozygous FATB quintuple mutant plants comprising one further mutant FATB allele are provided herein, wherein the genotype of the plant can be described as:
fatB-a1/fatB-a1, fatB-a2/fatB-a2, fatB-a3/fatB-a3, fatB-c1/fatB-c1, fatB-c2/fatB-c2, FATB-C3/fatB-c3,
fatB-a1/fatB-a1, fatB-a2/fatB-a2, fatB-a3/fatB-a3, fatB-c1/fatB-c1, fatB-c2/FATB-C2, fatB-c3/fatB-c3,
fatB-a1/fatB-a1, fatB-a2/fatB-a2, fatB-a3/fatB-a3, fatB-c1/FATB-C1, fatB-c2/fatB-c2, fatB-c3/fatB-c3,
fatB-a1/fatB-a1, fatB-a2/fatB-a2, fatB-a3/fatB-a3, FATB-A3, fatB-c1/fatB-c1, fatB-c2/fatB-c2, fatB-c3/fatB-c3,
fatB-a1/fatB-a1, fatB-a2/FATB-A2, fatB-a3/fatB-a3, fatB-c1/fatB-c1, fatB-c2/fatB-c2, fatB-c3/fatB-c3, or fatB-a1/FATB-A1, fatB-a2/fatB-a2, fatB-a3/fatB-a3, fatB-c1/fatB-c1, fatB-c2/fatB-c2, fatB-c3/fatB-c3.

Further provided herein are nucleic acid sequences of wild type and mutant FATB genes/alleles from *Brassica* species, as well as the wild type and mutant FATB proteins. Also provided are methods of generating and combining mutant and wild type FATB alleles in *Brassica* plants, as well as *Brassica* plants and plant parts comprising specific combinations of wild type and mutant FATB alleles in their genome, whereby these plants produce seed oil with low saturates or no saturates, and whereby the plants preferably grow normally and have a normal phenotype. The use of these plants for transferring mutant FATB alleles to other plants is also an embodiment of the invention, as are the plant products of any of the plants described. In addition kits and methods for marker assisted selection (MAS) for combining or detecting FATB genes and/or alleles are provided. Each of the embodiments of the invention is described in detail herein below.

Nucleic Acid Sequences According to the Invention

Provided are both wild type (FATB) nucleic acid sequences, encoding functional FATB proteins, and mutant (fatB) nucleic acid sequences (comprising one or more mutations, preferably mutations which result in a significantly reduced biological activity of the encoded FATB protein or in no FATB protein being produced) of FATB genes from *Brassica* species, especially from *Brassica napus*, but also from other *Brassica* crop species. For example, *Brassica* species comprising an A and/or a C genome may comprise different alleles of FATB-A or FATB-C genes which can be identified and combined in a single plant according to the invention. In addition, mutagenesis methods can be used to generate mutations in wild type FATB alleles, thereby generating mutant alleles for use according to the invention. Because specific FATB alleles are preferably combined in a *Brassica napus* plant by crossing and selection, in one embodiment the FATB and/or fatB nucleic acid sequences are provided within a *Brassica* plant (i.e. endogenously) which can be crossed with *Brassica napus* or which can be used to make a "synthetic" *Brassica napus* plant. Hybridization between different *Brassica* species is described in the art, e.g., as referred to in Snowdon (2007, Chromosome research 15: 85-95). Interspecific hybridization can, for example, be used to transfer genes from, e.g., the C genome in *B. napus* (AACC) to the C genome in *B. carinata* (BBCC), or even from, e.g., the C genome in *B. napus* (AACC) to the B genome in *B. juncea* (AABB) (by the sporadic event of illegitimate recombination between their C and B genomes). "Resynthesized" or "synthetic" *Brassica napus* lines can be produced by crossing the original ancestors, *B. oleracea* (CC) and *B. rapa* (AA). Interspecific, and also intergeneric, incompatibility barriers can be successfully overcome in crosses between *Brassica* crop species and their relatives, e.g., by embryo rescue techniques or protoplast fusion (see e.g. Snowdon, above).

However, isolated FATB and fatB nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional protein or a protein with significantly reduced or no functionality (e.g. by expression in a recombinant host cell and enzyme assays) and for selection and transfer of specific alleles from one *Brassica* plant into another, in order to generate a plant having the desired combination of functional and mutant alleles.

Nucleic acid sequences of FATB-A1, FATB-A2, FATB-A3, FATB-C1, FATB-C2 and FATB-C3 have been isolated from *Brassica napus* winter oilseed rape (WOSR) and spring oilseed rape (SOSR), as depicted in the sequence listing. The wild type FATB sequences are depicted, while the mutant fatB sequences of these sequences, and of sequences essentially similar to these, are described herein below and in the Examples, with reference to the wild type FATB sequences. The genomic FATB protein-encoding DNA, and corresponding pre-mRNA, comprises 5 exons (numbered exons 1-5 starting from the 5' end) interrupted by 4 introns (numbered introns 1-4, starting from the 5' end). In the cDNA and corresponding processed mRNA (i.e. the spliced RNA), introns are removed and exons are joined, as depicted in the sequence listing. Exon sequences are more conserved evolutionarily and are therefore less variable than intron sequences.

"FATB-A1 nucleic acid sequences" or "FATB-A1 variant nucleic acid sequences" according to the invention are nucleic acid sequences encoding an amino acid sequence having at least 80%, at least 85%, at least 90%, at least 95%, 98%, 99% or 100% sequence identity with SEQ ID NO: 2 (WOSR FATB-A1) when aligned with or without transit peptide and/or with SEQ ID NO: 14 (SOSR FATB-A1) when aligned with or without transit peptide or nucleic acid sequences having at least 80%, at least 85%, at least 90%, at least 95%, 96%, 97%, 98%, 99% or 100% sequence identity with SEQ ID NO: 1 (WOSR FATB-A1) when aligned with or without introns 1-4 and/or with SEQ ID NO: 13 (SOSR FATB-A1) when aligned with or without introns 1-4. These nucleic acid sequences may also be referred to as being "essentially similar" or "essentially identical" the FATB sequences provided in the sequence listing.

"FATB-A2 nucleic acid sequences" or "FATB-A2 variant nucleic acid sequences" according to the invention are nucleic acid sequences encoding an amino acid sequence having at least 80%, at least 85%, at least 90%, at least 95%, 98%, 99% or 100% sequence identity with SEQ ID NO: 4 (WOSR FATB-A2) when aligned with or without transit peptide and/or with SEQ ID NO: 16 (SOSR FATB-A2) when aligned with or without transit peptide or nucleic acid sequences having at least 80%, at least 85%, at least 90%, at least 95%, 96%, 97%, 98%, 99% or 100% sequence identity with SEQ ID NO: 3 (WOSR FATB-A2) when aligned with or without introns 1-4 and/or SEQ ID NO: 15 (SOSR FATB-A2) when aligned with or without introns 1-4. These nucleic acid sequences may also be referred to as being "essentially similar" or "essentially identical" the FATB sequences provided in the sequence listing.

"FATB-A3 nucleic acid sequences" or "FATB-A3 variant nucleic acid sequences" according to the invention are nucleic acid sequences encoding an amino acid sequence having at least 80%, at least 85%, at least 90%, at least 95%, 98%, 99% or 100% sequence identity with SEQ ID NO: 6 (WOSR FATB-A3) when aligned with or without transit peptide and/or with SEQ ID NO: 18 (SOSR FATB-A3) when aligned with or without transit peptide or nucleic acid sequences having at least 80%, at least 85%, at least 90%, at least 95%, 96%, 97%, 98%, 99% or 100% sequence identity with SEQ ID NO: 5 (WOSR FATB-A3) when aligned with or without introns 1-4 and/or SEQ ID NO: 17 (SOSR FATB-A3) when aligned with or without introns 1-4. These nucleic acid sequences may also be referred to as being "essentially similar" or "essentially identical" the FATB sequences provided in the sequence listing.

"FATB-C1 nucleic acid sequences" or "FATB-C1 variant nucleic acid sequences" according to the invention are nucleic acid sequences encoding an amino acid sequence having at least 80%, at least 85%, at least 90%, at least 95%, 98%, 99% or 100% sequence identity with SEQ ID NO: 8

(WOSR FATB-C1) when aligned with or without transit peptide and/or with SEQ ID NO: 20 (SOSR FATB-C1) when aligned with or without transit peptide or nucleic acid sequences having at least 80%, at least 85%, at least 90%, at least 95%, 96%, 97%, 98%, 99% or 100% sequence identity with SEQ ID NO: 7 (WOSR FATB-C1) when aligned with or without introns 1-4 and/or with SEQ ID NO: 19 (SOSR FATB-C1) when aligned with or without introns 1-4. These nucleic acid sequences may also be referred to as being "essentially similar" or "essentially identical" the FATB sequences provided in the sequence listing.

"FATB-C2 nucleic acid sequences" or "FATB-C2 variant nucleic acid sequences" according to the invention are nucleic acid sequences encoding an amino acid sequence having at least 80%, at least 85%, at least 90%, at least 95%, 98%, 99% or 100% sequence identity with SEQ ID NO: 10 (WOSR FATB-C2) when aligned with or without transit peptide and/or with SEQ ID NO: 22 (SOSR FATB-C2) when aligned with or without transit peptide or nucleic acid sequences having at least 80%, at least 85%, at least 90%, at least 95%, 96%, 97%, 98%, 99% or 100% sequence identity with SEQ ID NO: 9 (WOSR FATB-C2) when aligned with or without introns 1-4 and/or SEQ ID NO: 21 (SOSR FATB-C2) when aligned with or without introns 1-4. These nucleic acid sequences may also be referred to as being "essentially similar" or "essentially identical" the FATB sequences provided in the sequence listing.

"FATB-C3 nucleic acid sequences" or "FATB-C3 variant nucleic acid sequences" according to the invention are nucleic acid sequences encoding an amino acid sequence having at least 80%, at least 85%, at least 90%, at least 95%, 98%, 99% or 100% sequence identity with SEQ ID NO: 12 (WOSR FATB-C3) when aligned with or without transit peptide and/or with SEQ ID NO: 24 (SOSR FATB-C3) when aligned with or without transit peptide or nucleic acid sequences having at least at least 80%, at least 85%, at least 90%, at least 95%, 96%, 97%, 98%, 99% or 100% sequence identity with SEQ ID NO: 11 (WOSR FATB-C3) when aligned with or without introns 1-4 and/or SEQ ID NO: 23 (SOSR FATB-C3) when aligned with or without introns 1-4. These nucleic acid sequences may also be referred to as being "essentially similar" or "essentially identical" the FATB sequences provided in the sequence listing.

Thus, the invention provides both nucleic acid sequences encoding wild type, functional FATB-A1, FATB-A2, FATB-A3, FATB-C1, FATB-C2 and FATB-C3 proteins, including variants and fragments thereof (as defined further below), as well as mutant nucleic acid sequences of any of these, whereby the mutation in the nucleic acid sequence preferably results in one or more amino acids being inserted, deleted or substituted in comparison to the wild type protein. Preferably the mutation(s) in the nucleic acid sequence result in one or more amino acid changes (i.e. in relation to the wild type amino acid sequence one or more amino acids are inserted, deleted and/or substituted) whereby the biological activity of the FATB protein is significantly reduced. A significant reduction in biological activity of the mutant FATB protein, refers to a reduction in enzymatic activity (i.e. in acyl ACP-thioesterase activity) by at least 30%, at least 40%, 50% or more, at least 90% or 100% (no biological activity) compared to the activity of the wild type protein.

Both endogenous and isolated nucleic acid sequences are provided herein. Also provided are fragments of the FATB sequences and FATB variant nucleic acid sequences defined above, for use as primers or probes and as components of kits according to another aspect of the invention (see further below). A "fragment" of a FATB or fatB nucleic acid sequence or variant thereof (as defined) may be of various lengths, such as at least 10, 12, 15, 18, 20, 50, 100, 200, 500, 1000 contiguous nucleotides of the FATB or fatB sequence (or of the variant sequence).

Nucleic Acid Sequences Encoding Functional FATB Proteins

The nucleic acid sequences depicted in the sequence listing encode wild type, functional FATB proteins from *Brassica napus*. Thus, these sequences are endogenous to the WOSR and SOSR plants from which they were isolated. Other *Brassica* crop species, varieties, breeding lines or wild accessions may be screened for other FATB alleles, encoding the same FATB proteins or variants thereof. For example, nucleic acid hybridization techniques (e.g. Southern blot, using for example stringent hybridization conditions) or PCR-based techniques may be used to identify FATB alleles endogenous to other *Brassica* plants, such as various *Brassica napus* varieties, lines or accessions, but also *Brassica juncea* (especially FATB alleles on the A-genome), *Brassica carinata* (especially FATB alleles on the C-genome) and *Brassica rapa* (A-genome) and *Brassica oleracea* (C-genome) plants and tissues can be screened for other wild type FATB alleles. To screen such plants or plant tissues for the presence of FATB alleles, the FATB nucleic acid sequences provided in the sequence listing, or variants or fragments of any of these, may be used. For example whole sequences or fragments may be used as probes or primers. For example specific or degenerate primers may be used to amplify nucleic acid sequences encoding FATB proteins from the genomic DNA of the plant or plant tissue. These FATB nucleic acid sequences may be isolated and sequenced using standard molecular biology techniques. Bioinformatics analysis may then be used to characterize the allele(s), for example in order to determine which FATB allele the sequence corresponds to and which FATB protein or protein variant is encoded by the sequence.

Whether a nucleic acid sequence encodes a functional FATB protein can be analyzed by recombinant DNA techniques as known in the art, e.g. expressing the nucleic acid molecule in a host cell (e.g. a bacterium, such as *E. coli*) and analyzing the acyl-ACP thioesterase activity and/or substrate specificity of the resulting protein or cells. For example, fatty acyl-ACP hydrolysis after recombinant expression in *E. coli* is described by Doermann et al., 2000 (Plant Physiology 123: 637-643) and Doermann et al. 1995 (Arch Biochem Biophys 316: 612-618), by Yuan et al. (1995, PNAS Vol 92: 10639-10643), by Salas and Ohlrogge (2002, Archives of Biochemistry and Biophysics 403:25-34) and by Mayer and Shanklin (2007, BMC Plant Biology 7(1):1-11). Also, assays for fatty acyl-ACP hydrolysis using crude plant tissue homogenates have been described by Eccleston and Ohlrogge (for C12:0- and C18:1-ACP hydrolysis; 1998, Plant Cell 10: 613-622), by Salas and Ohlrogge (2002, Archives of Biochemistry and Biophysics 403:25-34) and by Bonaventure et al. (for C16:0-ACP and C18:1-ACP hydrolysis; 2003, Plant Cell 15:1020-1033).

In addition, it is understood that FATB nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below. Fragments include nucleic acid sequences encoding only the mature protein, or smaller fragments comprising all or part of the exon and/or intron sequences, etc.

Nucleic Acid Sequences Encoding Mutant FATB Proteins

Nucleic acid sequences comprising one or more nucleotide deletions, insertions or substitutions relative to the wild type nucleic acid sequences are another embodiment of the invention, as are fragments of such mutant nucleic acid molecules. Such mutant nucleic acid sequences (referred to as fatB sequences) can be generated and/or identified using various known methods, as described further below. Again, such nucleic acid molecules are provided both in endogenous form and in isolated form. In one embodiment, the mutation(s) result in one or more changes (deletions, insertions and/or substitutions) in the amino acid sequence of the encoded FATB protein (i.e. it is not a "silent mutation"). In another embodiment, the mutation(s) in the nucleic acid sequence result in a significantly reduced or completely abolished biological activity of the encoded FATB protein relative to the wild type protein.

The nucleic acid molecules may, thus, comprise one or more mutations, such as:

(a) a "missense mutation", which is a change in the nucleic acid sequence that results in the substitution of an amino acid for another amino acid;
(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.
(c) an "insertion mutation" of one or more amino acids, due to one or more codons having been added in the coding sequence of the nucleic acid;
(d) a "deletion mutation" of one or more amino acids, due to one or more codons having been deleted in the coding sequence of the nucleic acid;
(e) a "frameshift mutation", resulting in the nucleic acid sequence being translated in a different frame downstream of the mutation. A frameshift mutation can have various causes, such as the insertion, deletion or duplication of one or more nucleotides, but also mutations which affect pre-mRNA splicing (splice site mutations) can result in frameshifts;
(f) a "splice site mutation", which alters or abolishes the correct splicing of the pre-mRNA sequence, resulting in a protein of different amino acid sequence than the wild type. For example, one or more exons may be skipped during RNA splicing, resulting in a protein lacking the amino acids encoded by the skipped exons. Alternatively, the reading frame may be altered through incorrect splicing, or one or more introns may be retained, or alternate splice donors or acceptors may be generated, or splicing may be initiated at an alternate position (e.g. within an intron), or alternate polyadenylation signals may be generated. Correct pre-mRNA splicing is a complex process, which can be affected by various mutations in the nucleotide sequence of the FATB-encoding gene. In higher eukaryotes, such as plants, the major spliceosome splices introns containing GU at the 5' splice site (donor site) and AG at the 3' splice site (acceptor site). This GU-AG rule (or GT-AG rule; see Lewin, Genes VI, Oxford University Press 1998, pp 885-920, ISBN 0198577788) is followed in about 99% of splice sites of nuclear eukaryotic genes, while introns containing other dinucleotides at the 5' and 3' splice site, such as GC-AG and AU-AC account for only about 1% and 0.1% respectively.

As already mentioned, it is desired that the mutation(s) in the nucleic acid sequence preferably result in a mutant protein comprising significantly reduced or no enzymatic activity in vivo. Basically, any mutation which results in a protein comprising at least one amino acid insertion, deletion and/or substitution relative to the wild type protein can lead to significantly reduced or no enzymatic activity. It is, however, understood that mutations in certain parts of the protein are more likely to result in a reduced function of the mutant FATB protein, such as mutations leading to truncated proteins, whereby significant portions of the functional domains, such as the catalytic domain, are lacking.

The FATB proteins of Brassica described herein are about 412-424 amino acids in length and comprise a number of structural (and functional) domains. These include the following: An N-terminal plastid target peptide of about 60 amino acids followed by a hydrophobic region about 18 amino acids (proposed to form a helical trans-membrane anchor). This N-terminal part of roughly about 90 amino acids in total is followed by what constitutes the mature FATS protein (starting with the N-terminal amino acids LPDWSM (SEQ ID NO: 103)). It contains a tandem repeat of a helix/4-stranded sheet domain ("HEEEE" or "4HBT" domain, also "hot dog motif) separated by a linker region (Mayer and Shanklin, 2005, J. Biol. Chem. 280(5): 3621-3627). The first (N-terminal) helix/4-stranded sheet domain (which is encoded by a part of exon 1, the whole of exon 2 and 3 and a part of exon 4) comprises amino acid residues that are thought to affect substrate specificity, in particular two conserved methionines (Met or M), a conserved lysine (Lys or K), a conserved valine (Val or V), and a conserved serine (Ser or S) (Mayer and Shanklin, 2007, BMC Plant Biology 7(1):1-11) and the second (C-terminal) helix/4-stranded sheet domain (encoded largely by exon 5) comprises catalytic amino acid residues, in particular a papain-like catalytic triad of a conserved asparagine (Asn or N), a conserved histidine (His or H) residue and a conserved cysteine (Cys or C). The catalytic triad is located within the second helix/4-stranded sheet domain, encoded by exon 5 of the protein. The second HEEEE domain comprises further amino acid residues that are thought to affect substrate specificity, in particular a conserved tryptophan (Trp or W) (Mayer and Shanklin, 2007, supra).

TABLE 1a

WOSR FATB proteins - amino acids (aa) regions and positions

| | FATB-A1 SEQ ID: 2 | FATB-A2 SEQ ID: 4 | FATB-A3 SEQ ID: 6 | FATB-C1 SEQ ID: 8 | FATB-C2 SEQ ID: 10 | FATB-C3 SEQ ID: 12 | AtFATB SEQ ID: 80 |
|---|---|---|---|---|---|---|---|
| Protein size (aa) | 414 | 424 | 415 | 412 | 415 | 415 | 412 |
| N-terminal | 1-90 | 1-90 | 1-91 | 1-88 | 1-90 | 1-91 | 1-88 |
| Mature protein | 91-414 | 91-424 | 92-415 | 89-412 | 91-415 | 92-415 | 89-412 |

TABLE 1a-continued

WOSR FATB proteins - amino acids (aa) regions and positions

|  | FATB-A1 SEQ ID: 2 | FATB-A2 SEQ ID: 4 | FATB-A3 SEQ ID: 6 | FATB-C1 SEQ ID: 8 | FATB-C2 SEQ ID: 10 | FATB-C3 SEQ ID: 12 | AtFATB SEQ ID: 80 |
|---|---|---|---|---|---|---|---|
| aa encoded by exon 1 | 1-168 | 1-168 | 1-169 | 1-166 | 1-168 | 1-169 | 1-166 |
| aa encoded by exon 2 | 169-213 | 169-213 | 170-214 | 167-211 | 169-213 | 170-214 | 167-211 |
| aa encoded by exon 3 | 214-251 | 214-251 | 215-252 | 212-249 | 214-251 | 215-252 | 212-249 |
| aa encoded by exon 4 | 252-308 | 252-308 | 253-309 | 250-306 | 252-308 | 253-309 | 250-306 |
| aa encoded by exon 5 | 309-414 | 309-424 | 310-415 | 307-412 | 309-415 | 310-415 | 207-412 |
| 4HBT | 140-277 | 140-277 | 141-278 | 138-275 | 140-277 | 141-278 | 138-275 |
| linker | 278-302 | 278-302 | 279-303 | 276-300 | 278-302 | 279-303 | 276-300 |
| 4HBT Conserved | 303-407 | 303-407 | 304-408 | 301-405 | 303-407 | 304-408 | 301-405 |
| Met (M) | 164 | 164 | 165 | 162 | 164 | 165 | 162 |
| Lys (K) | 176 | 176 | 177 | 174 | 176 | 177 | 174 |
| Val (V) | 200 | 200 | 201 | 198 | 200 | 201 | 198 |
| Met (M) | 231 | 231 | 232 | 229 | 231 | 232 | 229 |
| Ser (S) | 264 | 264 | 265 | 262 | 264 | 265 | 262 |
| Trp (W) | 311 | 311 | 312 | 309 | 311 | 312 | 309 |
| Asn (N) | 317 | 317 | 318 | 315 | 317 | 318 | 315 |
| His (H) | 319 | 319 | 320 | 317 | 319 | 320 | 317 |
| Cys (C) | 354 | 354 | 355 | 352 | 354 | 355 | 352 |

TABLE 1b

SOSR FATB proteins - amino acid (aa) regions and positions

|  | FATB-A1 SEQ ID: 14 | FATB-A2 SEQ ID: 16 | FATB-A3 SEQ ID: 18 | FATB-C1 SEQ ID: 20 | FATB-C2 SEQ ID: 22 | FATB-C3 SEQ ID: 24 |
|---|---|---|---|---|---|---|
| Protein size (aa) | 413 | 415 | 415 | 412 | 415 | 415 |
| N-terminal | 1-89 | 1-90 | 1-91 | 1-88 | 1-90 | 1-91 |
| Mature protein | 90-413 | 91-415 | 92-415 | 89-412 | 91-415 | 92-415 |
| aa encoded by exon 1 | 1-167 | 1-168 | 1-169 | 1-166 | 1-168 | 1-169 |
| aa encoded by exon 2 | 168-212 | 169-213 | 170-214 | 167-211 | 169-213 | 170-214 |
| aa encoded by exon 3 | 213-250 | 214-251 | 215-252 | 212-249 | 214-251 | 215-252 |
| aa encoded by exon 4 | 251-307 | 252-308 | 253-309 | 250-306 | 252-308 | 253-309 |
| aa encoded by exon 5 | 308-413 | 309-415 | 310-415 | 307-412 | 309-415 | 310-415 |
| 4HBT | 139-276 | 140-277 | 141-278 | 138-275 | 140-277 | 141-278 |
| linker | 277-301 | 278-302 | 279-303 | 276-300 | 278-302 | 279-303 |
| 4HBT Conserved | 302-406 | 303-407 | 304-408 | 301-405 | 303-407 | 304-408 |
| Met (M) | 163 | 164 | 165 | 162 | 164 | 165 |
| Lys (K) | 175 | 176 | 177 | 174 | 176 | 177 |
| Val (V) | 199 | 200 | 201 | 198 | 200 | 201 |
| Met (M) | 230 | 231 | 232 | 229 | 231 | 232 |
| Ser (S) | 263 | 264 | 265 | 262 | 264 | 265 |
| Trp (W) | 310 | 311 | 312 | 309 | 311 | 312 |
| Asn (N) | 316 | 317 | 318 | 315 | 317 | 318 |
| His (H) | 318 | 319 | 320 | 317 | 319 | 320 |
| Cys (C) | 353 | 354 | 355 | 352 | 354 | 355 |

Thus in one embodiment, nucleic acid sequences comprising one or more of any of the types of mutations described above are provided. In another embodiment, fatB sequences comprising one or more deletion mutations, one or more stop codon (nonsense) mutations and/or one or more splice site mutations are provided. Any of the above mutant nucleic acid sequences are provided per se (in isolated form), as are plants and plant parts comprising such sequences endogenously.

A deletion mutation in a FATB allele, as used herein, is a mutation in a FATB allele whereby at least 1, at least 2, 3, 4, 5, 10, 20, 30, 50, 100, 200, 500, 1000 or more bases are deleted from the corresponding wild type FATB allele, and whereby the deletion results in the mutant FATB allele being transcribed and translated into a mutant protein which has significantly reduced or no activity in vivo. A deletion may lead to a frameshift and/or it may introduce a premature stop codon, or may lead to one amino acid or more amino acids (e.g. large parts) of coding sequence being removed, etc. The exact underlying molecular basis by which the deletion results in a mutant protein having significantly reduced biological activity is not important. Also provided herein are plants and plant parts in which specific FATB alleles are completely deleted, i.e. plants and plant parts lacking one or more FATB alleles.

A nonsense mutation in a FATB allele, as used herein, is a mutation in a FATB allele whereby one or more translation stop codons are introduced into the coding DNA and the corresponding mRNA sequence of the corresponding wild type FATB allele. Translation stop codons are TGA (UGA in the mRNA), TAA (UAA) and TAG (UAG). Thus, any mutation (deletion, insertion or substitution) which leads to the generation of an in-frame stop codon in the coding sequence (exon sequence) will result in termination of translation and truncation of the amino acid chain. In one embodiment, a mutant FATB allele comprising a nonsense mutation is a FATB allele wherein an in-frame stop codon is introduced in the FATB codon sequence by a single nucleotide substitution, such as the mutation of CAG to TAG, TGG to TAG, TGG to TGA, or CGA to TGA. In another embodiment, a mutant FATB allele comprising a nonsense mutation is a FATB allele wherein an in-frame stop codon is introduced in the FATB codon sequence by double nucleotide substitutions, such as the mutation of CAG to TAA, TGG to TAA, CGG to TAG or TGA, CGA to TAA. In yet another embodiment, a mutant FATB allele comprising a nonsense mutation is a FATB allele wherein an in-frame stop codon is introduced in the FATB codon sequence by triple nucleotide substitutions, such as the mutation of CGG to TAA. The truncated protein lacks the amino acids encoded by the coding DNA downstream of the mutation (i.e. the C-terminal part of the FATB protein) and maintains the amino acids encoded by the coding DNA upstream of the mutation (i.e. the N-terminal part of the FATB protein). In one embodiment, the nonsense mutation is present anywhere in front of the conserved Cys residue of the catalytic triad, so that at least the conserved Cys residue is lacking, resulting in significantly reduced activity of the truncated protein. The more truncated the mutant protein is in comparison to the wild type protein, the more likely it is that it will lack any enzymatic activity. Thus in another embodiment, a mutant FATB allele comprising a nonsense mutation which result in a truncated protein of less than 350 amino acids (lacking the conserved Cys), less than 315 amino acids (lacking all three conserved amino acids from the papain-like catalytic triad), less than 300 amino acids (lacking the second 4HBT domain), less than 262 amino acids (lacking the conserved Ser), less than 229 amino acids (lacking the second conserved Met), less than 198 amino acids (lacking the conserved Val), less than 174 amino acids (lacking the conserved Lys), less than 162 amino acids (lacking the first conserved Met), or even less amino acids in length are provided. In yet another embodiment, the nonsense mutation results in one or more exons not being translated into protein, such as exon 5, exons 4 and 5, exons 3-5, or even more.

The Tables herein below describe a range of possible nonsense mutations in the *Brassica napus* sequences provided herein:

TABLE 2a

Potential STOP codon mutations in FATB-A1 (WOSR, SEQ ID NO: 1 and 2)

| Exon number | Amino acid position | Nucleotide position | Wild type → mutant codon |
| --- | --- | --- | --- |
| exon 1 | 53 | 157 | cag → tag |
| exon 1 |  | 157 + 159 | cag → taa |
| exon 1 | 79 | 235 | cag → tag |
| exon 1 |  | 235 + 237 | cag → taa |
| exon 1 | 90 | 268 | cag → tag |
| exon 1 |  | 268 + 270 | cag → taa |
| exon 1 | 94 | 281 | tgg → tag |
| exon 1 |  | 282 | tgg → tga |
| exon 1 |  | 281 + 282 | tgg → taa |
| exon 1 | 111 | 331 | cag → tag |
| exon 1 |  | 331 + 333 | cag → taa |
| exon 1 | 112 | 335 | tgg → tag |
| exon 1 |  | 336 | tgg → tga |
| exon 1 |  | 335 + 336 | tgg → taa |
| exon 1 | 117 | 350 | tgg → tag |
| exon 1 |  | 351 | tgg → tga |
| exon 1 |  | 350 + 351 | tgg → taa |
| exon 1 | 136 | 406 | cag → tag |
| exon 1 |  | 406 + 408 | cag → taa |
| exon 1 | 143 | 427 | cag → tag |
| exon 1 |  | 427 + 429 | cag → taa |
| exon 1 | 148 | 442 + 443 | cgg → tag |
| exon 1 |  | 442 + 444 | cgg → tga |
| exon 1 |  | 442 + 443 + 444 | cgg → taa |
| exon 1 | 168 | 502 | cag → tag |
| exon 1 |  | 502 + 504 | cag → taa |
| exon 2 | 198 | 678 | tgg → tag |
| exon 2 |  | 679 | tgg → tga |
| exon 2 |  | 678 + 679 | tgg → taa |
| exon 2 | 204 | 695 | cag → tag |
| exon 2 |  | 695 + 697 | cag → taa |
| exon 2 | 213 | 723 | tgg → tag |
| exon 3 |  | 798 | tgg → tga |
| exon 2-3 |  | 723 + 798 | tgg → taa |
| exon 3 | 222 | 824 | tgg → tag |
| exon 3 |  | 825 | tgg → tga |

TABLE 2a-continued

Potential STOP codon mutations in FATB-A1 (WOSR, SEQ ID NO: 1 and 2)

| Exon number | Amino acid position | Nucleotide position | Wild type → mutant codon |
|---|---|---|---|
| exon 3 |  | 824 + 825 | tgg → taa |
| exon 3 | 225 | 832 | cag → tag |
| exon 3 |  | 832 + 834 | cag → taa |
| exon 3 | 235 | 863 | tgg → tag |
| exon 3 |  | 864 | tgg → tga |
| exon 3 |  | 863 + 864 | tgg → taa |
| exon 3 | 238 | 871 | cga → tga |
| exon 3 |  | 871 + 872 | cga → taa |
| exon 4 | 253 | 986 | tgg → tag |
| exon 4 |  | 987 | tgg → tga |
| exon 4 |  | 986 + 987 | tgg → taa |
| exon 4 | 271 | 1039 | cga → tga |
| exon 4 |  | 1039 + 1040 | cga → taa |
| exon 5 | 311 | 1250 | tgg → tag |
| exon 5 |  | 1251 | tgg → tga |
| exon 5 |  | 1250 + 1251 | tgg → taa |
| exon 5 | 318 | 1270 | cag → tag |
| exon 5 |  | 1270 + 1272 | cag → taa |
| exon 5 | 328 | 1301 | tgg → tag |
| exon 5 |  | 1302 | tgg → tga |
| exon 5 |  | 1301 + 1302 | tgg → taa |
| exon 5 | 341 | 1339 | cag → tag |
| exon 5 |  | 1339 + 1341 | cag → taa |
| exon 5 | 361 | 1399 | cag → tag |
| exon 5 |  | 1399 + 401 | cag → taa |
| exon 5 | 383 | 1465 | cag → tag |
| exon 5 |  | 1465 + 1467 | cag → taa |
| exon 5 | 389 | 1483 | cag → tag |
| exon 5 |  | 1483 + 1485 | cag → taa |
| exon 5 | 401 | 1520 | tgg → tag |
| exon 5 |  | 1521 | tgg → tga |
| exon 5 |  | 1520 + 1521 | tgg → taa |
| exon 5 | 410 | 1547 | tgg → tag |
| exon 5 |  | 1548 | tgg → tga |
| exon 5 |  | 1547 + 1548 | tgg → taa |

TABLE 2b

Potential STOP codon mutations in FATB-A1 (SOSR, SEQ ID NO: 13 and 14)

| Exon number | Amino acid position | Nucleotide position | Wild type → mutant codon |
|---|---|---|---|
| exon 1 | 53 | 157 | cag → tag |
| exon 1 |  | 157 + 159 | cag → taa |
| exon 1 | 78 | 232 | cag → tag |
| exon 1 |  | 232 + 234 | cag → taa |
| exon 1 | 89 | 265 | cag → tag |
| exon 1 |  | 265 + 267 | cag → taa |
| exon 1 | 93 | 278 | tgg → tag |
| exon 1 |  | 279 | tgg → tga |
| exon 1 |  | 278 + 279 | tgg → taa |
| exon 1 | 110 | 328 | cag → tag |
| exon 1 |  | 328 + 330 | cag → taa |
| exon 1 | 111 | 332 | tgg → tag |
| exon 1 |  | 333 | tgg → tga |
| exon 1 |  | 332 + 333 | tgg → taa |
| exon 1 | 116 | 347 | tgg → tag |
| exon 1 |  | 348 | tgg → tga |
| exon 1 |  | 347 + 348 | tgg → taa |
| exon 1 | 135 | 403 | cag → tag |
| exon 1 |  | 403 + 405 | cag → taa |
| exon 1 | 142 | 424 | cag → tag |
| exon 1 |  | 424 + 426 | cag → taa |
| exon 1 | 147 | 439 + 440 | cgg → tag |
| exon 1 |  | 439 + 441 | cgg → tga |
| exon 1 |  | 439 + 440 + 441 | cgg → taa |
| exon 1 | 167 | 499 | cag → tag |
| exon 1 |  | 499 + 501 | cag → taa |
| exon 2 | 197 | 675 | tgg → tag |
| exon 2 |  | 676 | tgg → tga |
| exon 2 |  | 675 + 676 | tgg → taa |
| exon 2 | 203 | 692 | cag → tag |
| exon 2 |  | 692 + 694 | cag → taa |
| exon 2 | 212 | 720 | tgg → tag |
| exon 3 |  | 795 | tgg → tga |
| exon 2-3 |  | 720 + 795 | tgg → taa |
| exon 3 | 221 | 821 | tgg → tag |
| exon 3 |  | 822 | tgg → tga |

TABLE 2b-continued

Potential STOP codon mutations in FATB-A1
(SOSR, SEQ ID NO: 13 and 14)

| Exon number | Amino acid position | Nucleotide position | Wild type → mutant codon |
|---|---|---|---|
| exon 3 | | 821 + 822 | tgg → taa |
| exon 3 | 224 | 829 | cag → tag |
| exon 3 | | 829 + 831 | cag → taa |
| exon 3 | 234 | 860 | tgg → tag |
| exon 3 | | 861 | tgg → tga |
| exon 3 | | 860 + 861 | tgg → taa |
| exon 3 | 237 | 868 | cga → tga |
| exon 3 | | 868 + 869 | cga → taa |
| exon 4 | 252 | 983 | tgg → tag |
| exon 4 | | 984 | tgg → tga |
| exon 4 | | 983 + 984 | tgg → taa |
| exon 4 | 270 | 1036 | cga → tga |
| exon 4 | | 1036 + 1037 | cga → taa |
| exon 5 | 310 | 1247 | tgg → tag |
| exon 5 | | 1248 | tgg → tga |
| exon 5 | | 1247 + 1248 | tgg → taa |
| exon 5 | 317 | 1267 | cag → tag |
| exon 5 | | 1267 + 1269 | cag → taa |
| exon 5 | 327 | 1298 | tgg → tag |
| exon 5 | | 1299 | tgg → tga |
| exon 5 | | 1298 + 1299 | tgg → taa |
| exon 5 | 340 | 1336 | cag → tag |
| exon 5 | | 1336 + 1338 | cag → taa |
| exon 5 | 360 | 1396 | cag → tag |
| exon 5 | | 1396 + 1398 | cag → taa |
| exon 5 | 382 | 1462 | cag → tag |
| exon 5 | | 1462 + 1464 | cag → taa |
| exon 5 | 388 | 1480 | cag → tag |
| exon 5 | | 1480 + 1482 | cag → taa |
| exon 5 | 400 | 1517 | tgg → tag |
| exon 5 | | 1518 | tgg → tga |
| exon 5 | | 1517 + 1518 | tgg → taa |
| exon 5 | 409 | 1544 | tgg → tag |
| exon 5 | | 1545 | tgg → tga |
| exon 5 | | 1544 + 1545 | tgg → taa |

TABLE 3a

Potential STOP codon mutations in FATB-A2
(WOSR, SEQ ID NO: 3 and 4)

| Exon number | Amino acid position | Nucleotide position | Wild type → mutant codon |
|---|---|---|---|
| exon 1 | 52 | 154 | cag → tag |
| exon 1 | | 154 + 156 | cag → taa |
| exon 1 | 79 | 235 | cag → tag |
| exon 1 | | 235 + 237 | cag → taa |
| exon 1 | 90 | 268 | cag → tag |
| exon 1 | | 268 + 270 | cag → taa |
| exon 1 | 94 | 281 | tgg → tag |
| exon 1 | | 282 | tgg → tga |
| exon 1 | | 281 + 282 | tgg → taa |
| exon 1 | 111 | 331 | cag → tag |
| exon 1 | | 331 + 333 | cag → taa |
| exon 1 | 112 | 335 | tgg → tag |
| exon 1 | | 336 | tgg → tga |
| exon 1 | | 335 + 336 | tgg → taa |
| exon 1 | 117 | 350 | tgg → tag |
| exon 1 | | 351 | tgg → tga |
| exon 1 | | 350 + 351 | tgg → taa |
| exon 1 | 136 | 406 | cag → tag |
| exon 1 | | 406 + 408 | cag → taa |
| exon 1 | 143 | 427 | cag → tag |
| exon 1 | | 427 + 429 | cag → taa |
| exon 1 | 168 | 502 | cag → tag |
| exon 1 | | 502 + 504 | cag → taa |
| exon 2 | 198 | 672 | tgg → tag |
| exon 2 | | 673 | tgg → tga |
| exon 2 | | 672 + 673 | tgg → taa |
| exon 2 | 204 | 689 | cag → tag |
| exon 2 | | 689 + 691 | cag → taa |
| exon 2 | 213 | 717 | tgg → tag |
| exon 3 | | 812 | tgg → tga |
| exon 2-3 | | 717 + 812 | tgg → taa |
| exon 3 | 222 | 838 | tgg → tag |
| exon 3 | | 839 | tgg → tga |
| exon 3 | | 838 + 839 | tgg → taa |
| exon 3 | 225 | 846 | cag → tag |
| exon 3 | | 846 + 848 | cag → taa |
| exon 3 | 235 | 877 | tgg → tag |

TABLE 3a-continued

Potential STOP codon mutations in FATB-A2
(WOSR, SEQ ID NO: 3 and 4)

| Exon number | Amino acid position | Nucleotide position | Wild type → mutant codon |
|---|---|---|---|
| exon 3 |  | 878 | tgg → tga |
| exon 3 |  | 877 + 878 | tgg → taa |
| exon 3 | 238 | 885 + 886 | cgg → tag |
| exon 3 |  | 885 + 887 | cgg → tga |
| exon 3 |  | 885 + 886 + 887 | cgg → taa |
| exon 3 | 248 | 915 | cga → tga |
| exon 3 |  | 915 + 916 | cga → taa |
| exon 4 | 253 | 1064 | tgg → tag |
| exon 4 |  | 1065 | tgg → tga |
| exon 4 |  | 1064 + 1065 | tgg → taa |
| exon 4 | 271 | 1117 | cga → tga |
| exon 4 |  | 1117 + 1118 | cga → taa |
| exon 5 | 311 | 1316 | tgg → tag |
| exon 5 |  | 1317 | tgg → tga |
| exon 5 |  | 1316 + 1317 | tgg → taa |
| exon 5 | 318 | 1336 | cag → tag |
| exon 5 |  | 1336 + 1338 | cag → taa |
| exon 5 | 328 | 1367 | tgg → tag |
| exon 5 |  | 1368 | tgg → tga |
| exon 5 |  | 1367 + 1368 | tgg → taa |
| exon 5 | 341 | 1405 | cag → tag |
| exon 5 |  | 1405 + 1407 | cag → taa |
| exon 5 | 361 | 1465 | cag → tag |
| exon 5 |  | 1465 + 1467 | cag → taa |
| exon 5 | 383 | 1531 | cag → tag |
| exon 5 |  | 1531 + 1533 | cag → taa |
| exon 5 | 387 | 1543 | cga → tga |
| exon 5 |  | 1543 + 1544 | cga → taa |
| exon 5 | 389 | 1549 | cag → tag |
| exon 5 |  | 1549 + 1551 | cag → taa |
| exon 5 | 401 | 1586 | tgg → tag |
| exon 5 |  | 1587 | tgg → tga |
| exon 5 |  | 1586 + 1587 | tgg → taa |
| exon 5 | 404 | 1594 | cag → tag |
| exon 5 |  | 1594 + 1596 | cag → taa |
| exon 5 | 410 | 1613 | tgg → tag |
| exon 5 |  | 1614 | tgg → tga |
| exon 5 |  | 1613 + 1614 | tgg → taa |

TABLE 3b

Potential STOP codon mutations in FATB-A2
(SOSR, SEQ ID NO: 15 and 16)

| Exon number | Amino acid position | Nucleotide position | Wild type → mutant codon |
|---|---|---|---|
| exon 1 | 52 | 154 | cag → tag |
| exon 1 |  | 154 + 156 | cag → taa |
| exon 1 | 79 | 235 | cag → tag |
| exon 1 |  | 235 + 237 | cag → taa |
| exon 1 | 90 | 268 | cag → tag |
| exon 1 |  | 268 + 270 | cag → taa |
| exon 1 | 94 | 281 | tgg → tag |
| exon 1 |  | 282 | tgg → tga |
| exon 1 |  | 281 + 282 | tgg → taa |
| exon 1 | 111 | 331 | cag → tag |
| exon 1 |  | 331 + 333 | cag → taa |
| exon 1 | 112 | 335 | tgg → tag |
| exon 1 |  | 336 | tgg → tga |
| exon 1 |  | 335 + 336 | tgg → taa |
| exon 1 | 117 | 350 | tgg → tag |
| exon 1 |  | 351 | tgg → tga |
| exon 1 |  | 350 + 351 | tgg → taa |
| exon 1 | 136 | 406 | cag → tag |
| exon 1 |  | 406 + 408 | cag → taa |
| exon 1 | 143 | 427 | cag → tag |
| exon 1 |  | 427 + 429 | cag → taa |
| exon 1 | 168 | 502 | cag → tag |
| exon 1 |  | 502 + 504 | cag → taa |
| exon 2 | 198 | 672 | tgg → tag |
| exon 2 |  | 673 | tgg → tga |
| exon 2 |  | 672 + 673 | tgg → taa |
| exon 2 | 204 | 689 | cag → tag |
| exon 2 |  | 689 + 691 | cag → taa |
| exon 2 | 213 | 717 | tgg → tag |

TABLE 3b-continued

Potential STOP codon mutations in FATB-A2
(SOSR, SEQ ID NO: 15 and 16)

| Exon number | Amino acid position | Nucleotide position | Wild type → mutant codon |
|---|---|---|---|
| exon 3 | | 812 | tgg → tga |
| exon 2-3 | | 717 + 812 | tgg → taa |
| exon 3 | 222 | 838 | tgg → tag |
| exon 3 | | 839 | tgg → tga |
| exon 3 | | 838 + 839 | tgg → taa |
| exon 3 | 225 | 846 | cag → tag |
| exon 3 | | 846 + 848 | cag → taa |
| exon 3 | 235 | 877 | tgg → tag |
| exon 3 | | 878 | tgg → tga |
| exon 3 | | 877 + 878 | tgg → taa |
| exon 3 | 238 | 885 + 886 | cgg → tag |
| exon 3 | | 885 + 887 | cgg → tga |
| exon 3 | | 885 + 886 + 887 | cgg → taa |
| exon 3 | 248 | 915 | cga → tga |
| exon 3 | | 915 + 916 | cga → taa |
| exon 4 | 253 | 1064 | tgg → tag |
| exon 4 | | 1065 | tgg → tga |
| exon 4 | | 1064 + 1065 | tgg → taa |
| exon 4 | 271 | 1117 | cga → tga |
| exon 4 | | 1117 + 1118 | cga → taa |
| exon 5 | 311 | 1316 | tgg → tag |
| exon 5 | | 1317 | tgg → tga |
| exon 5 | | 1316 + 1317 | tgg → taa |
| exon 5 | 318 | 1336 | cag → tag |
| exon 5 | | 1336 + 1338 | cag → taa |
| exon 5 | 328 | 1367 | tgg → tag |
| exon 5 | | 1368 | tgg → tga |
| exon 5 | | 1367 + 1368 | tgg → taa |
| exon 5 | 341 | 1405 | cag → tag |
| exon 5 | | 1405 + 1407 | cag → taa |
| exon 5 | 361 | 1465 | cag → tag |
| exon 5 | | 1465 + 1467 | cag → taa |
| exon 5 | 383 | 1531 | cag → tag |
| exon 5 | | 1531 + 1533 | cag → taa |
| exon 5 | 387 | 1543 | cga → tga |
| exon 5 | | 1543 + 1544 | cga → taa |
| exon 5 | 389 | 1549 | cag → tag |
| exon 5 | | 1549 + 1551 | cag → taa |
| exon 5 | 401 | 1586 | tgg → tag |
| exon 5 | | 1587 | tgg → tga |
| exon 5 | | 1586 + 1587 | tgg → taa |
| exon 5 | 410 | 1613 | tgg → tag |
| exon 5 | | 1614 | tgg → tga |
| exon 5 | | 1613 + 1614 | tgg → taa |

TABLE 4a

Potential STOP codon mutations in FATB-A3
(WOSR, SEQ ID NO: 5 and 6)

| Exon number | Amino acid position | Nucleotide position | Wild type → mutant codon |
|---|---|---|---|
| exon 1 | 52 | 154 | caa → taa |
| exon 1 | 81 | 241 | caa → taa |
| exon 1 | 82 | 244 | caa → taa |
| exon 1 | 91 | 271 | cag → tag |
| exon 1 | | 271 + 273 | cag → taa |
| exon 1 | 95 | 284 | tgg → tag |
| exon 1 | | 285 | tgg → tga |
| exon 1 | | 284 + 285 | tgg → taa |
| exon 1 | 112 | 334 | cag → tag |
| exon 1 | | 334 + 336 | cag → taa |
| exon 1 | 113 | 338 | tgg → tag |
| exon 1 | | 339 | tgg → tga |
| exon 1 | | 338 + 339 | tgg → taa |
| exon 1 | 137 | 409 | cag → tag |
| exon 1 | | 409 + 411 | cag → taa |
| exon 1 | 144 | 430 | cag → tag |
| exon 1 | | 430 + 432 | cag → taa |
| exon 1 | 169 | 505 | cag → tag |
| exon 1 | | 505 + 507 | cag → taa |
| exon 2 | 199 | 828 | tgg → tag |
| exon 2 | | 829 | tgg → tga |
| exon 2 | | 828 + 829 | tgg → taa |
| exon 2 | 205 | 845 | cag → tag |

TABLE 4a-continued

Potential STOP codon mutations in FATB-A3 (WOSR, SEQ ID NO: 5 and 6)

| Exon number | Amino acid position | Nucleotide position | Wild type → mutant codon |
|---|---|---|---|
| exon 2 |  | 845 + 847 | cag → taa |
| exon 2 | 214 | 873 | tgg → tag |
| exon 3 |  | 947 | tgg → tga |
| exon 2-3 |  | 873 + 947 | tgg → taa |
| exon 3 | 223 | 973 | tgg → tag |
| exon 3 |  | 974 | tgg → tga |
| exon 3 |  | 973 + 974 | tgg → taa |
| exon 3 | 236 | 1012 | tgg → tag |
| exon 3 |  | 1013 | tgg → tga |
| exon 3 |  | 1012 + 1013 | tgg → taa |
| exon 3 | 239 | 1020 + 1021 | cgg → tag |
| exon 3 |  | 1020 + 1022 | cgg → tga |
| exon 3 |  | 1020 + 1021 + 1022 | cgg → taa |
| exon 4 | 254 | 1146 | tgg → tag |
| exon 4 |  | 1147 | tgg → tga |
| exon 4 |  | 1146 + 1147 | tgg → taa |
| exon 4 | 272 | 1199 | cga → tga |
| exon 4 |  | 1199 + 1200 | cga → taa |
| exon 5 | 312 | 1420 | tgg → tag |
| exon 5 |  | 1421 | tgg → tga |
| exon 5 |  | 1420 + 1421 | tgg → taa |
| exon 5 | 319 | 1440 | cag → tag |
| exon 5 |  | 1440 + 1442 | cag → taa |
| exon 5 | 329 | 1471 | tgg → tag |
| exon 5 |  | 1472 | tgg → tga |
| exon 5 |  | 1471 + 1472 | tgg → taa |
| exon 5 | 362 | 1569 | cag → tag |
| exon 5 |  | 1569 + 1571 | cag → taa |
| exon 5 | 384 | 1635 | cag → tag |
| exon 5 |  | 1635 + 1637 | cag → taa |
| exon 5 | 388 | 1647 | cga → tga |
| exon 5 |  | 1647 + 1648 | cga → taa |
| exon 5 | 390 | 1653 | cag → tag |
| exon 5 |  | 1653 + 1655 | cag → taa |
| exon 5 | 399 | 1680 | cga → tga |
| exon 5 |  | 1680 + 1681 | cga → taa |
| exon 5 | 402 | 1690 | tgg → tag |
| exon 5 |  | 1691 | tgg → tga |
| exon 5 |  | 1690 + 1691 | tgg → taa |
| exon 5 | 411 | 1717 | tgg → tag |
| exon 5 |  | 1718 | tgg → tga |
| exon 5 |  | 1717 + 1718 | tgg → taa |

TABLE 4b

Potential STOP codon mutations in FATB-A3 (SOSR, SEQ ID NO: 17 and 18)

| Exon number | Amino acid position | Nucleotide position | Wild type → mutant codon |
|---|---|---|---|
| exon 1 | 52 | 154 | cag → tag |
| exon 1 |  | 154 + 156 | cag → taa |
| exon 1 | 81 | 241 | caa → taa |
| exon 1 | 82 | 244 | caa → taa |
| exon 1 | 91 | 271 | cag → tag |
| exon 1 |  | 271 + 273 | cag → taa |
| exon 1 | 95 | 284 | tgg → tag |
| exon 1 |  | 285 | tgg → tga |
| exon 1 |  | 284 + 285 | tgg → taa |
| exon 1 | 112 | 334 | cag → tag |
| exon 1 |  | 334 + 336 | cag → taa |
| exon 1 | 113 | 338 | tgg → tag |
| exon 1 |  | 339 | tgg → tga |
| exon 1 |  | 338 + 339 | tgg → taa |
| exon 1 | 137 | 409 | cag → tag |
| exon 1 |  | 409 + 411 | cag → taa |
| exon 1 | 144 | 430 | cag → tag |
| exon 1 |  | 430 + 432 | cag → taa |
| exon 1 | 169 | 505 | cag → tag |
| exon 1 |  | 505 + 507 | cag → taa |
| exon 2 | 199 | 828 | tgg → tag |
| exon 2 |  | 829 | tgg → tga |
| exon 2 |  | 828 + 829 | tgg → taa |
| exon 2 | 205 | 845 | cag → tag |
| exon 2 |  | 845 + 847 | cag → taa |

TABLE 4b-continued

Potential STOP codon mutations in FATB-A3 (SOSR, SEQ ID NO: 17 and 18)

| Exon number | Amino acid position | Nucleotide position | Wild type → mutant codon |
|---|---|---|---|
| exon 2 | 214 | 873 | tgg → tag |
| exon 3 | | 947 | tgg → tga |
| exon 2-3 | | 873 + 947 | tgg → taa |
| exon 3 | 223 | 973 | tgg → tag |
| exon 3 | | 974 | tgg → tga |
| exon 3 | | 973 + 974 | tgg → taa |
| exon 3 | 236 | 1012 | tgg → tag |
| exon 3 | | 1013 | tgg → tga |
| exon 3 | | 1012 + 1013 | tgg → taa |
| exon 4 | 254 | 1144 | tgg → tag |
| exon 4 | | 1145 | tgg → tga |
| exon 4 | | 1144 + 1145 | tgg → taa |
| exon 4 | 272 | 1197 | cga → tga |
| exon 4 | | 1197 + 1198 | cga → taa |
| exon 5 | 312 | 1402 | tgg → tag |
| exon 5 | | 1403 | tgg → tga |
| exon 5 | | 1402 + 1402 | tgg → taa |
| exon 5 | 319 | 1422 | cag → tag |
| exon 5 | | 1422 + 1424 | cag → taa |
| exon 5 | 329 | 1453 | tgg → tag |
| exon 5 | | 1454 | tgg → tga |
| exon 5 | | 1453 + 1454 | tgg → taa |
| exon 5 | 362 | 1551 | cag → tag |
| exon 5 | | 1551 + 1553 | cag → taa |
| exon 5 | 384 | 1617 | cag → tag |
| exon 5 | | 1617 + 1619 | cag → taa |
| exon 5 | 388 | 1629 | cga → tga |
| exon 5 | | 1629 + 1630 | cga → taa |
| exon 5 | 390 | 1635 | cag → tag |
| exon 5 | | 1635 + 1637 | cag → taa |
| exon 5 | 399 | 1662 | cga → tga |
| exon 5 | | 1662 + 1663 | cga → taa |
| exon 5 | 402 | 1672 | tgg → tag |
| exon 5 | | 1673 | tgg → tga |
| exon 5 | | 1672 + 1673 | tgg → taa |
| exon 5 | 411 | 1699 | tgg → tag |
| exon 5 | | 1700 | tgg → tga |
| exon 5 | | 1699 + 1700 | tgg → taa |

TABLE 5a

Potential STOP codon mutations in FATB-C1 (WOSR, SEQ ID NO: 7 and 8)

| Exon number | Amino acid position | Nucleotide position | Wild type → mutant codon |
|---|---|---|---|
| exon 1 | 52 | 154 | cag → tag |
| exon 1 | | 154 + 156 | cag → taa |
| exon 1 | 79 | 235 | caa → taa |
| exon 1 | 88 | 262 | cag → tag |
| exon 1 | | 262 + 264 | cag → taa |
| exon 1 | 92 | 275 | tgg → tag |
| exon 1 | | 276 | tgg → tga |
| exon 1 | | 275 + 276 | tgg → taa |
| exon 1 | 109 | 325 | cag → tag |
| exon 1 | | 325 + 327 | cag → taa |
| exon 1 | 110 | 329 | tgg → tag |
| exon 1 | | 330 | tgg → tga |
| exon 1 | | 329 + 330 | tgg → taa |
| exon 1 | 115 | 344 | tgg → tag |
| exon 1 | | 345 | tgg → tga |
| exon 1 | | 344 + 345 | tgg → taa |
| exon 1 | 134 | 400 | cag → tag |
| exon 1 | | 400 + 402 | cag → taa |
| exon 1 | 141 | 421 | cag → tag |
| exon 1 | | 421 + 423 | cag → taa |
| exon 1 | 146 | 436 + 437 | cgg → tag |
| exon 1 | | 436 + 438 | cgg → tga |
| exon 1 | | 436 + 437 + 438 | cgg → taa |
| exon 1 | 166 | 496 | cag → tag |
| exon 1 | | 496 + 498 | cag → taa |
| exon 2 | 196 | 667 | tgg → tag |
| exon 2 | | 668 | tgg → tga |
| exon 2 | | 667 + 668 | tgg → taa |
| exon 2 | 202 | 684 | cag → tag |

TABLE 5a-continued

Potential STOP codon mutations in FATB-C1
(WOSR, SEQ ID NO: 7 and 8)

| Exon number | Amino acid position | Nucleotide position | Wild type → mutant codon |
|---|---|---|---|
| exon 2 |  | 684 + 686 | cag → taa |
| exon 2 | 211 | 712 | tgg → tag |
| exon 3 |  | 791 | tgg → tga |
| exon 2-3 |  | 712 + 791 | tgg → taa |
| exon 3 | 220 | 817 | tgg → tag |
| exon 3 |  | 818 | tgg → tga |
| exon 3 |  | 817 + 818 | tgg → taa |
| exon 3 | 223 | 825 | cag → tag |
| exon 3 |  | 825 + 827 | cag → taa |
| exon 3 | 233 | 856 | tgg → tag |
| exon 3 |  | 857 | tgg → tga |
| exon 3 |  | 856 + 857 | tgg → taa |
| exon 3 | 236 | 864 | cga → tga |
| exon 3 |  | 864 + 865 | cga → taa |
| exon 4 | 251 | 1000 | tgg → tag |
| exon 4 |  | 1001 | tgg → tga |
| exon 4 |  | 1000 + 1001 | tgg → taa |
| exon 4 | 269 | 1053 | cga → tga |
| exon 4 |  | 1053 + 1054 | cga → taa |
| exon 5 | 309 | 1259 | tgg → tag |
| exon 5 |  | 1260 | tgg → tga |
| exon 5 |  | 1259 + 1260 | tgg → taa |
| exon 5 | 316 | 1279 | cag → tag |
| exon 5 |  | 1279 + 1281 | cag → taa |
| exon 5 | 326 | 1310 | tgg → tag |
| exon 5 |  | 1311 | tgg → tga |
| exon 5 |  | 1310 + 1311 | tgg → taa |
| exon 5 | 339 | 1348 | cag → tag |
| exon 5 |  | 1348 + 1350 | cag → taa |
| exon 5 | 359 | 1408 | cag → tag |
| exon 5 |  | 1408 + 1410 | cag → taa |
| exon 5 | 381 | 1474 | cag → tag |
| exon 5 |  | 1474 + 1476 | cag → taa |
| exon 5 | 387 | 1492 | cag → tag |
| exon 5 |  | 1492 + 1494 | cag → taa |
| exon 5 | 399 | 1529 | tgg → tag |
| exon 5 |  | 1530 | tgg → tga |
| exon 5 |  | 1529 + 1530 | tgg → taa |
| exon 5 | 408 | 1556 | tgg → tag |
| exon 5 |  | 1567 | tgg → tga |
| exon 5 |  | 1556 + 1557 | tgg → taa |

TABLE 5b

Potential STOP codon mutations in FATB-C1
(SOSR, SEQ ID NO: 19 and 20)

| Exon number | Amino acid position | Nucleotide position | Wild type → mutant codon |
|---|---|---|---|
| exon 1 | 52 | 154 | cag → tag |
| exon 1 |  | 154 + 156 | cag → taa |
| exon 1 | 79 | 235 | caa → taa |
| exon 1 | 88 | 262 | cag → tag |
| exon 1 |  | 262 + 264 | cag → taa |
| exon 1 | 92 | 275 | tgg → tag |
| exon 1 |  | 276 | tgg → tga |
| exon 1 |  | 275 + 276 | tgg → taa |
| exon 1 | 109 | 325 | cag → tag |
| exon 1 |  | 325 + 327 | cag → taa |
| exon 1 | 110 | 329 | tgg → tag |
| exon 1 |  | 330 | tgg → tga |
| exon 1 |  | 329 + 330 | tgg → taa |
| exon 1 | 115 | 344 | tgg → tag |
| exon 1 |  | 345 | tgg → tga |
| exon 1 |  | 344 + 345 | tgg → taa |
| exon 1 | 134 | 400 | cag → tag |
| exon 1 |  | 400 + 402 | cag → taa |
| exon 1 | 141 | 421 | cag → tag |
| exon 1 |  | 421 + 423 | cag → taa |
| exon 1 | 146 | 436 + 437 | cgg → tag |
| exon 1 |  | 436 + 438 | cgg → tga |
| exon 1 |  | 436 + 437 + 438 | cgg → taa |
| exon 1 | 166 | 496 | cag → tag |
| exon 1 |  | 496 + 498 | cag → taa |
| exon 2 | 196 | 667 | tgg → tag |

TABLE 5b-continued

Potential STOP codon mutations in FATB-C1
(SOSR, SEQ ID NO: 19 and 20)

| Exon number | Amino acid position | Nucleotide position | Wild type → mutant codon |
|---|---|---|---|
| exon 2 | | 668 | tgg → tga |
| exon 2 | | 667 + 668 | tgg → taa |
| exon 2 | 202 | 684 | cag → tag |
| exon 2 | | 684 + 686 | cag → taa |
| exon 2 | 211 | 712 | tgg → tag |
| exon 3 | | 791 | tgg → tga |
| exon 2-3 | | 712 + 791 | tgg → taa |
| exon 3 | 220 | 817 | tgg → tag |
| exon 3 | | 818 | tgg → tga |
| exon 3 | | 817 + 818 | tgg → taa |
| exon 3 | 223 | 825 | cag → tag |
| exon 3 | | 825 + 827 | cag → taa |
| exon 3 | 233 | 856 | tgg → tag |
| exon 3 | | 857 | tgg → tga |
| exon 3 | | 856 + 857 | tgg → taa |
| exon 3 | 236 | 864 | cga → tga |
| exon 3 | | 864 + 865 | cga → taa |
| exon 4 | 251 | 1000 | tgg → tag |
| exon 4 | | 1001 | tgg → tga |
| exon 4 | | 1000 + 1001 | tgg → taa |
| exon 4 | 269 | 1053 | cga → tga |
| exon 4 | | 1053 + 1054 | cga → taa |
| exon 5 | 309 | 1259 | tgg → tag |
| exon 5 | | 1260 | tgg → tga |
| exon 5 | | 1259 + 1260 | tgg → taa |
| exon 5 | 316 | 1279 | cag → tag |
| exon 5 | | 1279 + 1281 | cag → taa |
| exon 5 | 326 | 1309 | tgg → tag |
| exon 5 | | 1310 | tgg → tga |
| exon 5 | | 1309 + 1310 | tgg → taa |
| exon 5 | 339 | 1348 | cag → tag |
| exon 5 | | 1348 + 1350 | cag → taa |
| exon 5 | 359 | 1408 | cag → tag |
| exon 5 | | 1408 + 1410 | cag → taa |
| exon 5 | 381 | 1474 | cag → tag |
| exon 5 | | 1474 + 1476 | cag → taa |
| exon 5 | 387 | 1492 | cag → tag |
| exon 5 | | 1492 + 1494 | cag → taa |
| exon 5 | 399 | 1529 | tgg → tag |
| exon 5 | | 1530 | tgg → tga |
| exon 5 | | 1529 + 1530 | tgg → taa |
| exon 5 | 408 | 1556 | tgg → tag |
| exon 5 | | 1557 | tgg → tga |
| exon 5 | | 1556 + 1557 | tgg → taa |

TABLE 6a

Potential STOP codon mutations in FATB-C2
(WOSR, SEQ ID NO: 9 and 10)

| Exon number | Amino acid position | Nucleotide position | Wild type → mutant codon |
|---|---|---|---|
| exon 1 | 52 | 154 | cag → tag |
| exon 1 | | 154 + 156 | cag → taa |
| exon 1 | 79 | 235 | cag → tag |
| exon 1 | | 235 + 237 | cag → taa |
| exon 1 | 90 | 268 | cag → tag |
| exon 1 | | 268 + 270 | cag → taa |
| exon 1 | 94 | 281 | tgg → tag |
| exon 1 | | 282 | tgg → tga |
| exon 1 | | 281 + 282 | tgg → taa |
| exon 1 | 111 | 331 | cag → tag |
| exon 1 | | 331 + 333 | cag → taa |
| exon 1 | 112 | 335 | tgg → tag |
| exon 1 | | 336 | tgg → tga |
| exon 1 | | 335 + 336 | tgg → taa |
| exon 1 | 117 | 350 | tgg → tag |
| exon 1 | | 351 | tgg → tga |
| exon 1 | | 350 + 351 | tgg → taa |
| exon 1 | 136 | 406 | cag → tag |
| exon 1 | | 406 + 408 | cag → taa |
| exon 1 | 143 | 427 | cag → tag |
| exon 1 | | 427 + 429 | cag → taa |
| exon 1 | 168 | 502 | cag → tag |
| exon 1 | | 502 + 504 | cag → taa |

TABLE 6a-continued

Potential STOP codon mutations in FATB-C2 (WOSR, SEQ ID NO: 9 and 10)

| Exon number | Amino acid position | Nucleotide position | Wild type → mutant codon |
|---|---|---|---|
| exon 2 | 198 | 669 | tgg → tag |
| exon 2 |  | 670 | tgg → tga |
| exon 2 |  | 669 + 670 | tgg → taa |
| exon 2 | 204 | 686 | cag → tag |
| exon 2 |  | 686 + 688 | cag → taa |
| exon 2 | 213 | 714 | tgg → tag |
| exon 3 |  | 945 | tgg → tga |
| exon 2-3 |  | 714 + 945 | tgg → taa |
| exon 3 | 222 | 971 | tgg → tag |
| exon 3 |  | 972 | tgg → tga |
| exon 3 |  | 971 + 972 | tgg → taa |
| exon 3 | 225 | 979 | cag → tag |
| exon 3 |  | 979 + 981 | cag → taa |
| exon 3 | 235 | 1010 | tgg → tag |
| exon 3 |  | 1011 | tgg → tga |
| exon 3 |  | 1010 + 1011 | tgg → taa |
| exon 3 | 238 | 1018 + 1019 | cgg → tag |
| exon 3 |  | 1018 + 1020 | cgg → tga |
| exon 3 |  | 1018 + 1019 + 1020 | cgg → taa |
| exon 3 | 248 | 1048 | cga → tga |
| exon 3 |  | 1048 + 1049 | cga → taa |
| exon 4 | 253 | 1195 | tgg → tag |
| exon 4 |  | 1196 | tgg → tga |
| exon 4 |  | 1195 + 1196 | tgg → taa |
| exon 4 | 271 | 1248 | cga → tga |
| exon 4 |  | 1248 + 1249 | cga → taa |
| exon 5 | 311 | 1454 | tgg → tag |
| exon 5 |  | 1455 | tgg → tga |
| exon 5 |  | 1454 + 1455 | tgg → taa |
| exon 5 | 318 | 1474 | cag → tag |
| exon 5 |  | 1474 + 1476 | cag → taa |
| exon 5 | 328 | 1505 | tgg → tag |
| exon 5 |  | 1506 | tgg → tga |
| exon 5 |  | 1505 + 1506 | tgg → taa |
| exon 5 | 341 | 1543 | cag → tag |
| exon 5 |  | 1543 + 1545 | cag → taa |
| exon 5 | 361 | 1603 | cag → tag |
| exon 5 |  | 1603 + 1605 | cag → taa |
| exon 5 | 383 | 1669 | cag → tag |
| exon 5 |  | 1669 + 1671 | cag → taa |
| exon 5 | 389 | 1687 | cag → tag |
| exon 5 |  | 1687 + 1689 | cag → taa |
| exon 5 | 401 | 1724 | tgg → tag |
| exon 5 |  | 1725 | tgg → tga |
| exon 5 |  | 1724 + 1725 | tgg → taa |
| exon 5 | 410 | 1751 | tgg → tag |
| exon 5 |  | 1752 | tgg → tga |
| exon 5 |  | 1751 + 1752 | tgg → taa |

TABLE 6b

Potential STOP codon mutations in FATB-C2 (SOSR, SEQ ID NO: 21 and 22)

| Exon number | Amino acid position | Nucleotide position | Wild type → mutant codon |
|---|---|---|---|
| exon 1 | 52 | 154 | cag → tag |
| exon 1 |  | 154 + 156 | cag → taa |
| exon 1 | 79 | 235 | cag → tag |
| exon 1 |  | 235 + 237 | cag → taa |
| exon 1 | 90 | 268 | cag → tag |
| exon 1 |  | 268 + 270 | cag → taa |
| exon 1 | 94 | 281 | tgg → tag |
| exon 1 |  | 282 | tgg → tga |
| exon 1 |  | 281 + 282 | tgg → taa |
| exon 1 | 111 | 331 | cag → tag |
| exon 1 |  | 331 + 333 | cag → taa |
| exon 1 | 112 | 335 | tgg → tag |
| exon 1 |  | 336 | tgg → tga |
| exon 1 |  | 335 + 336 | tgg → taa |
| exon 1 | 117 | 350 | tgg → tag |
| exon 1 |  | 351 | tgg → tga |
| exon 1 |  | 350 + 351 | tgg → taa |
| exon 1 | 136 | 406 | cag → tag |
| exon 1 |  | 406 + 408 | cag → taa |

TABLE 6b-continued

Potential STOP codon mutations in FATB-C2
(SOSR, SEQ ID NO: 21 and 22)

| Exon number | Amino acid position | Nucleotide position | Wild type → mutant codon |
|---|---|---|---|
| exon 1 | 143 | 427 | cag → tag |
| exon 1 |  | 427 + 429 | cag → taa |
| exon 1 | 168 | 502 | cag → tag |
| exon 1 |  | 502 + 504 | cag → taa |
| exon 2 | 198 | 669 | tgg → tag |
| exon 2 |  | 670 | tgg → tga |
| exon 2 |  | 669 + 670 | tgg → taa |
| exon 2 | 204 | 686 | cag → tag |
| exon 2 |  | 686 + 688 | cag → taa |
| exon 2 | 213 | 714 | tgg → tag |
| exon 3 |  | 945 | tgg → tga |
| exon 2-3 |  | 714 + 945 | tgg → taa |
| exon 3 | 222 | 971 | tgg → tag |
| exon 3 |  | 972 | tgg → tga |
| exon 3 |  | 971 + 972 | tgg → taa |
| exon 3 | 225 | 979 | cag → tag |
| exon 3 |  | 979 + 981 | cag → taa |
| exon 3 | 235 | 1010 | tgg → tag |
| exon 3 |  | 1011 | tgg → tga |
| exon 3 |  | 1010 + 1011 | tgg → taa |
| exon 3 | 238 | 1018 + 1019 | cgg → tag |
| exon 3 |  | 1018 + 1020 | cgg → tga |
| exon 3 |  | 1018 + 1019 + 1020 | cgg → taa |
| exon 3 | 248 | 1048 | cga → tga |
| exon 3 |  | 1048 + 1049 | cga → taa |
| exon 4 | 253 | 1195 | tgg → tag |
| exon 4 |  | 1196 | tgg → tga |
| exon 4 |  | 1195 + 1196 | tgg → taa |
| exon 4 | 271 | 1248 | cga → tga |
| exon 4 |  | 1248 + 1249 | cga → taa |
| exon 5 | 311 | 1454 | tgg → tag |
| exon 5 |  | 1455 | tgg → tga |
| exon 5 |  | 1454 + 1455 | tgg → taa |
| exon 5 | 318 | 1474 | cag → tag |
| exon 5 |  | 1474 + 1476 | cag → taa |
| exon 5 | 328 | 1505 | tgg → tag |
| exon 5 |  | 1506 | tgg → tga |
| exon 5 |  | 1505 + 1506 | tgg → taa |
| exon 5 | 341 | 1543 | cag → tag |
| exon 5 |  | 1543 + 1545 | cag → taa |
| exon 5 | 361 | 1603 | cag → tag |
| exon 5 |  | 1603 + 1605 | cag → taa |
| exon 5 | 383 | 1669 | cag → tag |
| exon 5 |  | 1669 + 1671 | cag → taa |
| exon 5 | 389 | 1687 | cag → tag |
| exon 5 |  | 1687 + 1689 | cag → taa |
| exon 5 | 401 | 1724 | tgg → tag |
| exon 5 |  | 1725 | tgg → tga |
| exon 5 |  | 1724 + 1725 | tgg → taa |
| exon 5 | 410 | 1751 | tgg → tag |
| exon 5 |  | 1752 | tgg → tga |
| exon 5 |  | 1751 + 1752 | tgg → taa |

TABLE 7a

Potential STOP codon mutations in FATB-C3
(WOSR, SEQ ID NO: 11 and 12)

| Exon number | Amino acid position | Nucleotide position | Wild type → mutant codon |
|---|---|---|---|
| exon 1 | 52 | 154 | caa → taa |
| exon 1 | 81 | 241 | caa → taa |
| exon 1 | 82 | 244 | caa → taa |
| exon 1 | 91 | 271 | cag → tag |
| exon 1 |  | 271 + 273 | cag → taa |
| exon 1 | 95 | 284 | tgg → tag |
| exon 1 |  | 285 | tgg → tga |
| exon 1 |  | 284 + 285 | tgg → taa |
| exon 1 | 112 | 334 | cag → tag |
| exon 1 |  | 334 + 336 | cag → taa |
| exon 1 | 113 | 338 | tgg → tag |
| exon 1 |  | 339 | tgg → tga |
| exon 1 |  | 338 + 339 | tgg → taa |
| exon 1 | 137 | 409 | cag → tag |
| exon 1 |  | 409 + 411 | cag → taa |

TABLE 7a-continued

Potential STOP codon mutations in FATB-C3 (WOSR, SEQ ID NO: 11 and 12)

| Exon number | Amino acid position | Nucleotide position | Wild type → mutant codon |
|---|---|---|---|
| exon 1 | 144 | 430 | cag → tag |
| exon 1 |  | 430 + 432 | cag → taa |
| exon 1 | 169 | 505 | cag → tag |
| exon 1 |  | 505 + 507 | cag → taa |
| exon 2 | 199 | 1018 | tgg → tag |
| exon 2 |  | 1019 | tgg → tga |
| exon 2 |  | 1018 + 1019 | tgg → taa |
| exon 2 | 205 | 1035 | cag → tag |
| exon 2 |  | 1035 + 1037 | cag → taa |
| exon 2 | 214 | 1063 | tgg → tag |
| exon 3 |  | 1138 | tgg → tga |
| exon 2-3 |  | 1063 + 1138 | tgg → taa |
| exon 3 | 223 | 1164 | tgg → tag |
| exon 3 |  | 1165 | tgg → tga |
| exon 3 |  | 1164 + 1165 | tgg → taa |
| exon 3 | 236 | 1203 | tgg → tag |
| exon 3 |  | 1204 | tgg → tga |
| exon 3 |  | 1203 + 1204 | tgg → taa |
| exon 3 | 239 | 1211 + 1212 | cgg → tag |
| exon 3 |  | 1211 + 1213 | cgg → tga |
| exon 3 |  | 1211 + 1212 + 1213 | cgg → taa |
| exon 4 | 254 | 1329 | tgg → tag |
| exon 4 |  | 1330 | tgg → tga |
| exon 4 |  | 1329 + 1330 | tgg → taa |
| exon 4 | 272 | 1382 | cga → tga |
| exon 4 |  | 1382 + 1383 | cga → taa |
| exon 5 | 312 | 1578 | tgg → tag |
| exon 5 |  | 1579 | tgg → tga |
| exon 5 |  | 1578 + 1579 | tgg → taa |
| exon 5 | 319 | 1598 | cag → tag |
| exon 5 |  | 1598 + 1600 | cag → taa |
| exon 5 | 329 | 1629 | tgg → tag |
| exon 5 |  | 1630 | tgg → tga |
| exon 5 |  | 1629 + 1630 | tgg → taa |
| exon 5 | 362 | 1727 | cag → tag |
| exon 5 |  | 1727 + 1729 | cag → taa |
| exon 5 | 384 | 1793 | cag → tag |
| exon 5 |  | 1793 + 1795 | cag → taa |
| exon 5 | 388 | 1805 | cga → tga |
| exon 5 |  | 1805 + 1806 | cga → taa |
| exon 5 | 390 | 1811 | cag → tag |
| exon 5 |  | 1811 + 1813 | cag → taa |
| exon 5 | 399 | 1838 | cga → tga |
| exon 5 |  | 1838 + 1839 | cga → taa |
| exon 5 | 402 | 1848 | tgg → tag |
| exon 5 |  | 1849 | tgg → tga |
| exon 5 |  | 1848 + 1849 | tgg → taa |
| exon 5 | 411 | 1875 | tgg → tag |
| exon 5 |  | 1876 | tgg → tga |
| exon 5 |  | 1875 + 1876 | tgg → taa |

TABLE 7b

Potential STOP codon mutations in FATB-C3 (SOSR, SEQ ID NO: 23 and 24)

| Exon number | Amino acid position | Nucleotide position | Wild type → mutant codon |
|---|---|---|---|
| exon 1 | 52 | 154 | caa → taa |
| exon 1 | 81 | 241 | caa → taa |
| exon 1 | 82 | 244 | caa → taa |
| exon 1 | 91 | 271 | cag → tag |
| exon 1 |  | 271 + 273 | cag → taa |
| exon 1 | 95 | 284 | tgg → tag |
| exon 1 |  | 285 | tgg → tga |
| exon 1 |  | 284 + 285 | tgg → taa |
| exon 1 | 112 | 334 | cag → tag |
| exon 1 |  | 334 + 336 | cag → taa |
| exon 1 | 113 | 338 | tgg → tag |
| exon 1 |  | 339 | tgg → tga |
| exon 1 |  | 338 + 339 | tgg → taa |
| exon 1 | 137 | 409 | cag → tag |

TABLE 7b-continued

Potential STOP codon mutations in FATB-C3 (SOSR, SEQ ID NO: 23 and 24)

| Exon number | Amino acid position | Nucleotide position | Wild type → mutant codon |
|---|---|---|---|
| exon 1 |  | 409 + 411 | cag → taa |
| exon 1 | 144 | 430 | cag → tag |
| exon 1 |  | 430 + 432 | cag → taa |
| exon 1 | 169 | 505 | cag → tag |
| exon 1 |  | 505 + 507 | cag → taa |
| exon 2 | 199 | 1019 | tgg → tag |
| exon 2 |  | 1020 | tgg → tga |
| exon 2 |  | 1019 + 1020 | tgg → taa |
| exon 2 | 205 | 1036 | cag → tag |
| exon 2 |  | 1036 + 1038 | cag → taa |
| exon 2 | 214 | 1064 | tgg → tag |
| exon 3 |  | 1139 | tgg → tga |
| exon 2-3 |  | 1064 + 1139 | tgg → taa |
| exon 3 | 223 | 1165 | tgg → tag |
| exon 3 |  | 1166 | tgg → tga |
| exon 3 |  | 1165 + 1166 | tgg → taa |
| exon 3 | 236 | 1204 | tgg → tag |
| exon 3 |  | 1205 | tgg → tga |
| exon 3 |  | 1204 + 1205 | tgg → taa |
| exon 3 | 239 | 1212 + 1213 | cgg → tag |
| exon 3 |  | 1212 + 1214 | cgg → tga |
| exon 3 |  | 1212 + 1213 + 1214 | cgg → taa |
| exon 4 | 254 | 1330 | tgg → tag |
| exon 4 |  | 1331 | tgg → tga |
| exon 4 |  | 1330 + 1331 | tgg → taa |
| exon 4 | 272 | 1383 | cga → tga |
| exon 4 |  | 1383 + 1384 | cga → taa |
| exon 5 | 312 | 1579 | tgg → tag |
| exon 5 |  | 1580 | tgg → tga |
| exon 5 |  | 1579 + 1580 | tgg → taa |
| exon 5 | 319 | 1599 | cag → tag |
| exon 5 |  | 1599 + 1601 | cag → taa |
| exon 5 | 329 | 1630 | tgg → tag |
| exon 5 |  | 1631 | tgg → tga |
| exon 5 |  | 1630 + 1631 | tgg → taa |
| exon 5 | 362 | 1728 | cag → tag |
| exon 5 |  | 1728 + 1730 | cag → taa |
| exon 5 | 384 | 1794 | cag → tag |
| exon 5 |  | 1794 + 1796 | cag → taa |
| exon 5 | 388 | 1806 | cga → tga |
| exon 5 |  | 1806 + 1807 | cga → taa |
| exon 5 | 390 | 1812 | cag → tag |
| exon 5 |  | 1812 + 1814 | cag → taa |
| exon 5 | 399 | 1839 | cga → tga |
| exon 5 |  | 1839 + 1840 | cga → taa |
| exon 5 | 402 | 1849 | tgg → tag |
| exon 5 |  | 1850 | tgg → tga |
| exon 5 |  | 1849 + 1850 | tgg → taa |
| exon 5 | 411 | 1876 | tgg → tag |
| exon 5 |  | 1877 | tgg → tga |
| exon 5 |  | 1876 + 1877 | tgg → taa |

Obviously, mutations are not limited to the ones shown in the above tables and it is understood that analogous STOP mutations may be present in fatB alleles other than those depicted in the sequence listing and referred to in the tables above.

A splice site mutation in a FATB allele, as used herein, is a mutation in a FATB allele whereby a mutation in the corresponding wild type FATB allele results in aberrant splicing of the pre-mRNA thereby resulting in a mutant protein having significantly reduced or no activity. The mutation may be in the consensus splice site sequence. For example, the following table describes consensus sequences, which—if mutated—are likely to affect correct splicing. The GT-AG splice sites commonly have other conserved nucleotides, such as 2 highly conserved nucleotides on the 5' end of the intron (in the exon), often being 5'-AG-3'. On the 3'-side of the GT dinucleotide (thus in the intron) high conservation can be found for a tetranucleotide 5'-AAGT-3'. This means that 8 nucleotides can be identified as highly conserved at the donor site.

| Intron type | 5' splice junction (exon^intron) | Near 3'splice site | 3'splice junction (intron^exon) | Found in |
|---|---|---|---|---|
| GU-AG (Canonical introns; about 99%) | CRN^GU(A/G)AGU | A | YnAG^N | nuclear pre-mRNA |
| (about 1%) | ^GC | | AG^ | nuclear pre-mRNA |
| Non-canonical introns (< about 0.1%) | ^AU | | AC^ | nuclear pre-mRNA |
| Canonical branch sites | | CUPuAPy | | 20-50 nucleotides 5' to splice-site acceptor of nuclear pre mRNA |

^depicts the splice site; R = A or G; Y = C or T; N = A, C, G or T (but often G); n = multiple nucleotides; in bold = consensus dinucleotides in the intron sequence. Pu = purine base; Py = pyrimidine base.

Splice site structure and consensus sequences are described in the art and computer programs for identifying exons and splice site sequences, such as NetPLAntgene, BDGP or Genio, est2genome, FgeneSH, and the like, are available. Comparison of the genomic sequence or pre-mRNA sequence with the translated protein can be used to determine or verify splice sites and aberrant splicing.

Any mutation (insertion, deletion and/or substitution) of one or more nucleotides) which alters pre-mRNA splicing and thereby leads to a protein with significantly reduced biological activity is encompassed herein. In one embodiment, a mutant FATB allele comprising a splice site mutation is a FATB allele wherein altered splicing is caused by the introduction in the FATB transcribed DNA region of one or more nucleotide substitution(s) of the consensus dinucleotides depicted in bold above. For example, ^GU may for example be mutated to ^AU in the donor splice site and/or AG^ may be mutated to AA^ in the acceptor splice site sequence. In another embodiment, a mutant FATB allele comprising a splice site mutation is a FATB allele wherein altered splicing is caused by the introduction in the FATB transcribed DNA region of one or more nucleotide substitution(s) in the conserved nucleotides in the exon sequences.

The following tables indicate possible splice site mutations in FATB genes, especially in the conserved dinucleotides of canonical introns and the nucleotide immediately flanking these dinucleotides in the exon (the symbols '[' and ']' indicate the exon-intron and intron-exon boundaries and the splice site; underlined nucleotides are mutated).

TABLE 8a

Potential splice site mutations in FATB-A1 (WOSR, SEQ ID NO: 1)

| Intron number | Nucleotide position | Wild type → mutant splice site |
|---|---|---|
| intron 1 - donor | 504 | g[gt . . . → a[gt . . . |
| intron 1 - donor | 505 | g[gt . . . → g[at . . . |
| intron 1 - acceptor | 589 | . . . ag]g → . . . aa]g |
| intron 1 - acceptor | 590 | . . . ag]g → . . . ag]a |
| intron 2 - donor | 723 | g[gt . . . → a[gt . . . |
| intron 2 - donor | 724 | g[gt . . . → g[at . . . |
| intron 2 - acceptor | 797 | . . . ag]g → . . . aa]g |
| intron 2 - acceptor | 798 | . . . ag]g → . . . ag]a |
| intron 3 - donor | 911 | g[gt . . . → a[gt . . . |
| intron 3 - donor | 912 | g[gt . . . → g[at . . . |
| intron 3 - acceptor | 980 | . . . ag]t → . . . aa]t |
| intron 4 - donor | 1153 | t[gt . . . → t[at . . . |

TABLE 8a-continued

Potential splice site mutations in FATB-A1
(WOSR, SEQ ID NO: 1)

| Intron number | Nucleotide position | Wild type → mutant splice site |
|---|---|---|
| intron 4 - acceptor | 1242 | . . . ag]c → . . . aa]c |
| intron 4 - acceptor | 1243 | . . . ag]c → . . . ag]t |

TABLE 8b

Potential splice site mutations in FATB-A1
(SOSR, SEQ ID NO: 13)

| Intron number | Nucleotide position | Wild type → mutant splice site |
|---|---|---|
| intron 1 - donor | 501 | g[gt . . . → a[gt . . . |
| intron 1 - donor | 502 | g[gt . . . → g[at . . . |
| intron 1 - acceptor | 586 | . . . ag]g → . . . aa]g |
| intron 1 - acceptor | 587 | . . . ag]g → . . . ag]a |
| intron 2 - donor | 720 | g[gt . . . → a[gt . . . |
| intron 2 - donor | 721 | g[gt . . . → g[at . . . |
| intron 2 - acceptor | 794 | . . . ag]g → . . . aa]g |
| intron 2 - acceptor | 795 | . . . ag]g → . . . ag]a |
| intron 3 - donor | 908 | g[gt . . . → a[gt . . . |
| intron 3 - donor | 909 | g[gt . . . → g[at . . . |
| intron 3 - acceptor | 977 | . . . ag]t → . . . aa]t |
| intron 4 - donor | 1150 | t[gt . . . → t[at . . . |
| intron 4 - acceptor | 1239 | . . . ag]c → . . . aa]c |
| intron 4 - acceptor | 1240 | . . . ag]c → . . . ag]t |

TABLE 9a

Potential splice site mutations in FATB-A2
(WOSR, SEQ ID NO: 3)

| Intron number | Nucleotide position | Wild type → mutant splice site |
|---|---|---|
| intron 1 - donor | 504 | g[gt . . . → a[gt . . . |
| intron 1 - donor | 505 | g[gt . . . → g[at . . . |
| intron 1 - acceptor | 583 | . . . ag]g → . . . aa]g |
| intron 1 - acceptor | 584 | . . . ag]g → . . . ag]a |
| intron 2 - donor | 717 | g[gt . . . → a[gt . . . |
| intron 2 - donor | 718 | g[gt . . . → g[at . . . |
| intron 2 - acceptor | 811 | . . . ag]g → . . . aa]g |
| intron 2 - acceptor | 812 | . . . ag]g → . . . ag]a |
| intron 3 - donor | 925 | g[gt . . . → a[gt . . . |
| intron 3 - donor | 926 | g[gt . . . → g[at . . . |

TABLE 9a-continued

Potential splice site mutations in FATB-A2
(WOSR, SEQ ID NO: 3)

| Intron number | Nucleotide position | Wild type → mutant splice site |
|---|---|---|
| intron 3 - acceptor | 1058 | . . . ag]t → . . . a<u>a</u>]t |
| intron 4 - donor | 1231 | t[gt . . . → t[<u>a</u>t . . . |
| intron 4 - acceptor | 1308 | . . . ag]c → . . . a<u>a</u>]c |
| intron 4 - acceptor | 1309 | . . . ag]<u>c</u> → . . . ag]<u>t</u> |

TABLE 9b

Potential splice site mutations in FATB-A2
(SOSR, SEQ ID NO: 15)

| Intron number | Nucleotide position | Wild type → mutant splice site |
|---|---|---|
| intron 1 - donor | 504 | g[gt . . . → <u>a</u>[gt . . . |
| intron 1 - donor | 505 | g[gt . . . → g[<u>a</u>t . . . |
| intron 1 - acceptor | 583 | . . . ag]g → . . . a<u>a</u>]g |
| intron 1 - acceptor | 584 | . . . ag]g → . . . ag]<u>a</u> |
| intron 2 - donor | 717 | g[gt . . . → <u>a</u>[gt . . . |
| intron 2 - donor | 718 | g[gt . . . → g[<u>a</u>t . . . |
| intron 2 - acceptor | 811 | . . . ag]g → . . . a<u>a</u>]g |
| intron 2 - acceptor | 812 | . . . ag]g → . . . ag]<u>a</u> |
| intron 3 - donor | 925 | g[gt . . . → <u>a</u>[gt . . . |
| intron 3 - donor | 926 | g[gt . . . → g[<u>a</u>t . . . |
| intron 3 - acceptor | 1058 | . . . ag]t → . . . a<u>a</u>]t |
| intron 4 - donor | 1231 | t[gt . . . → t[<u>a</u>t . . . |
| intron 4 - acceptor | 1308 | . . . ag]c → . . . a<u>a</u>]c |
| intron 4 - acceptor | 1309 | . . . ag]<u>c</u> → . . . ag]<u>t</u> |

TABLE 10a

Potential splice site mutations in FATB-A3
(WOSR, SEQ ID NO: 5)

| Intron number | Nucleotide position | Wild type → mutant splice site |
|---|---|---|
| intron 1 - donor | 507 | g[gt . . . → <u>a</u>[gt . . . |
| intron 1 - donor | 508 | g[gt . . . → g[<u>a</u>t . . . |
| intron 1 - acceptor | 739 | . . . ag]g → . . . a<u>a</u>]g |
| intron 1 - acceptor | 740 | . . . ag]g → . . . ag]<u>a</u> |
| intron 2 - donor | 873 | g[gt . . . → <u>a</u>[gt . . . |
| intron 2 - donor | 874 | g[gt . . . → g[<u>a</u>t . . . |
| intron 2 - acceptor | 946 | . . . ag]g → . . . a<u>a</u>]g |
| intron 2 - acceptor | 947 | . . . ag]g → . . . ag]<u>a</u> |
| intron 3 - donor | 1060 | g[gt . . . → <u>a</u>[gt . . . |

TABLE 10a-continued

Potential splice site mutations in FATB-A3
(WOSR, SEQ ID NO: 5)

| Intron number | Nucleotide position | Wild type → mutant splice site |
|---|---|---|
| intron 3 - donor | 1061 | g[gt . . . → g[at . . . |
| intron 3 - acceptor | 1140 | . . . ag]t → . . . aa]t |
| intron 4 - donor | 1312 | c[gt . . . → t[gt . . . |
| intron 4 - donor | 1313 | c[gt . . . → c[at . . . |
| intron 4 - acceptor | 1412 | . . . ag]c → . . . aa]c |
| intron 4 - acceptor | 1413 | . . . ag]c → . . . ag]t |

TABLE 10b

Potential splice site mutations in FATB-A3
(SOSR, SEQ ID NO: 17)

| Intron number | Nucleotide position | Wild type → mutant splice site |
|---|---|---|
| intron 1 - donor | 507 | g[gt . . . → a[gt . . . |
| intron 1 - donor | 508 | g[gt . . . → g[at . . . |
| intron 1 - acceptor | 739 | . . . ag]g → . . . aa]g |
| intron 1 - acceptor | 740 | . . . ag]g → . . . ag]a |
| intron 2 - donor | 873 | g[gt . . . → a[gt . . . |
| intron 2 - donor | 874 | g[gt . . . → g[at . . . |
| intron 2 - acceptor | 946 | . . . ag]g → . . . aa]g |
| intron 2 - acceptor | 947 | . . . ag]g → . . . ag]a |
| intron 3 - donor | 1060 | g[gt . . . → a[gt . . . |
| intron 3 - donor | 1061 | g[gt . . . → g[at . . . |
| intron 3 - acceptor | 1138 | . . . ag]t → . . . aa]t |
| intron 4 - donor | 1310 | c[gt . . . → t[gt . . . |
| intron 4 - donor | 1311 | c[gt . . . → c[at . . . |
| intron 4 - acceptor | 1394 | . . . ag]c → . . . aa]c |
| intron 4 - acceptor | 1395 | . . . ag]c → . . . ag]t |

TABLE 11a

Potential splice site mutations in FATB-C1
(WOSR, SEQ ID NO: 7)

| Intron number | Nucleotide position | Wild type → mutant splice site |
|---|---|---|
| intron 1 - donor | 498 | g[gt . . . → a[gt . . . |
| intron 1 - donor | 499 | g[gt . . . → g[at . . . |
| intron 1 - acceptor | 578 | . . . ag]g → . . . aa]g |
| intron 1 - acceptor | 579 | . . . ag]g → . . . ag]a |
| intron 2 - donor | 712 | g[gt . . . → a[gt . . . |

TABLE 11a-continued

Potential splice site mutations in FATB-C1
(WOSR, SEQ ID NO: 7)

| Intron number | Nucleotide position | Wild type → mutant splice site |
|---|---|---|
| intron 2 - donor | 713 | g[gt . . . → g[at . . . |
| intron 2 - acceptor | 790 | . . . ag]g → . . . aa]g |
| intron 2 - acceptor | 791 | . . . ag]g → . . . ag]a |
| intron 3 - donor | 904 | g[gt . . . → a[gt . . . |
| intron 3 - donor | 905 | g[gt . . . → g[at . . . |
| intron 3 - acceptor | 994 | . . . ag]t → . . . aa]t |
| intron 4 - donor | 1167 | t[gt . . . → t[at . . . |
| intron 4 - acceptor | 1251 | . . . ag]c → . . . aa]c |
| intron 4 - acceptor | 1252 | . . . ag]c → . . . ag]t |

TABLE 11b

Potential splice site mutations in FATB-C1
(SOSR, SEQ ID NO: 19)

| Intron number | Nucleotide position | Wild type → mutant splice site |
|---|---|---|
| intron 1 - donor | 498 | g[gt . . . → a[gt . . . |
| intron 1 - donor | 499 | g[gt . . . → g[at . . . |
| intron 1 - acceptor | 578 | . . . ag]g → . . . aa]g |
| intron 1 - acceptor | 579 | . . . ag]g → . . . ag]a |
| intron 2 - donor | 712 | g[gt . . . → a[gt . . . |
| intron 2 - donor | 713 | g[gt . . . → g[at . . . |
| intron 2 - acceptor | 790 | . . . ag]g → . . . aa]g |
| intron 2 - acceptor | 791 | . . . ag]g → . . . ag]a |
| intron 3 - donor | 904 | g[gt . . . → a[gt . . . |
| intron 3 - donor | 905 | g[gt . . . → g[at . . . |
| intron 3 - acceptor | 994 | . . . ag]t → . . . aa]t |
| intron 4 - donor | 1167 | t[gt . . . → t[at . . . |
| intron 4 - acceptor | 1251 | . . . ag]c → . . . aa]c |
| intron 4 - acceptor | 1252 | . . . ag]c → . . . ag]t |

TABLE 12a

Potential splice site mutations in FATB-C2
(WOSR, SEQ ID NO: 9)

| Intron number | Nucleotide position | Wild type → mutant splice site |
|---|---|---|
| intron 1 - donor | 504 | g[gt . . . → a[gt . . . |
| intron 1 - donor | 505 | g[gt . . . → g[at . . . |
| intron 1 - acceptor | 580 | . . . ag]g → . . . aa]g |
| intron 1 - acceptor | 581 | . . . ag]g → . . . ag]a |

TABLE 12a-continued

Potential splice site mutations in FATB-C2
(WOSR, SEQ ID NO: 9)

| Intron number | Nucleotide position | Wild type → mutant splice site |
|---|---|---|
| intron 2 - donor | 714 | g[gt . . . → a[gt . . . |
| intron 2 - donor | 715 | g[gt . . . → g[at . . . |
| intron 2 - acceptor | 944 | . . . ag]g → . . . aa]g |
| intron 2 - acceptor | 945 | . . . ag]g → . . . ag]a |
| intron 3 - donor | 1058 | g[gt . . . → a[gt . . . |
| intron 3 - donor | 1059 | g[gt . . . → g[at . . . |
| intron 3 - acceptor | 1189 | . . . ag]t → . . . aa]t |
| intron 4 - donor | 1362 | t[gt . . . → t[at . . . |
| intron 4 - acceptor | 1446 | . . . ag]c → . . . aa]c |
| intron 4 - acceptor | 1447 | . . . ag]c → . . . ag]t |

TABLE 12b

Potential splice site mutations in FATB-C2
(SOSR, SEQ ID NO: 21)

| Intron number | Nucleotide position | Wild type → mutant splice site |
|---|---|---|
| intron 1 - donor | 504 | g[gt . . . → a[gt . . . |
| intron 1 - donor | 505 | g[gt . . . → g[at . . . |
| intron 1 - acceptor | 580 | . . . ag]g → . . . aa]g |
| intron 1 - acceptor | 581 | . . . ag]g → . . . ag]a |
| intron 2 - donor | 714 | g[gt . . . → a[gt . . . |
| intron 2 - donor | 715 | g[gt . . . → g[at . . . |
| intron 2 - acceptor | 944 | . . . ag]g → . . . aa]g |
| intron 2 - acceptor | 945 | . . . ag]g → . . . ag]a |
| intron 3 - donor | 1058 | g[gt . . . → a[gt . . . |
| intron 3 - donor | 1059 | g[gt . . . → g[at . . . |
| intron 3 - acceptor | 1189 | . . . ag]t → . . . aa]t |
| intron 4 - donor | 1362 | t[gt . . . → t[at . . . |
| intron 4 - acceptor | 1446 | . . . ag]c → . . . aa]c |
| intron 4 - acceptor | 1447 | . . . ag]c → . . . ag]t |

TABLE 13a

Potential splice site mutations in FATB-C3
(WOSR, SEQ ID NO: 11)

| Intron number | Nucleotide position | Wild type → mutant splice site |
|---|---|---|
| intron 1 - donor | 507 | g[gt . . . → a[gt . . . |
| intron 1 - donor | 508 | g[gt . . . → g[at . . . |
| intron 1 - acceptor | 929 | . . . ag]g → . . . aa]g |
| intron 1 - acceptor | 930 | . . . ag]g → . . . ag]a |
| intron 2 - donor | 1063 | g[gt . . . → a[gt . . . |
| intron 2 - donor | 1064 | g[gt . . . → g[at . . . |
| intron 2 - acceptor | 1137 | . . . ag]g → . . . aa]g |
| intron 2 - acceptor | 1138 | . . . ag]g → . . . ag]a |
| intron 3 - donor | 1251 | g[gt . . . → a[gt . . . |
| intron 3 - donor | 1252 | g[gt . . . → g[at . . . |
| intron 3 - acceptor | 1323 | . . . ag]t → . . . aa]t |
| intron 4 - donor | 1495 | c[gt . . . → t[gt . . . |
| intron 4 - donor | 1496 | c[gt . . . → c[at . . . |
| intron 4 - acceptor | 1570 | . . . ag]c → . . . aa]c |
| intron 4 - acceptor | 1571 | . . . ag]c → . . . ag]t |

TABLE 13b

Potential splice site mutations in FATB-C3
(SOSR, SEQ ID NO: 23)

| Intron number | Nucleotide position | Wild type → mutant splice site |
|---|---|---|
| intron 1 - donor | 507 | g[gt . . . → a[gt . . . |
| intron 1 - donor | 508 | g[gt . . . → g[at . . . |
| intron 1 - acceptor | 930 | . . . ag]g → . . . aa]g |
| intron 1 - acceptor | 931 | . . . ag]g → . . . ag]a |
| intron 2 - donor | 1064 | g[gt . . . → a[gt . . . |
| intron 2 - donor | 1065 | g[gt . . . → g[at . . . |
| intron 2 - acceptor | 1138 | . . . ag]g → . . . aa]g |
| intron 2 - acceptor | 1139 | . . . ag]g → . . . ag]a |
| intron 3 - donor | 1252 | g[gt . . . → a[gt . . . |
| intron 3 - donor | 1253 | g[gt . . . → g[at . . . |
| intron 3 - acceptor | 1324 | . . . ag]t → . . . aa]t |
| intron 4 - donor | 1496 | c[gt . . . → t[gt . . . |
| intron 4 - donor | 1497 | c[gt . . . → c[at . . . |
| intron 4 - acceptor | 1571 | . . . ag]c → . . . aa]c |
| intron 4 - acceptor | 1572 | . . . ag]c → . . . ag]t |

Amino Acid Sequences According to the Invention

Provided are both wild type (functional) FATB amino acid sequences and mutant FATB amino acid sequences (comprising one or more mutations, preferably mutations which result in a significantly reduced or no biological activity of the FATB protein) from *Brassica* species, especially from *Brassica napus*, but also from other *Brassica* crop species. For example, *Brassica* species comprising an A and/or a C genome may encode different FATB-A or FATB-C amino acids. In addition, mutagenesis methods can be used to generate mutations in wild type FATB alleles, thereby generating mutant alleles which can encode further mutant FATB proteins. In one embodiment the wild type and/or mutant FATB amino acid sequences are provided within a *Brassica* plant (i.e. endogenously). However, isolated FATB amino acid sequences (e.g. isolated from the plant or made synthetically), as well as variants thereof and fragments of any of these are also provided herein.

Amino acid sequences of FATB-A1, FATB-A2, FATB-A3, FATB-C1, FATB-C2 and FATB-C3 proteins have been isolated from *Brassica napus* winter oilseed rape (WOSR) and spring oilseed rape (SOSR), as depicted in the sequence listing. The wild type FATB sequences are depicted, while the mutant FATB sequences of these sequences, and of sequences essentially similar to these, are described herein below, with reference to the wild type FATB sequences.

As described above, the FATB proteins of *Brassica* described herein are about 412-424 amino acids in length and comprise a number of structural and functional domains. The sequences of the N-terminal part of the FATB proteins are less conserved evolutionarily than the sequences of the mature FATB proteins. The sequences of the mature FATB proteins are therefore less variable than the sequences of the precursor proteins.

"FATB-A1 amino acid sequences" or "FATB-A1 variant amino acid sequences" according to the invention are amino acid sequences having at least 80%, at least 85%, at least 90%, at least 95%, 98%, 99% or 100% sequence identity with SEQ ID NO: 2 (WOSR FATB-A1) when aligned with or without transit peptide and/or with SEQ ID NO: 14 (SOSR FATB-A1) when aligned with or without transit peptide. These amino acid sequences may also be referred to as being "essentially similar" or "essentially identical" the FATB sequences provided in the sequence listing.

"FATB-A2 amino acid sequences" or "FATB-A2 variant amino acid sequences" according to the invention are amino acid sequences having at least 80%, at least 85%, at least 90%, at least 95%, 96%, 97%, 98%, 99% or 100% sequence identity with SEQ ID NO: 4 (WOSR FATB-A2) when aligned with or without transit peptide and/or SEQ ID NO: 16 (SOSR FATB-A2) when aligned with or without transit peptide. These amino acid sequences may also be referred to as being "essentially similar" or "essentially identical" the FATB sequences provided in the sequence listing.

"FATB-A3 amino acid sequences" or "FATB-A3 variant amino acid sequences" according to the invention are amino acid sequences having at least 80%, at least 85%, at least 90%, at least 95%, 96%, 97%, 98%, 99% or 100% sequence identity with SEQ ID NO: 6 (WOSR FATB-A3) when aligned with or without transit peptide and/or SEQ ID NO: 18 (SOSR FATB-A3) when aligned with or without transit peptide. These amino acid sequences may also be referred to as being "essentially similar" or "essentially identical" the FATB sequences provided in the sequence listing.

"FATB-C1 amino acid sequences" or "FATB-C1 variant amino acid sequences" according to the invention are amino acid sequences having at least 80%, at least 85%, at least 90%, at least 95%, 96%, 97%, 98%, 99% or 100% sequence identity with SEQ ID NO: 8 (WOSR FATB-C1) when aligned with or without transit peptide and/or with SEQ ID NO: 20 (SOSR FATB-C1) when aligned with or without transit peptide. These amino acid sequences may also be referred to as being "essentially similar" or "essentially identical" the FATB sequences provided in the sequence listing.

"FATB-C2 amino acid sequences" or "FATB-C2 variant amino acid sequences" according to the invention are amino acid sequences having at least 80%, at least 85%, at least 90%, at least 95%, 96%, 97%, 98%, 99% or 100% sequence identity with SEQ ID NO: 10 (WOSR FATB-C2) when aligned with or without transit peptide and/or SEQ ID NO: 22 (SOSR FATB-C2) when aligned with or without transit peptide. These amino acid sequences may also be referred to as being "essentially similar" or "essentially identical" the FATB sequences provided in the sequence listing.

"FATB-C3 amino acid sequences" or "FATB-C3 variant amino acid sequences" according to the invention are amino acid sequences having at least at least 80%, at least 85%, at least 90%, at least 95%, 96%, 97%, 98%, 99% or 100% sequence identity with SEQ ID NO: 12 (WOSR FATB-C3) when aligned with or without transit peptide and/or SEQ ID NO: 24 (SOSR FATB-C3) when aligned with or without transit peptide. These amino acid sequences may also be referred to as being "essentially similar" or "essentially identical" the FATB sequences provided in the sequence listing.

Thus, the invention provides both amino acid sequences of wild type, functional FATB-A1, FATB-A2, FATB-A3, FATB-C1, FATB-C2 and FATB-C3 proteins, including variants and fragments thereof (as defined further below), as well as mutant amino acid sequences of any of these, whereby the mutation in the amino acid sequence preferably results in a significant reduction in the biological activity of the FATB protein. A significant reduction in biological activity of the mutant FATB protein, refers to a reduction in enzymatic activity (i.e. in acyl ACP-thioesterase activity) by at least 30%, at least 40%, 50% or more, at least 90% or 100% (no biological activity) compared to the activity of the wild type protein.

Both endogenous and isolated amino acid sequences are provided herein. A "fragment" of a FATB amino acid sequence or variant thereof (as defined) may be of various lengths, such as at least 10, 12, 15, 18, 20, 50, 100, 200, 400 contiguous amino acids of the FATB sequence (or of the valiant sequence).

Amino Acid Sequences of Functional FATB Proteins

The amino acid sequences depicted in the sequence listing are wild type, functional FATB proteins from *Brassica napus*. Thus, these sequences are endogenous to the WOSR and SOSR plants from which they were isolated. Other *Brassica* crop species, varieties, breeding lines or wild accessions may be screened for other functional FATB proteins with the same amino acid sequences or variants thereof, as described above.

In addition, it is understood that FATB amino acid sequences and variants thereof (or fragments of any of these) may be identified in silico, by screening amino acid databases for essentially similar sequences. Fragments of amino acid molecules according to the invention are also provided. Fragments include amino acid sequences of the mature protein, or smaller fragments comprising all or part of the amino acid sequences, etc.

Amino Acid Sequences of Mutant FATB Proteins.

Amino acid sequences comprising one or more amino acid deletions, insertions or substitutions relative to the wild type amino acid sequences are another embodiment of the invention, as are fragments of such mutant amino acid molecules.

Such mutant amino acid sequences can be generated and/or identified using various known methods, as described above. Again, such amino acid molecules are provided both in endogenous form and in isolated form.

In one embodiment, the mutation(s) in the amino acid sequence result in a significantly reduced or completely abolished biological activity of the FATB protein relative to the wild type protein. As described above, basically, any mutation which results in a protein comprising at least one amino acid insertion, deletion and/or substitution relative to the wild type protein can lead to significantly reduced (or no) enzymatic activity. It is, however, understood that mutations in certain parts of the protein are more likely to result in a reduced function of the mutant FATB protein, such as mutations leading to truncated proteins, whereby significant portions of the functional domains, such as the catalytic domain or amino acids involved in substrate specificity (see above), are lacking or mutations whereby conserved amino acid residues which have a catalytic function or which are involved in substrate specificity are substituted.

Thus in one embodiment, mutant FATB proteins are provided comprising one or more deletion or insertion mutations, whereby the deletion(s) or insertion(s) result(s) in a mutant protein which has significantly reduced or no activity in vivo. Such mutant FATB proteins are FATB proteins wherein at least 1, at least 2, 3, 4, 5, 10, 20, 30, 50, 100, 200, 300, 400 or more amino acids are deleted or inserted as compared to the wild type FATB protein, whereby the deletion(s) or insertion(s) result(s) in a mutant protein which has significantly reduced or no activity in vivo.

In another embodiment, mutant FATB proteins are provided which are truncated whereby the truncation results in a mutant protein which has significantly reduced or no activity in vivo. Such truncated FATB proteins are FATB proteins which lack functional domains in the C-terminal part of the corresponding wild type (mature) FATB protein and which maintain the N-terminal part of the corresponding wild type (mature) FATB protein. Thus in one embodiment, a truncated FATB protein comprising the N-terminal part of the corresponding wild type (mature) FATB protein up to but not including the conserved Cys residue of the papain-like catalytic triad (as described above) is provided. The more truncated the mutant protein is in comparison to the wild type protein, the more likely it is that it will lack any enzymatic activity. Thus in another embodiment, a truncated FATB protein comprising the N-terminal part of the corresponding wild type (mature) FATB protein up to but not including the conserved His or Asn residue of the papain-like catalytic triad (as described above) is provided. In yet another embodiment, a truncated FATB protein comprising the N-terminal part of the corresponding wild type (mature) FATB protein up to but not including the conserved Met, Lys, Val, Ser, or Trp residues involved in substrate specificity (as described above) are provided. In still another embodiment, a truncated FATB protein comprising the N-terminal part of the corresponding wild type (mature) FATB protein lacking part or all of the second 4HBT domain or lacking part or all of the first 4HBT domain (as described above), or even more amino acids are provided.

In yet another embodiment, mutant FATB proteins are provided comprising one or more substitution mutations, whereby the substitution(s) result(s) in a mutant protein which has significantly reduced or no activity in vivo. Such mutant FATB proteins are FATB proteins whereby conserved amino acid residues which have a catalytic function or which are involved in substrate specificity (for example, those described above) are substituted. Thus in one embodiment, a mutant FATB protein comprising a substitution of a conserved amino acid residue which has a catalytic function, such as the conserved Asn, His and Cys residues of the papain-like catalytic triad, is provided. In another embodiment, a mutant FATB protein comprising a substitution of a conserved amino acid residue involved in substrate specificity, such as the conserved Met, Lys, Val, Ser, or Trp residues, is provided.

Methods According to the Invention

Mutant fatB alleles may be generated (for example induced by mutagenesis) and/or identified using a range of methods, which are conventional in the art, for example using PCR based methods to amplify part or all of the fatB genomic or cDNA.

The term "mutagenesis", as used herein, refers to the process in which plant cells (e.g., a plurality of *Brassica* seeds or other parts, such as pollen) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), or a combination of two or more of these. Thus, the desired mutagenesis of one or more FATB alleles may be accomplished by use of chemical means such as by contact of one or more plant tissues with ethylmethylsulfonate (EMS), ethylnitrosourea, etc., by the use of physical means such as x-ray, etc, or by gamma radiation, such as that supplied by a Cobalt 60 source.

Following mutagenesis, *Brassica* plants are grown from the treated seeds, or regenerated from the treated cells using known techniques. For instance, the resulting *Brassica* seeds may be planted in accordance with conventional growing procedures and following self-pollination seed is formed on the plants. Alternatively, doubled haploid plantlets may be extracted from treated microspore or pollen cells to immediately form homozygous plants. Additional seed which is formed as a result of such self-pollination in the present or a subsequent generation may be harvested and screened for the presence of mutant FATB alleles, using techniques which are conventional in the art, for example polymerase chain reaction (PCR) based techniques (amplification of the fatB alleles) or hybridization based techniques, e.g. Southern blot analysis, and/or direct sequencing of fatB alleles. To screen for the presence of point mutations (so called Single Nucleotide Polymorphisms or SNPs) in mutant FATB alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type FATB allele results in the presence of one or more deleted, inserted, or substituted nucleotides (hereinafter called "mutation region") in the resulting mutant FATB allele. The mutant FATB allele can thus be characterized by the location and the configuration of the one or more deleted, inserted, or substituted nucleotides in the wild type FATB allele. The site in the wild type FATB allele where the one or more nucleotides have been inserted, deleted, or substituted, respectively, is also referred to as the "mutation region". A "5' or 3' flanking region or sequence" as used herein refers to a DNA region or sequence in the mutant (or the corresponding wild type) FATB allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) FATB allele which is located either immediately upstream of and contiguous with ("5' flanking region or sequence") or immediately downstream of and contiguous with ("3' flanking region or sequence") the mutation region in the mutant FATB allele (or in the corresponding wild type FATB allele).

The tools developed to identify a specific mutant FATB allele or the plant or plant material comprising a specific mutant FATB allele, or products which comprise plant material comprising a specific mutant FATB allele are based on the specific genomic characteristics of the specific mutant FATB allele as compared to the genomic characteristics of the corresponding wild type FATB allele, such as, a specific restriction map of the genomic region comprising the mutation region, molecular markers or the sequence of the flanking and/or mutation regions.

Once a specific mutant FATB allele has been sequenced, primers and probes can be developed which specifically recognize a sequence within the 5' flanking, 3' flanking and/or mutation regions of the mutant FATB allele in the nucleic acid (DNA or RNA) of a sample by way of a molecular biological technique. For instance a PCR method can be developed to identify the mutant FATB allele in biological samples (such as samples of plants, plant material or products comprising plant material). Such a PCR is based on at least two specific "primers": one recognizing a sequence within the 5' or 3' flanking region of the mutant FATB allele and the other recognizing a sequence within the 3' or 5' flanking region of the mutant FATB allele, respectively; or one recognizing a sequence within the 5' or 3' flanking region of the mutant FATB allele and the other recognizing a sequence within the mutation region of the mutant FATB allele; or one recognizing a sequence within the 5' or 3' flanking region of the mutant FATB allele and the other recognizing a sequence spanning the joining region between the 3' or 5' flanking region and the mutation region of the specific mutant FATB allele (as described further below), respectively.

The primers preferably have a sequence of between 15 and 35 nucleotides which under optimized PCR conditions "specifically recognize" a sequence within the 5' or 3' flanking region, a sequence within the mutation region, or a sequence spanning the joining region between the 3' or 5' flanking and mutation regions of the specific mutant FATB allele, so that a specific fragment ("mutant FATB specific fragment" or discriminating amplicon) is amplified from a nucleic acid sample comprising the specific mutant FATB allele. This means that only the targeted mutant FATB allele, and no other sequence in the plant genome, is amplified under optimized PCR conditions.

PCR primers suitable for the invention may be the following:
oligonucleotides ranging in length from 17 nt to about 200 nt, comprising a nucleotide sequence of at least 17 consecutive nucleotides, preferably 20 consecutive nucleotides selected from the 5' flanking sequence of a specific mutant FATB allele (i.e., for example, the sequence 5' flanking the one or more nucleotides deleted, inserted or substituted in the mutant FATB alleles of the invention, such as the sequence 5' flanking the deletion, non-sense or splice site mutations described above or the sequence 5' flanking the potential STOP codon or splice site mutations indicated in the above Tables) at their 3' end (primers recognizing 5' flanking sequences); or
oligonucleotides ranging in length from 17 nt to about 200 nt, comprising a nucleotide sequence of at least 17 consecutive nucleotides, preferably 20 consecutive nucleotides, selected from the 3' flanking sequence of a specific mutant FATB allele (i.e., for example, the complement of the sequence 3' flanking the one or more nucleotides deleted, inserted or substituted in the mutant FATB alleles of the invention, such as the complement of the sequence 3' flanking the deletion, non-sense or splice site mutations described above or the complement of the sequence 3' flanking the potential STOP codon or splice site mutations indicated in the above Tables) at their 3' end (primers recognizing 3' flanking sequences); or
oligonucleotides ranging in length from 17 nt to about 200 nt, comprising a nucleotide sequence of at least 17 consecutive nucleotides, preferably 20 nucleotides selected from the sequence of the mutation region of a specific mutant FATB allele (i.e., for example, the sequence of nucleotides inserted or substituted in the FATB genes of the invention, or the complement thereof) at their 3' end (primers recognizing mutation sequences).

The primers may of course be longer than the mentioned 17 consecutive nucleotides, and may e.g. be 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be not longer than 100, more preferably not longer than 50 or even 25 nucleotides.

Moreover, suitable primers may comprise or consist of a nucleotide sequence at their 3' end spanning the joining region between flanking and mutation sequences (i.e., for example, the joining region between a sequence 5' flanking one or more nucleotides deleted, inserted or substituted in the mutant FATB alleles of the invention and the sequence of the one or more nucleotides inserted or substituted or the sequence 3' flanking the one or more nucleotides deleted, such as the joining region between a sequence 5' flanking deletion, non-sense or splice site mutations in the FATB genes of the invention described above and the sequence of the non-sense or splice site mutations or the sequence 3' flanking the deletion mutation, or the joining region between a sequence 5' flanking a potential STOP codon or splice site mutation as indicated in the above Tables and the sequence of the potential STOP codon or splice site mutation), provided the mentioned 3'-located nucleotides are not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A⇔T; G⇔C) and reading the sequence in the 5' to 3' direction, i.e in opposite direction of the represented nucleotide sequence.

Examples of primers suitable to identify specific mutant FATB alleles are described in the Examples.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, a sequence within the mutation region, or a sequence spanning the joining region between the 3' or 5' flanking and mutation regions of the specific mutant FATB allele, provided the mismatches still allow specific identification of the specific mutant FATB allele with these primers under optimized PCR conditions. The range of allowable mismatches however, can easily be determined experimentally and are known to a person skilled in the art.

Detection and/or identification of a "mutant FATB specific fragment" can occur in various ways, e.g., via size estimation after gel or capillary electrophoresis or via fluorescence-based detection methods. The mutant FATB specific fragments may also be directly sequenced. Other sequence specific methods for detection of amplified DNA fragments are also known in the art.

Standard PCR protocols are described in the art; such as in 'PCR Applications Manual" (Roche Molecular Biochemicals, 2nd Edition, 1999) and other references. The optimal conditions for the PCR, including the sequence of the specific primers, is specified in a "PCR identification protocol" for each specific mutant FATB allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, $MgCl_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Examples of PCR identification protocols to identify specific mutant FATB alleles are described in the Examples.

Alternatively, specific primers can be used to amplify a mutant FATB specific fragment that can be used as a "specific probe" for identifying a specific mutant FATB allele in biological samples. Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant FATB allele. Such identification methods based on hybridization with a specific probe (either on a solid phase carrier or in solution) have been described in the art. The specific probe is preferably a sequence which, under optimized conditions, hybridizes specifically to a region within the 5' or 3' flanking region and/or within the mutation region of the specific mutant FATB allele (hereinafter referred to as "FATB mutation specific region"). Preferably, the specific probe comprises a sequence of between 20 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the specific mutant FATB allele.

Specific probes suitable for the invention may be the following:

oligonucleotides ranging in length from 20 nt to about 1000 nt, comprising a nucleotide sequence of at least 20 consecutive nucleotides selected from the 5' flanking sequence of a specific mutant FATB allele (i.e., for example, the sequence 5' flanking the one or more nucleotides deleted, inserted or substituted in the mutant FATB alleles of the invention, such as the sequence 5' flanking the deletion, non-sense or splice site mutations described above or the sequence 5' flanking the potential STOP codon or splice site mutations indicated in the above Tables), or a sequence having at least 80% sequence identity therewith (probes recognizing 5' flanking sequences); or oligonucleotides ranging in length from 20 nt to about 1000 nt, comprising a nucleotide sequence of at least 20 consecutive nucleotides selected from the 3' flanking sequence of a specific mutant FATB allele (i.e., for example, the sequence 3' flanking the one or more nucleotides deleted, inserted or substituted in the mutant FATB alleles of the invention, such as the sequence 3' flanking the deletion, non-sense or splice site mutations described above or the sequence 3' flanking the potential STOP codon or splice site mutations indicated in the above Tables), or a sequence having at least 80% sequence identity therewith (probes recognizing 3' flanking sequences); or oligonucleotides ranging in length from 20 nt to about 1000 nt, comprising a nucleotide sequence of at least 20 consecutive nucleotides selected from the mutation sequence of a specific mutant FATB allele (i.e., for example, the sequence of nucleotides inserted or substituted in the FATB genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be not longer than 50, more preferably not longer than 25 or even not longer than 20 or 15 nucleotides.

Moreover, suitable probes may comprise or consist of a nucleotide sequence spanning the joining region between flanking and mutation sequences (i.e., for example, the joining region between a sequence 5' flanking one or more nucleotides deleted, inserted or substituted in the mutant FATB alleles of the invention and the sequence of the one or more nucleotides inserted or substituted or the sequence 3' flanking the one or more nucleotides deleted, such as the joining region between a sequence 5' flanking deletion, non-sense or splice site mutations in the FATB genes of the invention described above and the sequence of the non-sense or splice site mutations or the sequence 3' flanking the deletion mutation, or the joining region between a sequence 5' flanking a potential STOP codon or splice site mutation as indicated in the above Tables and the sequence of the potential STOP codon or splice site mutation), provided the mentioned nucleotide sequence is not derived exclusively from either the mutation region or flanking regions.

Examples of specific probes suitable to identify specific mutant FATB alleles are described in the Examples.

Detection and/or identification of a "mutant FATB specific region" hybridizing to a specific probe can occur in various ways, e.g., via size estimation after gel electrophoresis or via fluorescence-based detection methods. Other sequence specific methods for detection of a "mutant FATB specific region" hybridizing to a specific probe are also known in the art.

Alternatively, plants or plant parts comprising one or more mutant fatB alleles can be generated and identified using other methods, such as the "Delete-a-gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants, seeds and tissues comprising one or more mutant fatB alleles in one or more tissues and methods for generating and identifying such plants is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in fatB alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant fatB alleles. As for the mutagenesis techniques above, preferably Brassica species are screened which comprise an A and/or a C genome, so that the identified fatB allele can subsequently be introduced into other Brassica species, such as Brassica napus, by crossing (inter- or intraspecific crosses) and selection. In ECOTILLING natural polymorphisms in breeding lines or related species are screened for by the TILLING methodology described above, in which individual or pools of plants are used for PCR amplification of the fatB target, heteroduplex formation and high-throughput analysis. This can be followed up by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested by expression in a homologous or heterologous host and testing the mutant FATB protein for functionality in an enzyme assay. Using this approach a plurality of mutant fatB alleles (and Brassica plants comprising one or more of these) can be identified. The desired mutant alleles can then be combined with the desired wild type alleles by crossing and selection methods as described further below. Finally a single plant comprising the desired number of mutant fatB and the desired number of wild type FATB alleles is generated.

Oligonucleotides suitable as PCR primers or specific probes for detection of a specific mutant FATB allele can also be used to develop methods to determine the zygosity status of the specific mutant FATB allele.

To determine the zygosity status of a specific mutant FATB allele, a PCR-based assay can be developed to determine the presence of a mutant and/or corresponding wild type FATB specific allele:

To determine the zygosity status of a specific mutant FATB allele, two primers specifically recognizing the wild-type FATB allele can be designed in such a way that they are directed towards each other and have the mutation region located in between the primers. These primers may be primers specifically recognizing the 5' and 3' flanking sequences, respectively. This set of primers allows simultaneous diagnostic PCR amplification of the mutant, as well as of the corresponding wild type FATB allele.

Alternatively, to determine the zygosity status of a specific mutant FATB allele, two primers specifically recognizing the wild-type FATB allele can be designed in such a way that they are directed towards each other and that one of them specifically recognizes the mutation region. These primers may be primers specifically recognizing the sequence of the 5' or 3' flanking region and the mutation region of the wild type FATB allele, respectively. This set of primers, together with a third primer which specifically recognizes the sequence of the mutation region in the mutant FATB allele, allow simultaneous diagnostic PCR amplification of the mutant FATB gene, as well as of the wild type FATB gene.

Alternatively, to determine the zygosity status of a specific mutant FATB allele, two primers specifically recognizing the wild-type FATB allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type FATB allele, respectively. This set of primers, together with a third primer which specifically recognizes the joining region between the mutation region and the 3' or 5' flanking region of the mutant FATB allele, respectively, allow simultaneous diagnostic PCR amplification of the mutant FATB gene, as well as of the wild type FATB gene.

Alternatively, the zygosity status of a specific mutant FATB allele can be determined by using alternative primer sets which specifically recognize mutant and wild type FATB alleles.

If the plant is homozygous for the mutant FATB gene or the corresponding wild type FATB gene, the diagnostic PCR assays described above will give rise to a single PCR product typical, preferably typical in length, for either the mutant or wild type FATB allele. If the plant is hemizygous for the mutant FATB allele, two specific PCR products will appear, reflecting both the amplification of the mutant and the wild type FATB allele.

Identification of the wild type and mutant FATB specific PCR products can occur e.g. by size estimation after gel or capillary electrophoresis (e.g. for mutant FATB alleles comprising a number of inserted or deleted nucleotides which results in a size difference between the fragments amplified from the wild type and the mutant FATB allele, such that said fragments can be visibly separated on a gel); by evaluating the presence or absence of the two different fragments after gel or capillary electrophoresis, whereby the diagnostic PCR amplification of the mutant FATB allele can, optionally, be performed separately from the diagnostic PCR amplification of the wild type FATB allele; by direct sequencing of the amplified fragments; or by fluorescence-based detection methods.

Examples of primers suitable to determine the zygosity of specific mutant FATB alleles are described in the Examples.

Alternatively, to determine the zygosity status of a specific mutant FATB allele, a hybridization-based assay can be developed to determine the presence of a mutant and/or corresponding wild type FATB specific allele:

To determine the zygosity status of a specific mutant FATB allele, two specific probes recognizing the wild-type FATB allele can be designed in such a way that each probe specifically recognizes a sequence within the FATB wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type FATB allele.

Alternatively, to determine the zygosity status of a specific mutant FATB allele, two specific probes recognizing the wild-type FATB allele can be designed in such a way that one of them specifically recognizes a sequence within the FATB wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type FATB allele, respectively. The use of one or, preferably, both of these probes, optionally, together with a third probe which specifically recognizes the sequence of the mutation region in the mutant FATB allele, allow diagnostic hybridization of the mutant and of the wild type FATB gene.

Alternatively, to determine the zygosity status of a specific mutant FATB allele, a specific probe recognizing the wild-type FATB allele can be designed in such a way that the probe specifically recognizes the joining region between the 5' or 3' flanking region, preferably the 5' flanking region, and the mutation region of the wild type FATB allele. This probe, optionally, together with a second probe which specifically recognizes the joining region between the 5' or 3' flanking region, preferably the 5' flanking region, and the mutation region of the mutant FATB allele, allows diagnostic hybridization of the mutant and of the wild type FATB gene.

Alternatively, the zygosity status of a specific mutant FATB allele can be determined by using alternative sets of probes which specifically recognize mutant and wild type FATB alleles.

If the plant is homozygous for the mutant FATB gene or the corresponding wild type FATB gene, the diagnostic hybridization assays described above will give rise to a single specific hybridization product, such as one or more hybridizing DNA (restriction) fragments, typical, preferably typical in length, for either the mutant or wild type FATB allele. If the plant is hemizygous for the mutant FATB allele, two specific hybridization products will appear, reflecting both the hybridization of the mutant and the wild type FATB allele.

Identification of the wild type and mutant FATB specific hybridization products can occur e.g. by size estimation after gel or capillary electrophoresis (e.g. for mutant FATB alleles comprising a number of inserted or deleted nucleotides which results in a size difference between the hybridizing DNA (restriction) fragments from the wild type and the mutant FATB allele, such that said fragments can be visibly separated on a gel); by evaluating the presence or absence of the two different specific hybridization products after gel or capillary electrophoresis, whereby the diagnostic hybridization of the mutant FATB allele can, optionally, be performed separately from the diagnostic hybridization of the wild type FATB allele; by direct sequencing of the hybridizing DNA (restriction) fragments; or by fluorescence-based detection methods.

Examples of probes suitable to determine the zygosity of specific mutant FATB alleles are described in the Examples.

Furthermore, detection methods specific for a specific mutant FATB allele which differ from PCR- or hybridization-based amplification methods can also be developed using the specific mutant FATB allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex.

Kits According to the Invention

A "kit" as used herein refers to a set of reagents for the purpose of performing the method of the invention, more particularly, the identification of a specific mutant FATB allele in biological samples or the determination of the zygosity status of plant material comprising a specific mutant FATB allele. More particularly, a preferred embodiment of the kit of the invention comprises at least two specific primers, as described above, for identification of a specific mutant FATB allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant FATB allele therein, as described above, for identification of a specific mutant FATB allele, or at least two or three specific probes for the determination of the zygosity status. Optionally, the kit can further comprise any other reagent (such as but not limited to hybridizing buffer, label) for identification of a specific mutant FATB allele in biological samples, using the specific probe.

The kit of the invention can be used, and its components can be specifically adjusted, for purposes of quality control (e.g., purity of seed lots), detection of the presence or absence of a specific mutant FATB allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant FATB allele under the conditions set forth in the method (such as the conditions of the PCR identification protocol), whereby the specificity is determined by the presence of positive and negative controls.

The term "hybridizing" as used herein when referring to specific probes, refers to the fact that the probe binds to a specific region in the nucleic acid sequence of a specific mutant FATB allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denaturated carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass *Brassica* plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for a specific mutant FATB allele, implying the presence of nucleic acids in the samples. Thus the methods referred to herein for identifying a specific mutant FATB allele in biological samples, relate to the identification in biological samples of nucleic acids which comprise the specific mutant FATB allele.

The present invention also relates to the transfer of one or more specific mutant FATB allele(s) in one *Brassica* plant to another *Brassica* plant, to the combination of specific FATB alleles in one plant, to the plants comprising one or more specific mutant FATB allele(s), the progeny obtained from these plants and to the plant cells, or plant material derived from these plants.

Thus, in one embodiment of the invention a method for transferring a mutant FATB allele from one *Brassica* plant to another *Brassica* plant is provided comprising the steps of:
(a) crossing a *Brassica* plant comprising a mutant FATB allele, as described above, with a second *Brassica* plant,
(b) collecting F1 hybrid seeds from the cross,
(c) optionally, backcrossing the F1 plants, derived from the F1 seeds, for one or more generations (x), collecting BCx seeds from the crosses, and identifying in every generation BCx plants, derived from the BCx seeds, comprising the mutant FATB allele as described above,
(d) optionally, extracting doubled haploid plants from treated microspore or pollen cells of F1 or BC1 plants to obtain homozygous plants,
(e) selfing the F1 or BCx plants, derived from the F1 or BCx seeds,
(f) collecting F1 S1 or BCx S1 seeds from the selfing,
(g) identifying F1 S1 or BCx S1 plants, derived from the F1 S1 or BCx S1 seeds, comprising the mutant FATB allele as described above.

In another embodiment of the invention a method for combining at least two mutant FATB alleles in one *Brassica* plant is provided comprising the steps of:

(a) transferring a mutant FATB allele(s) from one *Brassica* plant to another *Brassica* plant as described above,
(b) repeating step (a) until the desired number and/or types of mutant FATB alleles are combined in the second plant.

In yet another embodiment of the invention, a method is provided for making a *Brassica* plant comprising at least 3 mutant fatB alleles of three different FATB genes herein, comprising the steps of:
(a) combining at least three mutant FATB alleles of at least three different FATB genes in one *Brassica* plant, as described above,
(b) optionally, identifying a plant, or part thereof, which is homozygous or heterozygous for one or more mutant FATB alleles by determining the zygosity status of the one or more mutant FATB alleles, as described above,
(c) optionally, identifying a plant, or part thereof, with a significantly reduced amount of functional FATB protein,
(d) optionally, identifying a plant, which produces a seed oil, the fatty acid composition of which is significantly altered as compared to the fatty acid composition of the seed oil of a corresponding wild type *Brassica* plant,
(e) optionally, growing such plants and isolating seed oil from such plants for human consumption.

Plant Seed Oils According to the Invention

Provided are both "low sats" and "no sats" oil derived from seeds of *Brassica* plants according to the invention, especially of *Brassica napus* plants as provided herein, but also from other *Brassica* oilseed species. For example, *Brassica* oilseed species comprising mutant FATB-A and/or FATB-C genes, such as *Brassica juncea* and *Brassica rapa*.

It was found that *Brassica napus* plants comprising a mutation, which causes a significant reduction in the amount of functional FATB protein encoded by the wild type equivalent of the mutant fatB allele, in only one or two of the six FATB genes is not sufficient to significantly reduce the percentage (wt %) of saturated fatty acids in the seed oil of the plants. It is thought that at least three mutant fatB alleles, of three different FATB genes (selected from FATB-A1, FATB-A2, FATB-A3, FATB-C1, FATB-C2 and FATB-C3) need to be comprised in the plant in order to obtain plants which produce a low or no saturate seed oil.

Thus in one aspect of the invention, "low sats" or "no sats" seed oil is provided derived from seeds of *Brassica* plants comprising at least 3 mutant fatB alleles of three different FATB genes (selected from FATB-A1, FATB-A2, FATB-A3, FATB-C1, FATB-C2 and FATB-C3), whereby the mutant fatB alleles result in a significantly reduced amount of functional FATB protein of the type encoded by the wild-type equivalent of these mutant alleles and thus an overall significantly reduced amount of the functional FATB proteins produced in the plant cells, specifically in the developing seeds, in vivo.

In a further aspect of the invention, "low sats" or "no sats" seed oil is provided derived from seeds of homozygous FATB triple mutant-, homozygous FATB quadruple mutant- and/or homozygous FATB quintuple mutant-*Brassica* plants, whereby the mutant alleles are selected from the genes FATB-A1, FATB-A2, FATB-A3, FATB-C1, FATB-C2 and FATB-C3.

In yet a further aspect of the invention, "low sats" or "no sats" seed oil is provided derived from seeds of homozygous FATB triple mutant-, homozygous FATB quadruple mutant- and/or homozygous FATB quintuple mutant-*Brassica* plants, which comprise a further mutant FATB allele, wherein the mutant plants or plant parts are heterozygous for the additional mutant FATB allele, and wherein the mutant alleles are selected from the genes FATB-A1, FATB-A2, FATB-A3, FATB-C1, FATB-C2 and FATB-C3.

By combining sufficient copies of specific mutant fatB alleles with sufficient copies of specific wild type FATB alleles in one plant, it is possible to fine tune the amount and/or type of functional FATB proteins made, which in turn influences the export of (the amount and/or type of) free saturated fatty acids from the plastid and thus the fatty acid composition of the seed oil produced.

Thus in another embodiment of the invention, seed oil comprising a specific amount and/or type of saturated fatty acids is provided derived from seeds of *Brassica* plants comprising at least one specific mutant FATB allele according to the invention and at least one specific wild type FATB allele according to the invention, whereby the specific combination of the mutant and the wild type FATB allele(s) results in a specific amount and/or type of functional FATB proteins produced in the plant cells, specifically in the developing seeds, in vivo.

Also included in the invention is the use of the seed oil of this invention in food applications, in particular, food applications wherein a human health benefit is envisioned. While the oils of the present invention are primarily useful as oils for the human diet (food applications), they might also have utility in the diet of animals (feed applications). Other applications, such as mixing seed oil with a specific modified relative amount and/or composition of saturated fatty acids according to the invention, in particular, seed oil containing significantly less than 7% saturated fatty acids according to the invention, with other vegetable oils, in particular, vegetable oils containing significantly more than 7% saturated fatty acids, such as the ones mentioned in the background section, to decrease the level of saturated fatty acids in the latter one thus making it more suitable for certain applications, such as but not limited to, for the production of biodiesel, are also included in the invention.

Sequences

The sequence listing depicts the genomic FATB protein-encoding DNA of the wild type FATB sequences. These sequences comprises 5 exons interrupted by 4 introns. In the cDNA and corresponding processed mRNA (i.e. the spliced RNA), introns are removed and exons are joined. Thus, for example, the cDNA of the FATB-A1 gene encoding a wild-type FATB-A1 protein from winter oilseed rape (WOSR) *Brassica napus* has the sequence of SEQ ID NO:1 from position 1-504, 590-723, 798-911, 981-1152, and 1243-1560.

FATB Genes

SEQ ID NO 1: DNA of the FATB-A1 gene (with introns), encoding a wild-type FATB-A1 protein from winter oilseed rape (WOSR) *Brassica napus*.

SEQ ID NO 2: wild type FATB-A1 protein encoded by SEQ ID NO: 1.

SEQ ID NO 3: DNA of the FATB-A2 gene (with introns), encoding a wild-type FATB-A2 protein from winter oilseed rape (WOSR) *Brassica napus*.

SEQ ID NO 4: wild type FATB-A2 protein encoded by SEQ ID NO: 3.

SEQ ID NO 5: DNA of the FATB-A3 gene (with introns), encoding a wild-type FATB-A3 protein from winter oilseed rape (WOSR) *Brassica napus*.

SEQ ID NO 6: wild type FATB-A3 protein encoded by SEQ ID NO: 5.

SEQ ID NO 7: DNA of the FATB-C1 gene (with introns), encoding a wild-type FATB-C1 protein from winter oilseed rape (WOSR) *Brassica napus*.

SEQ ID NO 8: wild type FATB-C1 protein encoded by SEQ ID NO: 7.

SEQ ID NO 9: DNA of the FATB-C2 gene (with introns), encoding a wild-type FATB-C2 protein from winter oilseed rape (WOSR) *Brassica napus*.

SEQ ID NO 10: wild type FATB-C2 protein encoded by SEQ ID NO: 9.

SEQ ID NO 11: DNA of the FATB-C3 gene (with introns), encoding a wild-type FATB-C3 protein from winter oilseed rape (WOSR) *Brassica napus*.

SEQ ID NO 12: wild type FATB-C3 protein encoded by SEQ ID NO: 11.

SEQ ID NO 13: DNA of the FATB-A1 gene (with introns), encoding a wild-type FATB-A1 protein from spring oilseed rape (SOSR) *Brassica napus*.

SEQ ID NO 14: wild type FATB-A1 protein encoded by SEQ ID NO: 13.

SEQ ID NO 15: DNA of the FATB-A2 gene (with introns), encoding a wild-type FATB-A2 protein from spring oilseed rape (SOSR) *Brassica napus*.

SEQ ID NO 16: wild type FATB-A2 protein encoded by SEQ ID NO: 15.

SEQ ID NO 17: DNA of the FATB-A3 gene (with introns), encoding a wild-type FATB-A3 protein from spring oilseed rape (SOSR) *Brassica napus*.

SEQ ID NO 18: wild type FATB-A3 protein encoded by SEQ ID NO: 17.

SEQ ID NO 19: DNA of the FATB-C1 gene (with introns), encoding a wild-type FATB-C1 protein from spring oilseed rape (SOSR) *Brassica napus*.

SEQ ID NO 20: wild type FATB-C1 protein encoded by SEQ ID NO: 19.

SEQ ID NO 21: DNA of the FATB-C2 gene (with introns), encoding a wild-type FATB-C2 protein from spring oilseed rape (SOSR) *Brassica napus*.

SEQ ID NO 22: wild type FATB-C2 protein encoded by SEQ ID NO: 21.

SEQ ID NO 23: DNA of the FATB-C3 gene (with introns), encoding a wild-type FATB-C3 protein from spring oilseed rape (SOSR) *Brassica napus*.

SEQ ID NO 24: wild type FATB-C3 protein encoded by SEQ ID NO: 23.

SEQ ID NO 79: DNA of the FATB1 gene encoding a wild-type FATB1 protein from *Arabidopsis thaliana*

SEQ ID NO 80: wild type FATB1 protein encoded by SEQ ID NO: 79

Primers and Probes

SEQ ID NO 25: 5' At FATB1 probe

SEQ ID NO 26: oligonucleotide primer KVA05-14

SEQ ID NO 27: oligonucleotide primer KVA05-15

SEQ ID NO 28: 3' At FATB1 probe

SEQ ID NO 29: oligonucleotide primer KVA05-16

SEQ ID NO 30: oligonucleotide primer KVA05-17

SEQ ID NO 31: Forward oligonucleotide for detection of FATB-A1 (SEQ ID NO: 13)

SEQ ID NO 32: Reverse oligonucleotide for detection of FATB-A1 (SEQ ID NO: 13)

SEQ ID NO 33: Forward oligonucleotide for detection of FATB-A2 (SEQ ID NO: 15)

SEQ ID NO 34: Reverse oligonucleotide for detection of FATB-A2 (SEQ ID NO: 15)

SEQ ID NO 35: Forward oligonucleotide for detection of FATB-A3 (SEQ ID NO: 17)

SEQ ID NO 36: Reverse oligonucleotide for detection of FATB-A3 (SEQ ID NO: 17)

SEQ ID NO 37: Forward oligonucleotide for detection of FATB-C1 (SEQ ID NO: 19)

SEQ ID NO 38: Reverse oligonucleotide for detection of FATB-C1 (SEQ ID NO: 19)

SEQ ID NO 39: Forward oligonucleotide for detection of FATB-C2 (SEQ ID NO: 21)
SEQ ID NO 40: Reverse oligonucleotide for detection of FATB-C2 (SEQ ID NO: 21)
SEQ ID NO 41: Forward oligonucleotide for detection of FATB-C3 (SEQ ID NO: 23)
SEQ ID NO 42: Reverse oligonucleotide for detection of FATB-C3 (SEQ ID NO: 23)
SEQ ID NO 43: Reverse oligonucleotide for detection of FATB-A1
SEQ ID NO 44: Forward oligonucleotide for detection of FATB-A2
SEQ ID NO 45: Reverse oligonucleotide for detection of FATB-A2
SEQ ID NO 46: Reverse oligonucleotide for detection of FATB-A3
SEQ ID NO 47: Reverse oligonucleotide for detection of FATB-C1
SEQ ID NO 48: Reverse oligonucleotide for detection of FATB-C2
SEQ ID NO 49: Reverse oligonucleotide for detection of FATB-C3
SEQ ID NO 50: Forward oligonucleotide for detection of FATB-A1-EMS05
SEQ ID NO 51: Forward oligonucleotide for detection of FATB-A1
SEQ ID NO 52: Reverse oligonucleotide for detection of FATB-A1-EMS05 and -A1
SEQ ID NO 53: Forward oligonucleotide for detection of FATB-A1-EMS06
SEQ ID NO 54: Forward oligonucleotide for detection of FATB-A1
SEQ ID NO 55: Reverse oligonucleotide for detection of FATB-A1-EMS06 and -A1
SEQ ID NO 56: Reverse oligonucleotide for detection of FATB-A2-EMS05
SEQ ID NO 57: Reverse oligonucleotide for detection of FATB-A2
SEQ ID NO 58: Forward oligonucleotide for detection of FATB-A2-EMS05 and -A2
SEQ ID NO 59: Reverse oligonucleotide for detection of FATB-A2-EMS01
SEQ ID NO 60: Reverse oligonucleotide for detection of FATB-A2
SEQ ID NO 61: Forward oligonucleotide for detection of FATB-A2-EMS01 and -A2
SEQ ID NO 62: Reverse oligonucleotide for detection of FATB-A3-EMS01
SEQ ID NO 63: Reverse oligonucleotide for detection of FATB-A3
SEQ ID NO 64: Forward oligonucleotide for detection of FATB-A3-EMS01 and -A3
SEQ ID NO 65: Forward oligonucleotide for detection of FATB-C1-EMS05
SEQ ID NO 66: Forward oligonucleotide for detection of FATB-C1
SEQ ID NO 67: Reverse oligonucleotide for detection of FATB-C1-EMS05, -C1-EMS04, and -C1
SEQ ID NO 68: Forward oligonucleotide for detection of FATB-C1-EMS04
SEQ ID NO 69: Forward oligonucleotide for detection of FATB-C1
SEQ ID NO 70: Forward oligonucleotide for detection of FATB-C2-EMS02
SEQ ID NO 71: Forward oligonucleotide for detection of FATB-C2
SEQ ID NO 72: Reverse oligonucleotide for detection of FATB-C2-EMS02 and -C2
SEQ ID NO 73: Forward oligonucleotide for detection of FATB-C2-EMS03
SEQ ID NO 74: Forward oligonucleotide for detection of FATB-C2
SEQ ID NO 75: Reverse oligonucleotide for detection of FATB-C2-EMS03 and -C2
SEQ ID NO 76: Forward oligonucleotide for detection of FATB-C3-EMS02
SEQ ID NO 77: Forward oligonucleotide for detection of FATB-C3
SEQ ID NO 78: Reverse oligonucleotide for detection of FATB-C3-EMS02 and -C3
SEQ ID NO 81: Oligonucleotide for detection of FATB-A1-EMS05
SEQ ID NO 82: Oligonucleotide for detection of FATB-A1-EMS05
SEQ ID NO 83: Oligonucleotide for detection of FATB-A1-EMS06
SEQ ID NO 84: Oligonucleotide for detection of FATB-A1-EMS06
SEQ ID NO 85: Oligonucleotide for detection of FATB-A2-EMS01
SEQ ID NO 86: Oligonucleotide for detection of FATB-A2-EMS01
SEQ ID NO 87: Oligonucleotide for detection of FATB-A2-EMS05
SEQ ID NO 88: Oligonucleotide for detection of FATB-A2-EMS05
SEQ ID NO 89: Oligonucleotide for detection of FATB-A3-EMS01
SEQ ID NO 90: Oligonucleotide for detection of FATB-A3-EMS01
SEQ ID NO 91: Oligonucleotide for detection of FATB-C1-EMS04
SEQ ID NO 92: Oligonucleotide for detection of FATB-C1-EMS04
SEQ ID NO 93: Oligonucleotide for detection of FATB-C1-EMS05
SEQ ID NO 94: Oligonucleotide for detection of FATB-C1-EMS05
SEQ ID NO 95: Oligonucleotide for detection of FATB-C2-EMS02
SEQ ID NO 96: Oligonucleotide for detection of FATB-C2-EMS02
SEQ ID NO 97: Oligonucleotide for detection of FATB-C2-EMS03
SEQ ID NO 98: Oligonucleotide for detection of FATB-C2-EMS03
SEQ ID NO 99: Oligonucleotide for detection of FATB-C3-EMS02
SEQ ID NO 100: Oligonucleotide for detection of FATB-C3-EMS02
SEQ ID NO 101: Oligonucleotide for detection of ENDO1
SEQ ID NO 102: Oligonucleotide for detection of ENDO1

Unless stated otherwise in the Examples, all recombinant DNA techniques are carried out according to standard protocols as described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK). Standard materials and methods for plant molecular work are described in *Plant Molecular Biology Labfax* (1993) by R. D. D. Croy, jointly published by BIOS Scientific Pub-

EXAMPLES

Example 1

Determination of Number of FATB Genes in *Brassica napus* and Isolation of the DNA Sequences of the FATB Genes To determine the number of FATB genes in *Brassica napus* and the sequences of the different FATB genes, Bacterial Artificial Chromosome (BAC) libraries of different *Brassica napus* varieties were screened as follows:

1.1. Isolation of BAC Clones Comprising a FATB Sequence

To identify *Escherichia coli* colonies containing a BAC clone comprising a FATB sequence of different *Brassica napus* varieties, BAC libraries of an elite *Brassica napus* spring oilseed rape line (hereinafter called "SOSR") and of the *Brassica napus* winter oilseed rape variety Express (hereinafter called "WOSR Express") (average clone size of more than 120 kb) arrayed as individual duplicated clones on high density nylon filters were screened by standard Southern hybridization procedures:

DNA templates for the preparation of probes to detect the *Brassica* FATB genes were prepared by a polymerase chain reaction (PCR):

Templates:
(a) a pGEM5Zf(+) vector comprising a 487 bp fragment of the 5' part of the FATB1 gene from *Arabidopsis thaliana* cv. Colombia (At1g08510) (SEQ ID NO: 25) (pKVA48)
(b) a pGEM5Zf(+) vector comprising a 352 bp fragment of the 3' part of the FATB1 gene from *Arabidopsis thaliana* cv. Colombia (SEQ ID NO: 28). (pKVA49)

Primers:

```
(a) Forward primer:
                   (KVA05-14-SEQ ID NO: 26)
5'-GAACTTTCATCAACCAGTTACC-3'

Reverse primer:
                   (KVA05-15-SEQ ID NO: 27)
5'-TTATGC-AAGAGGATAGCTTACC-3'

(b) Forward primer:
                   (KVA05-16-SEQ ID NO: 29)
5-CAGTGTGTGGGTGATGATGA-3'

Reverse primer:
                   (KVA05-17-SEQ ID NO: 30)
5'-TATTCCCACTGGAGCACTCT-3'
```

PCR mix:
20 µl 10×PCR buffer, 2 µl dNTPs (25 mM), 1 µl Taq polymerase (5 U/µl), 168 µl H$_2$O, and
4 µl KVA05-14 (10 µM), 4 µl KVA05-15 (10 µM), 1 µl pKVA48 (20 pg/µl),
4 µl KVA05-16 (10 µM), 4 µl KVA05-17 (10 µM), 1 µl pKVA49 (20 pg/µl), divided in 4×50 µl Thermocycling profile: 4 min at 94° C.; 5×[1 min at 94° C. (denaturation) and 1 min at 50° C. (annealing) and 2 min at 72° C. (elongation)]; 25× [40 sec at 94° C. (denaturation) and 40 sec at 50° C. (annealing) and 1 min at 72° C. (elongation)]; 5 min at 72° C.; cool down to 10° C.

This generated:
(a) the 487 bp DNA fragment of the *Arabidopsis* FATB1 gene (SEQ ID NO: 25; "5' AtFATB1 probe") comprised in vector pKVA48.
(b) the 352 bp DNA fragment of the *Arabidopsis* FATB1 gene (SEQ ID NO: 28; "3' AtFATB1 probe") comprised in vector pKVA49.

The DNA fragments were purified and the 478 bp DNA fragments ("5' AtFATB1 probe") were labeled according to standard procedures (e.g., using α-$^{32}$P-dCTP and Ready-To-Go DNA labeling Beads—Amersham Bioscience®) and used for hybridizing to the DNA on the nylon membrane. Alternatively, the 352 bp DNA fragments ("3' AtFATB1 probe") can be labeled and used for hybridizing to the DNA on the nylon membrane.

Pre-hybridization was performed for 2 hour at 65° C. in 30 ml of the following hybridization buffer: 6×SSC (20× SSC contains 3.0 M NaCl, 0.3 M Na citrate, pH 7.0), 5×Denhardt's (100×Denhardt's contains 2% Ficoll, 2% Polyvinyl pyrollidone, 2% Bovine Serum Albumin), 0.5% SDS and 20 µg/ml denatured carrier DNA (single-stranded fish sperm DNA, with an average length of 120-3000 nucleotides)

Hybridization was performed under the following conditions:
The labeled probe was denatured by heating for 5 minutes at 95° C. and chilling on ice for 5 minutes and added to 15 ml of hybridization buffer (same buffer as for the pre-hybridization)
The hybridization was performed overnight at 65° C.

The blots were washed three times for 30 minutes at 65° C. in the hybridization tubes (once with 30 ml 6×SSC with 0.1% SDS and twice with 30 ml 2×SSC with 0.1% SDS) and one time for 10 minutes at 65° C. with 500 ml 2×SSC with 0.1% SDS in a box.

Kodak X-OMAT AR films were exposed to the radioactive blots for 4 hours at −70° C.

Based on the positive signals, 72 *E. coli* colonies containing a BAC clone comprising a FATB sequence were picked up by screening the BAC library from WOSR Express (total n° of positives: 114) and 40 by screening the BAC library from SOSR (total n° of positives: 135) in a second BAC library screening (hereinafter called "positive colonies").

1.2. Isolation of BAC Clones Comprising a Full-Length FATB Sequence

To identify positive colonies comprising a BAC clone with a full-length genomic sequence of one of the FATB genes, a Southern blot analysis was performed on BAC clone DNA isolated from the positive colonies and on genomic DNA isolated from *Brassica napus*:

BAC clone DNA was isolated through alkaline lysis as described in the art from the positive colonies grown up in 100 ml (for WOSR Express) or in 25 ml (for SOSR) Luria Broth medium containing 25 µg/ml chloramphenicol.

Genomic DNA was isolated from leaf tissue of the *B. napus* winter oilseed rape variety Darmor (hereinafter called "WOSR Darmor") according to the cetyltrimethylammoniumbromide (CTAB) method (Doyle and Doyle, 1987, Phytochemistry Bulletin 19:11-15).

The DNA concentration of each preparation was estimated by comparing the band intensity of 1 µl of each sample to the band intensity of 1, 2, 4, 8 and 20 µl of a solution containing 25 ng/µl Lambda DNA (Life Technologies®) on a 1% TBE (Invitrogen®) agarose gel (Roche®) containing ethidiumbromide (ICN Biochemicals®).

100-200 ng (for WOSR Express) or 10 ng (for SOSR) of BAC clone DNA and 1.7 µg genomic DNA isolated from WOSR Darmor were digested with restriction enzymes AseI and EcoRV in a final reaction volume of 20 µl, applying conditions proposed by the manufacturer (New England Biolabs). The time of digestion and/or amount of restriction enzyme were adjusted to ensure complete digestion of the genomic DNA samples without non-specific degradation.

After digestion, 2 µl of loading dye containing RNase (12.5 ml 1% xylene cyanol FF; 12.5 ml 1% bromophenol blue water soluble indicator; 25 ml glycerol; 100 µl 0.5M EDTA pH8; 1 µl RNase (10 mg/ml)) was added to the digested DNA samples and the samples were incubated for 30 min at 37° C.

The samples were loaded on a 1% TAE agarose gel.

Phage Lambda DNA (Fermentas®) digested with PstI (which generates 29 fragments (in bp): 11501, 5077, 4749, 4507, 2838, 2556, 2459, 2443, 2140, 1986, 1700, 1159, 1093, 805, 514, 468, 448, 339, 264, 247, 216, 211, 200, 164, 150, 94, 87, 72, 15—fragments in italic are not visible in standard electrophoresis) (for WOSR Express) or 1 kbp DNA Ladder (Life Technologies) (for SOSR) was included as size standard.

After electrophoresis, the DNA samples (digested BAC clone and genomic DNA) were transferred to a nylon membrane (Hybond-N+ Amersham Pharmacia Biotech®) by dry alkali capillary blotting.

The nylon membranes with digested BAC clone and genomic DNA were screened by standard Southern hybridization procedures as described above for the BAC library screenings, except that for the genomic DNA the Kodak XOMAT AR films were exposed to the radioactive blots for 2 days at −70° C.

Based on a comparison between the hybridization patterns obtained after digestion of BAC clone DNA of the identified positive colonies and of genomic DNA isolated from Brassica napus WOSR Darmor with restriction enzymes AseI and EcoRV and hybridization with the 5' AtFATB1 probe (SEQ ID NO: 25) (see Table 14) and the number of BAC clones displaying a particular restriction pattern, the BAC clones were grouped in 6 groups and for each of the 6 groups a BAC clone was selected containing a full-length FATB sequence (named FATB1 to 6).

The FATB sequences comprised in the BAC clones of the selected positive colonies were determined by standard sequencing techniques (Agowa).

TABLE 14

Hybridization pattern of digested BAC clone and genomic DNA hybridized to the 5' AtFATB1 probe (SEQ ID NO: 25)

| | DNA sample: | | | |
|---|---|---|---|---|
| restricted with: | Genomic DNA from WOSR Darmor | BAC clone DNA from WOSR Express | BAC clone DNA from SOSR | Corresponds to |
| | Estimated length of the hybridizing DNA fragments: | | | |
| AseI | 2.2 | 2.2 | 2.2 | FATB1 |
| | 8.8 | 8.8 | 4.5 | FATB2 |
| | 2.4 | 5.5 | 2.4 | FATB3 |
| | 2.2 | 2.2 | 2.2 | FATB4 |
| | 3.0 | 3.0 | 3.0 | FATB5 |
| | 1.7 | 1.7 | 1.7 | FATB6(a) |
| | 0.8 | 0.8 | 0.8 | FATB6(b) |
| EcoRV | 12 | | 11 | FATB1 |
| | 2.7 | | 2.7 | FATB2 |
| | 3.5 | | 3.5 | FATB3(a) |
| | 0.65 | | 0.65 | FATB3(b) |
| | 4.5 | | 4.5 | FATB4 |
| | 2.9 | | 2.9 | FATB5 |
| | 4.2 | | 4.2 | FATB6 |

The presence of 6 distinct groups of BAC clones was confirmed by AFLP analysis on the BAC clone DNA of the identified positive colonies and of genomic DNA isolated from Brassica napus WOSR Darmor (Vos et al., 1995, Nucleic Acids Research 23 (21):4407-4414).

Example 2

Characterization of FATB Gene Sequences from Brassica napus

After sequencing, the coding regions of the FATB sequences were determined with FgeneSH (Softberry, Inc. Mount Kisco, N.Y., USA) and est2genome (Rice et al., 2000, Trends in Genetics 16 (6): 276-277; Mott, 1997, Comput. Applic. 13:477-478) as depicted in the sequence listing.

Alignment of the different FATB sequences with partial FATB sequences isolated from B. rapa (AA) and B. oleracea (CC) indicated that the FATB1, FATB2, and FATB3 sequences originated from the A genome and the FATB4, FATB5, and FATB6 sequences from the C genome.

Multi-way alignment (Align Plus program—Scientific & Educational Software, USA; using the following default parameters: mismatch penalty=2, open gap penalty=4, extend gap penalty=1; for nucleotides the default scoring matrix used is Standard linear and for proteins the default scoring matrix is BLOSUM62) of the different FATB coding regions with or without intron sequences and FATB amino acid sequences showed that FATB1 and FATB4, FATB2 and FATB5, and FATB3 and FATB6 are more related to each other than to the other FATB genes, indicating that they are homeologous genes.

Based on these analyses, the sequences FATB1-FATB6 were renamed as FATB-A1, FATB-A2, FATB-A3, FATB-C1, FATB-C2 and FATB-C3, respectively, and this designation is used throughout the specification. Both protein and nucleic acid sequences of WOSR and SOSR *Brassica napus* genes are provided herein.

WOSR Sequences

The genomic sequences, i.e. the protein encoding regions of FATB-A1 to FATB-A3 and FATB-C1 to FATB-C3 including the intron sequences, of WOSR Express are represented in SEQ ID NO:1, SEQ ID NO:3, SEQ ID NO:5, SEQ ID NO:7, SEQ ID NO:9, and SEQ ID NO:11, respectively. The, by these nucleic acid sequence encoded, FATB-A1 to FATB-A3 and FATB-C1 to FATB-C3 protein sequences are depicted in SEQ ID NO:2, SEQ ID NO:4, SEQ ID NO:6, SEQ ID NO:8, SEQ ID NO:10, and SEQ ID NO:12, respectively.

SOSR Sequences

The genomic sequences, i.e. the protein encoding regions of FATB-A1 to FATB-A3 and FATB-C1 to FATB-C3 including the intron sequences, of SOSR are represented in SEQ ID NO: 13, SEQ ID NO: 15, SEQ ID NO: 17, SEQ ID NO: 19, SEQ ID NO:21, and SEQ ID NO:23. The, by these nucleic acid sequences encoded, FATB-A1 to FATB-A3 and FATB-C1 to FATB-C3 protein sequences are in SEQ ID NO: 14, SEQ ID NO: 16, SEQ ID NO: 18, SEQ ID NO: 20, SEQ ID NO: 22, and SEQ ID NO: 24, respectively.

Table 15 shows the percentage (nucleotide) sequence identity between the different FATB coding regions of WOSR Express (Table 15a) and SOSR (Table 15b), with and without intron sequences, and shows the higher degree of relatedness between the homologous FATB-A1 and FATB-C1, FATB-A2 and FATB-C2, and FATB-A3 and FATB-C3 (see underlines values) and indicates that the different FATB genes are more conserved in the exon than in the intron sequences.

TABLE 15a

Percentage (nucleotide) sequence identity between the different FATB coding regions obtained from WOSR Express, with/without intron sequences

| % sequence identity | FATB-A1 | FATB-A2 | FATB-A3 | FATB-C1 | FATB-C2 | FATB-C3 |
|---|---|---|---|---|---|---|
| FATB-A1 | 100/100 | 75.0/82.5 | 75.4/87.6 | <u>91.3/94.8</u> | 71.4/85.7 | 68.5/87.3 |
| FATB-A2 | | 100/100 | 70.6/83.0 | 77.5/83.4 | <u>85.2/94.3</u> | 64.4/83.3 |
| FATB-A3 | | | 100/100 | 75.3/88.0 | 67.4/85.4 | <u>83.5/96.7</u> |
| FATB-C1 | | | | 100/100 | 73.0/86.6 | 68.5/88.0 |
| FATB-C2 | | | | | 100/100 | 61.2/86.0 |
| FATB-C3 | | | | | | 100/100 |

TABLE 15b

Percentage (nucleotide) sequence identity between the different FATB coding regions obtained from SOSR with/without intron sequences

| % identity | FATB-A1 | FATB-A2 | FATB-A3 | FATB-C1 | FATB-C2 | FATB-C3 |
|---|---|---|---|---|---|---|
| FATB-A1 | 100/100 | 76.1/84.1 | 75.6/87.6 | <u>91.4/94.8</u> | 71.4/85.7 | 68.6/87.5 |
| FATB-A2 | | 100/100 | 72.3/84.8 | 78.8/85.3 | <u>86.6/96.4</u> | 65.3/85.1 |
| FATB-A3 | | | 100/100 | 76.1/87.9 | 68.0/85.3 | <u>84.2/96.4</u> |
| FATB-C1 | | | | 100/100 | 73.0/86.7 | 68.7/88.0 |
| FATB-C2 | | | | | 100/100 | 61.1/86.0 |
| FATB-C3 | | | | | | 100/100 |

Table 16, below, shows the percentage (nucleotide) sequence identity between the different FATB coding regions (with/without intron sequences) obtained from WOSR Express (W) and SOSR (S) and shows that the higher degree of relatedness between the homeologous FATB-A1 and FATB-C1, FATB-A2 and FAT-C2, and FATB-A3 and FATB-C3 is conserved between different *Brassica napus* varieties or breeding lines (see underlines values), i.e., the percentage of sequence identity between the homeologous FATB-A1 and FATB-C1, for example, between sequences from different varieties is higher than the percentage sequence identity between these FATB genes and the other FATB genes of the same variety.

In addition, it can be seen that there is a high percentage sequence identity between WOSR and SOSR alleles of the same gene (e.g. FATB-A1 from WOSR and FATB-A1 from SOSR; see bold values), indicating that *Brassica napus* varieties and breeding lines have closely related FATB alleles in their genomes.

TABLE 16

Sequence identity between the different FATB coding regions with/without intron sequences of WOSR Express (W) and of SOSR (S)

| % identity | FATB-A1 (W) | FATB-A2 (W) | FATB-A3 (W) | FATB-C1 (W) | FATB-C2 (W) | FATB-C3 (W) |
|---|---|---|---|---|---|---|
| FATB-A1 (S) | 99.7/99.6 | 76.3/84.3 | 75.4/87.4 | 91.2/94.6 | 71.4/85.7 | 68.4/87.2 |
| FATB-A2 (S) | 74.8/82.3 | 98.3/97.8 | 71.2/82.9 | 77.5/83.4 | 85.2/94.3 | 64.3/83.2 |
| FATB-A3 (S) | 75.6/87.9 | 71.7/84.9 | 97.8/98.6 | 75.4/88.0 | 67.4/85.4 | 83.4/96.6 |
| FATB-C1 (S) | 91.5/95.0 | 78.8/85.3 | 76.0/88.0 | 99.8/99.7 | 73.0/86.6 | 68.5/87.9 |
| FATB-C2 (S) | 71.4/85.7 | 86.6/96.4 | 68.0/85.3 | 73.0/86.7 | 100/100 | 61.1/86.0 |
| FATB-C3 (S) | 68.7/87.5 | 65.3/85.2 | 84.3/96.5 | 68.6/87.9 | 61.2/86.0 | 99.9/99.9 |

Table 17a and b show the percentage (amino acid) sequence identity between the different FATB amino acid sequences of WOSR Express (Table 17a) and SOSR (Table 17b).

TABLE 17a

Percentage sequence identity between the different FATB amino acid sequences of WOSR Express

| % identity | FATB-A1 | FATB-A2 | FATB-A3 | FATB-C1 | FATB-C2 | FATB-C3 |
|---|---|---|---|---|---|---|
| FATB-A1 | 100.0 | 86.5 | 90.2 | 96.2 | 88.5 | 89.3 |
| FATB-A2 | | 100.0 | 85.0 | 86.8 | 95.3 | 83.8 |
| FATB-A3 | | | 100.0 | 89.7 | 87.6 | 98.6 |
| FATB-C1 | | | | 100.0 | 88.9 | 88.7 |
| FATB-C2 | | | | | 100.0 | 86.4 |
| FATB-C3 | | | | | | 100.0 |

TABLE 17b

Percentage sequence identity between the different FATB amino acid sequences of SOSR

| % identity | FATB-A1 | FATB-A2 | FATB-A3 | FATB-C1 | FATB-C2 | FATB-C3 |
|---|---|---|---|---|---|---|
| FATB-A1 | 100.0 | 89.0 | 90.1 | 96.6 | 89.0 | 89.7 |
| FATB-A2 | | 100.0 | 87.3 | 88.9 | 98.6 | 86.6 |
| FATB-A3 | | | 100.0 | 89.4 | 87.3 | 97.8 |
| FATB-C1 | | | | 100.0 | 88.9 | 88.7 |
| FATB-C2 | | | | | 100.0 | 86.4 |
| FATB-C3 | | | | | | 100.0 |

Table 18 shows the percentage (amino acid) sequence identity between the different FATB amino acid sequences of WOSR Express (W) and of SOSR (S). The percentages sequence identity indicate that FATB-A1 and FATB-C1, FATB-A2 and FATB-C2, and FATB-A3 and FATB-C3, are homeologues genes (see underlines values) and that the higher degree of, relatedness between these homeologues is conserved between different varieties.

In addition, it can be seen that there is a high percentage sequence identity between WOSR and SOSR proteins of the same FATB gene (e.g. FATB-A1 from WOSR and FATB-A1 from SOSR; see bold values), indicating that *Brassica napus* varieties and breeding lines have closely related FATB alleles in their genomes, encoding the same or highly similar proteins.

TABLE 18

Percentage sequence identity between the different FATB amino acid sequences of WOSR Express (W) and of SOSR (S)

| % identity | FATB-A1 (W) | FATB-A2 (W) | FATB-A3 (W) | FATB-C1 (W) | FATB-C2 (W) | FATB-C3 (W) |
|---|---|---|---|---|---|---|
| FATB-A1 (S) | 99.5 | 88.6 | 89.7 | 96.2 | 88.5 | 89.3 |
| FATB-A2 (S) | 86.9 | 96.5 | 84.5 | 86.8 | 95.3 | 83.8 |
| FATB-A3 (S) | 90.7 | 87.8 | 99.3 | 89.7 | 87.6 | 98.6 |
| FATB-C1 (S) | 96.6 | 88.9 | 89.4 | 100.0 | 88.9 | 88.7 |
| FATB-C2 (S) | 89.0 | 98.6 | 87.3 | 88.9 | 100.0 | 86.4 |
| FATB-C3 (S) | 89.7 | 86.6 | 97.8 | 88.7 | 86.4 | 100.0 |

Example 3

Expression of *Brassica* FATB Genes

To analyze the expression of the different FATB genes in different tissues, semi-quantitative RT-PCR assays specific for each FATB gene were performed on total RNA isolated from various *Brassica* plant tissues:

Templates:
  A series of increasing amounts of total RNA, i.e., 0.1 ng, 1 ng, 10 ng and 100 ng, isolated from leaves, roots, unopened flower buds and apices, cotyledons, pods 11 days after anthesis with and without seeds and seeds of those pods, seeds of pods 21 and 34 days after anthesis and callus of *Brassica napus* SOSR, with the RNeasy Plant Minikit (Qiagen) according to the manufacturer's instructions.
  A series of increasing amounts of genomic DNA, i.e., 0.1 ng, 1 ng, and 10 ng, isolated from leaf tissue of the *Brassica napus* SOSR according to the CTAB method (Doyle and Doyle, 1987, Phytochemistry Bulletin 19:11-15).

Primers and Length of the Fragment Amplified from the Target FATB Gene:
  to determine the expression of the FATB-A1 gene (SEQ ID NO:13):

```
                                        (SEQ ID NO: 31)
Forward: 5'-CTGATAACGAGACGTCCTCAC-3'
                                        (SEQ ID NO: 32)
Reverse: 5'-CATCCTGGAGACGGAGCAGG-3'
→ 957 bp for FATB-A1 RNA template and
→ 1275 bp for FATB-A1 genomic DNA template
``` to determine the expression of the FATB-A2 gene (SEQ ID NO:15):

```
Forward:
5'-CTGCCTGACTGGAGTATGCTG-3'    (SEQ ID NO: 33)

Reverse:
5'-GTTGTTGCTCCTGTCTTGGAG-3'    (SEQ ID NO: 34)

→ 956 bp for FATB-A2 RNA template
and
→ 1340 bp for FATB-A2 genomic DNA template
``` to determine the expression of the FATB-A3 gene (SEQ ID NO:17):

```
Forward:
5'-GCAGTGGATGATGCTTGATAC-3'    (SEQ ID NO: 35)

Reverse:
5'-CAAGTCGTTGATGGTGTTTTC-3'    (SEQ ID NO: 36)

→ 900 bp for FATB-A3 RNA template
and
→ 1367 bp for FATB-A3 genomic DNA template
``` to determine the expression of the FATB-C1 gene (SEQ ID NO:19):

```
Forward:
5'-CTGCCTGACTGGAGCATGCTC-3'    (SEQ ID NO: 37)

Reverse:
5'-GTTCTTCCTCTCACCACTTCG-3'    (SEQ ID NO: 38/67)

→ 926 bp for FATB-C1 RNA template
and
→ 1259 bp for FATB-C1 genomic DNA template
``` to determine the expression of the FATB-C2 gene (SEQ ID NO:21):

```
Forward:
5'-ATCGTTCAGGATGGTCTTGTC-3'    (SEQ ID NO: 39)

Reverse:
5'-GCAGTCTTGTCATCAAGTTTG-3'    (SEQ ID NO: 40)

→ 500 bp for FATB-C2 RNA template
and

→ 937 bp for FATB-C2 genomic DNA template
``` to determine the expression of the FATB-C3 gene (SEQ ID NO:23):

```
Forward:
5'-ACAGTGGATGATGCTTGACTC-3'    (SEQ ID NO: 41)

Reverse:
5'-CGAACATAGTCAGCAGTCTTC-3'    (SEQ ID NO: 42)

→ 582 bp for FATB-C3 RNA template
and

→ 1151 bp for FATB-C3 genomic DNA template.
```

PCR Mix:
for RT-PCR on RNA (prepared with Superscript™ III One-Step RT-PCR System with Platinum® Taq DNA polymerase (Invitrogen)):12.5 µl 2× reaction mix, 1 µl Superscript™ III/Platinum® Taq DNA polymerase, 9.5 µl Milli-Q $H_2O$, 1 µl RNA (0.1 ng/µl, 1 ng/µl, 10 ng/µl and 100 ng/µl), 0.5 µl forward primer (20 µM), 0.5 µl reverse primer (20 µM))=Total volume of 25 µl;
for PCR on genomic DNA: 12.5 µl 2× reaction mix, 0.41 Platinum® Taq DNA polymerase (5 U/µl; Invitrogen), 0.5 µl forward primer (20 µM), 0.5 µl reverse primer (20 µM), 1 µl DNA (0.1 ng/µl, 1 ng/µl and 10 ng/µl), 10.3 µl Milli-Q $H_2O$=Total volume of 25 µl;

Thermocycling profile: 30 min at 55° C. (cDNA synthesis), 2 min at 94° C.; 30× [15 sec at 94° C. (denaturation) and 30 sec at 57° C. (annealing) and 2 min at 68° C. (elongation)]; 5 min at 68° C.; cool down to 10° C.

After amplification, 5 µl loading dye (2.5 ml 0.1% bromophenol blue, 2.5 ml 0.1% xyleencyanol, 5 ml glycerol, 50 µl 0.5M EDTA pH8) was added to the PCR samples and 15 µl of the samples were loaded on a 1% TAE (10×(400 mM Tris-Acetate+100 mM EDTA); Invitrogen®) agarose (Roche®) gel containing ethidiumbromide together with an appropriate molecular weight marker (1 Kb DNA ladder, GibcoBRL® Life Technologies).

The banding patterns obtained after amplification of the total RNA from different tissues and the genomic DNA of *Brassica napus* SOSR with the FATB gene-specific primers were evaluated as follows:

Data from the RNA samples within a single RT-PCR run and a single RT-PCR mix were not accepted unless the PCR products and the RT-PCR products (if any, in the case of the RT-PCR products; see below) amplified from the series of increasing amounts of genomic DNA and total RNA, respectively, showed the fragment lengths expected for the target FATB gene (as indicated above) and increased in amount proportionally to the increasing amount of template DNA and RNA, respectively.

Lanes comprising no RT-PCR products amplified from the series of increasing amounts of total RNA for the specific target FATB gene of the expected size, indicate that the specific target FATB gene is not expressed or expressed at very low levels in the corresponding tissue from which the template RNA was prepared.

Lanes comprising RT-PCR products amplified from the series of increasing amounts of total RNA for the specific target FATB gene of the expected size, indicate that the specific target FATB gene is expressed in the corresponding tissue from which the template RNA was prepared.

To determine the level of expression of each FATB gene in a specific tissue relative to the level of expression of the other FATB genes in that specific tissue, the intensity of the bands observed on the electrophoresis gel (resulting from ethidiumbromide staining of the DNA and observed under UV light) of the FATB RT-PCR products were compared with the intensity of the bands observed on the electrophoresis gel of the FATB PCR products amplified from the series of increasing amounts of genomic DNA.

Results

All FATB genes were expressed in all tissues analyzed (+ in Table 19). The level of expression of each FATB gene in leaves and seeds of pods of 11, 21 and 34 days (based on 10 ng RNA) expressed as the amount of genomic DNA (in ng) which generated a band intensity comparable with the band intensity of the FATB gene-specific RT-PCR product (as explained above) is indicated between brackets in Table 20.

TABLE 20

| Tissue | FATB-A1 | FATB-A2 | FATB-A3 | FATB-C1 | FATB-C2 | FATB-C3 |
|---|---|---|---|---|---|---|
| Leaf | + (0.1) | + (5) | + (>10) | + (<0.1) | + (5) | + (10) |
| Root | + | + | + | + | + | + |
| Unopened flowerbud + apex | + | + | + | + | + | + |
| Cotyledons | + | + | + | + | + | + |
| Callus | + | + | + | + | + | + |
| Pods 11d without seed | + | + | + | + | + | + |
| Pods 11d with seed | + | + | + | + | + | + |
| Seed from pods 11d | + (<0.1) | + (1) | + (10) | + (<0.1) | + (5) | + (1) |
| Pods 21d without seed | + | + | + | + | + | + |
| Pods 21d with seed | + | + | + | + | + | + |
| Seed from pods 21d | + (0.1) | + (1) | + (1) | + (0.1) | + (5) | + (1) |
| Pods 34d without seed | + | + | + | + | + | + |
| Seed from pods 34d | + (<0.01) | + (0.05) | + (0.05) | + (0.05) | + (0.5) | + (0.05) |

The timing (11, 21 and 34 days after anthesis) and the level of expression of each FATB gene in seed (based on 10 ng RNA) expressed as the amount of genomic DNA (in ng) which generated a band intensity comparable with the band intensity of the FATB gene-specific RT-PCR product (as explained above) is indicated in FIG. 1.

Example 4

Generation and Isolation of Mutant *Brassica* FATB Alleles (fatB)

Mutations in the FATB genes identified in Example 1 were generated and identified using the following approaches, described below. In section 4.1 the generation of fatB alleles which comprise deletions of one or more nucleotides, e.g. lacking parts or whole of the fatB allele ("deletion mutants"), is described. In section 4.2 the generation and isolation of fatB alleles comprising STOP codon mutations ("non-sense mutants") and/or one or more splice site mutations is described.

4.1 Generation of and Screening for fatB Deletion Mutants

Seeds from a *Brassica napus* SOSR (wild type, referred to as "M0" seeds) were mutagenized using the fast neutron mutagenesis approach as described in the art to generate a mutant seed population (referred to as "M1" seeds).

60,000 M1 plants were grown and selfed. The resulting M2 seeds were harvested for each individual M1 plant.

1000 M2 plants, derived from different M1 plants, were grown and DNA samples were prepared from leaf samples of each individual M2 plant according to the CTAB method (Doyle and Doyle, 1987, Phytochemistry Bulletin 19:11-15). The M2 plants were selfed to obtain M3 seeds.

The concentration of the DNA samples was estimated as described in Example 1. 1.7 μg of genomic DNA was digested with restriction enzymes AseI and EcoRV in a final reaction volume of 20 μl, under the following conditions (enzymes and buffers from New England Biolabs®):

AseI digest: 17 μl DNA (100 ng/μl), 1 μl AseI (10 U/μl), 2 μl NEB3 buffer

EcoRV digest: 17 μl DNA (100 ng/μl), 1 μl EcoRI (10 U/μl), 2 μl NEB3 buffer, 0.2 μl 100× Bovine Serum Albumin incubated overnight at 37° C. or for 4 hours at 37° C.

After digestion, 2 μl of loading dye containing RNase (12.5 ml 1% xylene cyanol FF; 12.5 ml 1% bromophenol blue water soluble indicator; 25 ml glycerol; 100 μl 0.5M EDTA pH8; 1 μl RNase (10 mg/ml)) was added to the digested DNA samples and the samples were incubated for 30 min at 37° C. The samples were loaded on a 1% TAE (Invitrogen®) agarose gel. Phage Lambda DNA (Fermentas®) digested with restriction enzyme PstI (which generates 29 fragments (in bp): 11501, 5077, 4749, 4507, 2838, 2556, 2459, 2443, 2140, 1986, 1700, 1159, 1093, 805, 514, 468, 448, 339, 264, 247, 216, 211, 200, 164, 150, 94, 87, 72, 15 (fragments in italic are not visible in standard electrophoresis) was included as size standard.

After electrophoresis, the DNA samples (digested genomic DNA) were transferred to a nylon membrane (Hybond-N+ Amersham Pharmacia Biotech®) by dry alkali capillary blotting. The nylon membranes with digested genomic DNA were screened by standard Southern hybridization procedures as described in Example 1 for the genomic DNA with the 5' At FATB1 probe (SEQ ID NO: 25). Kodak XOMAT AR films were exposed to the radioactive blots for 2 days at −70° C.

Results

The hybridization patterns obtained after digestion of genomic DNA of M2 *Brassica* plants with AseI and EcoRV and hybridization with the 5' At FATB1 probe (SEQ ID NO: 25) were compared with the hybridization patterns obtained after digestion of genomic DNA of wild-type *Brassica* SOSR plants with AseI and EcoRV and hybridization with the 5' At FATB1 probe (SEQ ID NO: 25) (Table 21). To determine the correspondence between the hybridizing DNA fragments and the different FATB genes, the latter hybridization pattern was compared with the hybridization pattern of the BAC clone DNA with a full-length sequence of one of the FATB genes identified in Example 1 digested with AseI and EcoRV and hybridized to the 5' At FATB1 probe (SEQ ID NO: 25) (see Table 14 above).

TABLE 21

Hybridization pattern of digested genomic DNA from *Brassica napus* hybridized to the 5' AtFATB1 probe

| Genomic DNA restricted with | Migration of hybridizing DNA fragments between size marker bands | | Estimated length of the hybridizing DNA fragments. | Corresponds to |
|---|---|---|---|---|
| | Larger than (kbp) | Smaller than (kbp) | | |
| AseI | 2.1 | 2.4 | 2.2 | FATB-A1 |
| | 2.8 | 4.7 | 4.5 | FATB-A2 |
| | 2.1 | 2.5 | 2.4 | FATB-A3 |
| | 2.1 | 2.4 | 2.2 | FATB-C1 |
| | 2.8 | 4.5 | 3.0 | FATB-C2 |
| | 1.1 | 2.0 | 1.7 | FATB-C3(a) |
| | 0.5 | 1.1 | 0.8 | FATB-C3(b) |
| EcoRV | 5.1 | 11.5 | 11 | FATB-A1 |
| | 2.6 | 2.8 | 2.7 | FATB-A2 |
| | 2.8 | 4.5 | 3.5 | FATB-A3(a) |
| | 0.5 | 0.8 | 0.65 | FATB-A3(b) |
| | 2.8 | 4.7 | 4.5 | FATB-C1 |
| | 2.8 | 4.5 | 2.9 | FATB-C2 |
| | 2.8 | 4.5 | 4.2 | FATB-C3 |

Absence of one of the hybridizing DNA fragments indicated in Table 21 indicated that complete FATB alleles were deleted in the mutagenized plants with the fast neutron mutagenesis approach.

Homozygous M2 *Brassica* plants comprising a fatB deletion thus identified and the missing hybridizing DNA fragment are indicated in Table 22.

TABLE 22

|  |  | Missing hybridizing DNA fragment: | | | | |
|---|---|---|---|---|---|---|
| Mutated FATB allele | Genomic DNA restricted with | Migration of missing hybridizing DNA fragments between size marker bands | | Estimated length of the missing hybridizing DNA fragments. | M2 Plant No. | Allele No. |
| | | Larger than (kbp) | Smaller than (kbp) | | | |
| FATB-A1 | AseI | 2.1 | 2.4 | 2.2 | LOSA018 | FATB-A1-FN1 |
| (SEQ ID NO: 13) | EcoRV | 5.1 | 11.5 | 11 | | |
| FATB-A2 | AseI | 2.8 | 4.7 | 4.5 | LOSA002, | FATB-A2-FN1, |
| (SEQ ID NO: 15) | EcoRV | 2.6 | 2.8 | 2.7 | LOSA003, | FATB-A2-FN2, |
| | | | | | LOSA005 | FATB-A2-FN3 |
| FATB-C2 | AseI | 2.4 | 4.5 | 3 | LOSA004 | FATB-C2-FN1 |
| (SEQ ID NO: 21) | EcoRV | 2.8 | 4.5 | 2.9 | | |

The absence of a specific FATB allele in the homozygous M2 *Brassica* plants was confirmed by the following PCR assays:

Template DNA:
Genomic DNA isolated from leaf material of the M2 *Brassica* plants identified to comprise a deletion in or of a specific FATB gene ("FATBx").

Positive control: BAC clone DNA of FATBx gene (Successful amplification of this positive control demonstrates that the PCR was run under conditions which allow for the amplification of the specific target FATBx sequence).

Negative controls: BAC clone DNA of FATB genes different from the FATBx gene (When the expected result, i.e., no amplification of the specific FATBx PCR product, is observed, this indicates that there is no detectable background amplification of other FATB genes).

A wild-type DNA control: This is a PCR in which the template DNA provided is genomic DNA prepared from a M2 *Brassica* plant without a deletion of the FATBx gene. When the expected result, i.e., only amplification of the specific FATBx PCR product, is observed this indicates that there is no detectable background amplification, e.g., of other FATB genes, in a genomic DNA sample.

Primers and length of the fragment amplified from the wild-type target FATBx gene ("FATBx-specific PCR fragment"):

to confirm the presence of a deletion in or of the FATB-A1 gene (SEQ ID NO: 13):

```
Forward:
5'-CTGATAACGAGACGTCCTCAC-3'    (SEQ ID NO: 31)

Reverse:
5'-CAGTCTTAACATGGTTGAGTG-3'    (SEQ ID NO: 43)

→ 403 bp
``` to confirm the presence of a deletion in or of the FATB-A2 gene (SEQ ID NO: 15):

```
Forward:
5'-CATGTTCCATCTTCTTCCTCG-3'    (SEQ ID NO: 44)

Reverse:
5'-TATTGGGACAACATGTGAGTG-3'    (SEQ ID NO: 45)

→ 513 bp
``` to confirm the presence of a deletion in or of the FATB-A3 gene (SEQ ID NO: 17):

```
Forward:
5'-GCAGTGGATGATGCTTGATAC-3'    (SEQ ID NO: 35)

Reverse:
5'-TTCTTCTTAACCATCTCAGGT-3'    (SEQ ID NO: 46)

→ 487 bp
``` to confirm the presence of a deletion in or of the FATB-C1 gene (SEQ ID NO: 19):

```
Forward:
5'-CTGCCTGACTGGAGCATGCTC-3'    (SEQ ID NO: 37)

Reverse:
5'-CCAAACCCATCTCCAAGCAGC-3'    (SEQ ID NO: 47)

→ 367 bp
``` to confirm the presence of a deletion in or of the FATB-C2 gene (SEQ ID NO: 21):

```
Forward:
5'-ATCGTTCAGGATGGTCTTGTC-3'    (SEQ ID NO: 39)

Reverse:
5'-TAACTCACAACGAGAACCAGG-3'    (SEQ ID NO: 48)

→ 397 bp
``` to confirm the presence of a deletion in or of the FATB-C3 gene (SEQ ID NO: 23):

```
Forward:
5'-ACAGTGGATGATGCTTGACTC-3'    (SEQ ID NO: 41)

Reverse:
5'-CTTTGATAATCTCCTTGTCAC-3'    (SEQ ID NO: 49)
```

→ 1035 bp

PCR mix: 2.5 µl 10×PCR buffer, 0.25 µl dNTP's (20 µM), 0.5 µl forward primer (10 µM), 0.5 µl reverse primer (10 µM), 0.25 µl Taq-polymerase (5 U/µl), 20 µl Milli-Q H₂O, 1 µA DNA (50 ng/µl)=Total volume of 25 µl;

Thermocycling profile: 4 min at 94° C.; 25× [1 min at 94° C. (denaturation) and 1 min at 57° C. (annealing) and 2 min at 72° C. (elongation)]; 5 min at 72° C.; cool down to 4° C.

After amplification, 5 µl loading dye (2.5 ml 0.1% bromophenol blue, 2.5 ml 0.1% xyleencyanol, 5 ml glycerol, 50 µl 0.5M EDTA pH8) was added to the PCR samples and the samples were loaded on a 1% TAE (10×(400 mM Tris-Acetate+100 mM EDTA); Invitrogen®) agarose (Roche®) gel together with an appropriate molecular weight marker (100 bp DNA marker; Invitrogen®).

The banding patterns obtained after amplification of genomic DNA of M2 *Brassica* plants with the FATBx-specific primers were evaluated as follows:

Data from DNA samples isolated from leaf material of the M2 *Brassica* plants identified to comprise a deletion mutation in or of a FATBx gene within a single PCR run and a single PCR mix should not be acceptable unless:
- the negative controls are negative for PCR amplification (no fragments),
- the positive control shows the expected PCR product (specific FATBx fragment),
- the wild-type DNA control shows the expected result (only specific FATBx fragment).

Lanes showing no PCR product for the specific FATBx gene of the expected size, indicate that the corresponding plant from which the genomic template DNA was prepared, comprises a deletion in or of the specific FATBx gene.

Lanes showing the PCR product for the specific FATBx gene of the expected size, indicate that the corresponding plant from which the genomic template DNA was prepared, does not comprise a deletion in or of a FATBx gene.

It was confirmed that homozygous M2 plant No. LOSA018 comprises a deletion of FATB-A1, homozygous M2 plant Nrs. LOSA002, 3, 5 comprise a deletion of FATB-A2, and homozygous M2 plant Nr. LOSA004 comprises a deletion of FATB-C2.

4.2 Generation and Isolation of FATB Alleles Comprising One or More Point Mutations 30,000 seeds from *Brassica napus* SOSR (M0 seeds) were preimbibed for two hours on wet filter paper in deionized or distilled water. Half of the seeds were exposed to 0.8% EMS and half to 1% EMS (Sigma: M0880) and incubated for 4 hours.

The mutagenized seeds (M1 seeds) were rinsed 3 times and dried in a fume hood overnight. 30,000 M1 plants were grown in soil and selfed to generate M2 seeds. M2 seeds were harvested for each individual M1 plant.

Two times 4800 M2 plants, derived from different M1 plants, were grown and DNA samples were prepared from leaf samples of each individual M2 plant according to the CTAB method (Doyle and Doyle, 1987, Phytochemistry Bulletin 19:11-15). The M2 plants were selfed to obtain M3 seeds.

The DNA samples were screened for the presence of point mutations in the FATB genes causing the introduction of STOP codons or mutations of splice sites by direct sequencing by standard sequencing techniques (Agowa) and analyzing the sequences for the presence of the point mutations using the NovoSNP software (VIB Antwerp).

The following mutant FATB alleles (fatB) were thus identified:

TABLE 23a

STOP codon mutations in FATB genes of SOSR

| Mutated FATB gene | Exon number | Amino acid position | Nucleotide position | Wild type → mutant codon | M2 Plant No. | Allele No. |
|---|---|---|---|---|---|---|
| FATB-A1 (SEQ ID NO: 13) | exon 1 | 93 | 279 | tgg → tga | LOSA101, LOSA103, LOSA102 | FATB-A1-EMS01, FATB-A1-EMS02, FATB-A1-EMS03 |
|  | exon 1 | 111 | 333 | tgg → tga | LOSA104 | FATB-A1-EMS05 [1] |
|  | exon 1 | 116 | 348 | tgg → tga | LOSA105 | FATB-A1-EMS06 [2] |
| FATB-A2 (SEQ ID NO: 15) | exon 1 | 94 | 282 | tgg → tga | LOSA111, LOSA112 | FATB-A2-EMS04, FATB-A2-EMS05 [3] |
|  | exon 1 | 136 | 406 | cag → tag | LOSA108 | FATB-A2-EMS01 [2] |
| FATB-A3 (SEQ ID NO: 17) | exon 2 | 205 | 845 | cag → tag | LOSA114 | FATB-A3-EMS01 [1] |
| FATB-C1 (SEQ ID NO: 19) | exon 2 | 196 | 668 | tgg → tga | LOSA129 | FATB-C1-EMS05 [2,3] |

TABLE 23a-continued

STOP codon mutations in FATB genes of SOSR

| Mutated FATB gene | Exon number | Amino acid position | Nucleotide position | Wild type → mutant codon | M2 Plant No. | Allele No. |
|---|---|---|---|---|---|---|
| FATB-C2 | exon 1 | 79 | 235 | cag → tag | LOSA119 | FATB-C2-EMS02 [3] |
| (SEQ ID | exon 1 | 111 | 331 | cag → tag | LOSA122 | FATB-C2-EMS05 |
| NO: 21) | exon 1 | 112 | 336 | tgg → tga | LOSA120, LOSA123 | FATB-C2-EMS03 [2], FATB-C2-EMS06 |

[1] Seeds comprising FATB-A1-EMS05, FATB-A3-EMS01, FATB-C1-EMS04 and FATB-C3-EMS02 (designated 08MBBN000584) have been deposited at the NCIMB Limited (Ferguson Building, Craibstone Estate, Bucksburn, Aberdeen, Scotland, AB21 9YA, UK) on Jun. 27, 2008, under accession number NCIMB 41568.
[2] Seeds comprising FATB-A1-EMS06, FATB-A2-EMS01, FATB-C1-EMS05 and FATB-C2-EMS03 (designated 08MBBN000572) have been deposited at the NCIMB Limited (Ferguson Building, Craibstone Estate, Bucksburn, Aberdeen, Scotland, AB21 9YA, UK) on Jun. 27, 2008, under accession number NCIMB 41567.
[3] Seeds comprising FATB-A2-EMS05, FATB-C1-EMS05 and FATB-C2-EMS02 (designated 08MBBN000553) have been deposited at the NCIMB Limited (Ferguson Building, Craibstone Estate, Bucksburn, Aberdeen, Scotland, AB21 9YA, UK) on Jun. 27, 2008, under accession number NCIMB 41566.

TABLE 23b

Splice site mutations in FATB genes of SOSR

| Mutated FATB gene | Intron number | Nucleotide position | Wild type → mutant codon | M2 Plant No. | Allele No. |
|---|---|---|---|---|---|
| FATB-A1 (SEQ ID NO: 13) | intron 1 - donor | 502 | g[gt . . . → g[at . . . | LOSA106 | FATB-A1-EMS07 |
|  | intron 1 - acceptor | 587 | . . . ag]g → . . . ag]a | LOSA107 | FATB-A1-EMS09 |
| FATB-A2 (SEQ ID NO: 15) | intron 1 - donor | 505 | g[gt . . . → g[at . . . | LOSA109 | FATB-A2-EMS02 |
|  |  | 504 | g[gt . . . → a[gt . . . | LOSA110 | FATB-A2-EMS03 |
| FATB-C1 (SEQ ID NO: 19) | intron 1 - donor | 498 | g[gt . . . → a[gt . . . | LOSA128 | FATB-C1-EMS04 [1] |
| FATB-C2 (SEQ ID NO: 21) | intron 1 - acceptor | 581 | . . . ag]g → . . . ag]a | LOSA121 | FATB-C2-EMS04 |
| FATB-C3 (SEQ ID NO: 23) | intron 1 - donor | 508 | g[gt . . . → g[at . . . | LOSA125 | FATB-C3-EMS02 [1] |

[1] Seeds comprising FATB-A1-EMS05, FATB-A3-EMS01, FATB-C1-EMS04 and FATB-C3-EMS02 (designated 08MBBN000584) have been deposited at the NCIMB Limited (Ferguson Building, Craibstone Estate, Bucksburn, Aberdeen, Scotland, AB21 9YA, UK) on Jun. 27, 2008, under accession number NCIMB 41568

In conclusion, the above examples show how mutant FATB alleles can be generated and isolated. Also, plant material comprising such mutant alleles can be used to combine the desired mutant and/or wild type alleles in a plant, as described in the following examples.

Example 5

Identification of a *Brassica* Plant Comprising a Mutant *Brassica* FATB Allele

*Brassica* plants comprising the mutations in the FATB genes identified in Example 5 were identified as follows:

5.1. Identification of *Brassica* Plants Comprising a Deletion of a FATB Allele

For each homozygous M2 plant identified to comprise a deletion of a FATB gene, M3 plants were grown and DNA samples were prepared from leaf samples of each individual M3 plant On each DNA sample of each individual M3 plant a PCR assay specific for the FATB gene identified to comprise a deletion mutation (as described in Example 4.1) was performed.

Homozygous M3 plants comprising the identified mutation were selfed and M4 seeds were harvested.

5.2. Identification of *Brassica* Plants Comprising a Point Mutation in a FATB Gene For each mutant FATB gene identified in the DNA sample of an M2 plant, 50 M2 plants derived from the same M1 plant as the M2 plant comprising the FATB mutation were grown and DNA samples were prepared from leaf samples of each individual M2 plant.

The DNA samples were screened for the presence of the identified point FATB mutation as described above in Example 4.2.

Heterozygous and homozygous (as determined based on the electropherograms) M2 plants comprising the same mutation were selfed and M3 seeds were harvested.

Example 6

Analysis of the Fatty Acid Composition of the Seed Oil of Brassica Plants Comprising a Mutant Brassica FATB Gene To determine the correlation between the presence of the mutant FATB genes in *Brassica* plants and the fatty acid composition of the seed oil of the *Brassica* plants, the fatty acid composition of the seed oil of *Brassica* plants comprising mutant FATB gene(s) was analyzed by extracting the fatty acyls from the seeds and analyzing their relative levels in the seed oil by capillary gas-liquid chromatography as follows:

Seed samples were dried and weighed. 0.8 g of seeds was put into plastic vials. A steel crushing rod was added to each vial. This vial was then filled with 2 ml methylation solution (10 g sodium methoxide in 500 ml methanol) and 0.8 ml of petroleum ether. The capped vials were shaken for 30 min on an Eberbach shaker. One ml of de-ionized water was added to each vial before recapping and shaking. The vials were centrifuged for 5 min at 3500 rpm.

25-50 µl of the petroleum ether layer from each sample were transferred into Gas Chromatography (GC) autosampler vials. 100 µl 0.4 M phosphate buffer and 800 µl petroleum ether were added to each vial before shaking them. 0.4 to 0.6 µl of the petroleum ether layer of the samples were injected for analysis in the gas chromatograph. Print outs from the gas chromatograph were analyzed and the content of each fatty acid was calculated.

6.1. Correlation Between the Presence of One Mutant Brassica FATB Allele in Brassica Plants and the Fatty Acid Composition of the Seed Oil of those Brassica Plants To determine the correlation between the presence of one mutant FATB allele in homozygous and/or heterozygous state in a *Brassica* plant and the fatty acid composition of the seed oil of the *Brassica* plant, the fatty acid composition of the seed oil of the *Brassica* plants identified in Example 5.1, was analyzed as described above.

No significant difference in seed oil fatty acid composition, in particular the level of total saturated fatty acids (i.e. level of C14:0, C16:0, C18:0, C20:0, C22:0 and C24:0 fatty acids), palmitic acid (C16:0) and stearic acid (C18:0), was observed for homozygous single mutant plants compared to the seed oil fatty acid composition of wild type plants (see Table 24).

TABLE 24

Level of total saturated fatty acids (i.e. C14:0, C16:0, C18:0, C20:0, C22:0, C24:0 fatty acids; 'sats'), palmitic acid (C16:0) and stearic acid (C18:0) (in weight percentage based on total amount of fatty acids) in seed oil of *Brassica* plants comprising one mutant FATB allele (i.e. a FATB-AX-FNY or FATB-CX-FNY allele as indicated in Table 22, referred to as 'aX-fnY' and 'cX-fnY' in column 2; wild-type FATB alleles are referred to as 'AX' and 'CX') in homozygous state

| Progeny of plant | Genotype | Total sats | SD | C16:0 | SD | C18:0 | SD |
|---|---|---|---|---|---|---|---|
| Wild-type | A1/A1, A2/A2, A3/A3, C1/C1, C2/C2, C3/C3 | 7.06 | 0.05 | 4.39 | 0.05 | 1.42 | 0.02 |
| LOSA002 | A1/A1, a2-fn1/a2-fn1, A3/A3, C1/C1, C2/C2, C3/C3 | 6.93 | 1.93 | 4.21 | 1.04 | 1.50 | 0.44 |
| LOSA003 | A1/A1, a2-fn2/a2-fn2, A3/A3, C1/C1, C2/C2, C3/C3 | 7.04 | 0.22 | 4.23 | 0.18 | 1.61 | 0.16 |
| LOSA005 | A1/A1, a2-fn3/a2-fn3, A3/A3, C1/C1, C2/C2, C3/C3 | 7.17 | 0.08 | 4.36 | 0.08 | 1.73 | 0.10 |
| LOSA004 | A1/A1, A2/A2, A3/A3, C1/C1, c2-fn1/c2-fn1, C3/C3 | 6.97 | 0.27 | 4.04 | 0.38 | 1.82 | 0.20 |

6.2. Correlation Between the Presence of One to Four Mutant Brassica FATB Alleles in Brassica Plants and the Fatty Acid Composition of the Seed Oil of those Brassica Plants To determine the correlation between the presence of one to four mutant FATB alleles in homozygous and/or heterozygous state in a *Brassica* plant and the fatty acid composition of the seed oil of the *Brassica* plant, the *Brassica* plants identified in Example 5.2, or progeny thereof comprising the mutant FATB alleles, were crossed with each other and the fatty acid composition of the seed oil of individual progeny *Brassica* plants was analyzed as described above.

Figure 8:
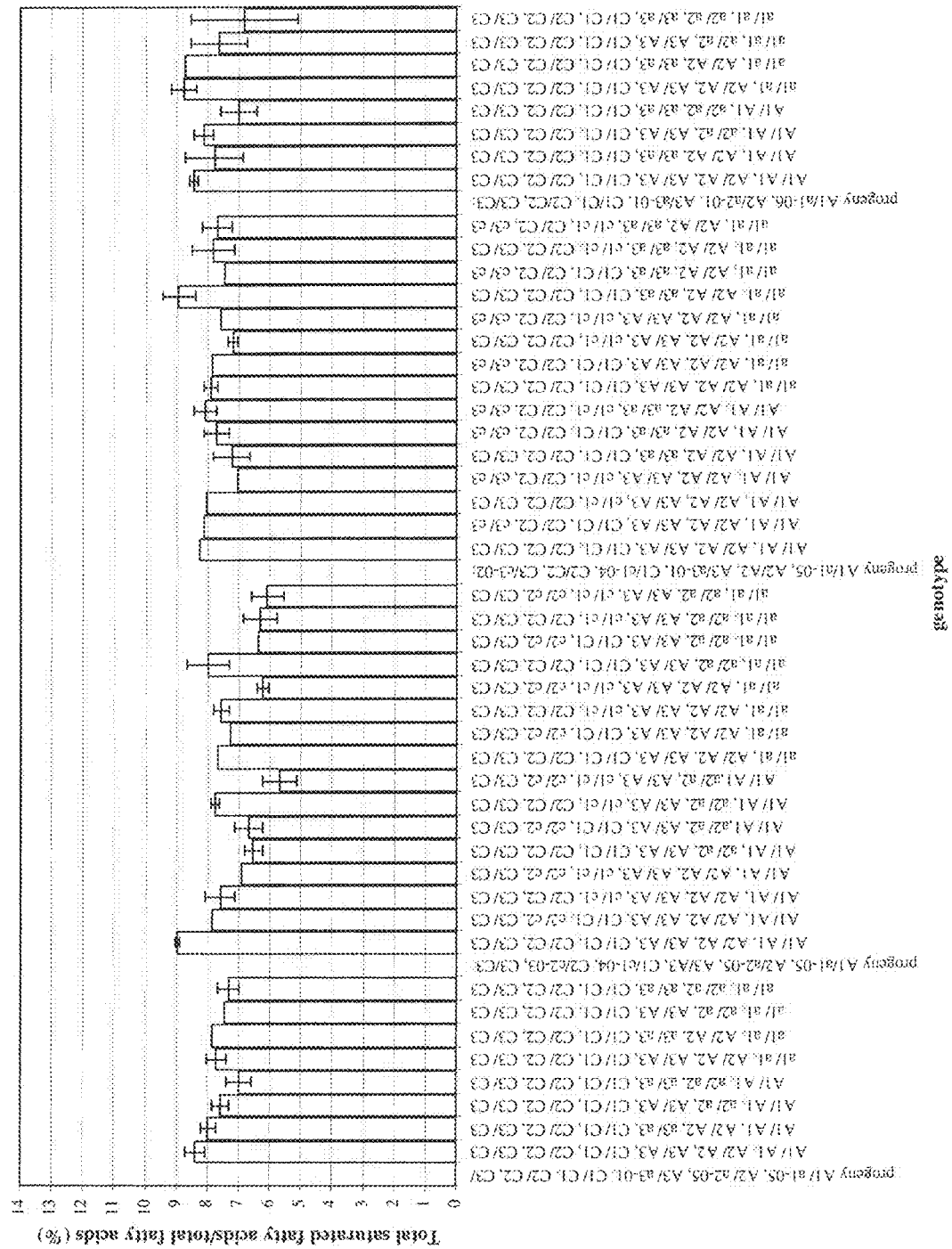
FIG. 8—Graph showing the correlation between the presence of none to four mutant FATB alleles in homozygous state in *Brassica* plants and the level of total saturated fatty acids (i.e. C14:0, C16:0, C18:0, C20:0, C22:0 and C24:0 fatty acids) (in weight percentage based on total amount of fatty acids) in seed oil of the *Brassica* plants.
Figure 9:
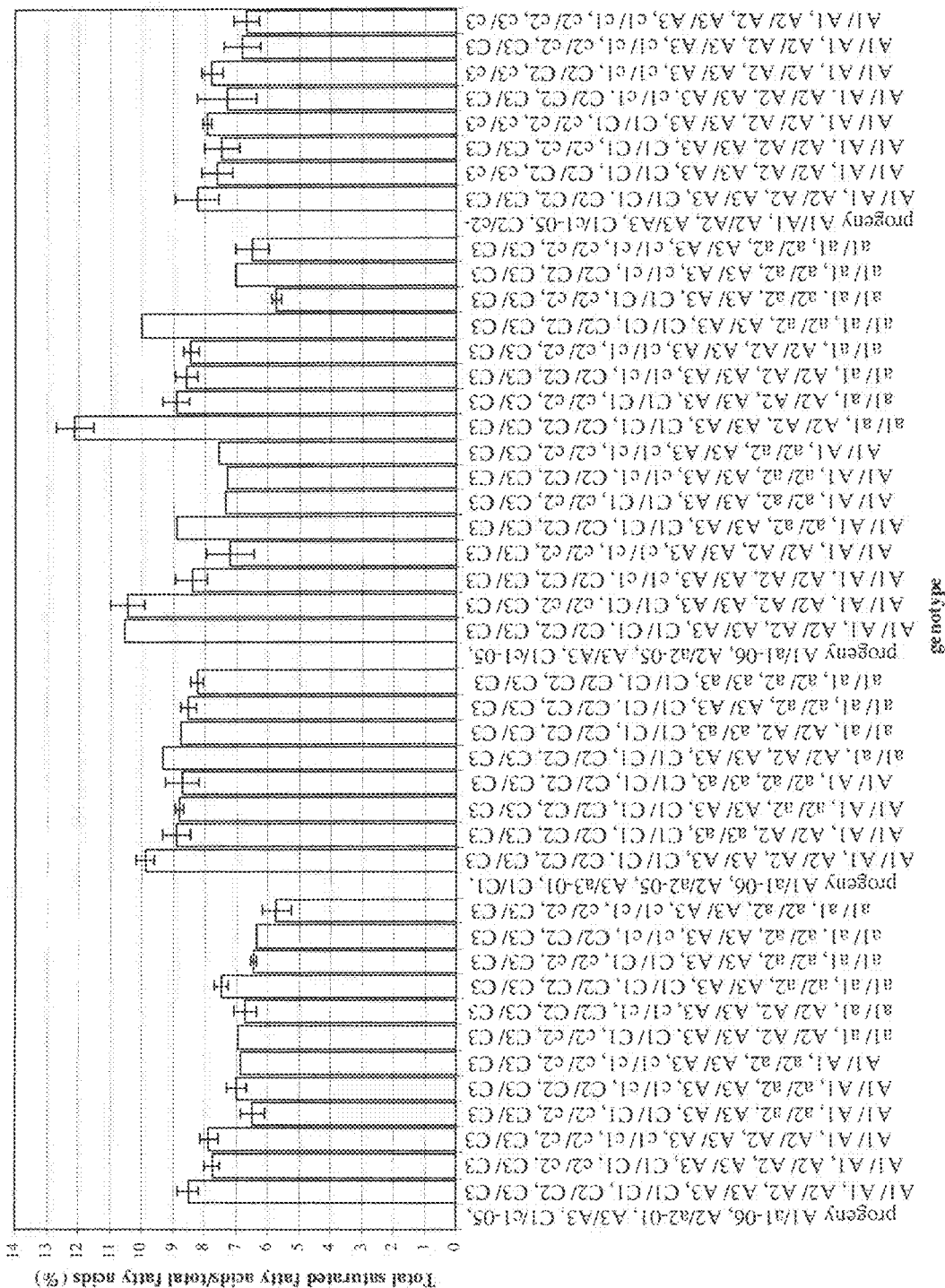
FIG. 9—Graph showing the correlation between the presence of none to four mutant FATB alleles in homozygous state in Brassica plants and the level of total saturated fatty acids (i.e. C14:0, C16:0, C18:0, C20:0, C22:0 and C24:0 fatty acids) (in weight percentage based on total amount of fatty acids) in seed oil of the Brassica plants.

Table 25 and FIG. 8 show that average total saturated fatty acid levels range from 8.24 to 10.52% in wildtype plants, from 6.53 to 12.12% in homozygous single mutant FATB plants, from 6:47 to 10.01% in homozygous double mutant FATB plants, from 5.68 to 8.43% in homozygous triple mutant FATB plants and from 5.72 to 7.7% in homozygous quadruple mutant FATB plants. Table 25 and FIG. 8 further indicate that mutations in specific FATB genes, such as FATB-A2 and FATB-C2, might have a stronger effect on the level of saturated fatty acids than mutations in other FATB genes.

The analysed plants were grown in the greenhouse. Since average total saturated fatty acid levels in seed oil from wildtype plants grown in the field are typically between about 6.5% and 7.5% instead of the 8.24 to 10.52% observed for the greenhouse grown plants, it is expected that total saturated fatty acid levels in seed oil from the mutant plants grown in the field will be lower. The mutant plants are grown in the field and the seed oil fatty acid composition is determined.

TABLE 25

Level of total saturated fatty acids (i.e. C14:0, C16:0, C18:0, C20:0, C22:0, C24:0 fatty acids; 'sats'), palmitic acid (C16:0) and stearic acid (C18:0) (in weight percentage based on total amount of fatty acids) in seed oil of *Brassica* plants comprising at least one mutant FATB allele (i.e. a FATB-AX-EMSY or FATB-CX-EMSY allele as indicated in Table 23, referred to as 'aX-emsY' and 'cX-emsY' in column 1 and as 'aX' and 'cX' in column 2; wild-type FATB alleles are referred to as 'AX' and 'CX') in homozygous state

| Progeny of plant comprising: | Genotype: | Total sats | SD | C16:0 | SD | C18:0 | SD |
|---|---|---|---|---|---|---|---|
| A1/a1-ems05, A2/a2-ems05, A3/a3-ems01, C1/C1, C2/C2, C3/C3 | A1/A1, A2/A2, A3/A3, C1/C1, C2/C2, C3/C3 | 8.39 | 0.69 | 5.43 | 0.19 | 1.52 | 0.35 |
| | A1/A1, A2/A2, a3/a3, C1/C1, C2/C2, C3/C3 | 7.98 | 0.37 | 4.83 | 0.19 | 1.64 | 0.13 |
| | A1/A1, a2/a2, A3/A3, C1/C1, C2/C2, C3/C3 | 7.58 | 0.51 | 4.38 | 0.22 | 1.64 | 0.16 |
| | A1/A1, a2/a2, a3/a3, C1/C1, C2/C2, C3/C3 | 7.00 | 0.32 | 4.17 | 0.14 | 1.43 | 0.16 |
| | a1/a1, A2/A2, A3/A3, C1/C1, C2/C2, C3/C3 | 7.71 | 0.25 | 4.88 | 0.44 | 1.40 | 0.13 |
| | a1/a1, A2/A2, a3/a3, C1/C1, C2/C2, C3/C3 | 7.88 | 0.28 | 4.85 | 0.22 | 1.52 | 0.20 |
| | a1/a1, a2/a2, A3/A3, C1/C1, C2/C2, C3/C3 | 7.47 | 0.39 | 4.21 | 0.30 | 1.66 | 0.30 |
| | a1/a1, a2/a2, a3/a3, C1/C1, C2/C2, C3/C3 | 7.34 | 0.30 | 3.88 | 0.12 | 1.73 | 0.12 |
| A1/a1-ems05, A2/a2-ems05, A3/A3, C1/c1-ems04, C2/c2-ems03, C3/C3 | A1/A1, A2/A2, A3/A3, C1/C1, C2/C2, C3/C3 | 8.97 | ND | 5.84 | ND | 1.52 | ND |
| | A1/A1, A2/A2, A3/A3, C1/C1, c2/c2, C3/C3 | 7.85 | 0.35 | 4.77 | 0.53 | 1.76 | 0.41 |
| | A1/A1, A2/A2, A3/A3, c1/c1, C2/C2, C3/C3 | 7.59 | 0.21 | 4.87 | 0.18 | 1.27 | 0.25 |
| | A1/A1, A2/A2, A3/A3, c1/c1, c2/c2, C3/C3 | 6.92 | 0.07 | 4.12 | 0.20 | 1.47 | 0.18 |
| | A1/A1, a2/a2, A3/A3, C1/C1, C2/C2, C3/C3 | 6.53 | ND | 4.05 | ND | 1.25 | ND |
| | A1/A1, a2/a2, A3/A3, C1/C1, a2/a2, C3/C3 | 6.68 | 0.48 | 4.02 | 0.25 | 1.35 | 0.11 |
| | A1/A1, a2/a2, A3/A3, c1/c1, C2/C2, C3/C3 | 7.76 | ND | 3.88 | ND | 1.92 | ND |
| | A1/A1, a2/a2, A3/A3, c1/c1, c2/c2, C3/C3 | 5.68 | 0.30 | 3.40 | 0.10 | 1.09 | 0.06 |
| | a1/a1, A2/A2, A3/A3, C1/C1, C2/C2, C3/C3 | 7.67 | 0.44 | 4.79 | 0.33 | 1.52 | 0.11 |
| | a1/a1, A2/A2, A3/A3, C1/C1, c2/c2, C3/C3 | 7.25 | 0.13 | 4.36 | 0.39 | 1.52 | 0.25 |
| | a1/a1, A2/A2, A3/A3, c1/c1, C2/C2, C3/C3 | 7.57 | 0.54 | 4.90 | 0.33 | 1.45 | 0.18 |
| | a1/a1, A2/A2, A3/A3, c1/c1, c2/c2, C3/C3 | 6.24 | ND | 3.88 | ND | 1.31 | ND |
| | a1/a1, a2/a2, A3/A3, C1/C1, C2/C2, C3/C3 | 8.00 | ND | 4.51 | ND | 1.92 | ND |
| | a1/a1, a2/a2, A3/A3, C1/C1, c2/c2, C3/C3 | 6.38 | 0.24 | 3.94 | 0.03 | 1.25 | 0.10 |
| | a1/a1, a2/a2, A3/A3, c1/c1, C2/C2, C3/C3 | 6.32 | 0.19 | 3.74 | 0.09 | 1.40 | 0.04 |
| | a1/a1, a2/a2, A3/A3, c1/c1, c2/c2, C3/C3 | 6.09 | 0.67 | 3.62 | 0.20 | 1.21 | 0.30 |
| A1/a1-ems05, A2/A2, A3/a3-ems01, C1/c1-ems04, C2/C2, C3/c3-ems02 | A1/A1, A2/A2, A3/A3, C1/C1, C2/C2, C3/C3 | 8.28 | 0.54 | 4.84 | 0.26 | 1.66 | 0.17 |
| | A1/A1, A2/A2, A3/A3, C1/C1, C2/C2, c3/c3 | 8.12 | 0.52 | 4.93 | 0.38 | 1.69 | 0.23 |
| | A1/A1, A2/A2, A3/A3, c1/c1, C2/C2, C3/C3 | 8.03 | 0.75 | 4.62 | 0.12 | 1.77 | 0.30 |
| | A1/A1, A2/A2, A3/A3, c1/c1, C2/C2, c3/c3 | 7.05 | ND | 4.42 | ND | 1.38 | ND |
| | A1/A1, A2/A2, a3/a3, C1/C1, C2/C2, C3/C3 | 7.23 | ND | 4.41 | ND | 1.44 | ND |
| | A1/A1, A2/A2, a3/a3, C1/C1, C2/C2, c3/c3 | 7.74 | ND | 4.38 | ND | 1.71 | ND |
| | A1/A1, A2/A2, a3/a3, c1/c1, C2/C2, c3/c3 | 8.08 | ND | 4.86 | ND | 1.72 | ND |
| | a1/a1, A2/A2, A3/A3, C1/C1, C2/C2, C3/C3 | 7.90 | 0.59 | 4.71 | 0.43 | 1.61 | 0.11 |
| | a1/a1, A2/A2, A3/A3, C1/C1, C2/C2, c3/c3 | 7.86 | 0.41 | 4.79 | 0.24 | 1.67 | 0.23 |
| | a1/a1, A2/A2, A3/A3, c1/c1, C2/C2, C3/C3 | 7.20 | 0.36 | 4.35 | 0.04 | 1.35 | 0.06 |
| | a1/a1, A2/A2, A3/A3, c1/c1, C2/C2, c3/c3 | 7.57 | 0.24 | 4.58 | 0.23 | 1.60 | 0.06 |
| | a1/a1, A2/A2, a3/a3, C1/C1, C2/C2, C3/C3 | 8.93 | ND | 5.46 | ND | 1.68 | ND |
| | a1/a1, A2/A2, a3/a3, C1/C1, C2/C2, c3/c3 | 7.45 | 0.17 | 4.44 | 0.12 | 1.57 | 0.07 |
| | a1/a1, A2/A2, a3/a3, c1/c1, C2/C2, C3/C3 | 7.82 | ND | 4.65 | ND | 1.56 | ND |
| | a1/a1, A2/A2, a3/a3, c1/c1, C2/C2, c3/c3 [1] | 7.70 | 0.53 | 4.39 | 0.12 | 1.81 | 0.28 |
| A1/a1-ems06, A2/a2-ems01, A3/a3-ems01, C1/C1, C2/C2, C3/C3 | A1/A1, A2/A2, A3/A3, C1/C1, C2/C2, C3/C3 | 8.46 | 0.67 | 4.74 | 0.11 | 1.85 | 0.29 |
| | A1/A1, A2/A2, a3/a3, C1/C1, C2/C2, C3/C3 | 7.79 | 0.48 | 4.62 | 0.18 | 1.57 | 0.17 |
| | A1/A1, a2/a2, A3/A3, C1/C1, C2/C2, C3/C3 | 8.14 | 0.55 | 4.45 | 0.40 | 1.80 | 0.12 |
| | A1/A1, a2/a2, a3/a3, C1/C1, C2/C2, C3/C3 | 7.01 | 0.13 | 4.24 | 0.10 | 1.43 | 0.16 |
| | a1/a1, A2/A2, A3/A3, C1/C1, C2/C2, C3/C3 | 8.77 | 0.93 | 4.99 | 0.49 | 2.02 | 0.31 |
| | a1/a1, A2/A2, a3/a3, C1/C1, C2/C2, C3/C3 | 8.73 | 0.32 | 5.44 | 0.40 | 1.65 | 0.54 |
| | a1/a1, a2/a2, A3/A3, C1/C1, C2/C2, C3/C3 | 7.64 | 0.58 | 4.44 | 0.54 | 1.51 | 0.18 |
| | a1/a1, a2/a2, a3/a3, C1/C1, C2/C2, C3/C3 | 6.82 | 0.40 | 3.93 | 0.16 | 1.41 | 0.11 |
| A1/a1-ems06, A2/a2-ems01, A3/A3, C1/c1-ems05, C2/c2-ems03, C3/C3 | A1/A1, A2/A2, A3/A3, C1/C1, C2/C2, C3/C3 | 8.51 | 0.91 | 5.49 | 0.73 | 1.46 | 0.16 |
| | A1/A1, A2/A2, A3/A3, C1/C1, c2/c2, C3/C3 | 7.74 | 1.72 | 5.05 | 1.22 | 1.28 | 0.06 |
| | A1/A1, A2/A2, A3/A3, c1/c1, c2/c2, C3/C3 | 7.85 | 0.23 | 4.70 | 0.35 | 1.54 | 0.35 |
| | A1/A1, a2/a2, A3/A3, C1/C1, C2/C2, C3/C3 | 6.47 | 0.77 | 4.13 | 0.59 | 1.14 | 0.07 |
| | A1/A1, a2/a2, A3/A3, C1/C1, c2/c2, C3/C3 | 6.98 | 0.54 | 4.21 | 0.21 | 1.36 | 0.23 |
| | A1/A1, a2/a2, A3/A3, c1/c1, c2/c2, C3/C3 | 6.83 | ND | 3.65 | ND | 1.59 | ND |
| | a1/a1, A2/A2, A3/A3, C1/C1, C2/C2, C3/C3 | 6.94 | 0.81 | 4.39 | 0.34 | 1.24 | 0.17 |
| | a1/a1, A2/A2, A3/A3, C1/C1, c2/c2, C3/C3 | 6.70 | 0.15 | 4.32 | 0.18 | 1.21 | 0.05 |
| | a1/a1, a2/a2, A3/A3, C1/C1, C2/C2, C3/C3 | 7.47 | 0.93 | 4.64 | 0.59 | 1.33 | 0.11 |
| | a1/a1, a2/a2, A3/A3, C1/C1, c2/c2, C3/C3 | 6.44 | 0.73 | 3.97 | 0.74 | 1.15 | 0.16 |
| | a1/a1, a2/a2, A3/A3, c1/c1, C2/C2, C3/C3 | 6.37 | 0.47 | 3.68 | 0.09 | 1.25 | 0.18 |
| | a1/a1, a2/a2, A3/A3, c1/c1, c2/c2, C3/C3 [2] | 5.72 | 0.34 | 3.24 | 0.04 | 1.22 | 0.20 |
| A1/a1-ems06, A2/a2-ems05, A3/a3-ems01, C1/C1, C2/C2, C3/C3 | A1/A1, A2/A2, A3/A3, C1/C1, C2/C2, C3/C3 | 9.88 | 1.03 | 6.03 | 1.29 | 1.96 | 0.39 |
| | A1/A1, A2/A2, a3/a3, C1/C1, C2/C2, C3/C3 | 8.89 | 0.63 | 5.06 | 0.57 | 2.03 | 0.33 |
| | A1/A1, a2/a2, A3/A3, C1/C1, C2/C2, C3/C3 | 8.79 | 0.72 | 5.17 | 0.95 | 1.81 | 0.36 |
| | A1/A1, a2/a2, a3/a3, C1/C1, C2/C2, C3/C3 | 8.70 | 0.72 | 5.04 | 1.17 | 1.81 | 0.43 |
| | a1/a1, A2/A2, A3/A3, C1/C1, C2/C2, C3/C3 | 9.34 | 0.41 | 4.93 | 0.67 | 2.31 | 0.30 |
| | a1/a1, A2/A2, a3/a3, C1/C1, C2/C2, C3/C3 | 8.78 | 1.00 | 5.14 | 0.98 | 1.89 | 0.02 |
| | a1/a1, a2/a2, A3/A3, C1/C1, C2/C2, C3/C3 | 8.52 | 0.60 | 4.35 | 0.38 | 2.24 | 0.37 |
| | a1/a1, a2/a2, a3/a3, C1/C1, C2/C2, C3/C3 | 8.24 | 1.06 | 4.59 | 0.61 | 1.87 | 0.46 |
| A1/a1-ems06, A2/a2-ems05, A3/A3, C1/c1-ems05, C2/c2- | A1/A1, A2/A2, A3/A3, C1/C1, C2/C2, C3/C3 | 10.52 | ND | 6.91 | ND | 1.83 | ND |
| | A1/A1, A2/A2, A3/A3, C1/C1, c2/c2, C3/C3 | 10.45 | 3.52 | 6.45 | 2.01 | 1.84 | 0.61 |
| | A1/A1, A2/A2, A3/A3, c1/c1, C2/C2, C3/C3 | 8.42 | 0.54 | 5.45 | 0.60 | 1.38 | 0.10 |
| | A1/A1, A2/A2, A3/A3, c1/c1, c2/c2, C3/C3 | 7.20 | 0.40 | 4.20 | 0.22 | 1.42 | 0.19 |

TABLE 25-continued

Level of total saturated fatty acids (i.e. C14:0, C16:0, C18:0, C20:0, C22:0, C24:0 fatty acids; 'sats'), palmitic acid (C16:0) and stearic acid (C18:0) (in weight percentage based on total amount of fatty acids) in seed oil of *Brassica* plants comprising at least one mutant FATB allele (i.e. a FATB-AX-EMSY or FATB-CX-EMSY allele as indicated in Table 23, referred to as 'aX-emsY' and 'cX-emsY' in column 1 and as 'aX' and 'cX' in column 2; wild-type FATB alleles are referred to as 'AX' and 'CX') in homozygous state

| Progeny of plant comprising: | Genotype: | Total sats | SD | C16:0 | SD | C18:0 | SD |
|---|---|---|---|---|---|---|---|
| ems02, C3/C3 | A1/A1, a2/a2, A3/A3, C1/C1, C2/C2, C3/C3 | 8.89 | ND | 5.50 | ND | 1.67 | ND |
| | A1/A1, a2/a2, A3/A3, C1/C1, c2/c2, C3/C3 | 7.32 | 0.47 | 4.26 | 0.21 | 1.47 | 0.11 |
| | A1/A1, a2/a2, A3/A3, c1/c1, C2/C2, C3/C3 | 7.31 | 1.23 | 4.63 | 1.00 | 1.25 | 0.16 |
| | A1/A1, a2/a2, A3/A3, c1/c1, c2/c2, C3/C3 [3] | 7.57 | 0.96 | 4.42 | 0.53 | 1.47 | 0.22 |
| | a1/a1, A2/A2, A3/A3, C1/C1, C2/C2, C3/C3 | 12.12 | ND | 7.04 | ND | 2.23 | ND |
| | a1/a1, A2/A2, A3/A3, C1/C1, c2/c2, C3/C3 | 8.91 | 0.95 | 5.50 | 0.70 | 1.65 | 0.28 |
| | a1/a1, A2/A2, A3/A3, c1/c1, C2/C2, C3/C3 | 8.59 | 0.81 | 5.41 | 0.77 | 1.50 | 0.20 |
| | a1/a1, A2/A2, A3/A3, c1/c1, c2/c2, C3/C3 | 8.43 | 1.72 | 4.71 | 0.96 | 1.92 | 0.23 |
| | a1/a1, a2/a2, A3/A3, C1/C1, C2/C2, C3/C3 | 10.01 | ND | 6.32 | ND | 1.79 | ND |
| | a1/a1, a2/a2, A3/A3, C1/C1, c2/c2, C3/C3 | 5.72 | ND | 3.53 | ND | 1.03 | ND |
| | a1/a1, a2/a2, A3/A3, c1/c1, C2/C2, C3/C3 | 7.01 | 1.14 | 4.32 | 0.59 | 1.27 | 0.27 |
| | a1/a1, a2/a2, A3/A3, c1/c1, c2/c2, C3/C3 | 6.47 | 0.54 | 3.55 | 0.42 | 1.39 | 0.15 |
| A1/A1, A2/A2, A3/A3, C1/c1-ems05, C2/c2-ems02, C3/c3-ems02 | A1/A1, A2/A2, A3/A3, C1/C1, C2/C2, C3/C3 | 8.24 | 0.62 | 4.66 | 0.21 | 1.66 | 0.29 |
| | A1/A1, A2/A2, A3/A3, C1/C1, C2/C2, c3/c3 | 7.59 | 0.95 | 4.47 | 0.27 | 1.64 | 0.43 |
| | A1/A1, A2/A2, A3/A3, C1/C1, c2/c2, C3/C3 | 7.46 | 0.42 | 4.06 | 0.01 | 1.48 | 0.20 |
| | A1/A1, A2/A2, A3/A3, C1/C1, c2/c2, c3/c3 | 7.91 | 0.30 | 4.12 | 0.11 | 2.06 | 0.12 |
| | A1/A1, A2/A2, A3/A3, c1/c1, C2/C2, C3/C3 | 7.31 | 0.49 | 4.14 | 0.05 | 1.48 | 0.15 |
| | A1/A1, A2/A2, A3/A3, c1/c1, C2/C2, c3/c3 | 7.76 | 0.33 | 4.55 | 0.15 | 1.67 | 0.16 |
| | A1/A1, A2/A2, A3/A3, c1/c1, c2/c2, C3/C3 | 6.81 | 0.23 | 3.73 | 0.01 | 1.39 | 0.13 |
| | A1/A1, A2/A2, A3/A3, c1/c1, c2/c2, c3/c3 | 6.66 | 0.48 | 3.84 | 0.16 | 1.44 | 0.21 |

[1] Seeds comprising FATB-A1-EMS05, FATB-A3-EMS01, FATB-C1-EMS04 and FATB-C3-EMS02 (designated 08MBBN000584) have been deposited at the NCIMB Limited (Ferguson Building, Craibstone Estate, Bucksburn, Aberdeen, Scotland, AB21 9YA, UK) on Jun. 27, 2008, under accession number NCIMB 41568.
[2] Seeds comprising FATB-A1-EMS06, FATB-A2-EMS01, FATB-C1-EMS05 and FATB-C2-EMS03 (designated 08MBBN000572) have been deposited at the NCIMB Limited (Ferguson Building, Craibstone Estate, Bucksburn, Aberdeen, Scotland, AB21 9YA, UK) on Jun. 27, 2008, under accession number NCIMB 41567.
[3] Seeds comprising FATB-A2-EMS05, FATB-C1-EMS05 and FATB-C2-EMS02 (designated 08MBBN000553) have been deposited at the NCIMB Limited (Ferguson Building, Craibstone Estate, Bucksburn, Aberdeen, Scotland, AB21 9YA, UK) on Jun. 27, 2008, under accession number NCIMB 41566.

6.3. Correlation Between the Presence of Five to Six Mutant *Brassica* FATB Alleles in Homozygous and/or Heterozygous State in *Brassica* Plants and the Fatty Acid Composition of the Seed Oil of those *Brassica* Plants To determine the correlation between the presence of five to six mutant FATB genes in homozygous and/or heterozygous state in a *Brassica* plant and the fatty acid composition of the seed oil of the *Brassica* plant, the *Brassica* plants identified in Example 5.2, or progeny thereof comprising the mutant FATB alleles, are crossed with each other and the fatty acid composition of the seed oil of the progeny *Brassica* plants is analyzed as described above.

Example 7

Transfer of Mutant FATB Genes into (Elite) *Brassica* Lines

The mutant FATB genes are transferred into (elite) *Brassica* breeding lines by the following method:

A plant containing a mutant FATB gene (donor plant), is crossed with an (elite) *Brassica* line (elite parent/recurrent parent) or variety lacking the mutant FATB gene. The following introgression scheme is used (the mutant FATB gene is abbreviated to fatB, while the wild type is depicted as FATB):

Initial cross: fatB/fatB (donor plant)×FATB/FATB (elite parent)

F1 plant: FATB/fatB

BC1 cross: FATB/fatB×FATB/FATB (recurrent parent)

BC1 plants: 50% FATB/fatB and 50% FATB/FATB

The 50% FATB/fatB are selected using e.g. AFLP or PCR markers for the mutant FATB allele (fatB).

BC2 cross: FATB/fatB (BC1 plant)×FATB/FATB (recurrent parent)

BC2 plants: 50% FATB/fatB and 50% FATB/FATB

The 50% FATB/fatB are selected using e.g. AFLP or PCR markers for the mutant FATB allele (fatB).

Backcrossing is repeated until BC3 to BC6

BC6 plants: 50% FATB/fatB and 50% FATB/FATB

The 50% FATB/fatB are selected using e.g. AFLP or PCR markers for the mutant FATB allele (fatB).

BC6 S1 cross: FATB/fatB×FATB/fatB

BC6 S1 plants: 25% FATB/FATB and 50% FATB/fatB and 25% fatB/fatB

Plants containing fatB are selected using e.g. AFLP or PCR markers for the mutant FATB allele (fatB).

Individual BC6 S1 plants that are homozygous for the mutant FATB allele (fatB/fatB) are selected using, e.g. AFLP or PCR markers for the mutant and the wild-type allele.

These plants are then used for seed production.

To select for plants comprising a deletion of a FATB allele, hybridization assays or PCR assays such as those described in Example 4.1. can be used.

To select for plants comprising a point mutation in a FATB allele, direct sequencing by standard sequencing techniques known in the art, such as those described in Example 4.2., can be used. Alternatively, PCR assays can be developed to discriminate plants comprising a specific point mutation in a FATB allele from plants not comprising that specific point mutation. The following discriminating PCR assays were thus developed to detect the presence or absence and the zygosity status of the mutant alleles identified in Example 4.2. (see Table 23):

Template DNA:
  Genomic DNA isolated from leaf material of homozygous or heterozygous mutant *Brassica* plants (comprising a mutant FATB allele, called hereinafter "FATB-Xx-EMSXX").
  Wild type DNA control: Genomic DNA isolated from leaf material of wild type *Brassica* plants (comprising the wild type equivalent of the mutant FATB allele, called hereinafter "FATB-Xx-WT").
  Positive DNA control: Genomic DNA isolated from leaf material of homozygous mutant *Brassica* plants known to comprise FATB-Xx-EMSXX.
Primers and length of the fragment amplified from the mutant and corresponding wild-type target FATB gene are indicated in Table 26. Each primer set consists of one primer specific for the mutant and the wild type target gene (e.g. primer LOSA104R5 is specific for FATB-A1-EMS06 and FATB-A1-WT) and one primer specific for the nucleotide difference (e.g. primer LOSA105MF1 is specific for the FATB-A1-EMS06 and primer LOSA105WF1 is specific for FATB-A1-WT). Usually, the last nucleotide of the latter primer matches with the nucleotide difference (underlined nucleotide in Table 26), but one (or more) additional target specific nucleotide(s) may be added to improve the annealing between the primer and its target sequence (see e.g. bold nucleotide in primer LOSA112MR2, which is specific for the FATB-A2-EMS05 allele, as compared to primer LOSA112WR2, which is specific for the FATB-A2-WT allele).
PCR mix: 2.5 µl 10×PCR buffer (15 mM MgCl2), 0.25 µl dNTP's (20 mM), 1 µl forward primer (10 µM), 1 µl reverse primer (10 µM), 0.25 µl Taq-polymerase (5 U/µl), 19.5 µl Milli-Q H$_2$O, 0.5 µA DNA (20-50 ng/µl)= Total volume of 25 µl;
Thermocycling profile: 4 min at 95° C.; 30× [1 min at 95° C. (denaturation) and 1 min at annealing temperature specified in Table 26 and 2 min at 72° C. (elongation)]; 5 min at 72° C.; cool down to 4° C. The optimal annealing temperature was determined by temperature gradient PCR wherein the annealing temperature was varied between 57° C. to 70° C. on a MJ Research thermocycler PTC-200 (Biozym). The optimal annealing temperature for the wild type FATB specific primers is that temperature at which a clear PCR fragment of the expected size can be detected (as described below) for the DNA sample from the wild type *Brassica* plant and not for the DNA sample from the mutant *Brassica* plant. The optimal annealing temperature for the mutant FATB specific primers is that temperature at which a clear PCR fragment of the expected size can be detected (as described below) for the DNA sample from the mutant *Brassica* plant and not for the DNA sample from the wild type *Brassica* plant.
After amplification, 5 µl loading dye (orange dye) was added to 15 µl of the PCR samples and the samples were loaded on a 1.5% agarose gel.
The banding patterns obtained after amplification of genomic DNA of mutant *Brassica* plants are evaluated as follows:
  Data from DNA samples isolated from leaf material of the mutant *Brassica* plants within a single PCR run and a single PCR mix should not be accepted unless:
    the wild-type DNA control shows the PCR fragment of the expected size for the FATB-Xx-WT specific PCR assay and no PCR fragment of the expected size for the FATB-Xx-EMSXX specific PCR assay
    the positive DNA control shows the PCR fragment of the expected size for the FATB-Xx-EMSXX specific PCR assay and no PCR fragment of the expected size for the FATB-Xx-WT specific PCR assay
  Lanes showing no PCR product of the expected size for the FATB-Xx-WT specific PCR assay and the PCR fragment of the expected size for the FATB-Xx-EMSXX specific PCR assay, indicate that the corresponding plant from which the genomic template DNA was prepared, is a homozygous mutant for FATB-Xx-EMSXX.
  Lanes showing the PCR fragment of the expected size for the FATB-Xx-WT specific PCR assay and the FATB-Xx-EMSXX specific PCR assay, indicate that the corresponding plant from which the genomic template DNA was prepared, is a heterozygous mutant for FATB-Xx-EMSXX.
  Lanes showing the PCR fragment of the expected size for the FATB-Xx-WT specific PCR assay and no PCR product of the expected size for the FATB-Xx-EMSXX specific PCR assay, indicate that the corresponding plant from which the genomic template DNA was prepared, is a wild type plant.

TABLE 26

| Allele No. | Primers | Annealing t° (° C.) | Size PCR fragment (bp) |
|---|---|---|---|
| FATB-A1-EMS05 | 5' GGCGGCTGAGAAGCAGTGAATA 3' (LOSA104MF1 - SEQ ID NO: 50) 5' GGACTGAAGCACACTGTCC 3' (LOSA104R3 - SEQ ID NO: 52) | 57 | 1087 |
| FATB-A1-WT | 5' GGCGGCTGAGAAGCAGTGGATG 3' (LOSA104WF1 - SEQ ID NO: 51) 5' GGACTGAAGCACACTGTCC 3' (LOSA104R3 - SEQ ID NO: 52) | 71.8 | 1087 |
| FATB-A1-EMS06 | 5' CAGTGGATGATGCTIGACTGA 3' (LOSA105MF1 - SEQ ID NO: 53) 5' GCATACGAGTAACAACCCAA 3' (LOSA104R5 - SEQ ID NO: 55) | 67 | 365 |
| FATB-A1-WT | 5' CAGTGGATGATGCTTGACTGG 3' (LOSA105WF1 - SEQ ID NO: 54) 5' GCATACGAGTAACAACCCAA 3' (LOSA104R5 - SEQ ID NO: 55) | 68.9 | 365 |

TABLE 26-continued

| Allele No. | Primers | Annealing t° (° C.) | Size PCR fragment (bp) |
|---|---|---|---|
| FATB-A2-EMS01 | 5' GAGTTGGGTCCACTAATTTTG 3'<br>(LOSA108F1 - SEQ ID NO: 58/59)<br>5' CGGAACACAAGACCATCCT<u>A</u> 3'<br>(LOSA108MR1' - SEQ ID NO: 60) | 67 | 346 |
| FATB-A2-WT | 5' GAGTTGGGTCCACTAATTTTG 3'<br>(LOSA108F1 - SEQ ID NO: 58/59)<br>5' CGGAACACAAGACCATCCT<u>G</u> 3'<br>(LOSA108WR1' - SEQ ID NO: 61) | 67 | 346 |
| FATB-A2-EMS05 | 5' GAGTTGGGTCCACTAATTTTG 3'<br>(LOSA108F1 - SEQ ID NO: 58/59)<br>5' AGCAGCAAGCAGCATACT<u>TC</u> 3'<br>(LOSA112MR2 - SEQ ID NO: 56) | 67 | 222 |
| FATB-A2-WT | 5' GAGTTGGGTCCACTAATTTTG 3'<br>(LOSA108F1 - SEQ ID NO: 58/59)<br>5' TAGCAGCAAGCAGCATACT<u>C</u> 3'<br>(LOSA112WR1 - SEQ ID NO: 57) | 67 | 222 |
| FATB-A3-EMS01 | 5' CAATGGCAAAACCAACAAAGC 3'<br>(LOSA114F1 - SEQ ID NO: 64)<br>5' TATTTATCAACTACAACCT<u>A</u> 3'<br>(LOSA114MR1 - SEQ ID NO: 62) | 60 | 805 |
| FATB-A3-WT | 5' CAATGGCAAAACCAACAAAGC 3'<br>(LOSA114F1 - SEQ ID NO: 64)<br>5' TATTTATCAACTACAACCT<u>G</u> 3'<br>(LOSA114WR1 - SEQ ID NO: 63) | 63 | 805 |
| FATB-C1-EMS04 | 5' CGGTTATGAATCATTTACA<u>A</u> 3'<br>(LOSA128MF1 - SEQ ID NO: 68)<br>5' GTTCTTCCTCTCACCACTTCG 3'<br>(LOSA116R1 - SEQ ID NO: 38/67) | 62.1 | 1045 |
| FATB-C1-WT | 5' CGGTTATGAATCATTTACA<u>G</u> 3'<br>(LOSA128WF1 - SEQ ID NO: 69)<br>5' GTTCTTCCTCTCACCACTTCG 3'<br>(LOSA116R1 - SEQ ID NO: 38/67) | 57-70 | 1045 |
| FATB-C1-EMS05 | 5' GTTAAGAAGAACTTGATATG<u>A</u> 3'<br>(LOSA129MF1 - SEQ ID NO: 65)<br>5' GTTCTTCCTCTCACCACTTCG 3'<br>(LOSA116R1 - SEQ ID NO: 67) | 60 | 876 |
| FATB-C1-WT | 5' GTTAAGAAGAACTTGATATG<u>G</u> 3'<br>(LOSA129WF1 - SEQ ID NO: 66)<br>5' GTTCTTCCTCTCACCACTTCG 3'<br>(LOSA116R1 - SEQ ID NO: 67) | 64.7 | 876 |
| FATB-C2-EMS02 | 5' GTCTGACAACGAGACTTCG<u>T</u> 3'<br>(LOSA119MF1 - SEQ ID NO: 70)<br>5' CAGTATTGCAATCCCGAACC 3'<br>(LOSAC2R3 - SEQ ID NO: 72) | 69.7 | 818 |
| FATB-C2-WT | 5' GTCTGACAACGAGACTTCG<u>C</u> 3'<br>(LOSA119WF1 - SEQ ID NO: 71)<br>5' CAGTATTGCAATCCCGAACC 3'<br>(LOSAC2R3 - SEQ ID NO: 72) | 57-70 | 818 |
| FATB-C2-EMS03 | 5' TGGCGGCTGAGAAACAGTG<u>A</u> 3'<br>(LOSA120MF1 - SEQ ID NO: 73)<br>5' AGGGTACTTACAGTGAGACCC 3'<br>(LOSAC2R1 - SEQ ID NO: 75) | 70 | 1056 |
| FATB-C2-WT | 5' TGGCGGCTGAGAAACAGTG<u>G</u> 3'<br>(LOSA120WF1 - SEQ ID NO: 74)<br>5' AGGGTACTTACAGTGAGACCC 3'<br>(LOSAC2R1 - SEQ ID NO: 75) | 71.1 | 1056 |
| FATB-C3-EMS02 | 5' CAGTCATGAACCACTTACAG<u>A</u> 3'<br>(LOSA125MF2 - SEQ ID NO: 76)<br>5' CAACCTGCATACGAGTAACG 3'<br>(LOSA124R2 - SEQ ID NO: 78) | 67 | 555 |

TABLE 26-continued

| Allele No. | Primers | Annealing t° (° C.) | Size PCR fragment (bp) |
|---|---|---|---|
| FATB-C3-WT | 5' CAGTCATGAACCACTTACAGG 3'<br>(LOSA125WF2 - SEQ ID NO: 77)<br>5' CAACCTGCATACGAGTAACG 3'<br>(LOSA124R2 - SEQ ID NO: 78) | 69.7 | 555 |

*ho = homozygous, he = heterozygous

Alternatively, Invader™ technology (Third Wave Agbio) can be used to discriminate plants comprising a specific point mutation in a FATB allele from plants not comprising that specific point mutation. The following discriminating Invader™ probes can thus be developed to detect the presence or absence and the zygosity status of the mutant alleles identified in Example 4 (see Table 23a and b):

Probes specific for the mutant (which can be discriminated by attaching a 'flap1' sequence) or corresponding wild-type (which can be discriminated by attaching a 'flap2' sequence) target FATB gene and "invading" probes which can be used in combination with them are developed. Generally, each probe set consists of one probe specific for the mutant or the wild type target gene of which the first nucleotide after the 5' flap sequence matches with the nucleotide difference (underlined nucleotide in Table 27) (the so-called "primary probe"; e.g. the probe with SEQ ID NO: 82 is specific for FATB-A1-EMS05) and one probe specific for the nucleotides upstream of the nucleotide difference (the so-called "Invader® oligo"; e.g. the probe with SEQ ID NO: 81 is specific for the nucleotides upstream of the nucleotide difference between FATB-A1-EMS05 and FATB-A1-WT). The last nucleotide of the latter primer may match with the nucleotide difference in the mutant, but other nucleotides may be used as well for this last nucleotide (as indicated by the bold nucleotides in Table 27) as long as the primary probe and the Invader® oligo are still able to form a single base overlap when hybridized to the target DNA to generate the specific invasive structure recognized by the Cleavase® enzymes (Third Wave Agbio). The Invader™ assay procedure and interpretation of the data are performed as prescribed by the manufacturer (Third Wave Agbio). Briefly, the nucleotide sequences indicated as "flap1" and "flap2" represent the sequences of the 5' "flaps" which are cleaved from the primary probes in the primary phase of the Invader™ assay and which are complementary to sequences in FRET™ cassette 1 and 2, respectively, and not complementary to the target mutant or wild type sequences. If the primary probes are cleaved in the primary phase and the flap1-probe and/or flap2-probe hybridise to FRET™ cassette 1 and 2, respectively, in the secondary phase, a signal is generated indicative of the presence in the sample of the mutant or corresponding wild-type target FATB gene, respectively.

Alternatively, probes specific for the mutant target FATB gene (indicated as "5' flap1-x" in Table 27) are used in combination with probes specific for an internal control gene (indicated as "5' flap2-x" in Table 27: control gene is indicated as ENDO1). If the primary probes are cleaved in the primary phase and the flap 1-probe and/or flap2-probe hybridise to FRET™ cassette 1 and 2, respectively, in the secondary phase, a signal is generated indicative of the presence in the sample of the mutant target FATB gene and the endogenous control gene, respectively. Based on the amount of signal generated from FRET™ cassette 1 relative to the amount of signal generated from FRET™ cassette 2, the zygosity status of the mutant FATB allele can be determined (homozygous FATB alleles generate about twice as much signal as heterozygous FATB alleles).

TABLE 27

| Allele No. | Probes | |
|---|---|---|
| FATB-A1-EMS05 | 5' GCGCCTCGGTTTCCAGTCAAGCATCATC 3' | (SEQ ID NO: 81) |
|  | 5' flap1-TCACTGCTTCTCAGCC 3' | (SEQ ID NO: 82) |
| FATB-A1-EMS06 | 5'GATCCATAATCACGTCAGAGCGCCTCGGTTTC3' | (SEQ ID NO: 83) |
|  | 5' flap1-TCAGTCAAGCATCATCC 3' | (SEQ ID NO: 84) |
| FATB-A2-EMS01 | 5'CCTAATGGAAAAATTCTGACGGAACACAAGAC CATCCTT 3' | (SEQ ID NO: 85) |
|  | 5' flap1-AAACAATTCTCCCTAAACCA 3' | (SEQ ID NO: 86) |
| FATB-A2-EMS05 | 5'TGCCAAGAAAATGGTAGTTATAGCAGCAAGCA GCATACTC 3' | (SEQ ID NO: 87) |
|  | 5' flap1-TCAGTCAGGCAGCT 3' | (SEQ ID NO: 88) |
| FATB-A3-EMS01 | 5'AAGAGAGCTTACCAAGTAGGATATTTATCAACT ACAACCTT 3' | (SEQ ID NO: 89) |
|  | 5' flap1-ACATACGAGTAACAACCC 3' | (SEQ ID NO: 90) |
| FATB-C1-EMS04 | 5'CCAGTAACAACAAGCGACTACAATCATAATCA TAATCAGTACC 3' | (SEQ ID NO: 91) |
|  | 5' flap1-TTGTAAATGATTCATAACCGTTT 3' | (SEQ ID NO: 92) |

TABLE 27-continued

| Allele No. | Probes | |
|---|---|---|
| FATB-C1-EMS05 | 5'TAGGATATTTATCAACGACAACCTGCATACGAG TAACAACC 3' | (SEQ ID NO: 93) |
| | 5' flap1-TCATATCAAGTTCTTCTTAACCA 3' | (SEQ ID NO: 94) |
| FATB-C2-EMS02 | 5'CCTGGTTCTGTAGAGATATCAAAGTCTGACAAC GAGACTTCGC 3' | (SEQ ID NO: 95) |
| | 5' flap1-TAGCCCGCACCC 3' | (SEQ ID NO: 96) |
| FATB-C2-EMS03 | 5' AGAACGCCTGGGTTTCCAGTCAAGCATCATC 3' | (SEQ ID NO: 97) |
| | 5' flap1-TCACTGTTTCTCAGCC 3' | (SEQ ID NO: 98) |
| FATB-C3-EMS02 | 5'CGCTCTGCGTCTATAGAAACAGTCATGAACCAC TTACAGT 3' | (SEQ ID NO: 99) |
| | 5' flap1-ATATATTACAATCACACTCGATTG 3' | (SEQ ID NO: 100) |
| ENDO1 | 5' TGAGGAGCGTGGTGGTCCCACACCTT 3' | (SEQ ID NO: 101) |
| | 5' flap2-CGATGCGACCAGC 3' | (SEQ ID NO: 102) |

The invention claimed is:

1. An induced mutant FATB allele comprising
   (a) a nucleic acid molecule comprising at least 90% sequence identity to SEQ ID NO: 1, SEQ ID NO: 3, SEQ ID NO: 5, SEQ ID NO: 7, SEQ ID NO: 9, or SEQ ID NO: 11; or
   (b) a nucleic acid molecule comprising at least 90% sequence identity to SEQ ID NO: 1, SEQ ID NO: 3, SEQ ID NO: 5, SEQ ID NO: 7, SEQ ID NO: 9, or SEQ ID NO: 11 when aligned without introns 1 to 4;
   wherein said induced mutant FATB allele comprises a mutated DNA region including one or more inserted, deleted, or substituted nucleotides compared to a corresponding wild-type DNA, and wherein said mutant FATB allele does not encode a functional FATB protein.

2. A mutant allele of a gene encoding a functional FATB protein, wherein the functional FATB gene comprises:
   (a) a nucleic acid molecule
      (i) comprising at least 90% sequence identity to SEQ ID NO: 1, SEQ ID NO: 3, SEQ ID NO: 5, SEQ ID NO: 7, SEQ ID NO: 9, or SEQ ID NO: 11; and
      (ii) encoding an amino acid sequence comprising at least 90% sequence identity to SEQ ID NO: 2, SEQ ID NO: 4, SEQ ID NO: 6, SEQ ID NO: 8 SEQ ID NO: 10, or SEQ ID NO: 12, or
   (b) a nucleic acid molecule
      (i) comprising at least 90% sequence identity to SEQ ID NO: 1, SEQ ID NO: 3, SEQ ID NO: 5, SEQ ID NO: 7, SEQ ID NO: 9, or SEQ ID NO: 11 when aligned without introns 1 to 4; and
      (ii) encoding an amino acid sequence comprising at least 90% sequence identity to SEQ ID NO: 2, SEQ ID NO: 4, SEQ ID NO: 6, SEQ ID No: 8, SEQ ID NO: 10, or SEQ ID NO: 12,
   wherein said mutant FATB allele comprises a mutated DNA region including one or more inserted, deleted, or substituted nucleotides compared to a corresponding wild-type DNA region in the functional FATB gene, and wherein said mutant FATB allele does not encode a functional FATB protein,
   wherein said mutant FATB allele is FATB-A1-FN1, FATB-A2-FN1, FATB-A2-FN 2, FATB-A2-FN3, FATB-C2-FN1, FATB-A1-EMS01, FATB-A1-EMS02, FATB-A1-EMS03, FATB-A1-EMS05, FATB-A1-EMS 06, FATB-A2-EMS01, FATB-A2-EMS04, FATB-A2-EMS05, FATB-A3-EMS01, FATB-C1-EMS05, FATB-C2-EMS02, FATB-C2-EMS03, FATB-C2-EMS05, FATB-C2-EMS06, FATB-A1-EMS07, FATB-A1-EMS09, FATB-A2-EMS02, FATB-A2-EMS03, FATB-C1-EMS 04, FATB-C2-EMS04, or FATB-C3-EMS02.

3. A *Brassica napus* plant, or cell, part, seed or progeny thereof, comprising at least three FATE alleles in its genome selected from FATB-A1-EMS05, FATB-A1-EMS06, FATB-A2-EMS01, FATB-A2-EMS05, FATB-A3-EMS01, FATB-C1-EMS04, FATB-C1-EMS05, FATB-C2-EMS02, FATB-C2-EMS03 or FATB-C3-EMS02, obtainable by propagation of and/or breeding with a *Brassica* plant grown from a seed (a) comprising FATB-A1-EMS05, FATB-A3-EMS01, FATB-C1-EMS04 and FATB-C3-EMS02 having been deposited at the NCIMB Limited on Jun. 27, 2008, under accession number NCIMB 41568,
   (b) comprising FATB-A1-EMS06, FATB-A2-EMS01, FATB-C1-EMS05 and FATB-C2-EMS03 having been deposited at the NCIMB Limited on Jun. 27, 2008, under accession number NCIMB 41567, or
   (c) comprising FATB-A2-EMS05, FATB-C1-EMS05 and FATB-C2-EMS02 having been deposited at the NCIMB Limited on Jun. 27, 2008, under accession number NCIMB 41566.

4. A *Brassica napus*, *Brassica juncea* or *Brassica carinata* plant, or cell, part, seed or progeny thereof, wherein said plant, or cell, part, seed or progeny thereof comprises at least three induced mutant FATB alleles in its genome, said at least three mutant alleles being an induced mutant allele comprising:
   (a) a nucleic acid molecule comprising at least 90% sequence identity to SEQ ID NO: 1, SEQ ID NO: 3, SEQ ID NO: 5, SEQ ID NO: 7, SEQ ID NO: 9, or SEQ ID NO: 11; or
   (b) a nucleic acid molecule comprising at least 90% sequence identity to SEQ ID NO: 1, SEQ ID NO: 3, SEQ ID NO: 5, SEQ ID NO: 7, SEQ ID NO: 9, or SEQ ID NO: 11 when aligned without introns 1 to 4;
   wherein said at least three induced mutant FATB alleles comprise a mutated DNA region including one or more inserted, deleted, or substituted nucleotides compared to a corresponding wild-type DNA, and wherein said at least three mutant FATB alleles do not encode a functional FATB protein, and
   whereby the at least three mutant FATB alleles are alleles of at least three different FATB genes.

5. The plant of claim 4, wherein the level of saturated fatty acids in the seed oil is less than 7 wt % based on the total amount of fatty acids in the seed oil.

6. The plant of claim 5, wherein the level of saturated fatty acids, especially palmitic and/or stearic acid, in the seed oil is less than 3.5 wt % based on the total amount of fatty acids in the seed oil.

7. The plant of claim 4, wherein said plant is *B. napus*.

8. The induced mutant FATB allele of claim 1, wherein the induced mutant FATB allele is an allele of a wild-type gene that encodes an amino acid sequence comprising at least 90% sequence identity to SEQ ID NO: 2, SEQ ID NO: 4, SEQ ID NO: 6, SEQ ID NO: 8, SEQ ID NO: 10, or SEQ ID NO: 12.

9. The induced mutant FATB allele of claim 1, wherein the induced mutant FATB allele comprises a gene that encodes a truncated FATB protein comprising an N-terminal part of the corresponding wild-type FATB protein of less than 229 amino acids lacking the second conserved Methionine.

10. The plant of claim 4, wherein the induced mutant FATB allele is an allele of a wild-type gene that encodes an amino acid sequence comprising at least 90% sequence identity to SEQ ID NO: 2, SEQ ID NO: 4, SEQ ID NO: 6, SEQ ID NO: 8, SEQ ID NO: 10, or SEQ ID NO: 12.

11. The plant of claim 4, wherein the induced mutant FATB allele comprises a gene that encodes a truncated FATB protein comprising an N-terminal part of the corresponding wild-type FATB protein of less than 229 amino acids and lacking the second conserved Methionine.

12. The induced mutant FATB allele of claim 1, wherein the mutant FATB allele comprises:
   (a) a nucleic acid molecule comprising at least 90% sequence identity to SEQ ID NO: 3, SEQ ID NO: 7 or SEQ ID NO: 9, or
   (b) a nucleic acid molecule comprising at least 90% sequence identity to SEQ ID NO: 3, SEQ ID NO: 7, or SEQ ID NO: 9 when aligned without introns 1 to 4.

13. The induced mutant FATB allele of claim 1, wherein the mutant FATB allele comprises:
   (a) a nucleic acid molecule comprising at least 98% sequence identity to SEQ ID NO: 1, SEQ ID NO: 3, SEQ ID NO: 5, SEQ ID NO: 7, SEQ ID NO: 9, or SEQ ID NO: 11; or
   (b) a nucleic acid molecule comprising at least 98% sequence identity to SEQ ID NO: 1, SEQ ID NO: 3, SEQ ID NO: 5, SEQ ID NO: 7, SEQ ID NO: 9, or SEQ ID NO: 11 when aligned without introns 1 to 4.

14. The plant of claim 4, wherein said at least three mutant alleles comprise:
   (a) a nucleic acid molecule comprising at least 90% sequence identity to SEQ ID NO: 3, SEQ ID NO: 7 or SEQ ID NO: 9, or
   (b) a nucleic acid molecule comprising at least 90% sequence identity to SEQ ID NO: 3, SEQ ID NO: 7, or SEQ ID NO: 9 when aligned without introns 1 to 4.

15. The plant of claim 4, which is *Brassica napus*, and wherein said at least three mutant alleles comprise:
   (a) a nucleic acid molecule comprising at least 98% sequence identity to SEQ ID NO: 1, SEQ ID NO: 3, SEQ ID NO: 5, SEQ ID NO: 7, SEQ ID NO: 9, or SEQ ID NO: 11; or
   (b) a nucleic acid molecule comprising at least 98% sequence identity to SEQ ID NO: 1, SEQ ID NO: 3, SEQ ID NO: 5, SEQ ID NO: 7, SEQ ID NO: 9, or SEQ ID NO: 11 when aligned without introns 1 to 4.

* * * * *

UNITED STATES PATENT AND TRADEMARK OFFICE
CERTIFICATE OF CORRECTION

| | | |
|---|---|---|
| PATENT NO. | : 8,981,180 B2 | Page 1 of 1 |
| APPLICATION NO. | : 12/668303 | |
| DATED | : March 17, 2015 | |
| INVENTOR(S) | : Benjamin Laga et al. | |

It is certified that error appears in the above-identified patent and that said Letters Patent is hereby corrected as shown below:

In the claims

In claim 3, column 237, line 62, delete "FATE" and insert --FATB--.

Signed and Sealed this
Twenty-seventh Day of October, 2015

Michelle K. Lee
*Director of the United States Patent and Trademark Office*